(12) United States Patent
Lee et al.

(10) Patent No.: US 9,515,269 B2
(45) Date of Patent: Dec. 6, 2016

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUKSAN HIGH METAL CO., LTD., Ulsan (KR)

(72) Inventors: Bumsung Lee, Cheonan-si (KR); Yeonhee Choi, Cheonan-si (KR); Sunhee Lee, Cheonan-si (KR); Daesung Kim, Yongin-si (KR); Kiho So, Cheonan-si (KR); Jinho Yun, Incheon (KR); Daehwan Oh, Cheonan-si (KR); Seongje Park, Busan (KR); Soungyun Mun, Yongin-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 92 days.

(21) Appl. No.: 14/442,608

(22) PCT Filed: Nov. 12, 2013

(86) PCT No.: PCT/KR2013/010220
§ 371 (c)(1),
(2) Date: May 13, 2015

(87) PCT Pub. No.: WO2014/077558
PCT Pub. Date: May 22, 2014

(65) Prior Publication Data
US 2016/0293846 A1     Oct. 6, 2016

(30) Foreign Application Priority Data

Nov. 13, 2012  (KR) .......................... 10-2012-0128114
Oct. 30, 2013  (KR) .......................... 10-2013-0130267

(51) Int. Cl.
*H01L 51/00* (2006.01)
*C07D 209/82* (2006.01)
*C09K 11/06* (2006.01)
*H01L 51/50* (2006.01)

(52) U.S. Cl.
CPC ......... *H01L 51/0061* (2013.01); *C07D 209/82* (2013.01); *C09K 11/06* (2013.01);
(Continued)

(58) Field of Classification Search
CPC .................... H01L 2251/552; H01L 51/5012
See application file for complete search history.

(56) References Cited

U.S. PATENT DOCUMENTS

| 2005/0221124 | A1  | 10/2005 | Hwang et al. |
| 2009/0302313 | A1* | 12/2009 | Choi ................... H01L 51/5012 257/40 |
| 2012/0205636 | A1* | 8/2012  | Kim ...................... C09K 11/06 257/40 |

FOREIGN PATENT DOCUMENTS

| JP | 2001-39934 A  | 2/2001 |
| JP | 2012-136498 A | 7/2012 |

(Continued)

OTHER PUBLICATIONS

International Search Report for International Application No. PCT/KR2013/010220; two pages; mailed Feb. 5, 2014; with English translation, two pages.

*Primary Examiner* — Charles Garber
*Assistant Examiner* — Ankush Singal
(74) *Attorney, Agent, or Firm* — Vorys, Sater, Seymour & Pease LLP; Min Suhn Koh

(57) ABSTRACT

The present invention provides a novel compound capable of improving light emitting efficiency, stability, and lifespan of the element, an organic element using the same, and an electric device for the same.

12 Claims, 1 Drawing Sheet

(52) U.S. Cl.
CPC .... *H01L 51/006* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1092* (2013.01); *H01L 51/0003* (2013.01); *H01L 51/0004* (2013.01); *H01L 51/0005* (2013.01); *H01L 51/0052* (2013.01); *H01L 51/0056* (2013.01); *H01L 51/0058* (2013.01); *H01L 51/0067* (2013.01); *H01L 51/0072* (2013.01); *H01L 51/0074* (2013.01); *H01L 51/504* (2013.01); *H01L 51/5056* (2013.01)

(56) References Cited

FOREIGN PATENT DOCUMENTS

| | | |
|---|---|---|
| KR | 10-2010-0023783 A | 3/2010 |
| KR | 10-2010-0106014 A | 10/2010 |
| KR | 10-2011-0044587 A | 4/2011 |
| KR | 10-2011-0049665 A | 5/2011 |
| KR | 10-2011-0134201 A | 12/2011 |
| KR | 10-2012-0034140 A | 4/2012 |
| KR | 10-1181281 B1 | 9/2012 |
| KR | 10-2012-0111670 A | 10/2012 |
| WO | 2012/090806 A1 | 7/2012 |

\* cited by examiner

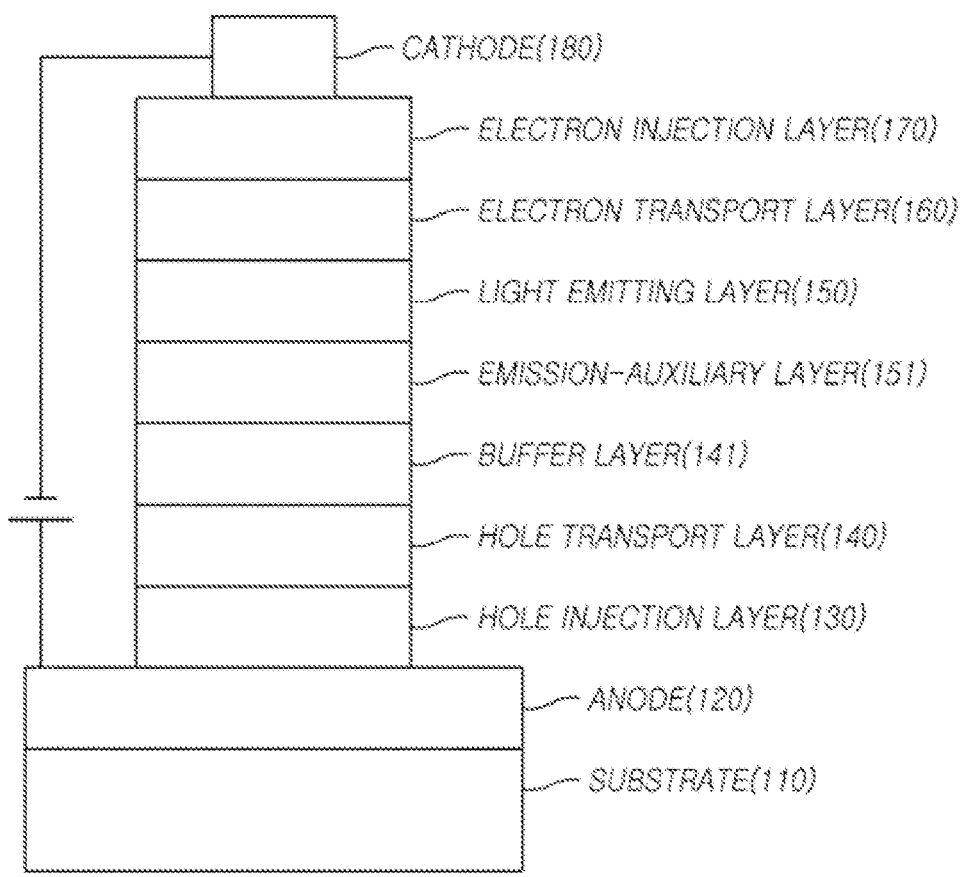

COMPOUND FOR ORGANIC ELECTRIC ELEMENT, ORGANIC ELECTRIC ELEMENT COMPRISING THE SAME AND ELECTRONIC DEVICE THEREOF

BACKGROUND

Technical Field

The present invention relates to a compound for an organic electric element, an organic electric element using the same, and an electronic device thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. Here, in many cases, the organic material layer may have a multi-layered structure including multiple layers made of different materials in order to improve the efficiency and stability of an organic electric element, and for example, may include a hole injection layer, a hole transport layer, a light emitting layer, an electron transport layer, an electron injection layer, and the like.

A material used as an organic material layer in an organic electric element may be classified into a light emitting material and a charge transport material, for example, a hole injection material, a hole transport material, an electron transport material, an electron injection material, and the like according to its function.

The most problematic issues in an organic electric element are life span and efficiency, and the situation is such that this life span or efficiency issue must be solved as displays become larger and larger. Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, in order to solve the emission problem with a hole transport layer in a recent organic electric element, an emission-auxiliary layer is present between the hole transport layer and a light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton.

However, since materials to be used in the hole transport layer must have low HOMO values, they mostly have low T1 values, and on account of this, the exciton formed in the light emitting layer is transferred into the hole transport layer, which causes charge unbalance in the light emitting layer and thus light emission at the light emitting layer-hole transport layer interface.

The light emission at the light emitting layer-hole transport layer interface has a problem in that color purity and efficiency are lowered and life span is shortened. Therefore, there is an urgent need to develop an emission-auxiliary layer which has a high T1 value and the HOMO level of which is between the HOMO energy level of a hole transport layer and the HOMO energy level of a light emitting layer.

In addition, it is required to develop a hole injection layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus there is an actual need to develop a material that is durable to such a deposition method, that is, a highly heat-resistant material.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

SUMMARY

In order to solve one or more of the above-mentioned problems occurring in the prior art, an aspect of the present invention is to provide a compound which allows an organic electric element to have high luminous efficiency, low driving voltage and high heat-resistant and to be improved in color purity and life span, an organic electric element using the same, and an electronic device including the organic electric element.

In accordance with an aspect of the present invention, there is provided a compound represented by Formula below.

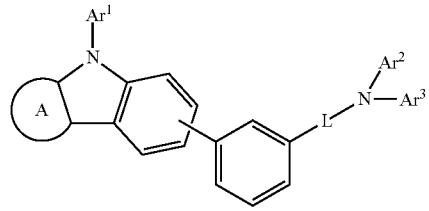

In another aspect of the present invention, there are provided an organic electric element using the compound represented by Formula above and an electronic device including the organic electric element.

By using the compound according to embodiments of the present invention, an organic electric element according to one or more embodiments of the present invention not only has high luminous efficiency, low driving voltage and high heat-resistant and, but can also be significantly improved in color purity, luminous efficiency, and life span.

BRIEF DESCRIPTION OF THE DRAWINGS

FIG. 1 illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

Unless otherwise stated, the term "halo" or "halogen" as used herein includes fluorine, chlorine, bromine, or iodine.

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "haloalkyl" or "halogen alkyl" as used herein includes an alkyl group substituted with a halogen.

Unless otherwise stated, the term "heteroalkyl" as used herein means alkyl substituted one or more carbon atoms with heteroatom.

Unless otherwise stated, the term "alkenyl" or "alkynyl" as used herein has, but not limited to, double or triple bonds of 2 to 60 carbon atoms, and includes a linear alkyl group, or a branched chain alkyl group, Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "alkenoxyl group", "alkenoxy group", "alkenyloxy group" or "alkenyloxy group" as used herein means an oxygen radical attached to an alkenyl group, but not limited to, and has 2 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "aryl group" or "arylene group" as used herein has, but not limited to, 6 to 60 carbon atoms. Herein, the aryl group or arylene group means a monocyclic or polycyclic aromatic group, and may also be formed in conjunction with an adjacent group. Examples of "aryl group" or "arylene group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "heteroalkyl" as used herein means alkyl containing one or more heteroatoms. Unless otherwise stated, the term "heteroaryl group" or "heteroarylene group" as used herein means, but not limited to, a $C_2$ to $C_{60}$ aryl or arylene group containing one or more heteroatoms, includes both monocyclic and polycyclic rings, and may also be formed in conjunction with an adjacent group.

Unless otherwise stated, the term "heterocyclic group" as used herein contains one or more heteroatoms, but not limited to, has 2 to 60 carbon atoms, includes both monocyclic and polycyclic rings, and may include alicyclic and/or aromatic group containing heteroatoms. Also, the heterocyclic group may also be formed in conjunction with an adjacent group.

Unless otherwise stated, the term "heteroatom" as used herein represents at least one of N, O, S, P, and Si.

Also, the term "heterocyclic group" may include $SO_2$ instead of carbon consisting of cycle. For example, "heterocyclic group" includes compound below.

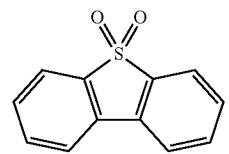 [SMILES: O=S1(=O)c2ccccc2-c2ccccc21]

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more heteroatoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

Otherwise specified, the Formulas used in the present invention are as defined in the index definition of the substituent of the following Formula:

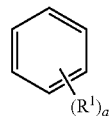

wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$'s may be the same and different, and are linked to the benzene ring as follows:

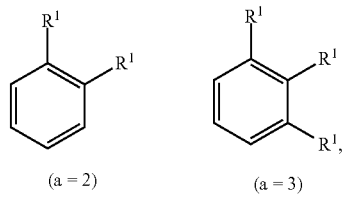

(a = 2)            (a = 3)

and when a is an integer of 4 to 6, the substituents $R^1$'s may be the same and different, and are linked to the benzene ring in a similar manner to that when a is an integer of 2 or 3, hydrogen atoms linked to carbon constituents of the benzene ring being not represented as usual.

FIG. 1 illustrates an organic electric element according to an embodiment of the present invention.

Referring to FIG. 1, an organic electric element 100 according to an embodiment of the present invention includes a first formed on a substrate 100, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as the light emitting layer 150, the hole transport layer 140, and/or the emission-auxiliary layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

As already described above, in order to solve the emission problem with a hole transport layer in a conventional organic electric element, an emission-auxiliary layer is preferably formed between the hole transport layer and a light emitting layer, and it is time to develop different emission-auxiliary layers according to respective light emitting layers (R, G, B). However, even when a similar core is used, it is very difficult to infer the characteristics of an emission-auxiliary layer if a used organic material layer varies because the correlation between the emission-auxiliary layer and a hole transport layer and the correlation between the emission-auxiliary layer and a light emitting layer (host) mused be discovered.

Accordingly, in the present invention, a combination of energy levels and T1 values, inherent material properties (mobility, interfacial properties, etc.), and the like among the respective layers included in the organic material layer is optimized by forming a light emitting layer or an emission-auxiliary layer by using the compound represented by Formula 1, and thus the life span and efficiency of the organic electric element can be improved at the same time.

The organic electric element according to an embodiment of the present invention may be manufactured using a PVD (physical vapor deposition) method. For example, the organic electric element may be manufactured by depositing a metal, a conductive metal oxide, or a mixture thereof on the substrate 110 to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R(Red), G(Green), B(Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

[Formula 1]

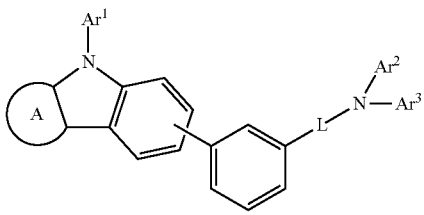

In Formula 1 above,

A ring may be a $C_{10}$-$C_{60}$ aromatic ring; or a $C_2$-$C_{60}$ heterocyclic group containing at least one heteroatom selected from the group consisting of O, N, S, Si, and P, and may be naphthalene or phenanthrene and so on.

$Ar^1$ to $Ar^3$ may be independently selected from the group consisting of a $C_6$-$C_{60}$ aryl group, a fluorenyl group, a $C_2$-$C_{60}$ heterocyclic group containing at least one heteroatom selected from O, N, S, Si, and P, a fused ring group of a $C_3$-$C_{60}$ aliphatic ring and a $C_6$-$C_{60}$ aromatic ring, a $C_1$-$C_{20}$ alkyl group, and a $C_2$-$C_{20}$ alkenyl group.

L may be selected from the group consisting of a single bond, a $C_6$-$C_{60}$ arylene group, and a fluorenylene group.

The above aromatic ring, aryl group, fluorenyl group, heterocyclic group, fused ring group, alkyl group, alkenyl group, arylene group, and fluorenylene group may be substituted by one or more substituents selected from the group consisting of deuterium, halogen, a silane group, a boron group, a germanium group, a cyano group, a nitro group, -L'-N($R^a$)($R^b$) (wherein, L' may be selected from the group consisting of a single bond, a $C_6$-$C_{60}$ arylene group, a fluorenylene group, a $C_2$-$C_{60}$ heterocyclic group containing at least one heteroatom selected from O, N, S, Si, and P, a fused ring group of a $C_3$-$C_{60}$ aliphatic ring and a $C_6$-$C_{60}$ aromatic ring, and a $C_1$-$C_{60}$ aliphatic hydrocarbon group, and the $R^a$ and $R^b$ may be independently selected from the group consisting of a $C_6$-$C_{60}$ aryl group, a fluorenyl group, a $C_2$-$C_{60}$ heterocyclic group containing at least one heteroatom selected from O, N, S, Si, and P, a $C_1$-$C_{20}$ alkyl group, and a $C_2$-$C_{20}$ alkenyl group), a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

Specially, the compound represented by Formula 1 above may be represented by one of Formulas below.

<Formula A1>

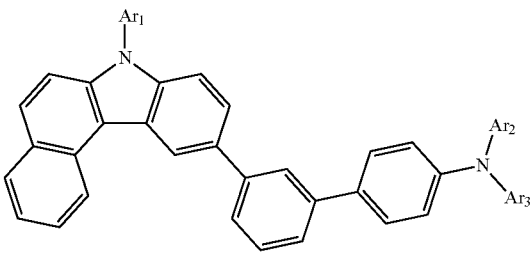

<Formula B1>

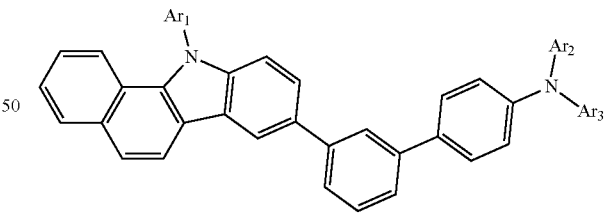

<Formula C1>

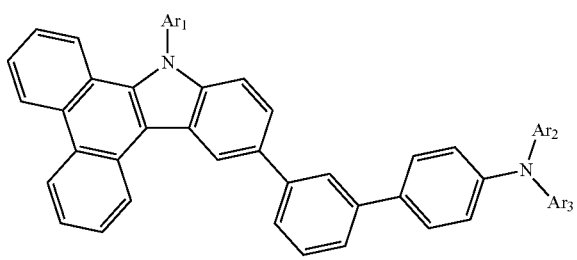

<Formula A2>
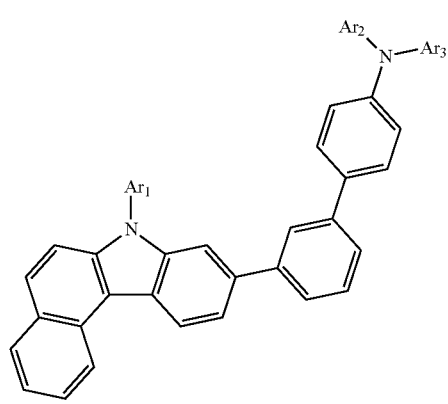
<Formula B2>
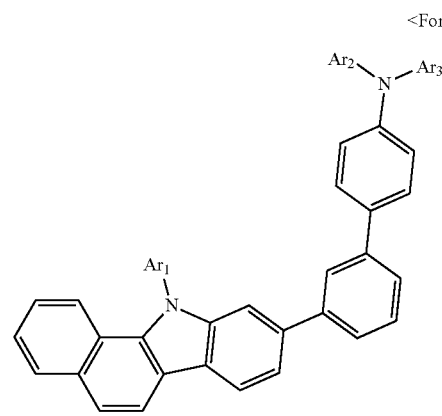
<Formula C2>
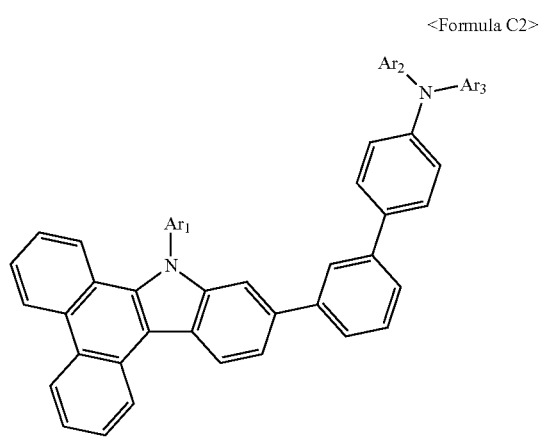
<Formula A3>
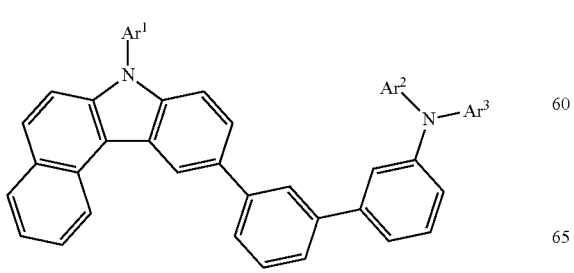
<Formula B3>
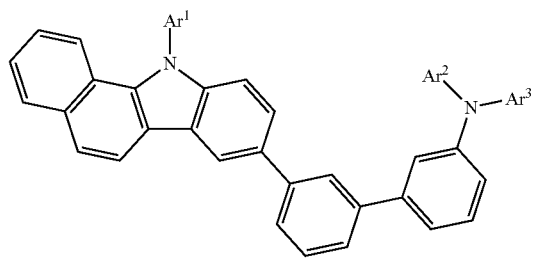
<Formula C3>
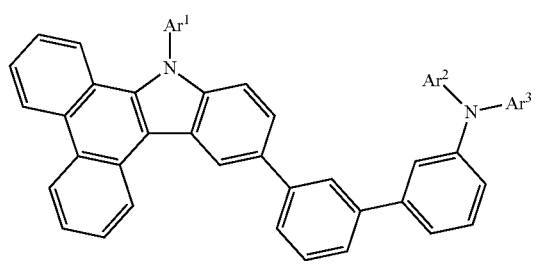
<Formula A4>
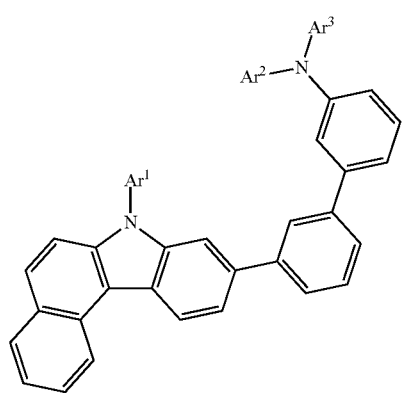
<Formula B4>
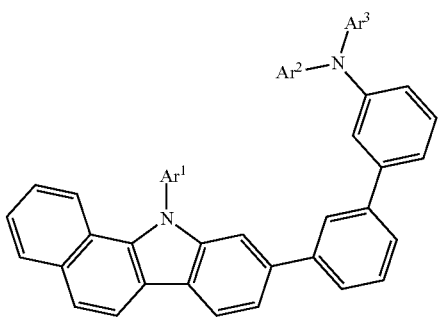

<Formula C4>
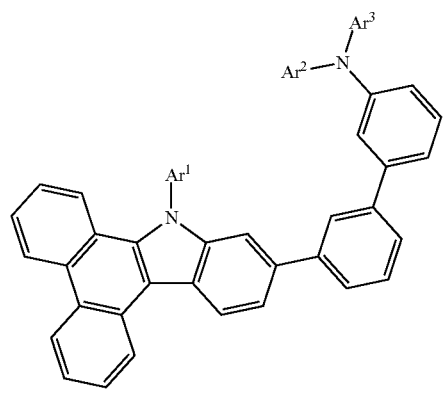
<Formula A5>
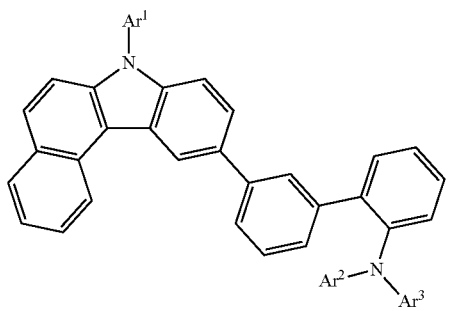
<Formula B5>
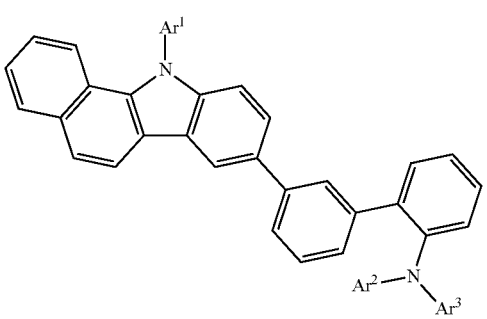
<Formula C5>
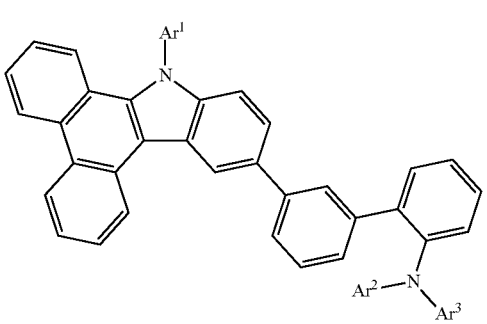
<Formula A6>
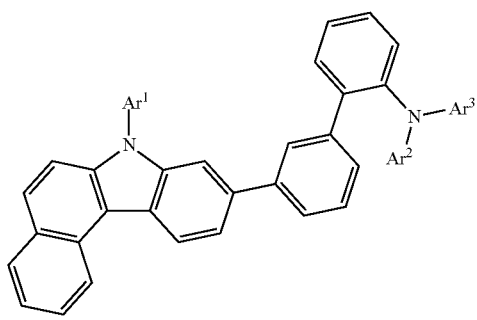
<Formula B6>
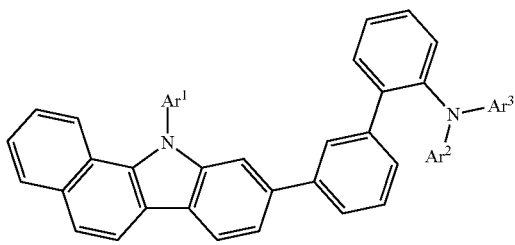
<Formula C6>
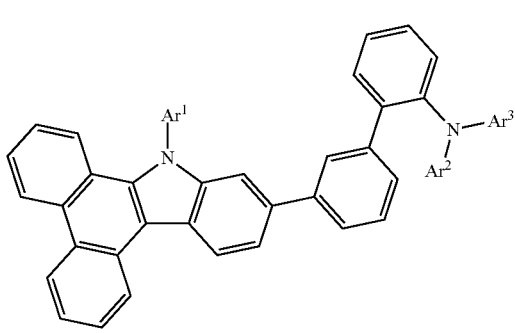
<Formula A7>
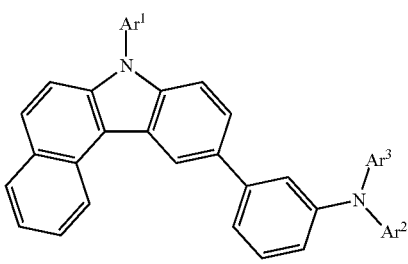
<Formula B7>
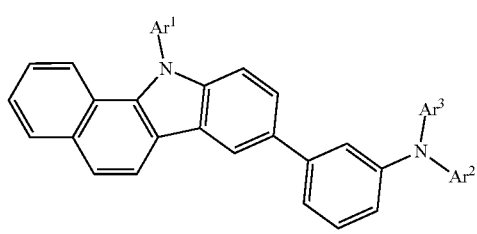

-continued

<Formula C7>

<Formula A8>

<Formula B8>

<Formula C8>

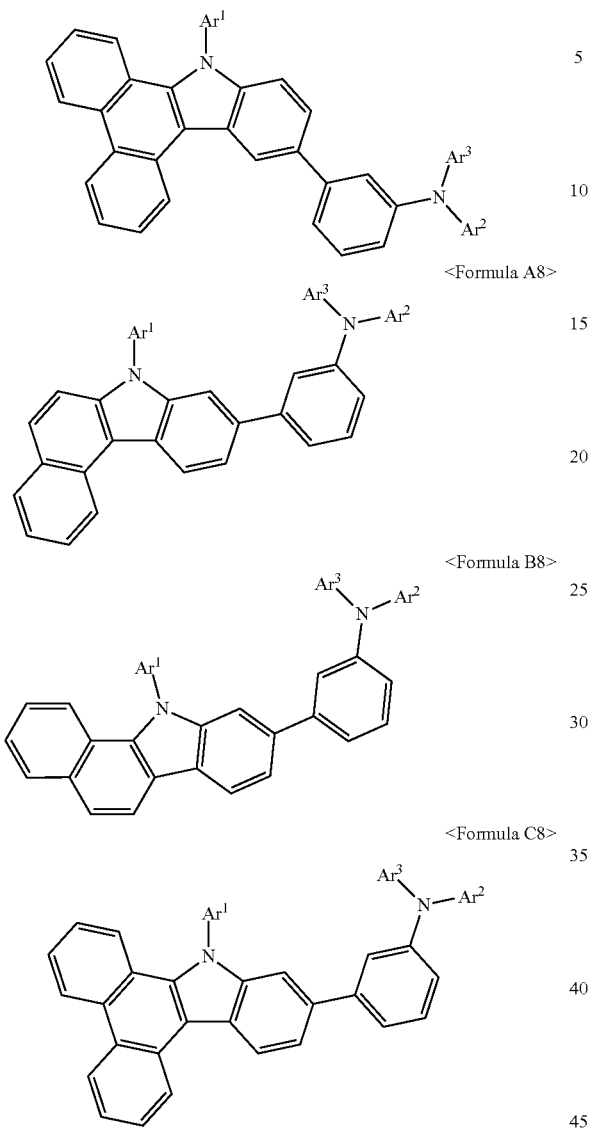

In formulas A1 to C8 above, Ar¹ to Ar³ are as defined in Formula 1 above.

Also, in formulas A1 to C8 above, Ar¹ to Ar³ may be independently any one of H1 to H22 below.

Namely, Ar¹ to Ar³ may be independently substituted any one of H1 to H22 below, more specially, the above Ar¹ may be substituted any one of H1 to H20 below, and Ar² and Ar³ may be independently substituted any one of H1 to H18, H21 and H22 below.

H1

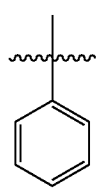

-continued

H2

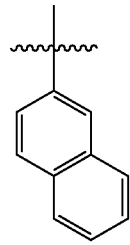

H3

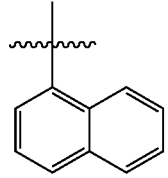

H4

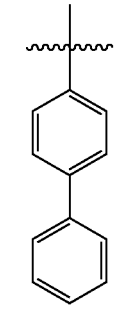

H5

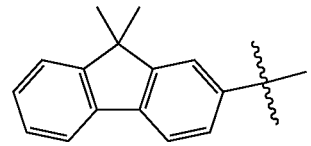

H6

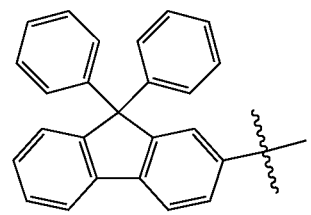

H7

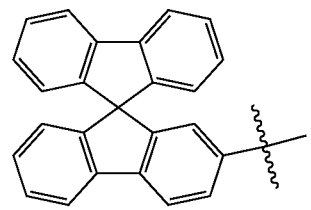

H8

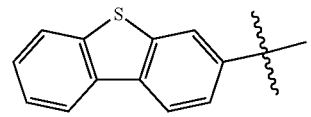

H9

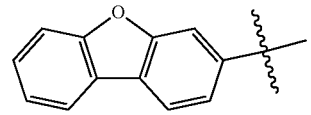

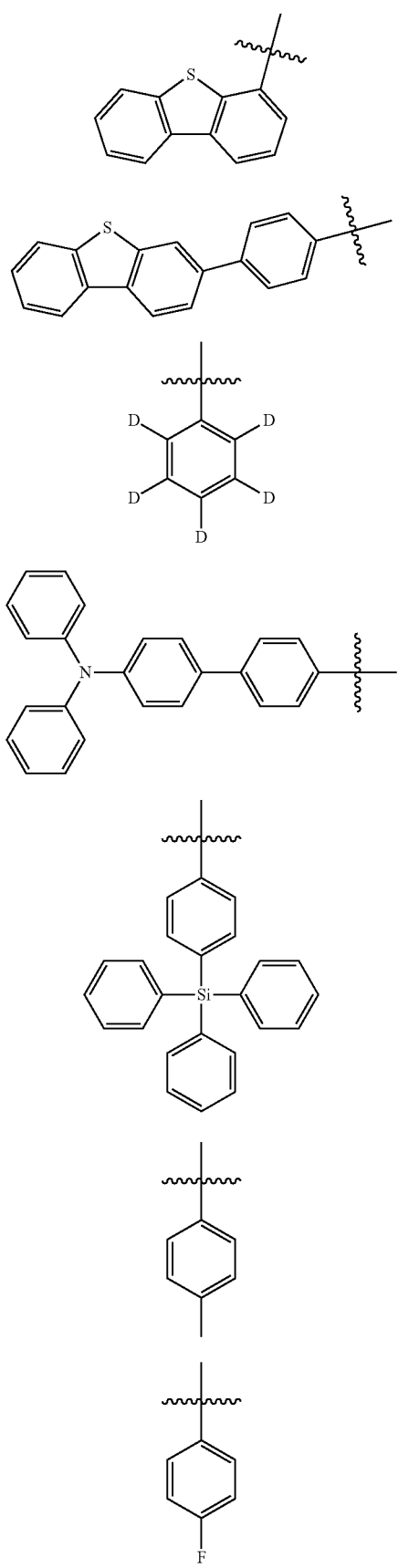
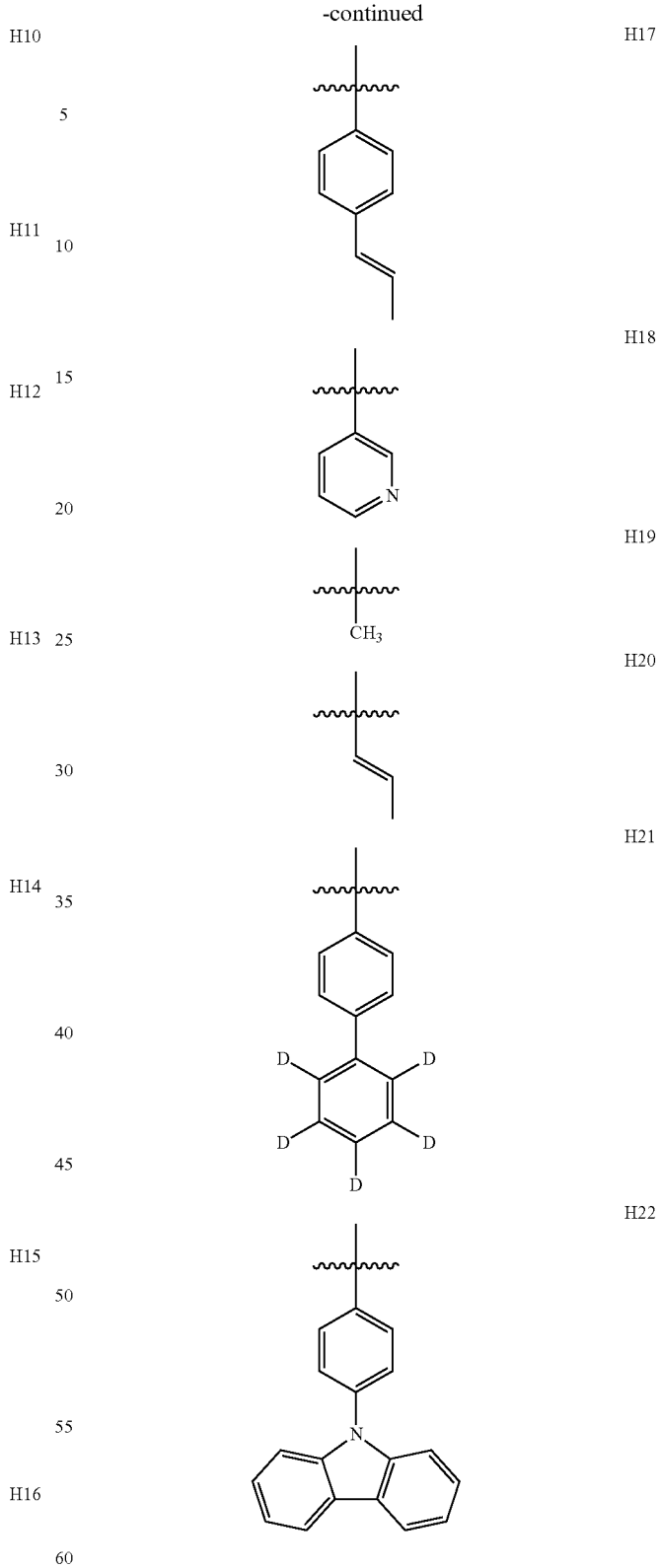
The tables 1 to 8 below are examples that the combinations of $Ar^1$ to $Ar^3$ of Formulas A1 to C8 may be independently any one of H1 to H22 above. The first two letters of each compound refer to Chemical Formulas A1 to C8.
Namely, the Formula A1 above is any one of A1-1 to A1-104 in the Tables below, the Formula B1 above is any one of B1-1 to B1-86 in the Tables below, the Formula C1 above is any one of C1-1 to C1-86 in the Tables below, the Formula A2 above is any one of A2-1 to A2-24 in the Tables below, the Formula B2 above is any one of B2-1 to B2-10 in the Tables below, the Formula C2 above is any one of C2-1 to C2-12 in the Tables below, the Formula A3 above is any one of A3-1 to A3-24 in the Tables below, the Formula B3 above is any one of B3-1 to B3-10 in the Tables below, the Formula C3 above is any one of C3-1 to C3-12 in the Tables below, the Formula A4 above is any one of A4-1 to A4-24 in the Tables below, the Formula B4 above is any one of B4-1 to B4-10 in the Tables below, the Formula C4 above is any one of C4-1 to C4-12 in the Tables below, the Formula A5 above is any one of A5-1 to A5-24 in the Tables below, the Formula B5 above is any one of B5-1 to B5-10 in the Tables below, the Formula 5 above is any one of C5-1 to C5-12 in the Tables below, the Formula A6 above is any one of A6-1 to A6-24 in the Tables below, the Formula B6 above is any one of B6-1 to B6-10 in the Tables below, the Formula C6 above is any one of C6-1 to C6-12 in the Tables below, the Formula A7 above is any one of A7-1 to A7-24 in the Tables below, the Formula B7 above is any one of B7-1 to B7-10 in the Tables below, the Formula C7 above is any one of C7-1 to C7-12 in the Tables below, and the Formula A8 above is any one of A8-1 to A8-24 in the Tables below, the Formula B8 above is any one of B8-1 to B8-10 in the Tables below, the Formula C8 above is any one of C8-1 to C8-12 in the Tables below.

For example, when $Ar^1$ is H1, $Ar^2$ is H5, and $Ar^3$ is H4 in Formula A1, Formula A1 may be represented by Formula below, and this is the compound A1-5.

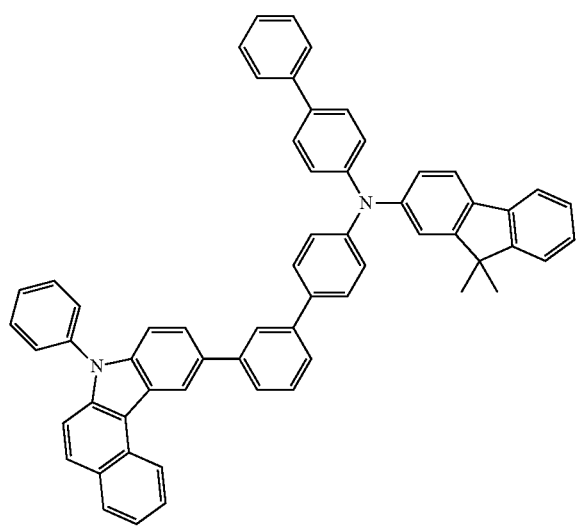

A1-5

When $Ar^1$ is H1, $Ar^2$ is H6 and $Ar^3$ is H4 in Formula C4, Formula C4 may be represented by Formula below, and this is the compound A4-4.

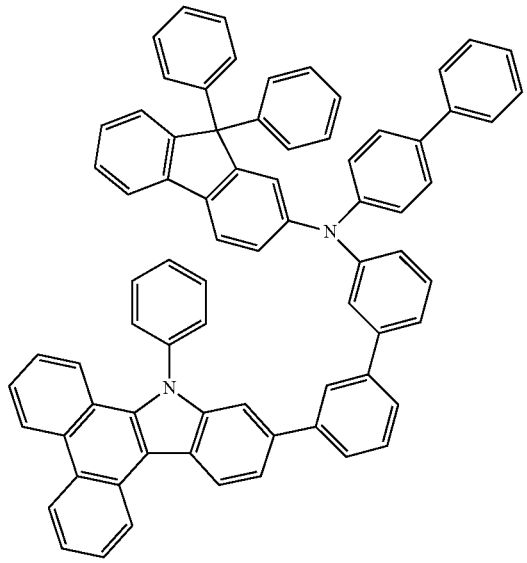

C4-4

When $Ar^1$ is H1, $Ar^2$ is H8 and $Ar^3$ is H4 in Formula B7, Formula B7 may be represented by Formula below, and this is the compound B7-6.

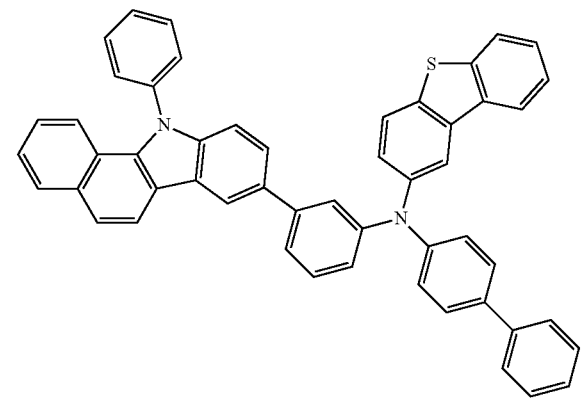

B7-6

In Tables 1 to 8, combinations of $Ar^1$ to $Ar^3$ of Formulas A1 to C8 for compounds A1-1 to C8-12 are summarized.

TABLE 1

| Compound | $Ar^1$ | $Ar^2$ | $Ar^3$ | Compound | $Ar^1$ | $Ar^2$ | $Ar^3$ |
|---|---|---|---|---|---|---|---|
| A1-1 | H1 | H5 | H12 | A1-2 | H4 | H5 | H1 |
| A1-3 | H2 | H5 | H1 | A1-4 | H3 | H5 | H1 |
| A1-5 | H1 | H5 | H4 | A1-6 | H4 | H5 | H4 |
| A1-7 | H2 | H5 | H4 | A1-8 | H3 | H5 | H4 |
| A1-9 | H1 | H5 | H3 | A1-10 | H4 | H5 | H3 |
| A1-11 | H2 | H5 | H3 | A1-12 | H3 | H5 | H3 |
| A1-13 | H1 | H6 | H1 | A1-14 | H4 | H6 | H1 |
| A1-15 | H2 | H6 | H1 | A1-16 | H3 | H6 | H1 |
| A1-17 | H1 | H6 | H4 | A1-18 | H4 | H6 | H4 |
| A1-19 | H2 | H6 | H4 | A1-20 | H3 | H6 | H4 |
| A1-21 | H1 | H6 | H3 | A1-22 | H4 | H6 | H3 |
| A1-23 | H2 | H6 | H3 | A1-24 | H3 | H6 | H3 |
| A1-25 | H1 | H7 | H1 | A1-26 | H4 | H7 | H1 |
| A1-27 | H2 | H7 | H1 | A1-28 | H3 | H7 | H1 |

TABLE 1-continued

| Compound | Ar¹ | Ar² | Ar³ | Compound | Ar¹ | Ar² | Ar³ |
|---|---|---|---|---|---|---|---|
| A1-29 | H1 | H7 | H3 | A1-30 | H4 | H7 | H3 |
| A1-31 | H2 | H7 | H3 | A1-32 | H3 | H7 | H3 |
| A1-33 | H1 | H7 | H4 | A1-34 | H4 | H7 | H4 |
| A1-35 | H2 | H7 | H4 | A1-36 | H3 | H7 | H4 |
| A1-37 | H1 | H4 | H1 | A1-38 | H4 | H4 | H1 |
| A1-39 | H2 | H4 | H1 | A1-40 | H3 | H4 | H1 |
| A1-41 | H1 | H4 | H4 | A1-42 | H4 | H4 | H4 |
| A1-43 | H2 | H4 | H4 | A1-44 | H3 | H4 | H4 |
| A1-45 | H1 | H4 | H3 | A1-46 | H4 | H4 | H3 |
| A1-47 | H2 | H4 | H3 | A1-48 | H3 | H4 | H3 |
| A1-49 | H1 | H4 | H2 | A1-50 | H4 | H4 | H2 |
| A1-51 | H2 | H4 | H2 | A1-52 | H3 | H4 | H2 |
| A1-53 | H1 | H1 | H3 | A1-54 | H4 | H1 | H3 |
| A1-55 | H2 | H1 | H3 | A1-56 | H3 | H1 | H3 |
| A1-57 | H1 | H1 | H2 | A1-58 | H4 | H1 | H2 |
| A1-59 | H2 | H1 | H2 | A1-60 | H3 | H1 | H2 |
| A1-61 | H1 | H3 | H3 | A1-62 | H4 | H3 | H3 |
| A1-63 | H2 | H3 | H3 | A1-64 | H3 | H3 | H3 |
| A1-65 | H1 | H3 | H2 | A1-66 | H4 | H3 | H2 |
| A1-67 | H2 | H3 | H2 | A1-68 | H3 | H3 | H2 |
| A1-69 | H1 | H2 | H2 | A1-70 | H4 | H2 | H2 |
| A1-71 | H2 | H2 | H2 | A1-72 | H3 | H2 | H2 |
| A1-73 | H1 | H8 | H1 | A1-74 | H4 | H8 | H1 |
| A1-75 | H2 | H8 | H1 | A1-76 | H3 | H8 | H1 |
| A1-77 | H1 | H9 | H1 | A1-78 | H4 | H9 | H1 |
| A1-79 | H2 | H9 | H1 | A1-80 | H3 | H9 | H1 |
| A1-81 | H1 | H8 | H4 | A1-82 | H4 | H8 | H4 |
| A1-83 | H2 | H8 | H4 | A1-84 | H3 | H8 | H4 |
| A1-85 | H1 | H9 | H4 | A1-86 | H4 | H9 | H4 |
| A1-87 | H2 | H9 | H4 | A1-88 | H3 | H9 | H4 |
| A1-89 | H1 | H8 | H3 | A1-90 | H4 | H8 | H3 |
| A1-91 | H2 | H8 | H3 | A1-92 | H3 | H8 | H3 |
| A1-93 | H1 | H9 | H3 | A1-94 | H4 | H9 | H3 |
| A1-95 | H2 | H9 | H3 | A1-96 | H3 | H9 | H3 |
| A1-97 | H1 | H11 | H1 | A1-98 | H4 | H10 | H1 |
| A1-99 | H1 | H1 | H1 | A1-100 | H4 | H1 | H1 |
| A1-101 | H1 | H5 | H15 | A1-102 | H18 | H5 | H2 |
| A1-103 | H1 | H5 | H21 | A1-104 | H1 | H5 | H22 |
| B1-1 | H1 | H5 | H1 | B1-2 | H4 | H5 | H1 |
| B1-3 | H2 | H5 | H1 | B1-4 | H3 | H5 | H1 |
| B1-5 | H1 | H5 | H4 | B1-6 | H4 | H5 | H4 |
| B1-7 | H2 | H5 | H4 | B1-8 | H3 | H5 | H4 |
| B1-9 | H1 | H5 | H3 | B1-10 | H4 | H5 | H3 |
| B1-11 | H2 | H5 | H3 | B1-12 | H3 | H5 | H3 |
| B1-13 | H1 | H6 | H1 | B1-14 | H4 | H6 | H1 |
| B1-15 | H2 | H6 | H1 | B1-16 | H3 | H6 | H1 |
| B1-17 | H1 | H6 | H4 | B1-18 | H4 | H6 | H4 |
| B1-19 | H2 | H6 | H4 | B1-20 | H3 | H6 | H4 |
| B1-21 | H1 | H6 | H3 | B1-22 | H4 | H6 | H3 |
| B1-23 | H2 | H6 | H3 | B1-24 | H3 | H6 | H3 |
| B1-25 | H1 | H7 | H1 | B1-26 | H4 | H7 | H1 |
| B1-27 | H2 | H7 | H1 | B1-28 | H3 | H7 | H1 |
| B1-29 | H1 | H7 | H3 | B1-30 | H4 | H7 | H3 |
| B1-31 | H2 | H7 | H3 | B1-32 | H3 | H7 | H3 |
| B1-33 | H1 | H7 | H4 | B1-34 | H4 | H7 | H4 |
| B1-35 | H2 | H7 | H4 | B1-36 | H3 | H7 | H4 |
| B1-37 | H1 | H4 | H1 | B1-38 | H4 | H4 | H1 |
| B1-39 | H2 | H4 | H1 | B1-40 | H3 | H4 | H1 |
| B1-41 | H1 | H4 | H4 | B1-42 | H4 | H4 | H4 |
| B1-43 | H2 | H4 | H4 | B1-44 | H3 | H4 | H4 |
| B1-45 | H1 | H4 | H3 | B1-46 | H4 | H4 | H3 |
| B1-47 | H2 | H4 | H3 | B1-48 | H3 | H4 | H3 |
| B1-49 | H1 | H4 | H2 | B1-50 | H4 | H4 | H2 |
| B1-51 | H2 | H4 | H2 | B1-52 | H3 | H4 | H2 |
| B1-53 | H1 | H1 | H3 | B1-54 | H4 | H1 | H3 |
| B1-55 | H2 | H1 | H3 | B1-56 | H3 | H1 | H3 |
| B1-57 | H1 | H1 | H2 | B1-58 | H4 | H1 | H2 |
| B1-59 | H2 | H1 | H2 | B1-60 | H3 | H1 | H2 |
| B1-61 | H1 | H8 | H1 | B1-62 | H4 | H8 | H1 |
| B1-63 | H2 | H8 | H1 | B1-64 | H3 | H8 | H1 |
| B1-65 | H1 | H9 | H1 | B1-66 | H4 | H9 | H1 |
| B1-67 | H2 | H9 | H1 | B1-68 | H3 | H9 | H1 |
| B1-69 | H1 | H8 | H4 | B1-70 | H4 | H8 | H4 |
| B1-71 | H2 | H8 | H4 | B1-72 | H3 | H8 | H4 |
| B1-73 | H1 | H9 | H4 | B1-74 | H4 | H9 | H4 |
| B1-75 | H2 | H9 | H4 | B1-76 | H3 | H9 | H4 |
| B1-77 | H1 | H8 | H3 | B1-78 | H4 | H8 | H3 |
| B1-79 | H2 | H8 | H3 | B1-80 | H3 | H8 | H3 |
| B1-81 | H1 | H9 | H3 | B1-82 | H4 | H9 | H3 |
| B1-83 | H2 | H9 | H3 | B1-84 | H3 | H9 | H3 |
| B1-85 | H1 | H1 | H14 | B1-86 | H1 | H1 | H13 |
| C1-1 | H1 | H5 | H1 | C1-2 | H4 | H5 | H1 |
| C1-3 | H2 | H5 | H1 | C1-4 | H3 | H5 | H1 |
| C1-5 | H1 | H5 | H4 | C1-6 | H4 | H5 | H4 |
| C1-7 | H2 | H5 | H4 | C1-8 | H3 | H5 | H4 |
| C1-9 | H1 | H5 | H3 | C1-10 | H4 | H5 | H3 |
| C1-11 | H2 | H5 | H3 | C1-12 | H3 | H5 | H3 |
| C1-13 | H1 | H6 | H1 | C1-14 | H4 | H6 | H1 |
| C1-15 | H2 | H6 | H1 | C1-16 | H3 | H6 | H1 |
| C1-17 | H1 | H6 | H4 | C1-18 | H4 | H6 | H4 |
| C1-19 | H2 | H6 | H4 | C1-20 | H3 | H6 | H4 |
| C1-21 | H1 | H6 | H3 | C1-22 | H4 | H6 | H3 |
| C1-23 | H2 | H6 | H3 | C1-24 | H3 | H6 | H3 |
| C1-25 | H1 | H7 | H1 | C1-26 | H4 | H7 | H1 |
| C1-27 | H2 | H7 | H1 | C1-28 | H3 | H7 | H1 |
| C1-29 | H1 | H7 | H3 | C1-30 | H4 | H7 | H3 |
| C1-31 | H2 | H7 | H3 | C1-32 | H3 | H7 | H3 |
| C1-33 | H1 | H7 | H4 | C1-34 | H4 | H7 | H4 |
| C1-35 | H2 | H7 | H4 | C1-36 | H3 | H7 | H4 |
| C1-37 | H1 | H4 | H1 | C1-38 | H4 | H4 | H1 |
| C1-39 | H2 | H4 | H1 | C1-40 | H3 | H4 | H1 |
| C1-41 | H1 | H4 | H4 | C1-42 | H4 | H4 | H4 |
| C1-43 | H2 | H4 | H4 | C1-44 | H3 | H4 | H4 |
| C1-45 | H1 | H4 | H3 | C1-46 | H4 | H4 | H3 |
| C1-47 | H2 | H4 | H3 | C1-48 | H3 | H4 | H3 |
| C1-49 | H1 | H4 | H2 | C1-50 | H4 | H4 | H2 |
| C1-51 | H2 | H4 | H2 | C1-52 | H3 | H4 | H2 |
| C1-53 | H1 | H1 | H3 | C1-54 | H4 | H1 | H3 |
| C1-55 | H2 | H1 | H3 | C1-56 | H3 | H1 | H3 |
| C1-57 | H1 | H1 | H2 | C1-58 | H4 | H1 | H2 |
| C1-59 | H2 | H1 | H2 | C1-60 | H3 | H1 | H2 |
| C1-61 | H1 | H8 | H1 | C1-62 | H4 | H8 | H1 |
| C1-63 | H2 | H8 | H1 | C1-64 | H3 | H8 | H1 |
| C1-65 | H1 | H9 | H1 | C1-66 | H4 | H9 | H1 |
| C1-67 | H2 | H9 | H1 | C1-68 | H3 | H9 | H1 |
| C1-69 | H1 | H8 | H4 | C1-70 | H4 | H8 | H4 |
| C1-71 | H2 | H8 | H4 | C1-72 | H3 | H8 | H4 |
| C1-73 | H1 | H9 | H4 | C1-74 | H4 | H9 | H4 |
| C1-75 | H2 | H9 | H4 | C1-76 | H3 | H9 | H4 |
| C1-77 | H1 | H8 | H3 | C1-78 | H4 | H8 | H3 |
| C1-79 | H2 | H8 | H3 | C1-80 | H3 | H8 | H3 |
| C1-81 | H1 | H9 | H3 | C1-82 | H4 | H9 | H3 |
| C1-83 | H2 | H9 | H3 | C1-84 | H3 | H9 | H3 |
| C1-85 | H19 | H1 | H1 | C1-86 | H20 | H1 | H1 |

TABLE 2

| Compound | Ar¹ | Ar² | Ar³ | Compound | Ar¹ | Ar² | Ar³ |
|---|---|---|---|---|---|---|---|
| A2-1 | H1 | H5 | H1 | A2-2 | H1 | H5 | H4 |
| A2-3 | H1 | H5 | H3 | A2-4 | H1 | H6 | H1 |
| A2-5 | H1 | H6 | H4 | A2-6 | H1 | H6 | H3 |
| A2-7 | H1 | H7 | H1 | A2-8 | H1 | H7 | H3 |
| A2-9 | H1 | H7 | H4 | A2-10 | H1 | H4 | H1 |
| A2-11 | H4 | H4 | H1 | A2-12 | H1 | H4 | H4 |
| A2-13 | H4 | H4 | H4 | A2-14 | H1 | H4 | H3 |
| A2-15 | H1 | H4 | H2 | A2-16 | H1 | H1 | H3 |
| A2-17 | H1 | H1 | H2 | A2-18 | H1 | H8 | H1 |
| A2-19 | H1 | H9 | H1 | A2-20 | H1 | H8 | H4 |
| A2-21 | H1 | H9 | H4 | A2-22 | H1 | H8 | H3 |
| A2-23 | H1 | H9 | H3 | A2-24 | H1 | H1 | H1 |
| B2-1 | H1 | H5 | H1 | B2-2 | H1 | H6 | H1 |
| B2-3 | H4 | H4 | H1 | B2-4 | H4 | H4 | H4 |
| B2-5 | H1 | H8 | H1 | B2-6 | H1 | H8 | H4 |
| B2-7 | H3 | H9 | H4 | B2-8 | H1 | H1 | H1 |
| B2-9 | H1 | H1 | H16 | B2-10 | H1 | H1 | H17 |
| C2-1 | H1 | H5 | H1 | C2-2 | H1 | H5 | H4 |
| C2-3 | H1 | H6 | H1 | C2-4 | H1 | H6 | H4 |
| C2-5 | H1 | H7 | H1 | C2-6 | H1 | H4 | H1 |
| C2-7 | H1 | H4 | H4 | C2-8 | H1 | H1 | H3 |
| C2-9 | H1 | H1 | H2 | C2-10 | H1 | H8 | H1 |
| C2-11 | H1 | H9 | H1 | C2-12 | H1 | H1 | H1 |

TABLE 3

| Compound | Ar¹ | Ar² | Ar³ | Compound | Ar¹ | Ar² | Ar³ |
|---|---|---|---|---|---|---|---|
| A3-1 | H1 | H5 | H1 | A3-2 | H1 | H5 | H4 |
| A3-3 | H1 | H5 | H3 | A3-4 | H1 | H6 | H1 |
| A3-5 | H1 | H6 | H4 | A3-6 | H1 | H6 | H3 |
| A3-7 | H1 | H7 | H1 | A3-8 | H1 | H7 | H3 |
| A3-9 | H1 | H7 | H4 | A3-10 | H1 | H4 | H1 |
| A3-11 | H4 | H4 | H1 | A3-12 | H1 | H4 | H4 |
| A3-13 | H4 | H4 | H4 | A3-14 | H1 | H4 | H3 |
| A3-15 | H1 | H4 | H2 | A3-16 | H1 | H1 | H3 |
| A3-17 | H1 | H1 | H2 | A3-18 | H1 | H8 | H1 |
| A3-19 | H1 | H9 | H1 | A3-20 | H1 | H8 | H4 |
| A3-21 | H1 | H9 | H4 | A3-22 | H1 | H8 | H3 |
| A3-23 | H1 | H9 | H3 | A3-24 | H1 | H1 | H1 |
| B3-1 | H1 | H5 | H1 | B3-2 | H1 | H6 | H1 |
| B3-3 | H4 | H4 | H1 | B3-4 | H4 | H4 | H4 |
| B3-5 | H1 | H8 | H1 | B3-6 | H1 | H8 | H4 |
| B3-7 | H3 | H9 | H4 | B3-8 | H1 | H1 | H1 |
| B3-9 | H1 | H1 | H16 | B3-10 | H1 | H1 | H17 |
| C3-1 | H1 | H5 | H1 | C3-2 | H1 | H5 | H4 |
| C3-3 | H1 | H6 | H1 | C3-4 | H1 | H6 | H4 |
| C3-5 | H1 | H7 | H1 | C3-6 | H1 | H4 | H1 |
| C3-7 | H1 | H4 | H4 | C3-8 | H1 | H1 | H3 |
| C3-9 | H1 | H1 | H2 | C3-10 | H1 | H8 | H1 |
| C3-11 | H1 | H9 | H1 | C3-12 | H1 | H1 | H1 |

TABLE 4

| Compound | Ar¹ | Ar² | Ar³ | Compound | Ar¹ | Ar² | Ar³ |
|---|---|---|---|---|---|---|---|
| A4-1 | H1 | H5 | H1 | A4-2 | H1 | H5 | H4 |
| A4-3 | H1 | H5 | H3 | A4-4 | H1 | H6 | H1 |
| A4-5 | H1 | H6 | H4 | A4-6 | H1 | H6 | H3 |
| A4-7 | H1 | H7 | H1 | A4-8 | H1 | H7 | H3 |
| A4-9 | H1 | H7 | H4 | A4-10 | H1 | H4 | H1 |
| A4-11 | H4 | H4 | H1 | A4-12 | H1 | H4 | H4 |
| A4-13 | H4 | H4 | H4 | A4-14 | H1 | H4 | H3 |
| A4-15 | H1 | H4 | H2 | A4-16 | H1 | H1 | H3 |
| A4-17 | H1 | H1 | H2 | A4-18 | H1 | H8 | H1 |
| A4-19 | H1 | H9 | H1 | A4-20 | H1 | H8 | H4 |
| A4-21 | H1 | H9 | H4 | A4-22 | H1 | H8 | H3 |
| A4-23 | H1 | H9 | H3 | A4-24 | H1 | H1 | H1 |
| B4-1 | H1 | H5 | H1 | B4-2 | H1 | H6 | H1 |
| B4-3 | H4 | H4 | H1 | B4-4 | H4 | H4 | H4 |
| B4-5 | H1 | H8 | H1 | B4-6 | H1 | H8 | H4 |
| B4-7 | H3 | H9 | H4 | B4-8 | H1 | H1 | H1 |
| B4-9 | H1 | H1 | H16 | B4-10 | H1 | H1 | H17 |
| C4-1 | H1 | H5 | H1 | C4-2 | H1 | H5 | H4 |
| C4-3 | H1 | H6 | H1 | C4-4 | H1 | H6 | H4 |
| C4-5 | H1 | H7 | H1 | C4-6 | H1 | H4 | H1 |
| C4-7 | H1 | H4 | H4 | C4-8 | H1 | H1 | H3 |
| C4-9 | H1 | H1 | H2 | C4-10 | H1 | H8 | H1 |
| C4-11 | H1 | H9 | H1 | C4-12 | H1 | H1 | H1 |

TABLE 5

| Compound | Ar¹ | Ar² | Ar³ | Compound | Ar¹ | Ar² | Ar³ |
|---|---|---|---|---|---|---|---|
| A5-1 | H1 | H5 | H1 | A5-2 | H1 | H5 | H4 |
| A5-3 | H1 | H5 | H3 | A5-4 | H1 | H6 | H1 |
| A5-5 | H1 | H6 | H4 | A5-6 | H1 | H6 | H3 |
| A5-7 | H1 | H7 | H1 | A5-8 | H1 | H7 | H3 |
| A5-9 | H1 | H7 | H4 | A5-10 | H1 | H4 | H1 |
| A5-11 | H4 | H4 | H1 | A5-12 | H1 | H4 | H4 |
| A5-13 | H4 | H4 | H4 | A5-14 | H1 | H4 | H3 |
| A5-15 | H1 | H4 | H2 | A5-16 | H1 | H1 | H3 |
| A5-17 | H1 | H1 | H2 | A5-18 | H1 | H8 | H1 |
| A5-19 | H1 | H9 | H1 | A5-20 | H1 | H8 | H4 |
| A5-21 | H1 | H9 | H4 | A5-22 | H1 | H8 | H3 |
| A5-23 | H1 | H9 | H3 | A5-24 | H1 | H1 | H1 |
| B5-1 | H1 | H5 | H1 | B5-2 | H1 | H6 | H1 |
| B5-3 | H4 | H4 | H1 | B5-4 | H4 | H4 | H4 |
| B5-5 | H1 | H8 | H1 | B5-6 | H1 | H8 | H4 |
| B5-7 | H3 | H9 | H4 | B5-8 | H1 | H1 | H1 |
| B5-9 | H1 | H1 | H16 | B5-10 | H1 | H1 | H17 |

TABLE 5-continued

| Compound | Ar¹ | Ar² | Ar³ | Compound | Ar¹ | Ar² | Ar³ |
|---|---|---|---|---|---|---|---|
| C5-1 | H1 | H5 | H1 | C5-2 | H1 | H5 | H4 |
| C5-3 | H1 | H6 | H1 | C5-4 | H1 | H6 | H4 |
| C5-5 | H1 | H7 | H1 | C5-6 | H1 | H4 | H1 |
| C5-7 | H1 | H4 | H4 | C5-8 | H1 | H1 | H3 |
| C5-9 | H1 | H1 | H2 | C5-10 | H1 | H8 | H1 |
| C5-11 | H1 | H9 | H1 | C5-12 | H1 | H1 | H1 |

TABLE 6

| Compound | Ar¹ | Ar² | Ar³ | Compound | Ar¹ | Ar² | Ar³ |
|---|---|---|---|---|---|---|---|
| A6-1 | H1 | H5 | H1 | A6-2 | H1 | H5 | H4 |
| A6-3 | H1 | H5 | H3 | A6-4 | H1 | H6 | H1 |
| A6-5 | H1 | H6 | H4 | A6-6 | H1 | H6 | H3 |
| A6-7 | H1 | H7 | H1 | A6-8 | H1 | H7 | H3 |
| A6-9 | H1 | H7 | H4 | A6-10 | H1 | H4 | H1 |
| A6-11 | H4 | H4 | H1 | A6-12 | H1 | H4 | H4 |
| A6-13 | H4 | H4 | H4 | A6-14 | H1 | H4 | H3 |
| A6-15 | H1 | H4 | H2 | A6-16 | H1 | H1 | H3 |
| A6-17 | H1 | H1 | H2 | A6-18 | H1 | H8 | H1 |
| A6-19 | H1 | H9 | H1 | A6-20 | H1 | H8 | H4 |
| A6-21 | H1 | H9 | H4 | A6-22 | H1 | H8 | H3 |
| A6-23 | H1 | H9 | H3 | A6-24 | H1 | H1 | H1 |
| B6-1 | H1 | H5 | H1 | B6-2 | H1 | H6 | H1 |
| B6-3 | H4 | H4 | H1 | B6-4 | H4 | H4 | H4 |
| B6-5 | H1 | H8 | H1 | B6-6 | H1 | H8 | H4 |
| B6-7 | H3 | H9 | H4 | B6-8 | H1 | H1 | H1 |
| B6-9 | H1 | H1 | H16 | B6-10 | H1 | H1 | H17 |
| C6-1 | H1 | H5 | H1 | C6-2 | H1 | H5 | H4 |
| C6-3 | H1 | H6 | H1 | C6-4 | H1 | H6 | H4 |
| C6-5 | H1 | H7 | H1 | C6-6 | H1 | H4 | H1 |
| C6-7 | H1 | H4 | H4 | C6-8 | H1 | H1 | H3 |
| C6-9 | H1 | H1 | H2 | C6-10 | H1 | H8 | H1 |
| C6-11 | H1 | H9 | H1 | C6-12 | H1 | H1 | H1 |
| A7-1 | H1 | H5 | H1 | A7-2 | H1 | H5 | H4 |
| A7-3 | H1 | H5 | H3 | A7-4 | H1 | H6 | H1 |
| A7-5 | H1 | H6 | H4 | A7-6 | H1 | H6 | H3 |
| A7-7 | H1 | H7 | H1 | A7-8 | H1 | H7 | H3 |
| A7-9 | H1 | H7 | H4 | A7-10 | H1 | H4 | H1 |
| A7-11 | H4 | H4 | H1 | A7-12 | H1 | H4 | H4 |
| A7-13 | H4 | H4 | H4 | A7-14 | H1 | H4 | H3 |
| A7-15 | H1 | H4 | H2 | A7-16 | H1 | H1 | H3 |
| A7-17 | H1 | H1 | H2 | A7-18 | H1 | H8 | H1 |
| A7-19 | H1 | H9 | H1 | A7-20 | H1 | H8 | H4 |
| A7-21 | H1 | H9 | H4 | A7-22 | H1 | H8 | H3 |
| A7-23 | H1 | H9 | H3 | A7-24 | H1 | H1 | H1 |
| B7-1 | H1 | H5 | H1 | B7-2 | H1 | H6 | H1 |
| B7-3 | H4 | H4 | H1 | B7-4 | H4 | H4 | H4 |
| B7-5 | H1 | H8 | H1 | B7-6 | H1 | H8 | H4 |
| B7-7 | H3 | H9 | H4 | B7-8 | H1 | H1 | H1 |
| B7-9 | H1 | H1 | H16 | B7-10 | H1 | H1 | H17 |
| C7-1 | H1 | H5 | H1 | C7-2 | H1 | H5 | H4 |
| C7-3 | H1 | H6 | H1 | C7-4 | H1 | H6 | H4 |
| C7-5 | H1 | H7 | H1 | C7-6 | H1 | H4 | H1 |
| C7-7 | H1 | H4 | H4 | C7-8 | H1 | H1 | H3 |
| C7-9 | H1 | H1 | H2 | C7-10 | H1 | H8 | H1 |
| C7-11 | H1 | H9 | H1 | C7-12 | H1 | H1 | H1 |

TABLE 7

| Compound | Ar¹ | Ar² | Ar³ | Compound | Ar¹ | Ar² | Ar³ |
|---|---|---|---|---|---|---|---|
| A8-1 | H1 | H5 | H1 | A8-2 | H1 | H5 | H4 |
| A8-3 | H1 | H5 | H3 | A8-4 | H1 | H6 | H1 |
| A8-5 | H1 | H6 | H4 | A8-6 | H1 | H6 | H3 |
| A8-7 | H1 | H7 | H1 | A8-8 | H1 | H7 | H3 |
| A8-9 | H1 | H7 | H4 | A8-10 | H1 | H4 | H1 |
| A8-11 | H4 | H4 | H1 | A8-12 | H1 | H4 | H4 |
| A8-13 | H4 | H4 | H4 | A8-14 | H1 | H4 | H3 |
| A8-15 | H1 | H4 | H2 | A8-16 | H1 | H1 | H3 |
| A8-17 | H1 | H1 | H2 | A8-18 | H1 | H8 | H1 |
| A8-19 | H1 | H9 | H1 | A8-20 | H1 | H8 | H4 |
| A8-21 | H1 | H9 | H4 | A8-22 | H1 | H8 | H3 |

TABLE 7-continued

| Compound | Ar¹ | Ar² | Ar³ | Compound | Ar¹ | Ar² | Ar³ |
|---|---|---|---|---|---|---|---|
| A8-23 | H1 | H9 | H3 | A8-24 | H1 | H1 | H1 |
| B8-1 | H1 | H5 | H1 | B8-2 | H1 | H6 | H1 |
| B8-3 | H4 | H4 | H1 | B8-4 | H4 | H4 | H4 |
| B8-5 | H1 | H8 | H1 | B8-6 | H1 | H8 | H4 |
| B8-7 | H3 | H9 | H4 | B8-8 | H1 | H1 | H1 |
| B8-9 | H1 | H1 | H16 | B8-10 | H1 | H1 | H17 |
| C8-1 | H1 | H5 | H1 | C8-2 | H1 | H5 | H4 |
| C8-3 | H1 | H6 | H1 | C8-4 | H1 | H6 | H4 |
| C8-5 | H1 | H7 | H1 | C8-6 | H1 | H4 | H1 |
| C8-7 | H1 | H4 | H4 | C8-8 | H1 | H1 | H3 |
| C8-9 | H1 | H1 | H2 | C8-10 | H1 | H8 | H1 |
| C8-11 | H1 | H9 | H1 | C8-12 | H1 | H1 | H1 |

TABLE 8

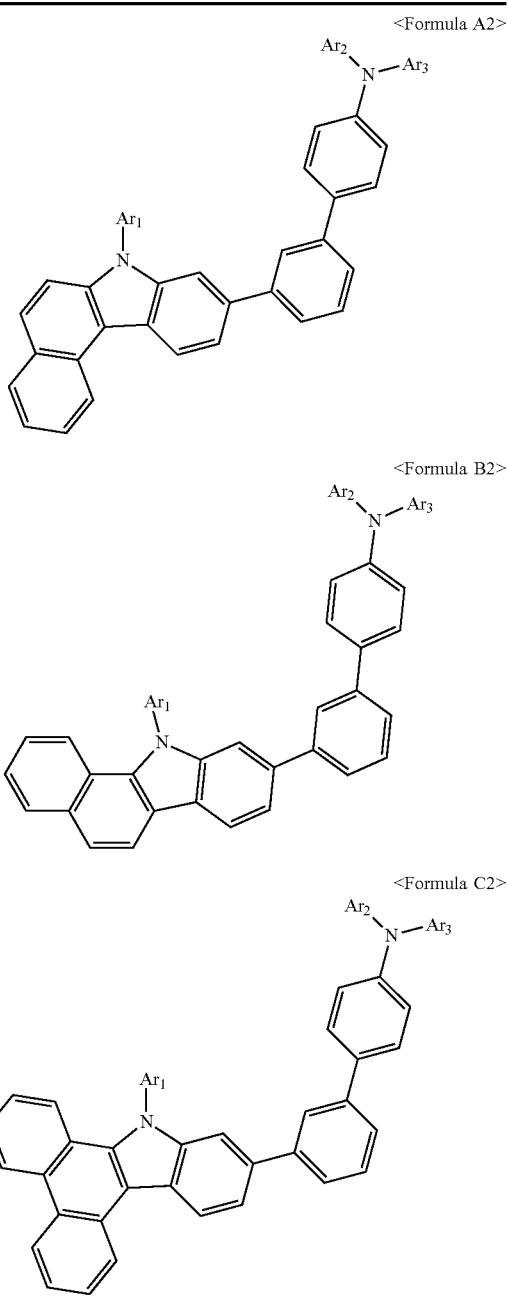

<Formula A2>

<Formula B2>

<Formula C2>

TABLE 8-continued

| Compound | Ar¹ | Ar² | Ar³ |
|---|---|---|---|
| A2-1 | H1 | H5 | H1 |
| A2-2 | H1 | H5 | H4 |
| A2-3 | H1 | H5 | H3 |
| A2-4 | H1 | H6 | H1 |
| A2-5 | H1 | H6 | H4 |
| A2-6 | H1 | H6 | H3 |
| A2-7 | H1 | H7 | H1 |
| A2-8 | H1 | H7 | H3 |
| A2-9 | H1 | H7 | H4 |
| A2-10 | H1 | H4 | H1 |
| A2-11 | H4 | H4 | H1 |
| A2-12 | H1 | H4 | H4 |
| A2-13 | H4 | H4 | H4 |
| A2-14 | H1 | H4 | H3 |
| A2-15 | H1 | H4 | H2 |
| A2-16 | H1 | H1 | H3 |
| A2-17 | H1 | H1 | H2 |
| A2-18 | H1 | H8 | H1 |
| A2-19 | H1 | H9 | H1 |
| A2-20 | H1 | H8 | H4 |
| A2-21 | H1 | H9 | H4 |
| A2-22 | H1 | H8 | H3 |
| A2-23 | H1 | H9 | H3 |
| A2-24 | H1 | H1 | H1 |
| B2-1 | H1 | H5 | H1 |
| B2-2 | H1 | H6 | H1 |
| B2-3 | H4 | H4 | H1 |
| B2-4 | H4 | H4 | H4 |
| B2-5 | H1 | H8 | H1 |
| B2-6 | H1 | H8 | H4 |
| B2-7 | H3 | H9 | H4 |
| B2-8 | H1 | H1 | H1 |
| B2-9 | H1 | H1 | H16 |
| B2-10 | H1 | H1 | H17 |
| C2-1 | H1 | H5 | H1 |
| C2-2 | H1 | H5 | H4 |
| C2-3 | H1 | H6 | H1 |
| C2-4 | H1 | H6 | H4 |
| C2-5 | H1 | H7 | H1 |
| C2-6 | H1 | H4 | H1 |
| C2-7 | H1 | H4 | H4 |
| C2-8 | H1 | H1 | H3 |
| C2-9 | H1 | H1 | H2 |
| C2-10 | H1 | H8 | H1 |
| C2-11 | H1 | H9 | H1 |
| C2-12 | H1 | H1 | H1 |

In another specific example of the present invention, the present invention provides an organic electric element comprising a first electrode, a second electrode, and an organic material layer disposed between the first electrode and the second electrode, wherein the organic material layer comprising the compound of claim 1. Specifically, the present invention provides an organic electric element comprising any one of the compounds represented by Formulas A1 to C8 in the organic material layer. More specifically, the present invention provides an organic electric element comprising the compound represented by the combination of the Tables 1 to 8 above in the organic material layer.

In another specific example of the present invention, the present invention provides an organic electric element further including one capping layer formed on at least one side opposite to the organic material layer of sides of the first or second electrodes.

In another specific example of the present invention, the present invention provides an organic electric element including the organic material layer formed by any one of the process of spin coating, nozzle printing, inkjet printing, slot coating, dip coating and roll-to-roll.

In another specific example of the present invention, the present invention provides an organic electric element comprising the organic material layer which includes an emission-auxiliary layer, and the emission-auxiliary layer includes the compound.

In another specific example of the present invention, the present invention provides an organic electric element comprising the organic material layer which includes a hole transport layer, and the hole transport layer includes the compound.

In another specific example of the present invention, the present invention provides an electronic device comprising a display device, which comprises the organic electric element, and a control unit for driving the display device.

In another specific example of the present invention, the electronic device according to the present invention may be at least one of an organic light emitting diode (OLED), an organic solar cell, an organic photo conductor (OPC), an organic transistor (organic TFT), and an element for monochromatic or white illumination.

Hereinafter, Synthesis Examples of the inventive compound represented by Formula 1 above and Preparation Examples of an organic electric element will be described in detail by way of example. However, the following examples are only for illustrative purposes and are not intended to limit the scope of the invention.

Synthesis Example

The final product according to the present invention can be synthesized by reaction between Sub 1 and Sub 2 as illustrated in, but not limited to, the following Reaction Scheme 1.

<Reaction Scheme 1>

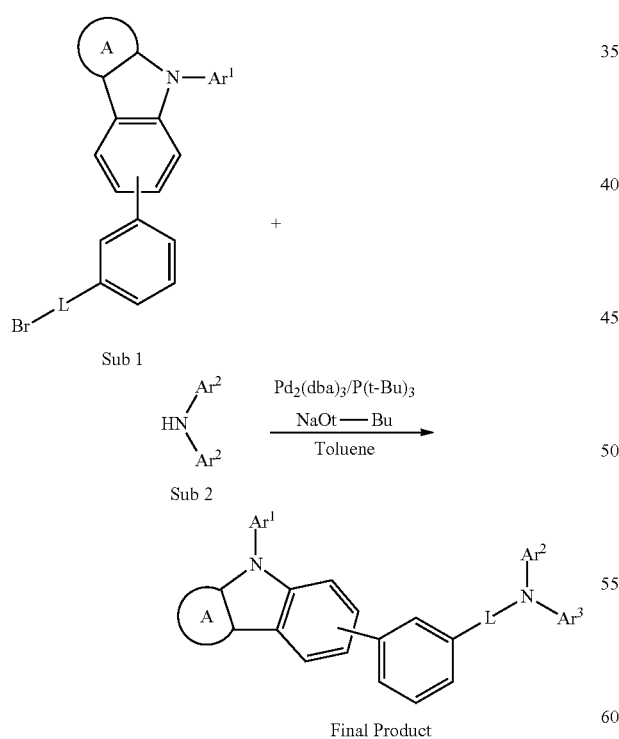

I. Synthesis of Intermediate Sub 1

Sub 1 of Reaction Scheme 1 can be synthesized according to, but not limited to, the following Reaction Scheme 2.

<Reaction Scheme 2>

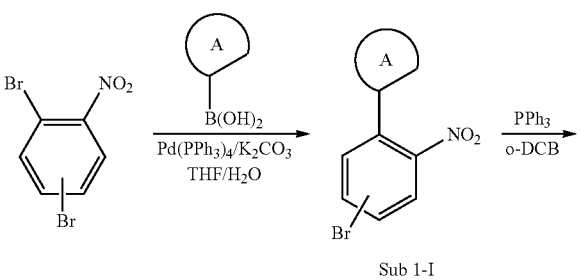

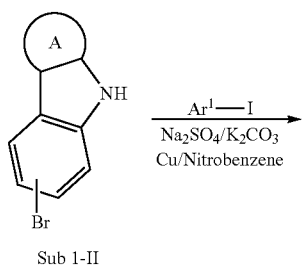

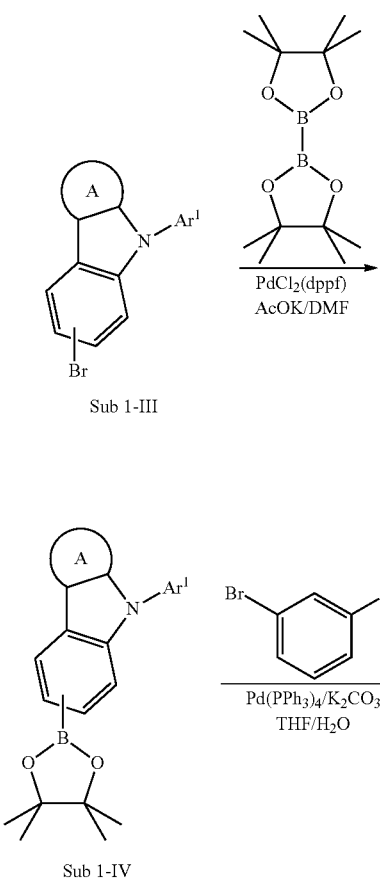

-continued

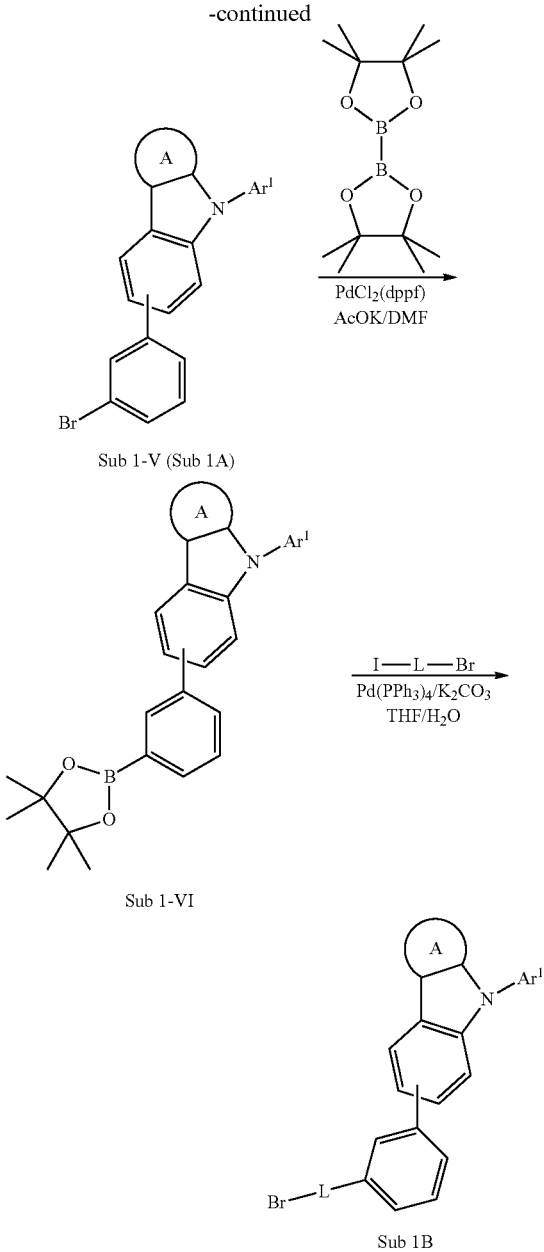

Sub 1-V (Sub 1A)

Sub 1-VI

Sub 1B (1) Sub 1-I Synthesis

To the solution of the starting material 1-bromo-2-nitrobenzene (1 eq.) in THF in a round-bottom flask were added boronic acid (1.5 eqs.), Pd(PPh$_3$)$_4$ (0.05 eqs.), K$_2$CO$_3$ (3 eqs.), and water, followed by stirring at 80° C. After completion of the reaction, extraction was conducted with CH$_2$Cl$_2$ and water, and the organic layer was dried over MgSO$_4$ and concentrated. The concentrate was purified using silica gel column chromatography and recrystallized to afford the product.

(2) Sub 1-II Synthesis

To a solution of the obtained Sub 1-I (1 eq.) in o-dichlorobenzene in a round-bottom flask was added triphenylphosphine (2.5 eqs.), followed by stirring at 200° C. After completion of the reaction, o-dichlorobenzene was removed by distillation, and then extraction was conducted with CH$_2$Cl$_2$ and water. The organic layer was dried over MgSO$_4$ and concentrated. The concentrate was purified using silica gel column chromatography and recrystallized to afford the product.

(3) Sub 1-III Synthesis

To a solution of the obtained Sub 1-II (1 eq.) in nitrobenzene in a round-bottom flask were added the iodo-substituted compound (1.5 eqs.), Na$_2$SO$_4$ (1 eq.), K$_2$CO$_3$ (1 eq.), and Cu (0.3 eqs.), followed by stirring at 200° C. After completion of the reaction, nitrobenzene was removed by distillation, and then extraction was conducted with CH$_2$Cl$_2$ and water. The organic layer was dried over MgSO$_4$ and concentrated. The concentrate was purified using silica gel column chromatography and recrystallized to afford the product.

(4) Sub 1-IV Synthesis

To a solution of the obtained Sub 1-III (1 eq.) in DMF in a round-bottom flask were added bis(pinacolato)diboron (1.1 eq.), Pd(dppf)Cl$_2$ (0.03 eqs.), and KOAc (3 eqs.), followed by stirring at 90° C. After completion of the reaction, DMF was removed by distillation, and then extraction was conducted with CH$_2$Cl$_2$ and water. The organic layer was dried over MgSO$_4$ and concentrated. The concentrate was purified using silica gel column chromatography and recrystallized to afford the product.

(5) Sub 1-V (Sub 1A) Synthesis

To a solution of the obtained Sub 1-IV (1 eq.) in THF in a round-bottom flask were added 1,3-dibromobenzene (1.5 eqs.), Pd(PPh$_3$)$_4$ (0.05 eqs.), K$_2$CO$_3$ (3 eqs.), and water, followed by stirring at 80° C. After completion of the reaction, extraction was conducted with CH$_2$Cl$_2$ and water. The organic layer was dried over MgSO$_4$ and concentrated. The concentrate was purified using silica gel column chromatography and recrystallized to afford the product.

(6) Sub 1-VI Synthesis

To a solution of the obtained Sub 1-V (39.27 g, 87.6 mmol) in DMF in a round-bottom flask were added bis(pinacolato)diboron (1.1 eq.), Pd(dppf)Cl$_2$ (0.03 eqs.), and KOAc (3 eqs.), followed by stirring at 90° C. After completion of the reaction, DMF was removed by distillation, and then extraction was conducted with CH$_2$Cl$_2$ and water. The organic layer was dried over MgSO$_4$ and concentrated. The concentrate was purified using silica gel column chromatography and recrystallized to afford the product.

(7) Sub 1B Synthesis

To a solution of the obtained Sub 1-VI (35.58 g, 71.8 mmol) in THF in a round-bottom flask were added the I-L-Br compound (1.5 eqs.), Pd(PPh$_3$)$_4$ (0.05 eqs.), K$_2$CO$_3$ (3 eqs.), and water, followed by stirring at 80° C. After completion of the reaction, extraction was conducted with CH$_2$Cl$_2$ and water. The organic layer was dried over MgSO$_4$ and concentrated. The concentrate was purified using silica gel column chromatography and recrystallized to afford the product.

1. Synthesis of Sub 1-A1-1

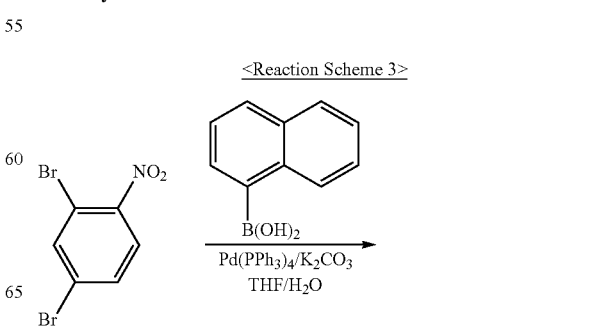

<Reaction Scheme 3>

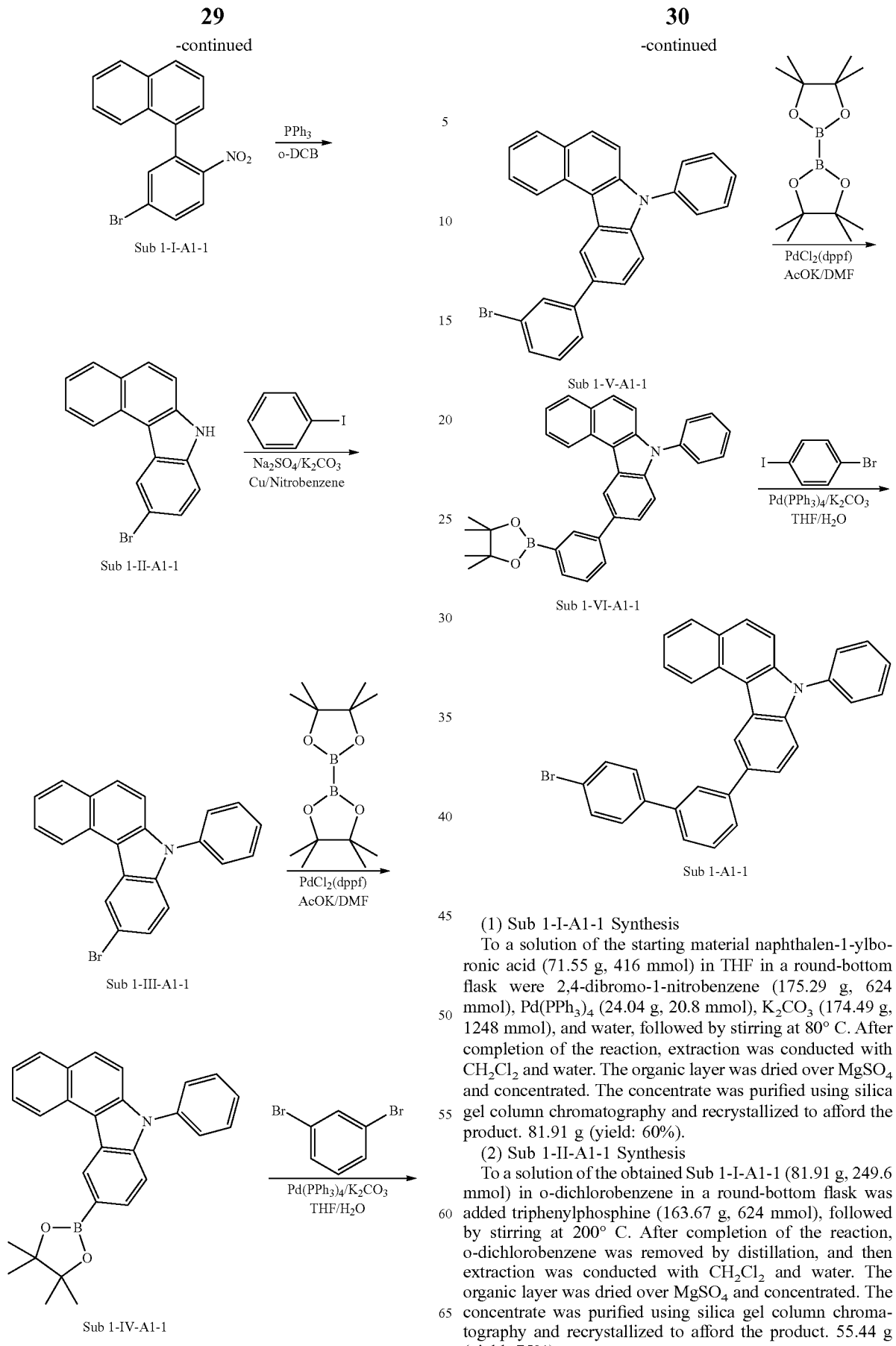

(1) Sub 1-I-A1-1 Synthesis

To a solution of the starting material naphthalen-1-ylboronic acid (71.55 g, 416 mmol) in THF in a round-bottom flask were 2,4-dibromo-1-nitrobenzene (175.29 g, 624 mmol), Pd(PPh$_3$)$_4$ (24.04 g, 20.8 mmol), K$_2$CO$_3$ (174.49 g, 1248 mmol), and water, followed by stirring at 80° C. After completion of the reaction, extraction was conducted with CH$_2$Cl$_2$ and water. The organic layer was dried over MgSO$_4$ and concentrated. The concentrate was purified using silica gel column chromatography and recrystallized to afford the product. 81.91 g (yield: 60%).

(2) Sub 1-II-A1-1 Synthesis

To a solution of the obtained Sub 1-I-A1-1 (81.91 g, 249.6 mmol) in o-dichlorobenzene in a round-bottom flask was added triphenylphosphine (163.67 g, 624 mmol), followed by stirring at 200° C. After completion of the reaction, o-dichlorobenzene was removed by distillation, and then extraction was conducted with CH$_2$Cl$_2$ and water. The organic layer was dried over MgSO$_4$ and concentrated. The concentrate was purified using silica gel column chromatography and recrystallized to afford the product. 55.44 g (yield: 75%).

(3) Sub 1-III-A1-1 Synthesis

To a solution of the obtained Sub 1-II-A1-1 (55.44 g, 187.2 mmol) in nitrobenzene in a round-bottom flask were added iodobenzene (57.29 g, 280.8 mmol), Na₂SO₄ (26.59 g, 187.2 mmol), K₂CO₃ (25.87 g, 187.2 mmol), and Cu (3.57 g, 56.2 mmol), followed by stirring at 200° C. After completion of the reaction, nitrobenzene was removed by distillation, and then extraction was conducted with CH₂Cl₂ and water. The organic layer was dried over MgSO₄ and concentrated. The concentrate was purified using silica gel column chromatography and recrystallized to afford the product. 52.96 g (yield: 76%)

(4) Sub 1-IV-A1-1 Synthesis

To a solution of the obtained Sub 1-III-A1-1 (52.96 g, 142.3 mmol) in DMF in a round-bottom flask were added bis(pinacolato)diboron (39.74 g, 156.5 mmol), Pd(dppf)Cl₂ (3.49 g, 4.3 mmol), and KOAc (41.89 g, 426.8 mmol), followed by stirring at 90° C. After completion of the reaction, DMF was removed by distillation, and then extraction was conducted with CH₂Cl₂ and water. The organic layer was dried over MgSO₄ and concentrated. The concentrate was purified using silica gel column chromatography and recrystallized to afford the product. 48.32 g (yield: 81%).

(5) Sub 1-V-A1-1 Synthesis

To a solution of the obtained Sub 1-IV-A1-1 (48.32 g, 115.2 mmol) in THF in a round-bottom flask were added 1,3-dibromobenzene (40.78 g, 172.9 mmol), Pd(PPh₃)₄ (6.66 g, 5.8 mmol), K₂CO₃ (47.78 g, 345.7 mmol), and water, followed by stirring at 80° C. After completion of the reaction, extraction was conducted with CH₂Cl₂ and water. The organic layer was dried over MgSO₄ and concentrated. The concentrate was purified using silica gel column chromatography and recrystallized to afford the product. 39.27 g (yield: 76%).

(6) Sub 1-VI-A1-1 Synthesis

To a solution of the obtained Sub 1-V-A1-1 (39.27 g, 87.6 mmol) in DMF in a round-bottom flask were added bis (pinacolato)diboron (24.47 g, 96.3 mmol), Pd(dppf)Cl₂ (2.15 g, 2.6 mmol), and KOAc (25.79 g, 262.8 mmol), followed by stirring at 90° C. After completion of the reaction, DMF was removed by distillation, and then extraction was conducted with CH₂Cl₂ and water. The organic layer was dried over MgSO₄ and concentrated. The concentrate was purified using silica gel column chromatography and recrystallized to afford the product. 35.58 g (yield: 82%).

(7) Sub 1-A1-1 Synthesis

To a solution of the obtained Sub 1-VI-A1-1 (35.58 g, 71.8 mmol) in THF in a round-bottom flask were added 1-bromo-4-iodobenzene (30.48 g, 107.7 mmol), Pd(PPh₃)₄ (4.15 g, 3.6 mmol), K₂CO₃ (29.78 g, 215.5 mmol), and water, followed by stirring at 80° C. After completion of the reaction, extraction was conducted with CH₂Cl₂ and water. The organic layer was dried over MgSO₄ and concentrated. The concentrate was purified using silica gel column chromatography and recrystallized to afford the product. 32.39 g (yield: 86%).

2. Synthesis of Sub 1-B1-4

<Reaction Scheme 4>

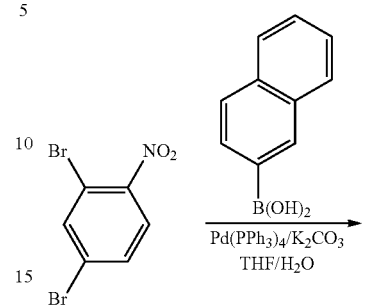

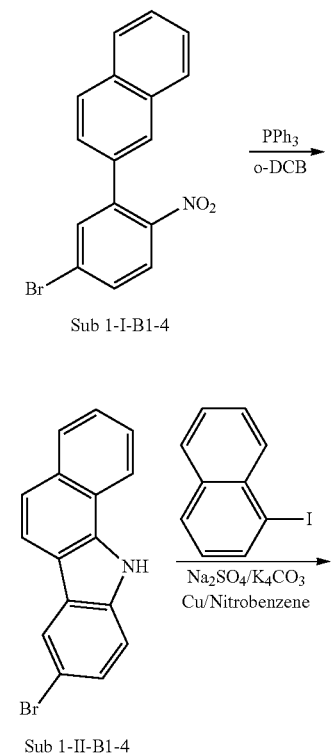

Sub 1-I-B1-4

Sub 1-II-B1-4

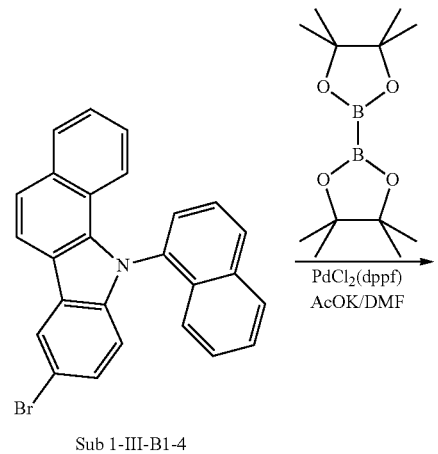

Sub 1-III-B1-4

-continued

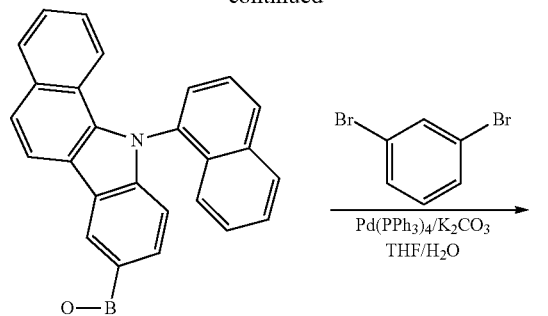
Sub 1-IV-B1-4

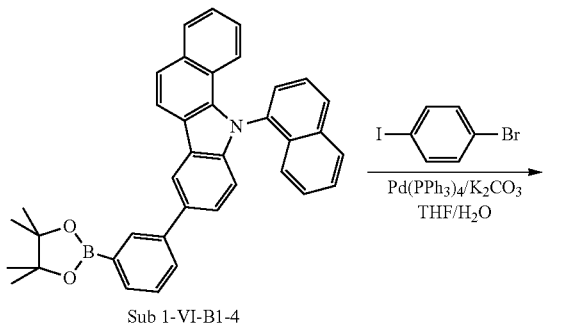
Sub 1-V-B1-4

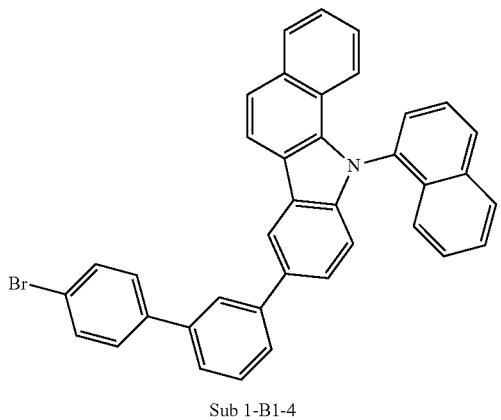
Sub 1-VI-B1-4

Sub 1-B1-4

(1) Sub 1-I-B1-4 Synthesis

Except for using naphthalen-2-ylboronic acid (72.68 g, 422.6 mmol) as a starting material plus 2,4-dibromo-1-nitrobenzene (178.06 g, 633.9 mmol), Pd(PPh₃)₄ (24.42 g, 21.1 mmol), K₂CO₃ (175.22 g, 1267.7 mmol), THF, and water, the same procedure as in the Sub 1-I-A1-1 synthesis was repeated to afford the product 80.43 g (yield: 58%).

(2) Sub 1-II-B1-4 Synthesis

Except for using the obtained Sub 1-I-B1-4 (80.43 g, 245.1 mmol) plus triphenylphosphine (160.7 g, 612.7 mmol), and o-dichlorobenzene, the same procedure as in the Sub 1-II-A1-1 was repeated to afford the product. 55.17 g (yield: 76%).

(3) Sub 1-III-B1-4 Synthesis

Except for using the obtained Sub 1-II-B1-4 (55.17 g, 186.3 mmol) plus 1-iodonaphthalene (70.99 g, 279.4 mmol), Na₂SO₄ (26.46 g, 186.3 mmol), K₂CO₃ (25.75 g, 186.3 mmol), Cu (3.55 g, 55.9 mmol), and nitrobenzene, the same procedure as in the Sub 1-III-A1-1 was repeated to afford the product. 56.64 g (yield: 72%).

(4) Sub 1-IV-B1-4 Synthesis

Except for using the obtained Sub 1-III-B1-4 (56.64 g, 134.1 mmol) plus bis(pinacolato)diboron (37.46 g, 147.5 mmol), Pd(dppf)Cl₂ (3.29 g, 4 mmol), KOAc (39.49 g, 402.3 mmol), and DMF, the same procedure as in the Sub 1-IV-A1-1 was repeated to afford the product. 49.73 g (yield: 79%).

(5) Sub 1-V-B1-4 Synthesis

Except for using the obtained Sub 1-IV-B1-4 (49.73 g, 105.9 mmol) plus 1,3-dibromobenzene (37.49 g, 158.9 mmol), Pd(PPh₃)₄ (6.12 g, 5.3 mmol), K₂CO₃ (43.93 g, 317.8 mmol), THF, and water, the same procedure as in the Sub 1-V-A1-1 was repeated to afford the product. 41.19 g (yield: 78%).

(6) Sub 1-VI-B1-4 Synthesis

Except for using the obtained Sub 1-V-B1-4 (41.19 g, 82.6 mmol) plus biss(pinacolato)diboron (23.08 g, 90.9 mmol), Pd(dppf)Cl₂ (2.02 g, 2.5 mmol), KOAc (24.33 g, 247.9 mmol), and DMF, the same procedure as in the Sub 1-VI-A1-1 was repeated to afford the product. 36.51 g (yield: 81%).

(7) Sub 1-B1-4 Synthesis

Except for using the obtained Sub 1-VI-B1-4 (36.51 g, 66.9 mmol) plus 1-bromo-4-iodobenzene (28.4 g, 100.4 mmol), Pd(PPh₃)₄ (3.87 g, 3.3 mmol), K₂CO₃ (27.75 g, 200.8 mmol), THF, and water, the same procedure as in the Sub 1-A1-1 was repeated to afford the product. 32.3 g (yield: 84%).

3. Synthesis of Sub 1-C1-1

<Reaction Scheme 5>

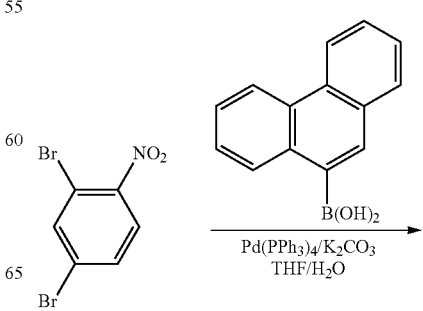

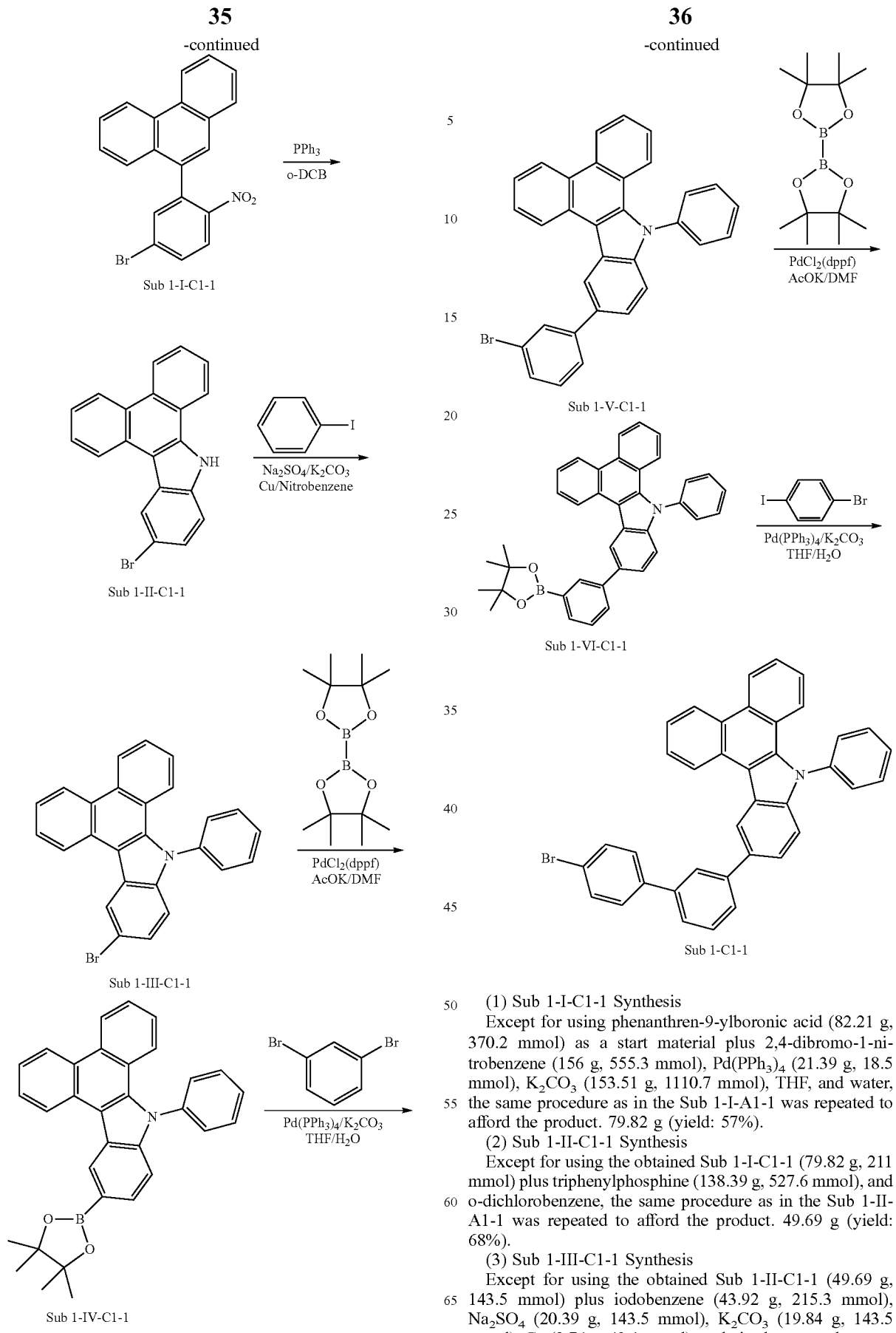

(1) Sub 1-I-C1-1 Synthesis
Except for using phenanthren-9-ylboronic acid (82.21 g, 370.2 mmol) as a start material plus 2,4-dibromo-1-nitrobenzene (156 g, 555.3 mmol), Pd(PPh$_3$)$_4$ (21.39 g, 18.5 mmol), K$_2$CO$_3$ (153.51 g, 1110.7 mmol), THF, and water, the same procedure as in the Sub 1-I-A1-1 was repeated to afford the product. 79.82 g (yield: 57%).

(2) Sub 1-II-C1-1 Synthesis
Except for using the obtained Sub 1-I-C1-1 (79.82 g, 211 mmol) plus triphenylphosphine (138.39 g, 527.6 mmol), and o-dichlorobenzene, the same procedure as in the Sub 1-II-A1-1 was repeated to afford the product. 49.69 g (yield: 68%).

(3) Sub 1-III-C1-1 Synthesis
Except for using the obtained Sub 1-II-C1-1 (49.69 g, 143.5 mmol) plus iodobenzene (43.92 g, 215.3 mmol), Na$_2$SO$_4$ (20.39 g, 143.5 mmol), K$_2$CO$_3$ (19.84 g, 143.5 mmol), Cu (2.74 g, 43.1 mmol), and nitrobenzene, the same procedure as in the Sub 1-III-A1-1 was repeated to afford the product. 42.43 g (yield: 70%).

(4) Sub 1-IV-C1-1 Synthesis

Except for using the obtained Sub 1-III-C1-1 (42.43 g, 100.5 mmol) plus bis(pinacolato)diboron (28.06 g, 110.5 mmol), Pd(dppf)Cl$_2$ (2.46 g, 3 mmol), KOAc (29.58 g, 301.4 mmol), and DMF, the same procedure as in the Sub 1-IV-A1-1 was repeated to afford the product. 35.84 g (yield: 76%).

(5) Sub 1-V-C1-1 Synthesis

Except for using the obtained Sub 1-IV-C1-1 (35.84 g, 76.4 mmol) plus 1,3-dibromobenzene (27.02 g, 114.5 mmol), Pd(PPh$_3$)$_4$ (4.41 g, 3.8 mmol), K$_2$CO$_3$ (31.66 g, 229.1 mmol), THF, and water, the same procedure as in the Sub 1-V-A1-1 was repeated to afford the product. 27.78 g (yield: 73%).

(6) Sub 1-VI-C1-1 Synthesis

Except for using the obtained Sub 1-V-C1-1 (27.78 g, 55.7 mmol) plus bis(pinacolato)diboron (15.57 g, 61.3 mmol), Pd(dppf)Cl$_2$ (1.37 g, 1.7 mmol), KOAc (16.41 g, 167.2 mmol), and DMF, the same procedure as in the Sub 1-VI-A1-1 was repeated to afford the product. 23.71 g (yield: 78%).

(7) Sub 1-C1-1 Synthesis

Except for using the obtained Sub 1-VI-C1-1 (23.71 g, 43.5 mmol) plus 1-bromo-4-iodobenzene (18.44 g, 65.2 mmol), Pd(PPh$_3$)$_4$ (2.51 g, 2.2 mmol), K$_2$CO$_3$ (18.02 g, 130.4 mmol), THF, and water, the same procedure as in the Sub 1-A1-1 was repeated to afford the product. 20.23 g (yield: 81%).

4. Synthesis of Sub 1-A2-1

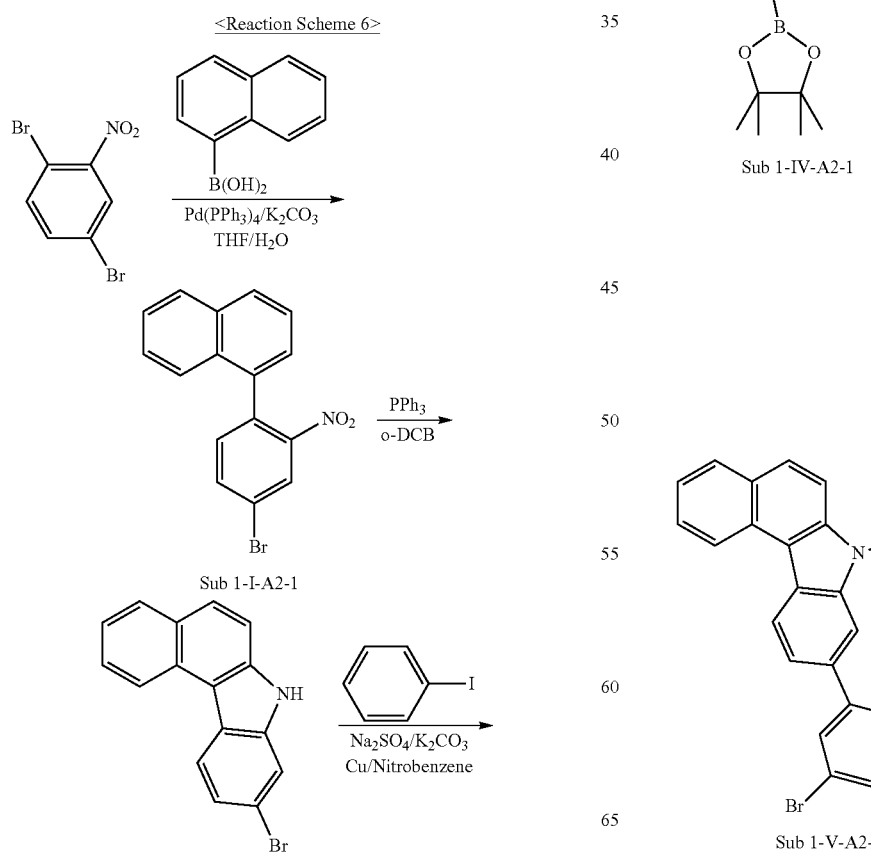

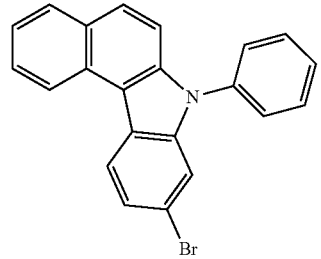

Sub 1-III-A2-1

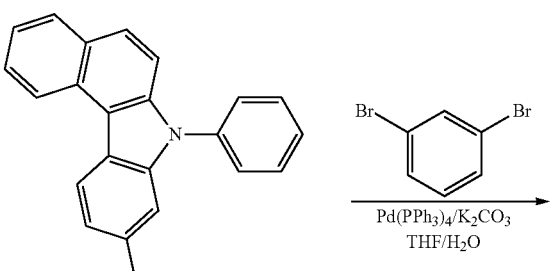

Sub 1-IV-A2-1

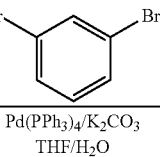

Sub 1-V-A2-1

-continued

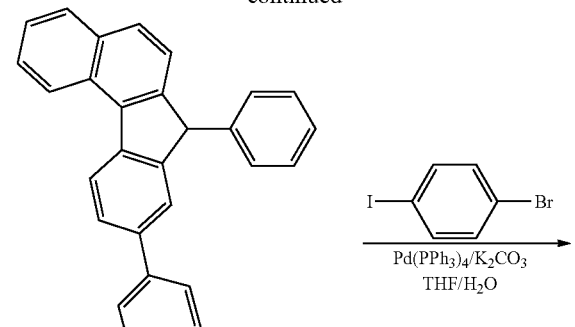

Sub 1-VI-A2-1

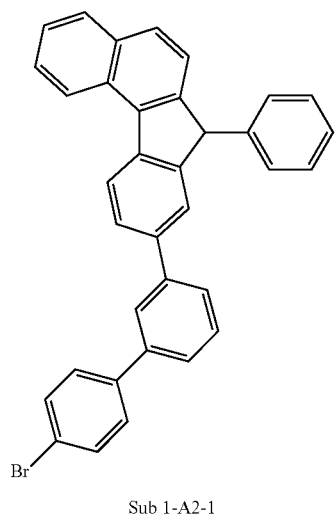

Sub 1-A2-1

(1) Sub 1-I-A2-1 Synthesis

Except for using naphthalen-1-ylboronic acid (73.6 g, 427.9 mmol) as a starting material plus 1,4-dibromo-2-nitrobenzene (180.31 g, 641.9 mmol), Pd(PPh$_3$)$_4$ (24.73 g, 21.4 mmol), K$_2$CO$_3$ (177.43 g, 1283.8 mmol), THF, and water, the same procedure as in the Sub 1-I-A1-1 was repeated to afford the product. 68.81 g (yield: 49%).

(2) Sub 1-II-A2-1 Synthesis

Except for using the obtained Sub 1-I-A2-1 (68.81 g, 209.7 mmol) plus triphenylphosphine (137.5 g, 524.2 mmol) and o-dichlorobenzene, the same procedure as in the Sub 1-II-A1-1 was repeated to afford the product. 44.09 g (yield: 71%).

(3) Sub 1-III-A2-1 Synthesis

Except for using the obtained Sub 1-II-A2-1 (44.09 g, 148.9 mmol) plus iodobenzene (45.56 g, 223.3 mmol), Na$_2$SO$_4$ (21.15 g, 148.9 mmol), K$_2$CO$_3$ (20.58 g, 148.9 mmol), Cu (2.84 g, 44.7 mmol), and nitrobenzene, the same procedure as in the Sub 1-III-A1-1 was repeated to afford the product. 41.01 g (yield: 74%).

(4) Sub 1-IV-A2-1 Synthesis

Except for using the obtained Sub 1-III-A2-1 (41.01 g, 110.2 mmol) plus bis(pinacolato)diboron (30.77 g, 121.2 mmol), Pd(dppf)Cl$_2$ (2.7 g, 3.3 mmol), KOAc (32.43 g, 330.5 mmol), and DMF, the same procedure as in the Sub 1-IV-A1-1 was repeated to afford the product. 36.96 g (yield: 80%).

(5) Sub 1-V-A2-1 Synthesis

Except for using the obtained Sub 1-IV-A2-1 (36.96 g, 88.1 mmol) plus 1,3-dibromobenzene (31.19 g, 132.2 mmol), Pd(PPh$_3$)$_4$ (5.09 g, 4.4 mmol), K$_2$CO$_3$ (36.55 g, 264.4 mmol), THF, and water, the same procedure as in the Sub 1-V-A1-1 was repeated to afford the product. 30.43 g (yield: 77%).

(6) Sub 1-VI-A2-1 Synthesis

Except for using the obtained Sub 1-V-A2-1 (30.43 g, 67.9 mmol) plus bis(pinacolato)diboron (18.96 g, 74.7 mmol), Pd(dppf)Cl$_2$ (1.66 g, 2.0 mmol), KOAc (19.98 g, 203.6 mmol), and DMF, the same procedure as in the Sub 1-VI-A1-1 was repeated to afford the product. 26.9 g (yield: 80%).

(7) Sub 1-A2-1 Synthesis

Except for using the obtained Sub 1-VI-A2-1 (26.9 g, 54.3 mmol) plus 1-bromo-4-iodobenzene (23.04 g, 81.4 mmol), Pd(PPh$_3$)$_4$ (3.14 g, 2.7 mmol), K$_2$CO$_3$ (22.51 g, 162.9 mmol), THF, and water, the same procedure as in the Sub 1-A1-1 was repeated to afford the product. 25.06 g (yield: 88%).

5. Synthesis of Sub 1-A3-1

<Reaction Scheme 7>

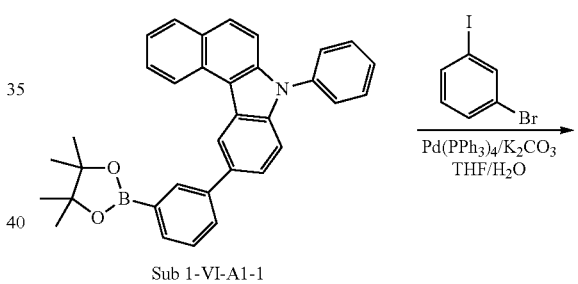

Sub 1-VI-A1-1

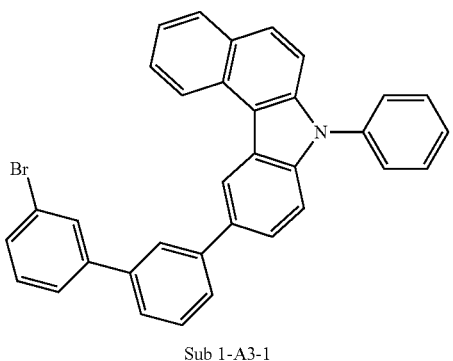

Sub 1-A3-1

Except for using the obtained Sub 1-VI-A1-1 (26.9 g, 54.3 mmol) plus 1-bromo-3-iodobenzene (23.04 g, 81.4 mmol), Pd(PPh$_3$)$_4$ (3.14 g, 2.7 mmol), K$_2$CO$_3$ (22.51 g, 162.9 mmol), THF, and water, the same procedure as in the Sub 1-A1-1 was repeated to afford the product. 23.6 g (yield: 83%).

6. Synthesis of Sub 1-B4-1

<Reaction Scheme 8>

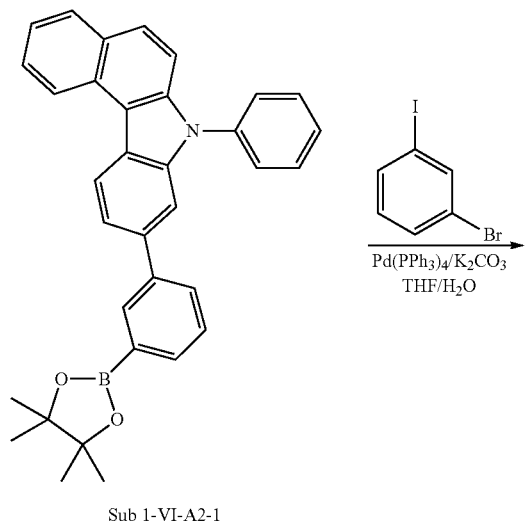

Sub 1-VI-A2-1

Sub 1-B4-1

Except for using the obtained Sub 1-VI-A2-1 (26.9 g, 54.3 mmol) plus 1-bromo-3-iodobenzene (23.04 g, 81.4 mmol), Pd(PPh$_3$)$_4$ (3.14 g, 2.7 mmol), K$_2$CO$_3$ (22.51 g, 162.9 mmol), THF, and water, the same procedure as in the Sub 1-A1-1 was repeated to afford the product. 22.8 g (yield: 80%).

7. Synthesis of Sub 1-C5-1

<Reaction Scheme 9>

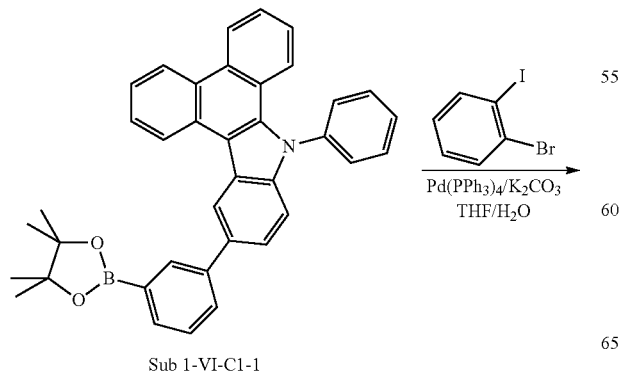

Sub 1-VI-C1-1

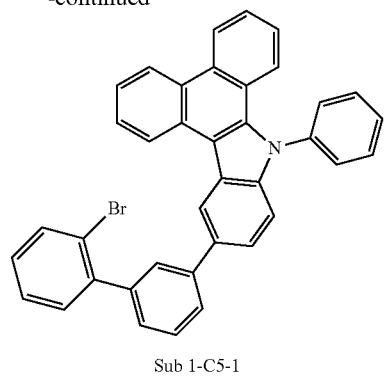

Sub 1-C5-1

Except for using the obtained Sub 1-VI-C1-1 (29.6 g, 54.3 mmol) plus 1-bromo-2-iodobenzene (23.04 g, 81.4 mmol), Pd(PPh$_3$)$_4$ (3.14 g, 2.7 mmol), K$_2$CO$_3$ (22.51 g, 162.9 mmol), THF, and water, the same procedure as in the Sub 1-A1-1 was repeated to afford the product. 25.3 g (yield: 81%).

8. Synthesis of Sub 1-A6-1

<Reaction Scheme 10>

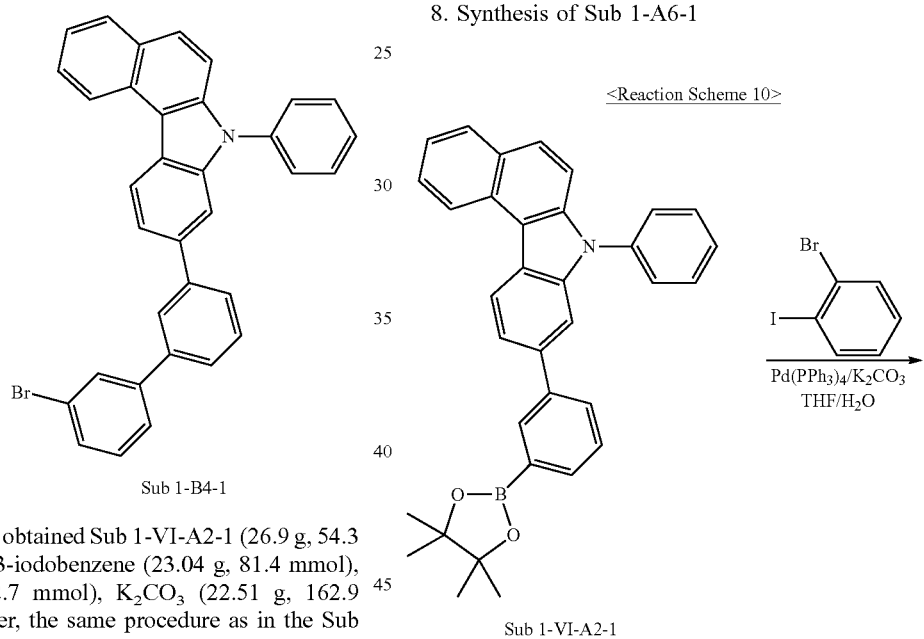

Sub 1-VI-A2-1

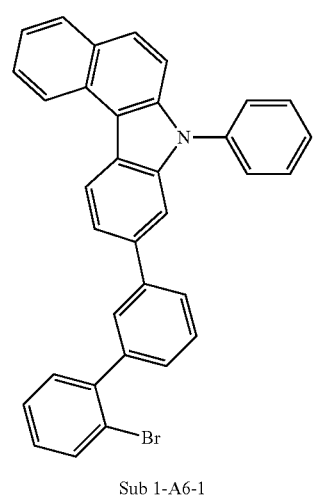

Sub 1-A6-1

Except for using the obtained Sub 1-VI-A2-1 (26.9 g, 54.3 mmol) plus 1-bromo-2-iodobenzene (23.04 g, 81.4 mmol), Pd(PPh₃)₄ (3.14 g, 2.7 mmol), K₂CO₃ (22.51 g, 162.9 mmol), THF, and water, the same procedure as in the Sub 1-A1-1 was repeated to afford the product. 21.4 g (yield: 75%).
Meanwhile, examples of Sub 1 compounds include, but are not limited to, the following compounds:
Sub 1-A1-1
Sub 1-A1-2
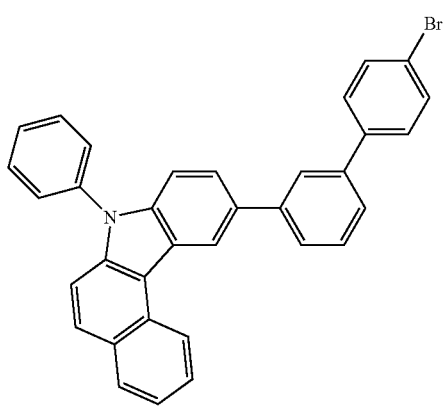
Sub 1-A1-3
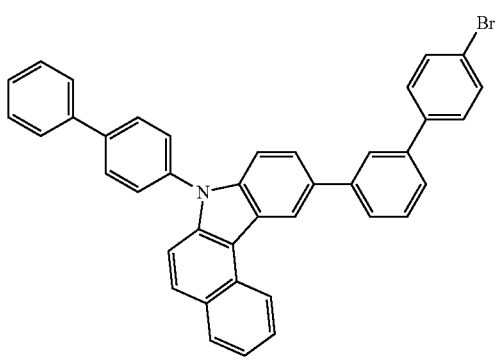
Sub 1-A1-4
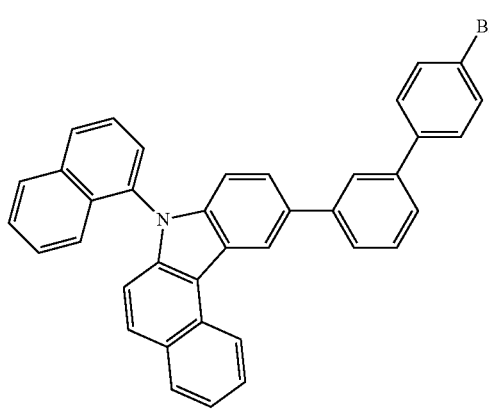
Sub 1-A1-5
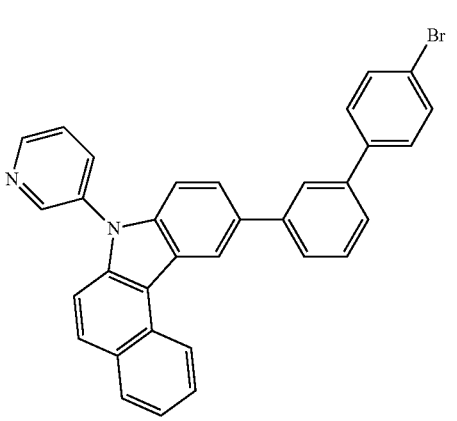
Sub 1-B1-1
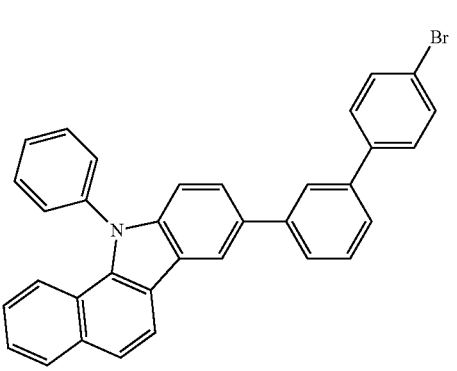
Sub 1-B1-2
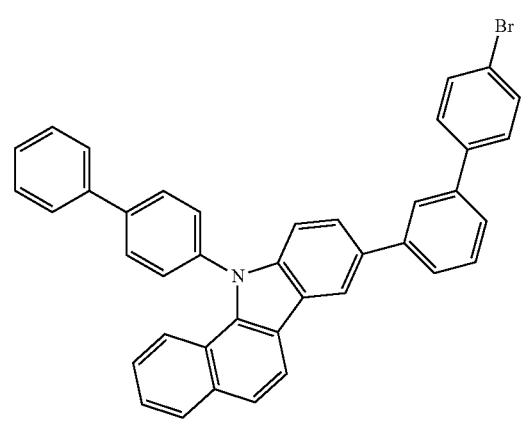
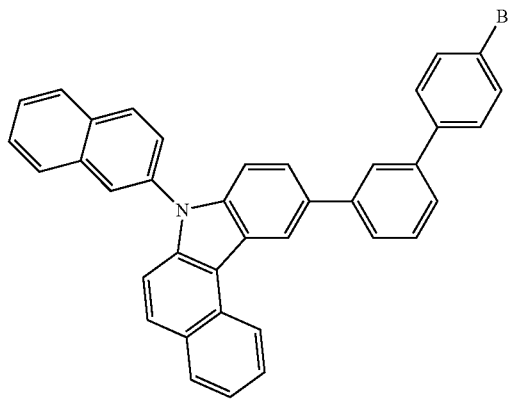

Sub 1-B1-3
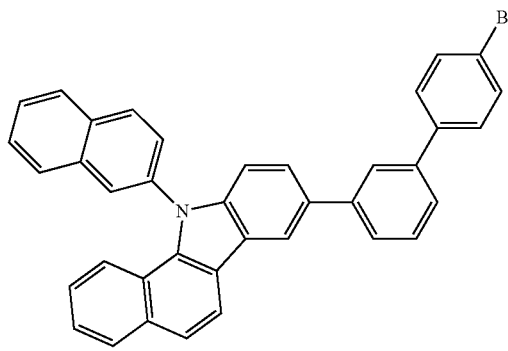
Sub 1-B1-4
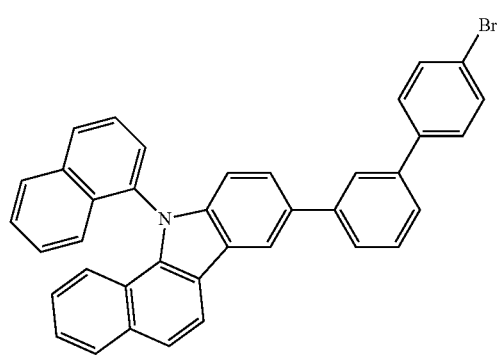
Sub 1-C1-1
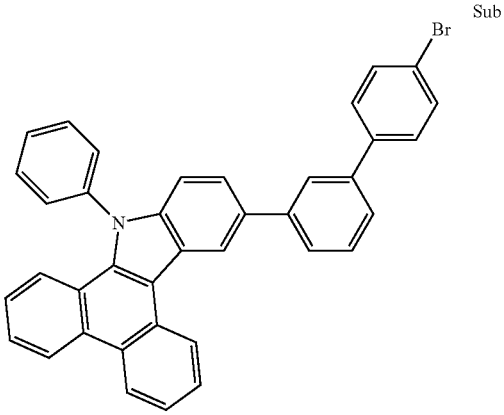
Sub 1-C1-2
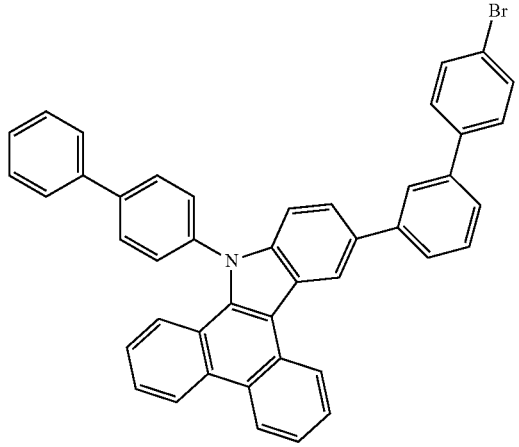
Sub 1-C1-3
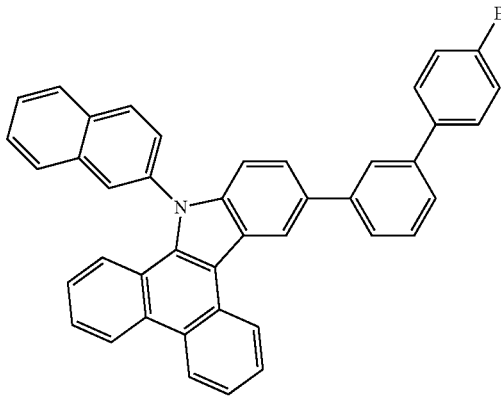
Sub 1-C1-4
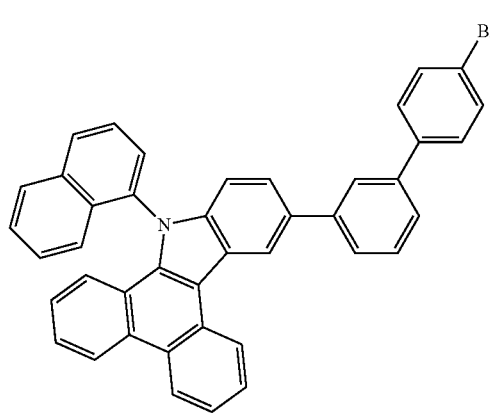
Sub 1-C1-5
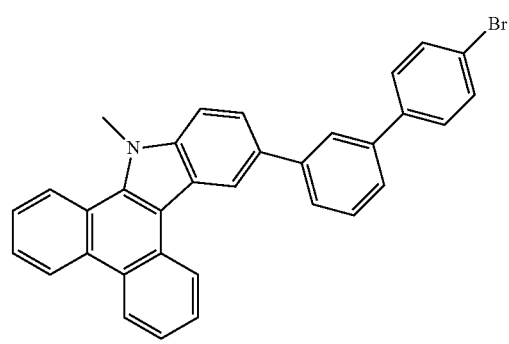
Sub 1-C1-6
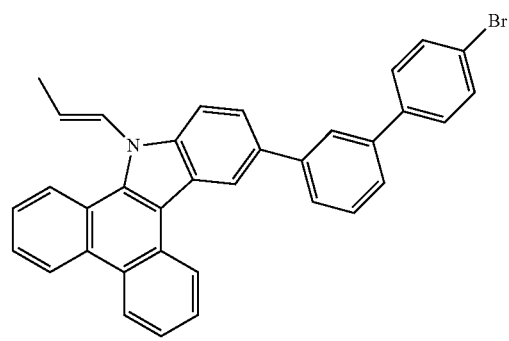

Sub 1-A2-1
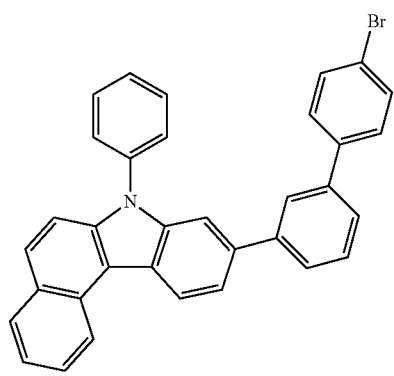
Sub 1-A2-2
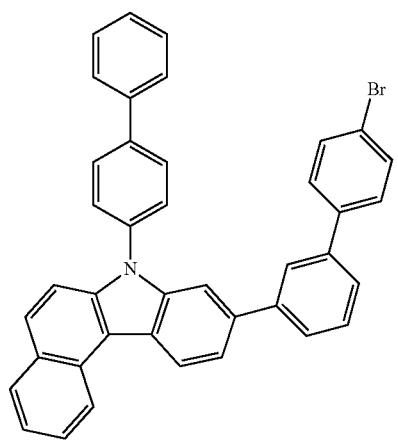
Sub 1-B2-1
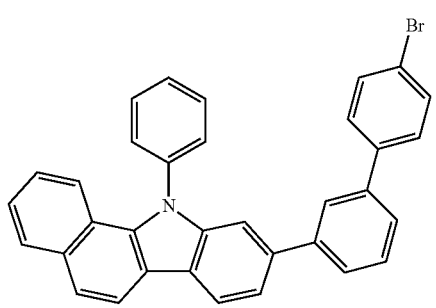
Sub 1-B2-2
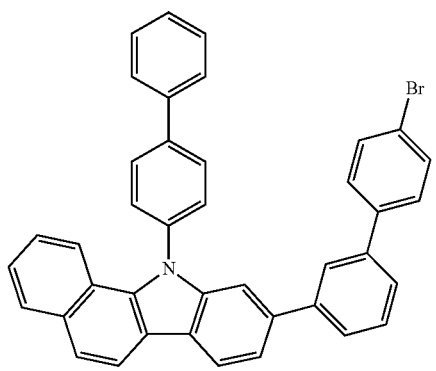
Sub 1-C2-1
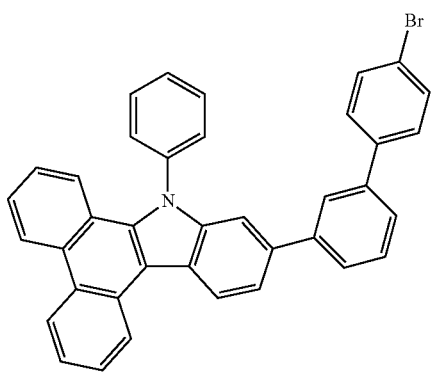
Sub 1-A3-1
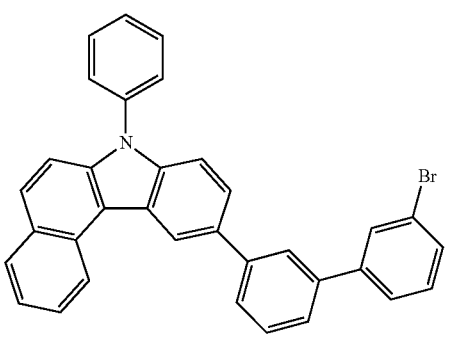
Sub 1-A4-1
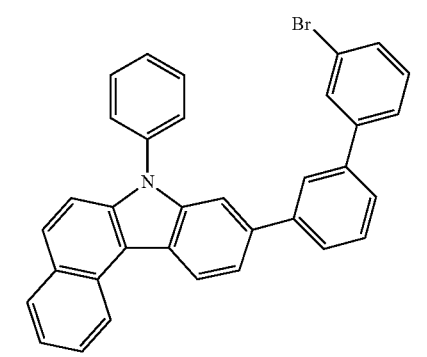
Sub 1-A5-1
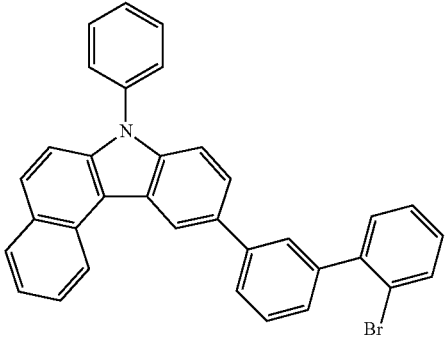

-continued
Sub 1-A6-1
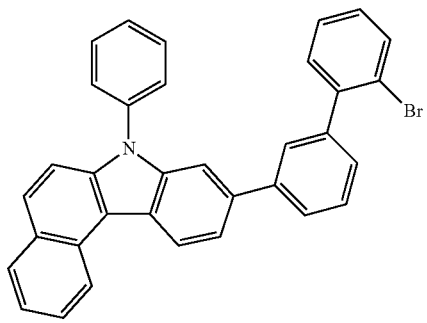
Sub 1-A6-2
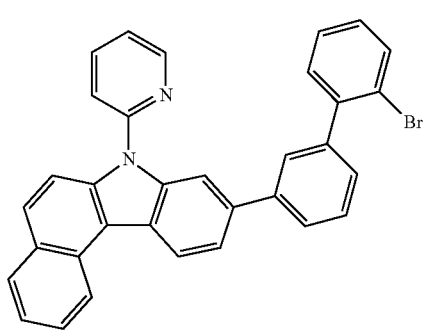
Sub 1-B3-1
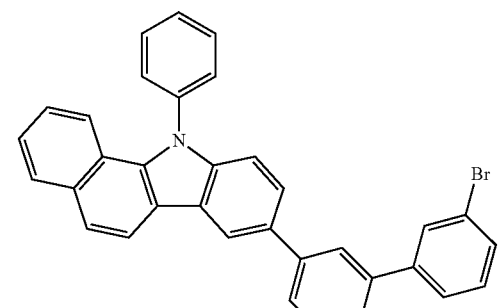
Sub 1-B4-1
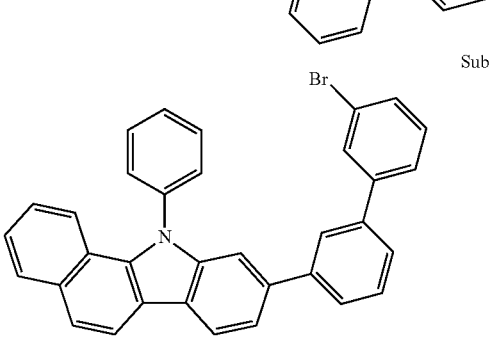
Sub 1-B5-1
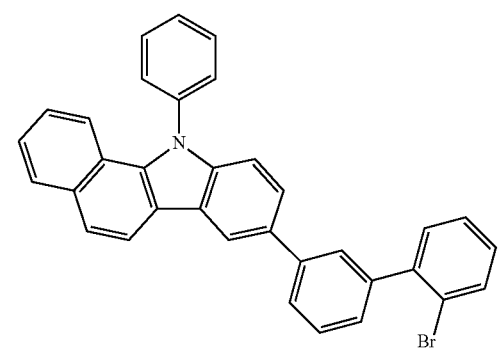
-continued
Sub 1-B6-1
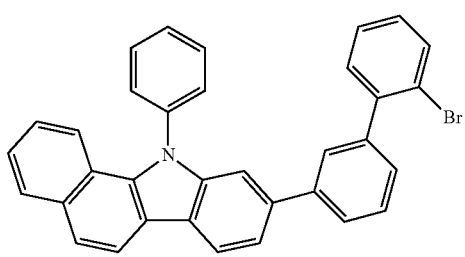
Sub 1-B6-2
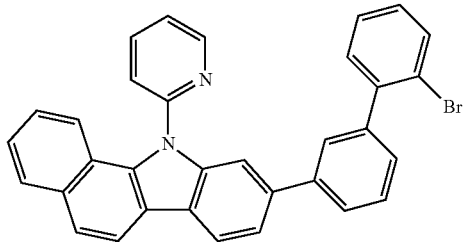
Sub 1-C3-1
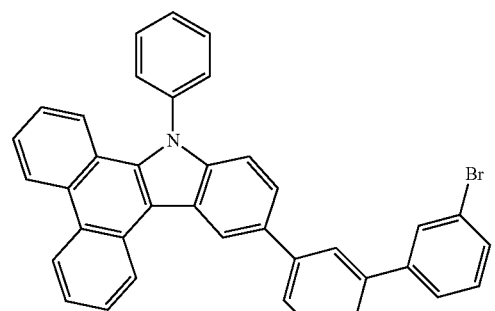
Sub 1-C4-1
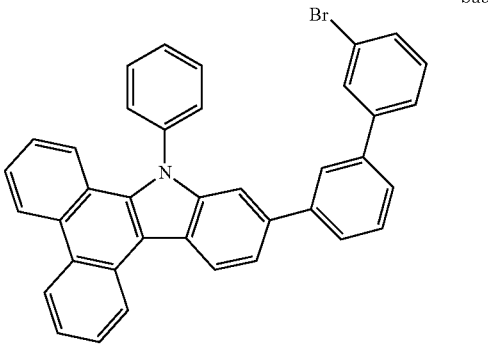
Sub 1-C5-1
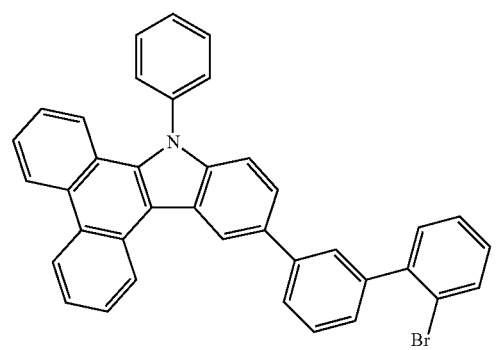

-continued

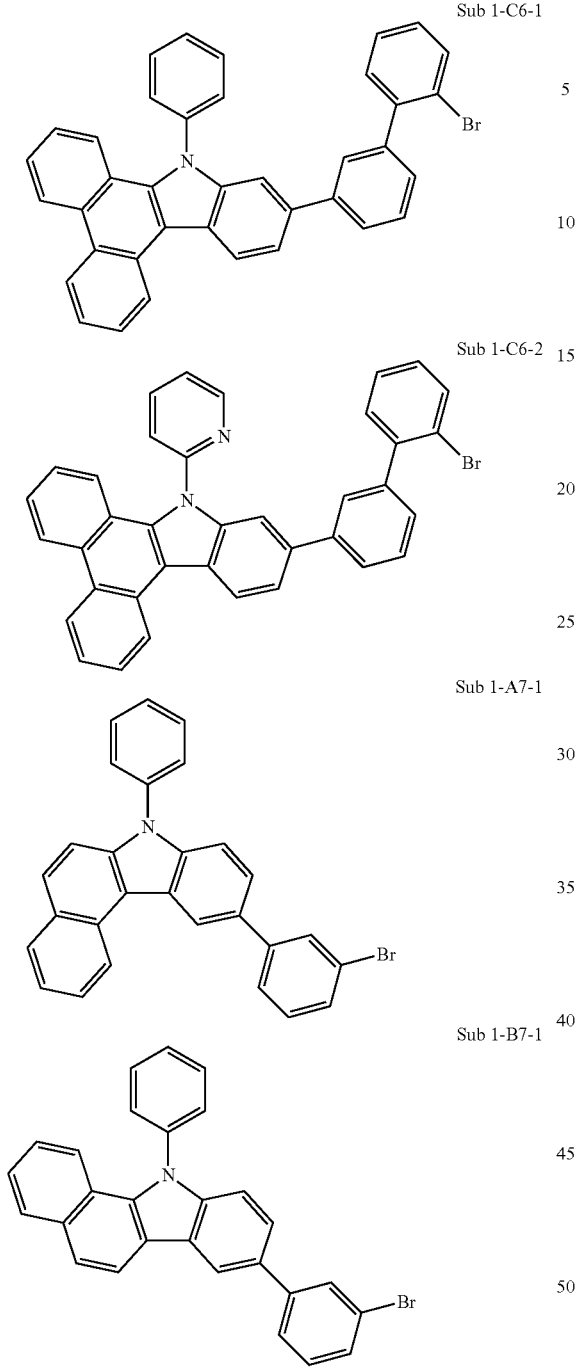

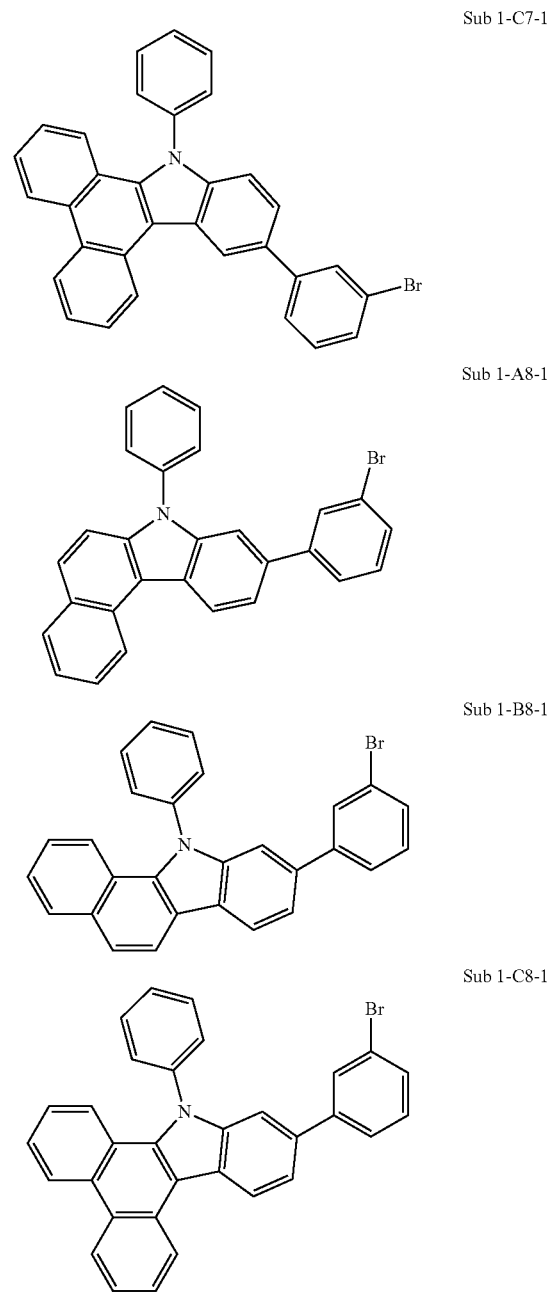

Field desorption mass spectrometry (FD-MS) data of the Sub 1 compounds are given in Table 9 below.

TABLE 9

| Compound | FD-MS | Compound | FD-MS |
|---|---|---|---|
| Sub 1-A1-1 | m/z = 523.09($C_{34}H_{22}BrN$ = 524.45) | Sub 1-A1-2 | m/z = 599.12($C_{40}H_{26}BrN$ = 600.55) |
| Sub 1-A1-3 | m/z = 573.11($C_{38}H_{24}BrN$ = 574.51) | Sub 1-A1-4 | m/z = 573.11($C_{38}H_{24}BrN$ = 574.51) |
| Sub 1-A1-5 | m/z = 524.09($C_{33}H_{21}BrN_2$ = 525.44) | Sub 1-B1-1 | m/z = 523.09($C_{34}H_{22}BrN$ = 524.45) |
| Sub 1-B1-2 | m/z = 599.12($C_{40}H_{26}BrN$ = 600.55) | Sub 1-B1-3 | m/z = 573.11($C_{38}H_{24}BrN$ = 574.51) |
| Sub 1-B1-4 | m/z = 573.11($C_{38}H_{24}BrN$ = 574.51) | Sub 1-C1-1 | m/z = 573.11($C_{38}H_{24}BrN$ = 574.51) |
| Sub 1-C1-2 | m/z = 649.14($C_{44}H_{28}BrN$ = 650.60) | Sub 1-C1-3 | m/z = 623.12($C_{42}H_{26}BrN$ = 624.57) |
| Sub 1-C1-4 | m/z = 623.12($C_{42}H_{26}BrN$ = 624.57) | Sub 1-C1-5 | m/z = 511.09($C_{33}H_{22}BrN$ = 512.44) |
| Sub 1-C1-6 | m/z = 537.11($C_{35}H_{24}BrN$ = 538.48) | Sub 1-A2-1 | m/z = 523.09($C_{34}H_{22}BrN$ = 524.45) |
| Sub 1-A2-2 | m/z = 599.12($C_{40}H_{26}BrN$ = 600.55) | Sub 1-B2-1 | m/z = 523.09($C_{34}H_{22}BrN$ = 524.45) |
| Sub 1-B2-2 | m/z = 599.12($C_{40}H_{26}BrN$ = 600.55) | Sub 1-C2-1 | m/z = 573.11($C_{38}H_{24}BrN$ = 574.51) |

TABLE 9-continued

| Compound | FD-MS | Compound | FD-MS |
|---|---|---|---|
| Sub 1-A3-1 | m/z = 523.09($C_{34}H_{22}BrN$ = 524.45) | Sub 1-A4-1 | m/z = 523.09($C_{34}H_{22}BrN$ = 524.45) |
| Sub 1-A5-1 | m/z = 523.09($C_{34}H_{22}BrN$ = 524.45) | Sub 1-A6-1 | m/z = 523.09($C_{34}H_{22}BrN$ = 524.45) |
| Sub 1-A6-2 | m/z = 524.09($C_{33}H_{21}BrN_2$ = 525.44) | Sub 1-B3-1 | m/z = 523.09($C_{34}H_{22}BrN$ = 524.45) |
| Sub 1-B4-1 | m/z = 523.09($C_{34}H_{22}BrN$ = 524.45) | Sub 1-B5-1 | m/z = 523.09($C_{34}H_{22}BrN$ = 524.45) |
| Sub 1-B6-1 | m/z = 523.09($C_{34}H_{22}BrN$ = 524.45) | Sub 1-B6-2 | m/z = 524.09($C_{33}H_{21}BrN_2$ = 525.44) |
| Sub 1-C3-1 | m/z = 573.11($C_{38}H_{24}BrN$ = 574.51) | Sub 1-C4-1 | m/z = 573.11($C_{38}H_{24}BrN$ = 574.51) |
| Sub 1-C5-1 | m/z = 573.11($C_{38}H_{24}BrN$ = 574.51) | Sub 1-C6-1 | m/z = 573.11($C_{38}H_{24}BrN$ = 574.51) |
| Sub 1-C6-2 | m/z = 574.10($C_{37}H_{23}BrN_2$ = 575.50) | Sub 1-A7-1 | m/z = 447.06($C_{28}H_{18}BrN$ = 448.35) |
| Sub 1-B7-1 | m/z = 447.06($C_{28}H_{18}BrN$ = 448.35) | Sub 1-C7-1 | m/z = 497.08($C_{32}H_{20}BrN$ = 498.41) |
| Sub 1-A8-1 | m/z = 447.06($C_{28}H_{18}BrN$ = 448.35) | Sub 1-B8-1 | m/z = 447.06($C_{28}H_{18}BrN$ = 448.35) |
| Sub 1-C8-1 | m/z = 497.08($C_{32}H_{20}BrN$ = 498.41) | | |

II. Synthesis of the Intermediate Sub 2

Sub 2 in Reaction Scheme 1 may be synthesized according to, but not limited to, the Reaction Scheme 11.

<Reaction Scheme 11>

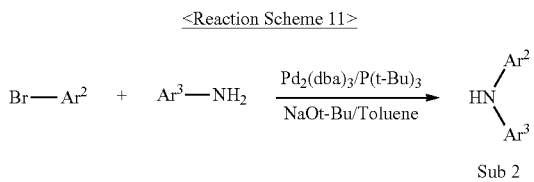

Concrete Sub 2 compounds may be synthesized as follows.

1. Sub 2-1 Synthesis

<Reaction Scheme 12>

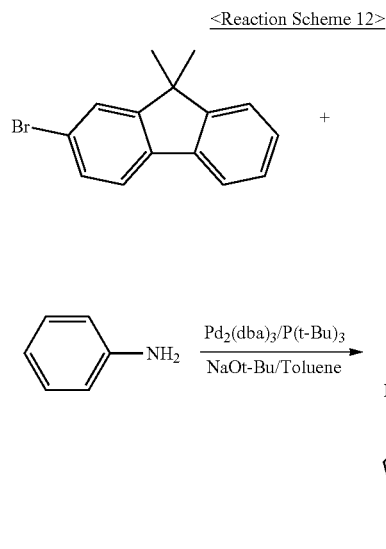

To a solution of the starting material 2-bromo-9,9-dimethyl-9H-fluorene (63.75 g, 233.4 mmol) in toluene in a round-bottom flask were added aniline (43.47 g, 466.7 mmol), $Pd_2(dba)_3$ (6.41 g, 7 mmol), $P(t-Bu)_3$ (9.1 ml, 18.7 mmol), and NaOt-Bu (67.29 g, 700.1 mmol), followed by stirring at 40° C. After completion of the reaction, extraction was made with $CH_2Cl_2$ and water, and the organic layer thus formed was dried over $MgSO_4$ and concentrated. The concentrate was purified by silica gel column chromatography, and recrystallized to afford the product. 55.94 g (yield: 84%).

2. Sub 2-3 Synthesis

<Reaction Scheme 13>

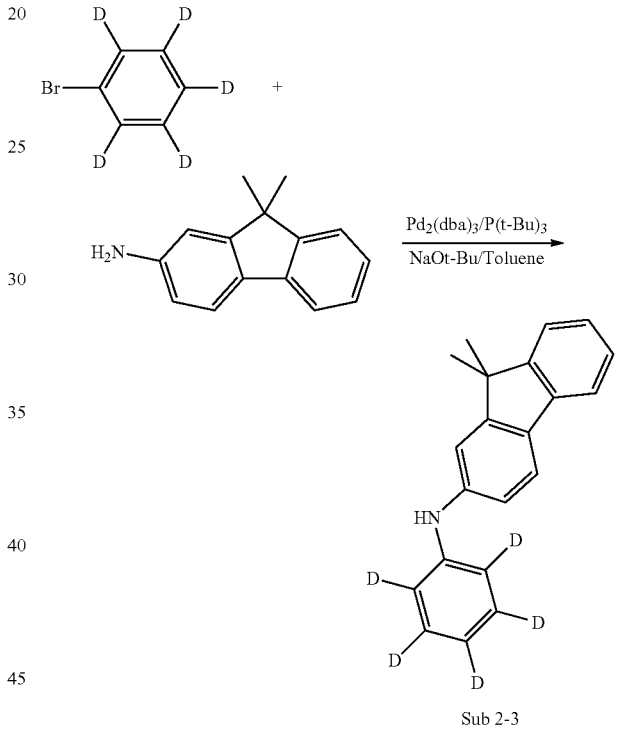

Except for using bromobenzene-d5 (23.76 g, 146.6 mmol) as a starting material plus 9,9-dimethyl-9H-fluoren-2-amine (61.38 g, 293.3 mmol), $Pd_2(dba)_3$ (4.03 g, 4.4 mmol), 50% $P(t-Bu)_3$ (5.7 ml, 11.7 mmol), NaOt-Bu (42.28 g, 439.9 mmol), and toluene, the same procedure as in the Sub 2-1 synthesis was repeated to afford the product. 30.66 g (yield: 72%).

3. Sub 2-6 Synthesis

<Reaction Scheme 14>

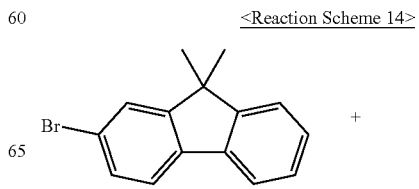

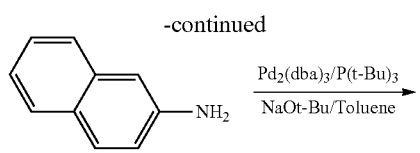

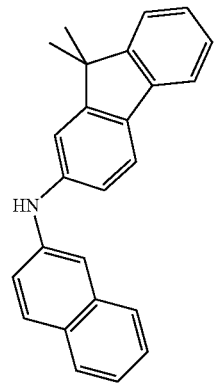

Sub 2-6

Except for using 2-bromo-9,9-dimethyl-9H-fluorene (51.93 g, 190.1 mmol) as a starting material plus naphthalen-2-amine (54.44 g, 380.2 mmol), Pd$_2$(dba)$_3$ (5.22 g, 5.7 mmol), 50% P(t-Bu)$_3$ (7.4 ml, 15.2 mmol), NaOt-Bu (54.81 g, 570.3 mmol), and toluene, the same procedure as in the Sub 2-1 synthesis was repeated to afford the product. 50.38 g (yield: 79%).

4. Sub 2-7 Synthesis

<Reaction Scheme 15>

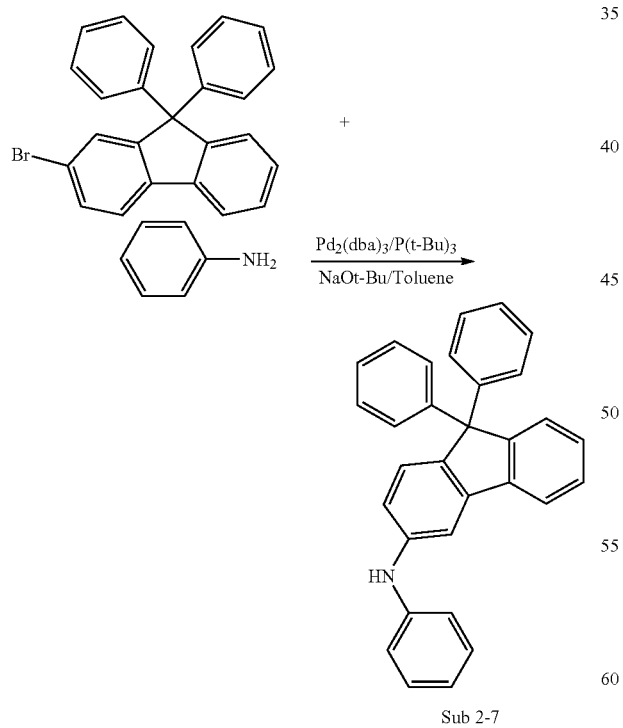

Sub 2-7

Except for using 2-bromo-9,9-diphenyl-9H-fluorene (58.11 g, 146.3 mmol) as a starting material plus aniline (27.24 g, 292.5 mmol), Pd$_2$(dba)$_3$ (4.02 g, 4.4 mmol), 50% P(t-Bu)$_3$ (5.7 ml, 11.7 mmol), NaOt-Bu (42.17 g, 438.8 mmol), and toluene, the same procedure as in the Sub 2-1 synthesis was repeated to afford the product. 45.52 g (yield: 76%).

5. Sub 2-8 Synthesis

<Reaction Scheme 16>

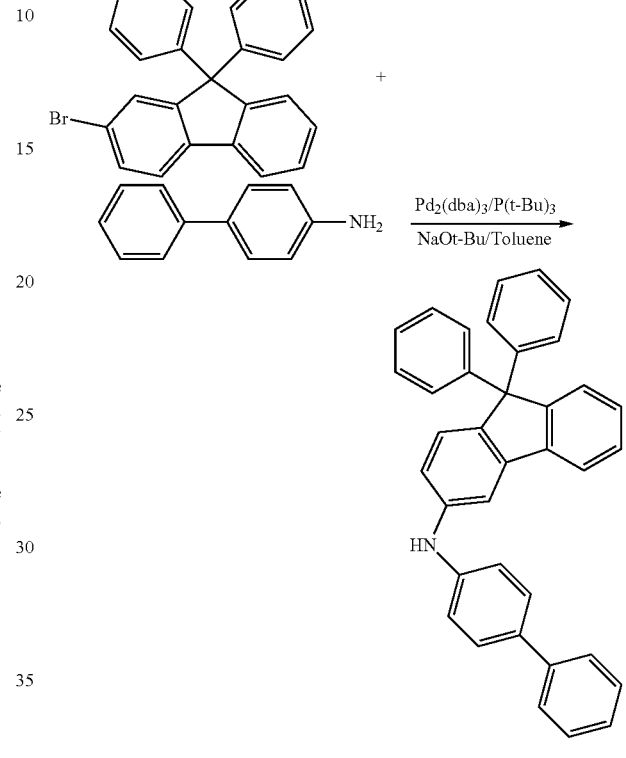

Sub 2-8

Except for using 2-bromo-9,9-diphenyl-9H-fluorene (53.95 g, 135.8 mmol) as a starting material plus [1,1'-biphenyl]-4-amine (45.96 g, 271.6 mmol), Pd$_2$(dba)$_3$ (3.73 g, 4.1 mmol), 50% P(t-Bu)$_3$ (5.3 ml, 10.9 mmol), NaOt-Bu (39.15 g, 407.4 mmol), and toluene, the same procedure as in the Sub 2-1 synthesis was repeated to afford the product. 49.46 g (yield: 75%).

6. Sub 2-12 Synthesis

<Reaction Scheme 17>

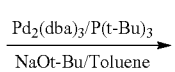

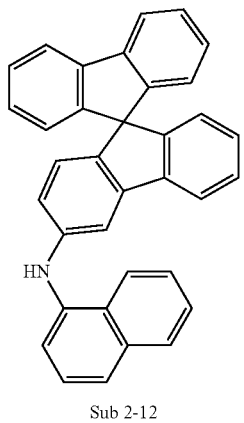

Sub 2-12

Except for using 2-bromo-9,9'-spirobi[fluorene] (55.31 g, 139.9 mmol) as a starting material plus naphthalen-1-amine (40.07 g, 279.8 mmol), Pd$_2$(dba)$_3$ (3.84 g, 4.2 mmol), 50% P(t-Bu)$_3$ (5.5 ml, 11.2 mmol), NaOt-Bu (40.34 g, 419.8 mmol), and toluene, the same procedure as in the Sub 2-1 synthesis was repeated to afford the product. 40.97 g (yield: 64%).

7. Sub 2-13 Synthesis

<Reaction Scheme 18>

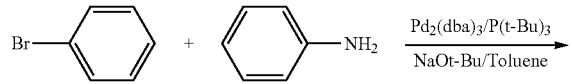

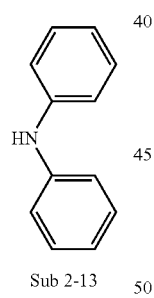

Sub 2-13

Except for using bromobenzene (58.53 g, 372.8 mmol) as a starting material plus aniline (69.43 g, 745.6 mmol), Pd$_2$(dba)$_3$ (10.24 g, 11.2 mmol), 50% P(t-Bu)$_3$ (14.5 ml, 29.8 mmol), NaOt-Bu (107.48 g, 1118.3 mmol), and toluene, the same procedure as in the Sub 2-1 synthesis was repeated to afford the product. 54.88 g (yield: 87%).

8. Sub 2-14 Synthesis

<Reaction Scheme 19>

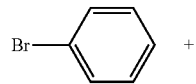

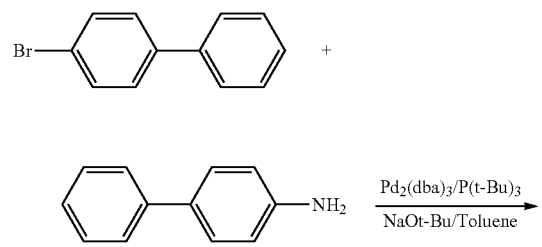

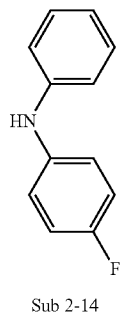

Sub 2-14

Except for using bromobenzene (30.47 g, 194.1 mmol) as a starting material plus 4-fluoroaniline (43.13 g, 388.1 mmol), Pd$_2$(dba)$_3$ (5.33 g, 5.8 mmol), 50% P(t-Bu)$_3$ (7.6 ml, 15.5 mmol), NaOt-Bu (55.95 g, 582.2 mmol), and toluene, the same procedure as in the Sub 2-1 synthesis was repeated to afford the product. 29.79 g (yield: 82%).

9. Sub 2-17 Synthesis

<Reaction Scheme 20>

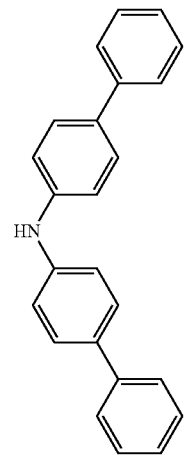

Sub 2-17

Except for using 4-bromo-1,1'-biphenyl (55.61 g, 238.6 mmol) as a starting material plus [1,1'-biphenyl]-4-amine (80.74 g, 477.1 mmol), Pd$_2$(dba)$_3$ (6.55 g, 7.2 mmol), 50% P(t-Bu)$_3$ (9.3 ml, 19.1 mmol), NaOt-Bu (68.79 g, 715.7 mmol), and toluene, the same procedure as in the Sub 2-1 synthesis was repeated to afford the product. 62.11 g (yield: 81%).

10. Sub 2-28 Synthesis

<Reaction Scheme 20>

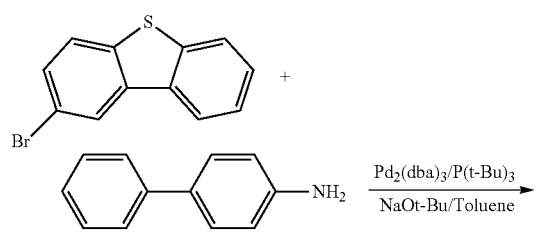

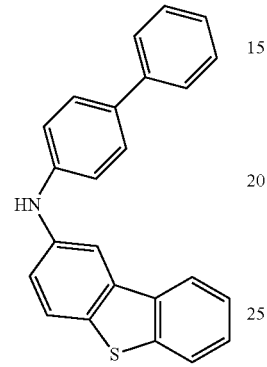

Sub 2-28

Except for using 2-bromodibenzo[b,d]thiophene (49.61 g, 188.5 mmol) as a starting material plus [1,1'-biphenyl]-4-amine (63.8 g, 377 mmol), Pd$_2$(dba)$_3$ (5.18 g, 5.7 mmol), 50% P(t-Bu)$_3$ (7.4 ml, 15.1 mmol), NaOt-Bu (54.36 g, 565.6 mmol), and toluene, the same procedure as in the Sub 2-1 synthesis was repeated to afford the product. 51.02 g (yield: 77%).

Meanwhile, examples of Sub 2 compounds include, but are not limited to, the following compounds:

Sub 2-1

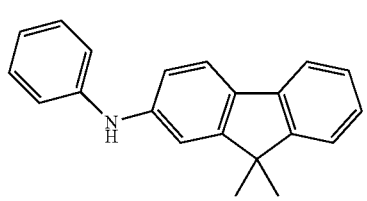

Sub 2-2

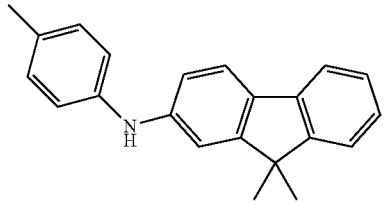

Sub 2-3

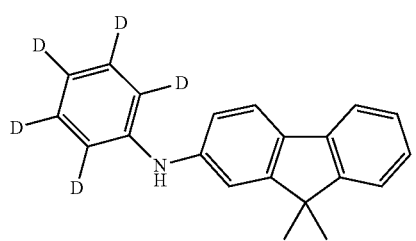

Sub 2-4

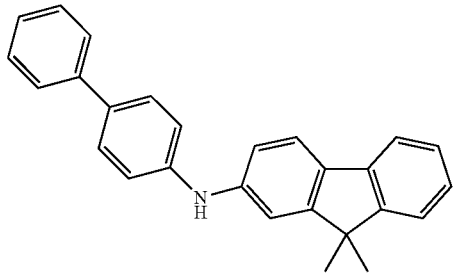

Sub 2-5

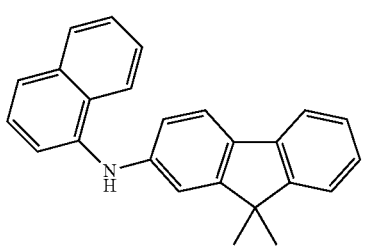

Sub 2-6

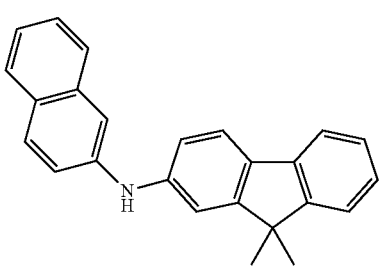

Sub 2-7

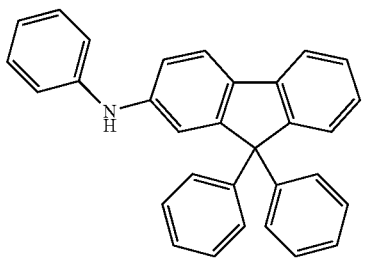

Sub 2-8

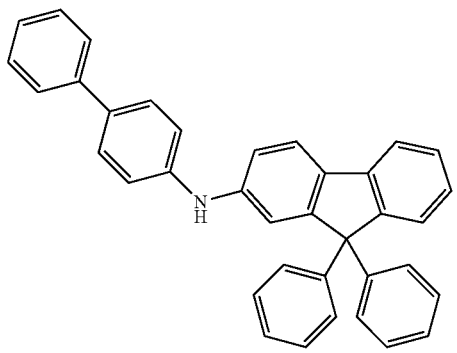

-continued
Sub 2-9
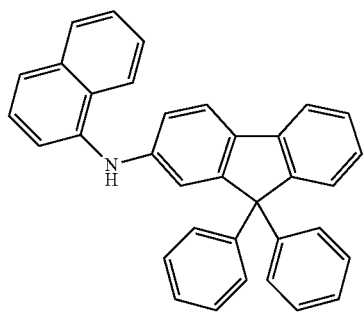
Sub 2-10
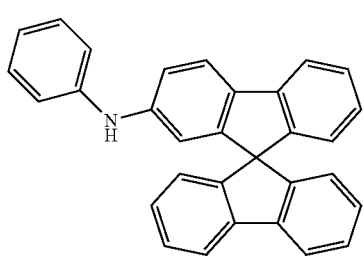
Sub-2-11
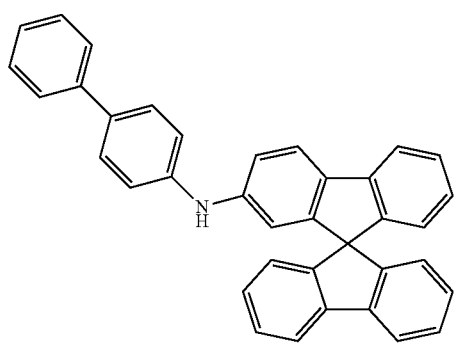
Sub 2-12
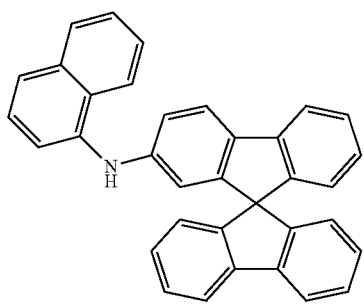
Sub 2-13
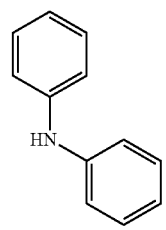
-continued
Sub 2-14
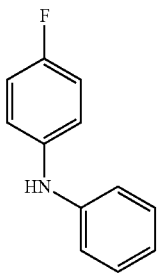
Sub 2-15
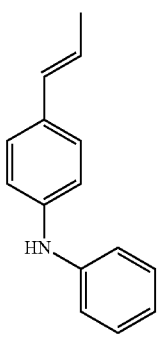
Sub 2-16
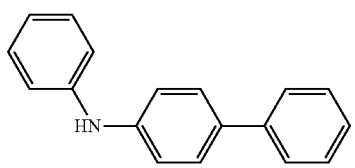
Sub 2-17
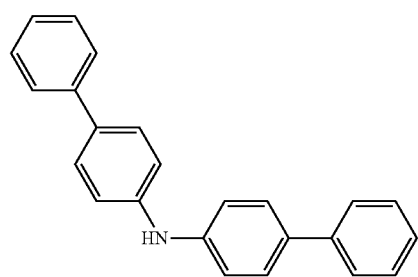
Sub 2-18
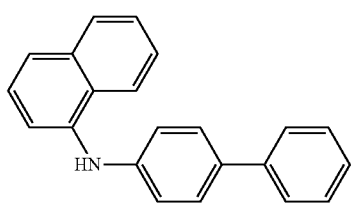
Sub 2-19
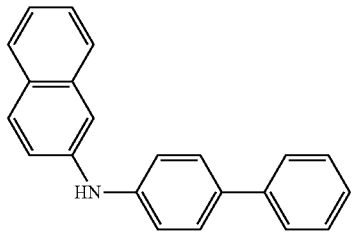

Sub 2-20
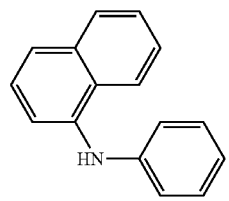
Sub 2-21
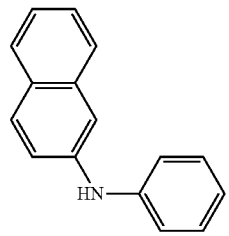
Sub 2-22
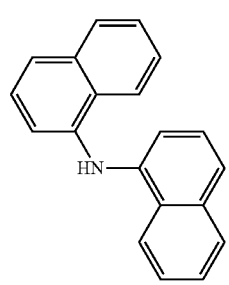
Sub 2-23
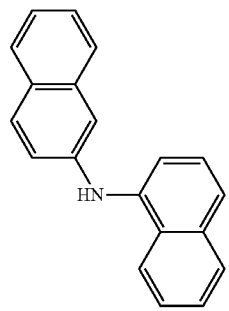
Sub 2-24
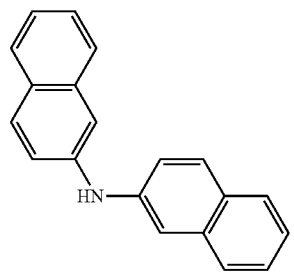
Sub 2-25
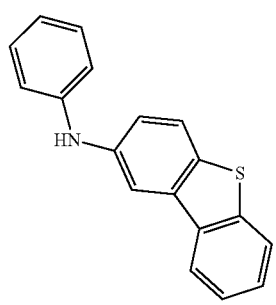
Sub 2-26
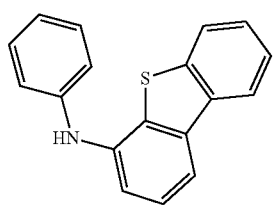
Sub 2-27
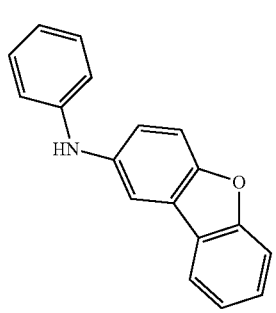
Sub 2-28
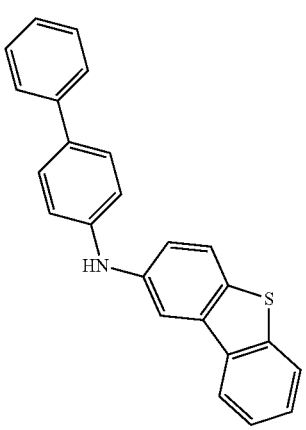
Sub 2-29
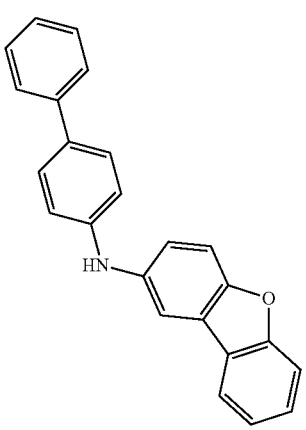

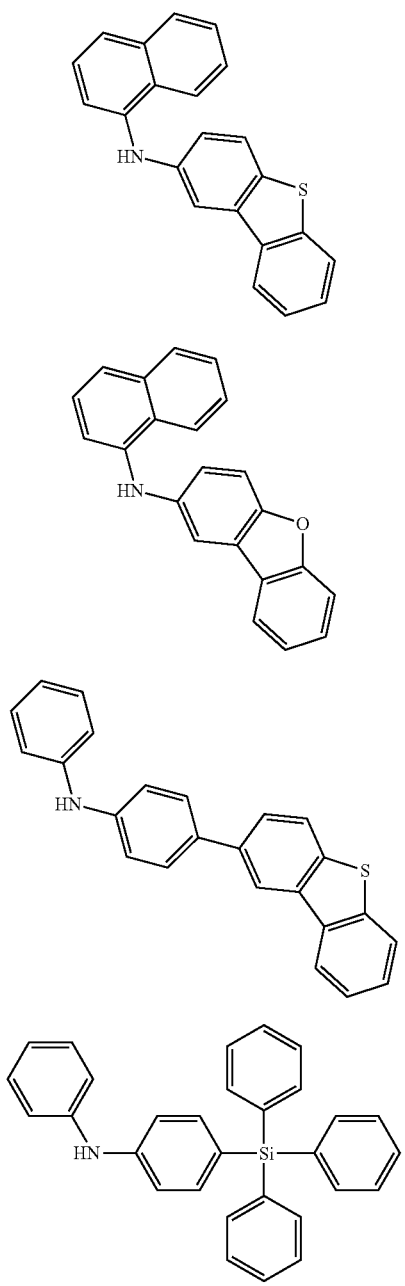

Sub 2-30

Sub 2-31

Sub 2-32

Sub 2-33

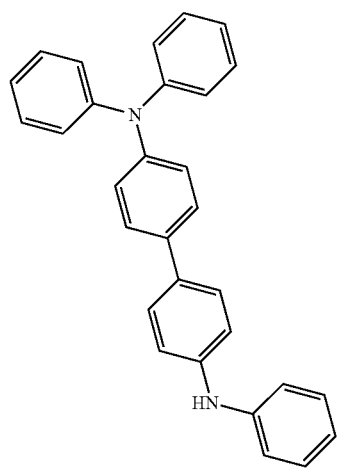

Sub 2-34

Sub 2-35

Sub 2-36

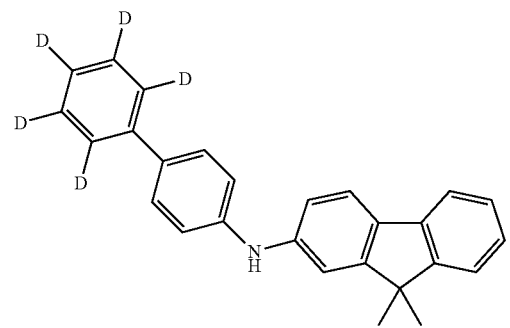

FD-MS data of the Sub 2 compounds are given in Table 10 below.

TABLE 10

| Compound | FD-MS | Compound | FD-MS |
|---|---|---|---|
| Sub 2-1 | m/z = 285.15($C_{21}H_{19}N$ = 285.38) | Sub 2-2 | m/z = 299.17($C_{22}H_{21}N$ = 299.41) |
| Sub 2-3 | m/z = 290.18($C_{21}H_{14}D_5N$ = 290.41) | Sub 2-4 | m/z = 361.18($C_{27}H_{23}N$ = 361.48) |
| Sub 2-5 | m/z = 335.17($C_{25}H_{21}N$ = 335.44) | Sub 2-6 | m/z = 335.17($C_{25}H_{21}N$ = 335.44) |
| Sub 2-7 | m/z = 409.18($C_{31}H_{23}N$ = 409.52) | Sub 2-8 | m/z = 485.21($C_{37}H_{27}N$ = 485.62) |
| Sub 2-9 | m/z = 459.20($C_{35}H_{25}N$ = 459.58) | Sub 2-10 | m/z = 407.17($C_{31}H_{21}N$ = 407.51) |
| Sub 2-11 | m/z = 483.20($C_{37}H_{25}N$ = 483.60) | Sub 2-12 | m/z = 457.18($C_{35}H_{23}N$ = 457.56) |
| Sub 2-13 | m/z = 169.09($C_{12}H_{11}N$ = 169.22) | Sub 2-14 | m/z = 187.08($C_{12}H_{10}FN$ = 187.21) |
| Sub 2-15 | m/z = 209.12($C_{15}H_{15}N$ = 209.29) | Sub 2-16 | m/z = 245.12($C_{18}H_{15}N$ = 245.32) |
| Sub 2-17 | m/z = 321.15($C_{24}H_{19}N$ = 321.41) | Sub 2-18 | m/z = 295.14($C_{22}H_{17}N$ = 295.38) |
| Sub 2-19 | m/z = 295.14($C_{22}H_{17}N$ = 295.38) | Sub 2-20 | m/z = 219.10($C_{16}H_{13}N$ = 219.28) |
| Sub 2-21 | m/z = 219.10($C_{16}H_{13}N$ = 219.28) | Sub 2-22 | m/z = 269.12($C_{20}H_{15}N$ = 269.34) |
| Sub 2-23 | m/z = 269.12($C_{20}H_{15}N$ = 269.34) | Sub 2-24 | m/z = 269.12($C_{20}H_{15}N$ = 269.34) |
| Sub 2-25 | m/z = 275.08($C_{18}H_{13}NS$ = 275.37) | Sub 2-26 | m/z = 275.08($C_{18}H_{13}NS$ = 275.37) |

TABLE 10-continued

| Compound | FD-MS | Compound | FD-MS |
|---|---|---|---|
| Sub 2-27 | m/z = 259.10($C_{18}H_{13}NO$ = 259.30) | Sub 2-28 | m/z = 351.11($C_{24}H_{17}NS$ = 351.46) |
| Sub 2-29 | m/z = 335.13($C_{24}H_{17}NO$ = 335.40) | Sub 2-30 | m/z = 325.09($C_{22}H_{15}NS$ = 325.43) |
| Sub 2-31 | m/z = 309.12($C_{22}H_{15}NO$ = 309.36) | Sub 2-32 | m/z = 351.11($C_{24}H_{17}NS$ = 351.46) |
| Sub 2-33 | m/z = 427.18($C_{30}H_{25}NSi$ = 427.61) | Sub 2-34 | m/z = 412.19($C_{30}H_{24}N_2$ = 412.52) |
| Sub 2-35 | m/z = 366.21($C_{27}H_{18}D_5N$ = 366.51) | Sub 2-36 | m/z = 450.21($C_{33}H_{26}N_2$ = 450.57) |

III. Synthesis of Final Product

To a solution of Sub 2 (1 eq.) in toluene in a round-bottom flask were added Sub 1 (1.2 eqs.), Pd$_2$(dba)$_3$ (0.03 eqs.), P(t-Bu)$_3$ (0.08 eqs.), and NaOt-Bu (3 eqs.), followed by stirring at 100° C. After completion of the reaction, extraction was made with CH$_2$Cl$_2$ and water, and the organic layer thus formed was dried over MgSO$_4$ and concentrated. The concentrate was purified by silica gel column chromatography, and recrystallized to afford the final product.

1. Product A1-1 Synthesis

<Reaction Scheme 22>

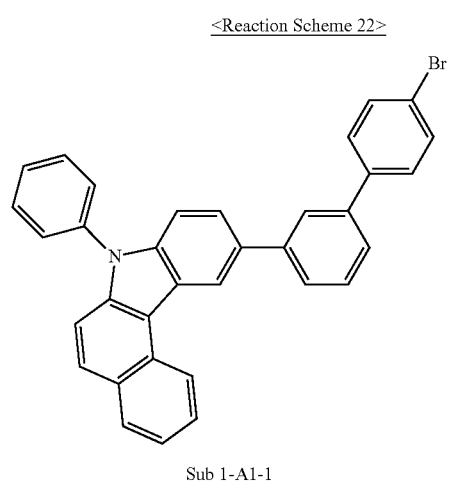

Sub 1-A1-1

+

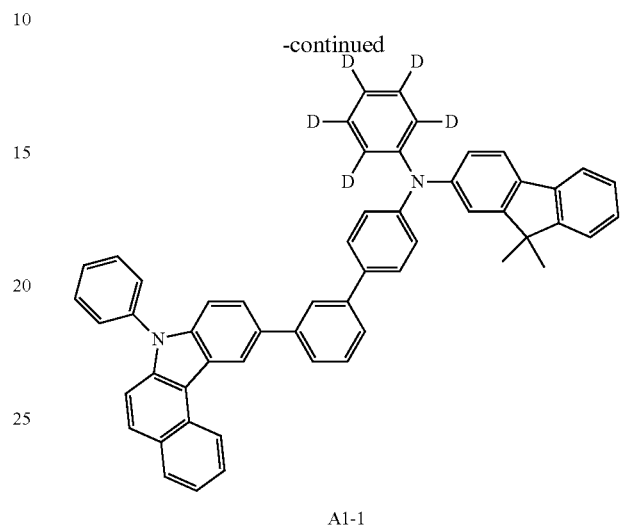

A1-1

To a solution of the obtained Sub 2-3 (7.41 g, 25.5 mmol) in toluene in a round-bottom flask were added Sub 1-A1-1 (16.06 g, 30.6 mmol), Pd$_2$(dba)$_3$ (0.7 g, 0.8 mmol), 50% P(t-Bu)$_3$ (1 ml, 2 mmol), and NaOt-Bu (7.36 g, 76.5 mmol), followed by stirring at 100° C. After completion of the reaction, extraction was made with CH$_2$Cl$_2$ and water, and the organic layer thus formed was dried over MgSO$_4$ and concentrated. The concentrate was purified by silica gel column chromatography, and recrystallized to afford the product. 12.73 g (yield: 68%).

2. Product A1-17 Synthesis

<Reaction Scheme 23>

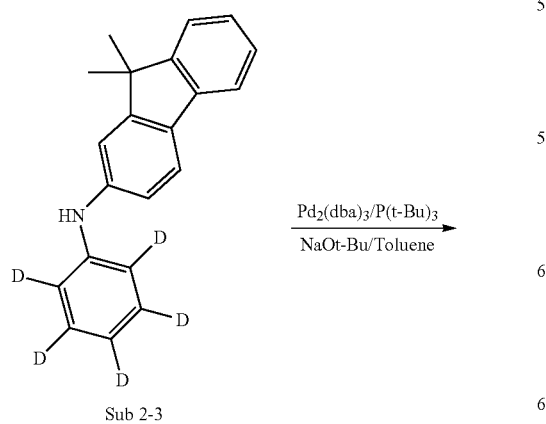

Sub 2-3

Pd$_2$(dba)$_3$/P(t-Bu)$_3$
NaOt-Bu/Toluene

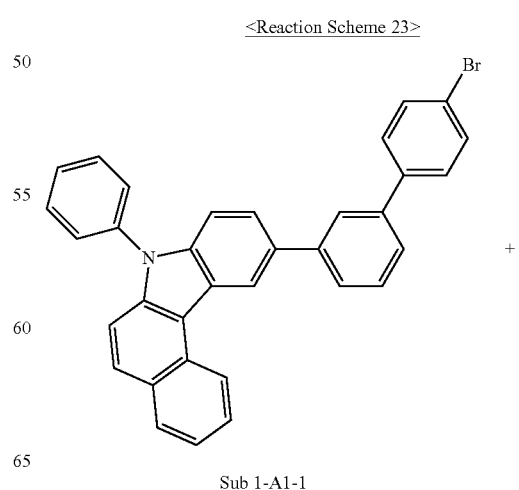

Sub 1-A1-1

+

3. Product A1-42 Synthesis

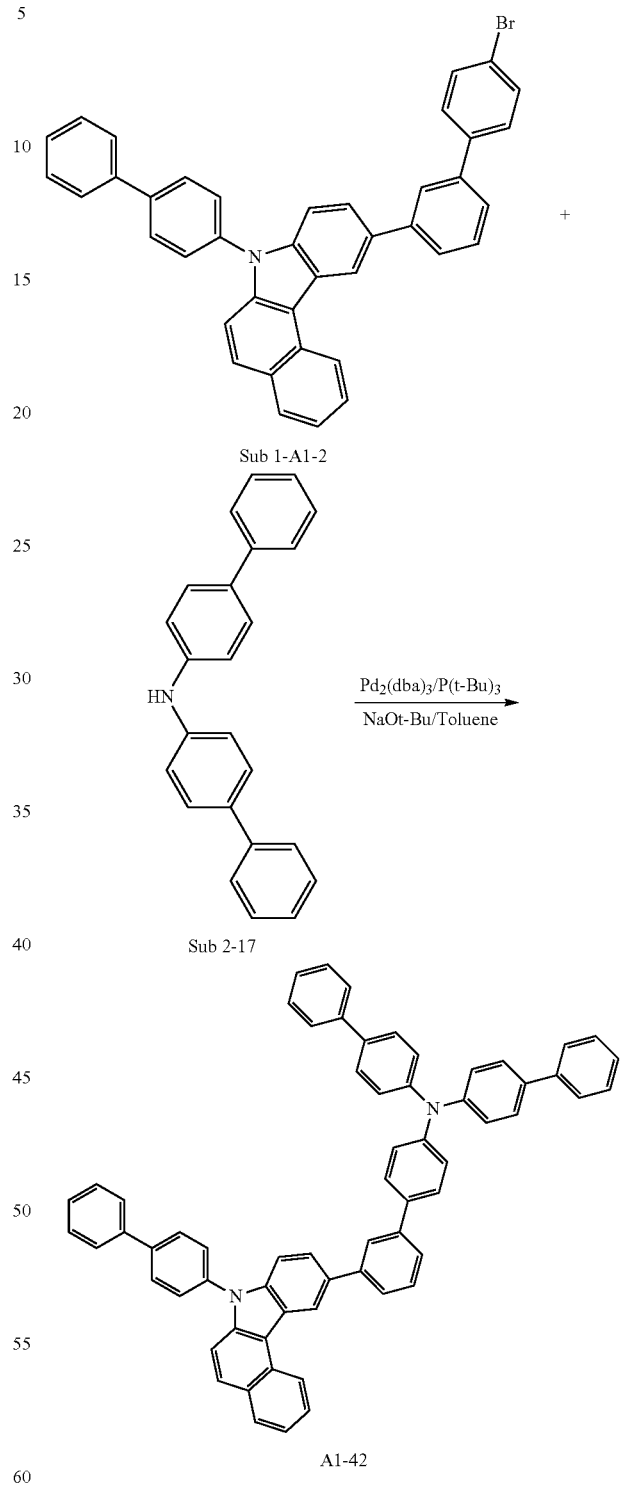

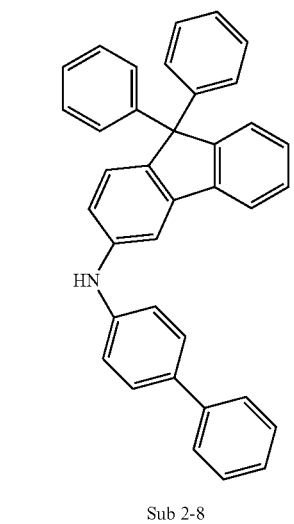

Sub 2-8

A1-17

Except for using the obtained Sub 2-8 (8.96 g, 18.5 mmol) plus Sub 1-A1-1 (11.61 g, 22.1 mmol), Pd$_2$(dba)$_3$ (0.51 g, 0.6 mmol), 50% P(t-Bu)$_3$ (0.7 ml, 1.5 mmol), NaOt-Bu (5.32 g, 55.4 mmol), and toluene, the same procedure as in the Product A1-1 synthesis was repeated to afford the product. 12.17 g (yield: 71%).

Except for using the obtained Sub 2-17 (6.07 g, 18.9 mmol) plus Sub 1-A1-2 (13.61 g, 22.7 mmol), Pd$_2$(dba)$_3$ (0.52 g, 0.6 mmol), 50% P(t-Bu)$_3$ (0.7 ml, 1.5 mmol), NaOt-Bu (5.45 g, 56.7 mmol), and toluene, the same procedure as in the Product A1-1 synthesis was repeated to afford the product. 11.91 g (yield: 75%).

4. Product A1-102 Synthesis

<Reaction Scheme 25>

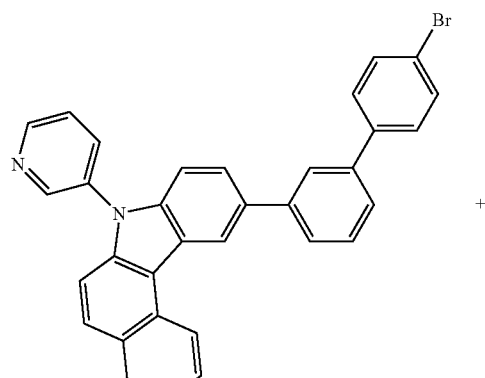

Sub 1-A1-5

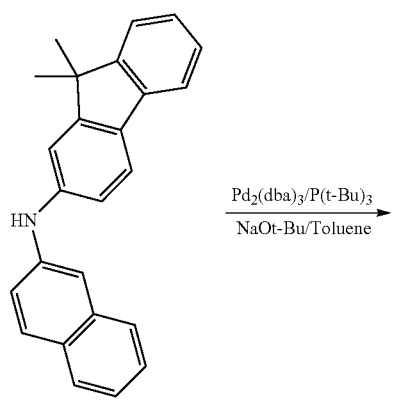

Sub 2-6

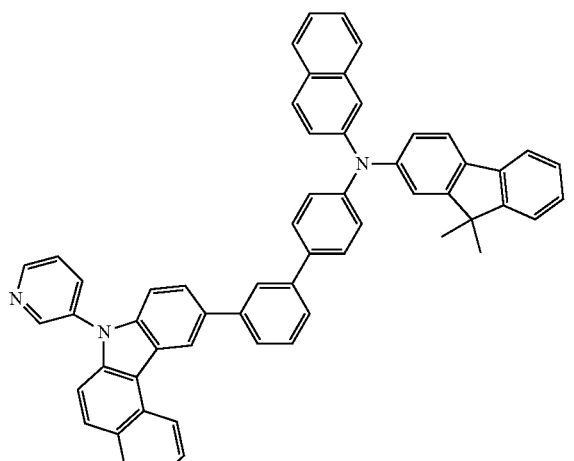

A1-102

Except for using the obtained Sub 2-6 (6.32 g, 18.8 mmol) plus Sub 1-A1-5 (11.88 g, 22.6 mmol), Pd$_2$(dba)$_3$ (0.52 g, 0.6 mmol), 50% P(t-Bu)$_3$ (0.7 ml, 1.5 mmol), NaOt-Bu (5.43 g, 56.5 mmol), and toluene, the same procedure as in the Product A1-1 synthesis was repeated to afford the product. 10.29 g (yield: 70%).

5. Product B1-32 Synthesis

<Reaction Scheme 26>

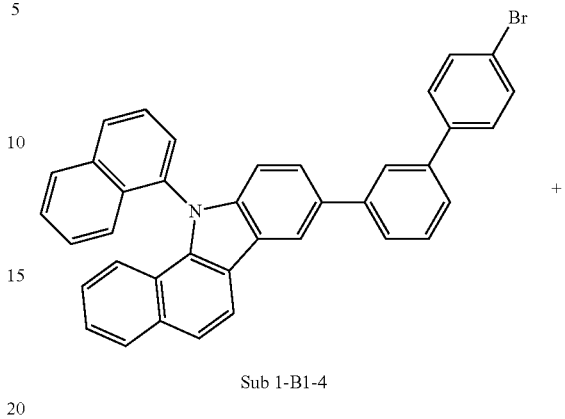

Sub 1-B1-4

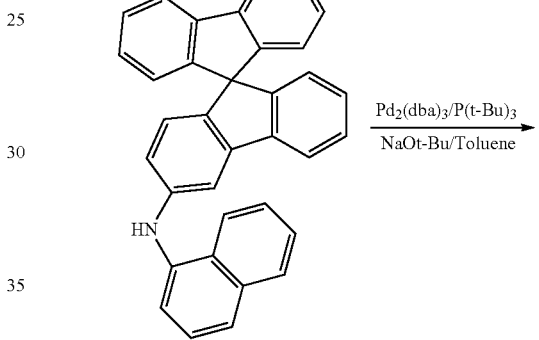

Sub 2-12

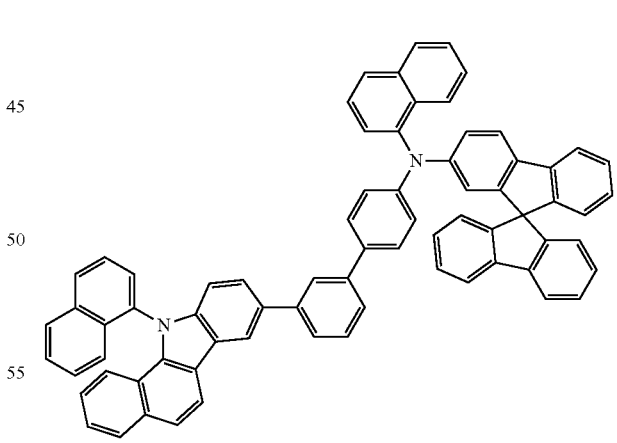

B1-32

Except for using the obtained Sub 2-12 (8.29 g, 18.1 mmol) plus Sub 1-B1-4 (12.49 g, 21.7 mmol), Pd$_2$(dba)$_3$ (0.5 g, 0.5 mmol), 50% P(t-Bu)$_3$ (0.7 ml, 1.4 mmol), NaOt-Bu (5.22 g, 54.4 mmol), and toluene, the same procedure as in the Product A1-1 synthesis was repeated to afford the product. 10.68 g (yield: 62%).

6. Product C1-1 Synthesis

7. Product C1-85 Synthesis

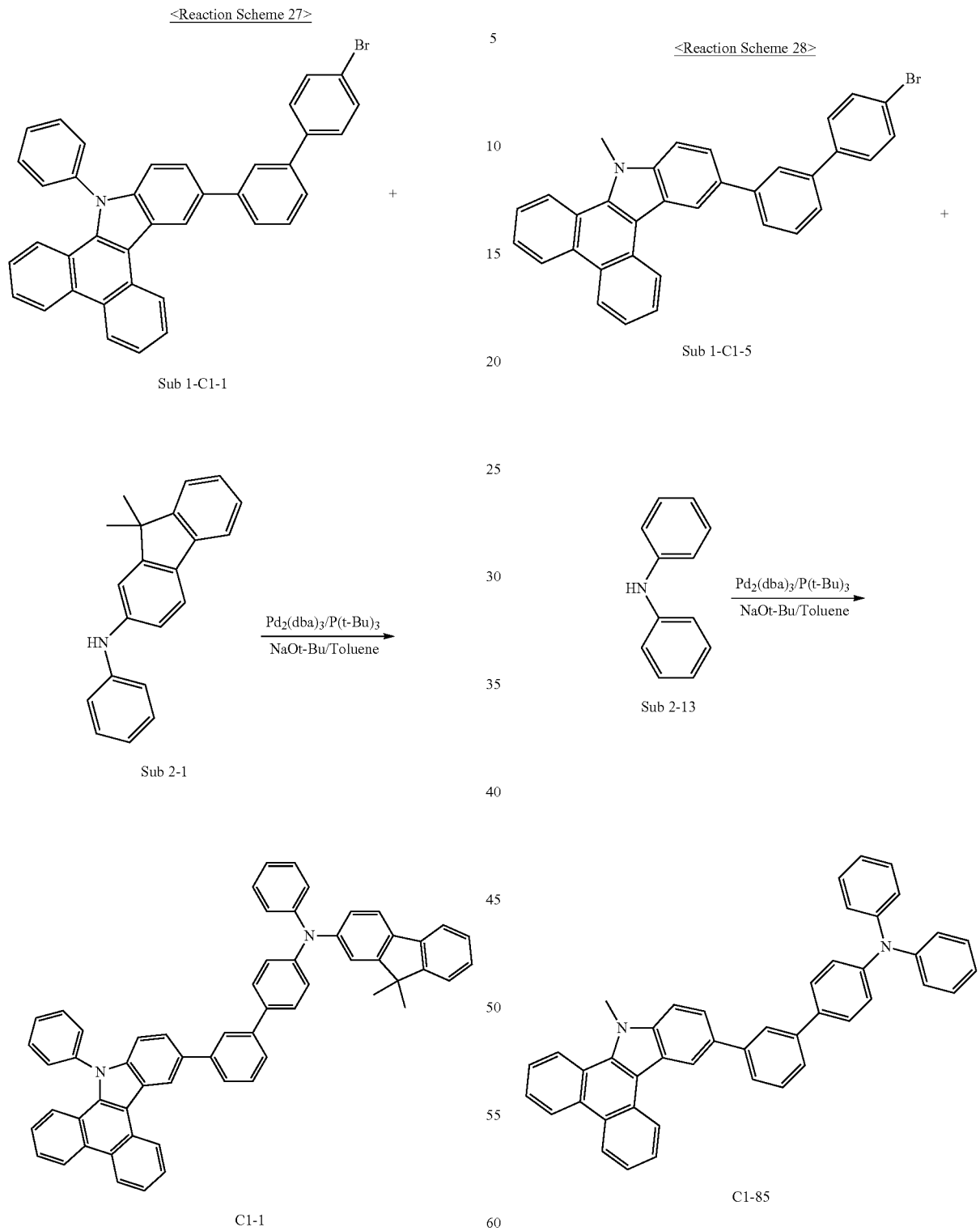

Except for using the obtained Sub 2-1 (5.97 g, 20.9 mmol) plus Sub 1-C1-1 (14.42 g, 25.1 mmol), Pd$_2$(dba)$_3$ (0.57 g, 0.6 mmol), 50% P(t-Bu)$_3$ (0.8 ml, 1.7 mmol), NaOt-Bu (6.03 g, 62.8 mmol), and toluene, the same procedure as in the Product A1-1 was repeated to afford the product. 12.06 g (yield: 74%).

Except for using the obtained Sub 2-13 (4.13 g, 24.4 mmol) plus Sub 1-C1-5 (15.01 g, 29.3 mmol), Pd$_2$(dba)$_3$ (0.67 g, 0.7 mmol), 50% P(t-Bu)$_3$ (1 ml, 2 mmol), NaOt-Bu (7.04 g, 73.2 mmol), and toluene, the same procedure as in the Product A1-1 synthesis was repeated to afford the product. 11.29 g (yield: 77%).

8. Product A2-20 Synthesis

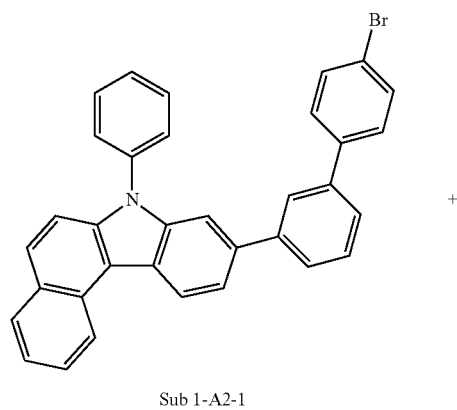

Sub 1-A2-1

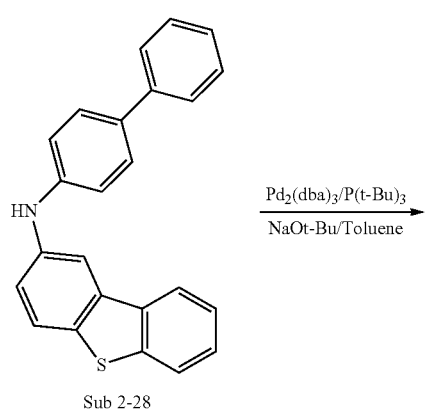

Sub 2-28

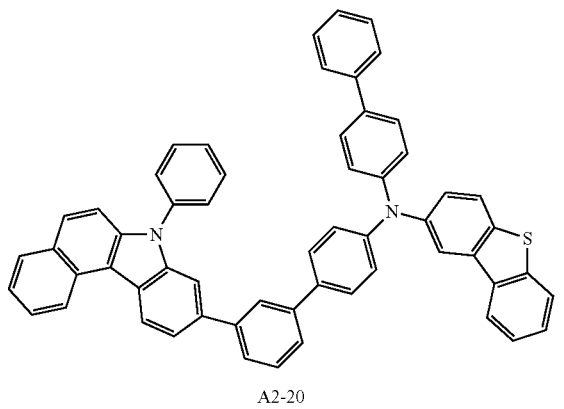

A2-20

Except for using the obtained Sub 2-28 (6.51 g, 18.5 mmol) plus Sub 1-A2-1 (11.66 g, 22.2 mmol), Pd$_2$(dba)$_3$ (0.51 g, 0.6 mmol), 50% P(t-Bu)$_3$ (0.7 ml, 1.5 mmol), NaOt-Bu (5.34 g, 55.6 mmol), and toluene, the same procedure as in the Product A1-1 synthesis was repeated to afford the product. 12.07 g (yield: 82%).

9. Product B2-9 Synthesis

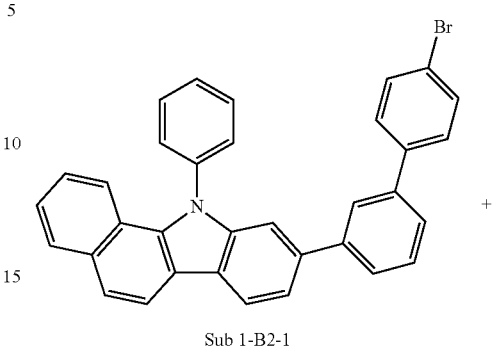

Sub 1-B2-1

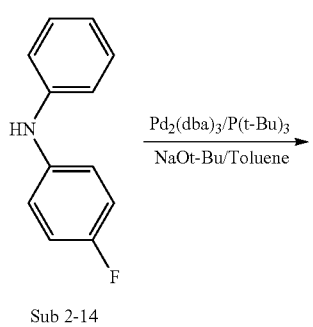

Sub 2-14

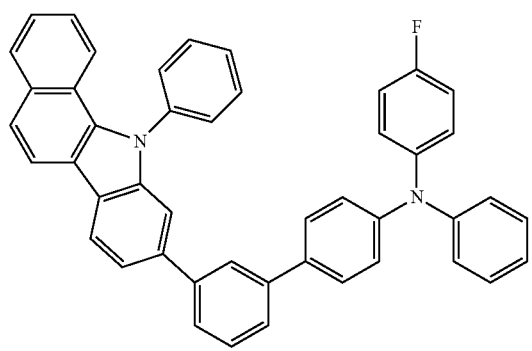

B2-9

Except for using the obtained Sub 2-14 (5.03 g, 26.9 mmol) plus Sub 1-B2-1 (16.91 g, 32.2 mmol), Pd$_2$(dba)$_3$ (0.74 g, 0.8 mmol), 50% P(t-Bu)$_3$ (1 ml, 2.1 mmol), NaOt-Bu (7.75 g, 80.6 mmol), and toluene, the same procedure as in the Product A1-1 synthesis was repeated to afford the product. 12.54 g (yield: 74%).

10. Product C2-3 Synthesis

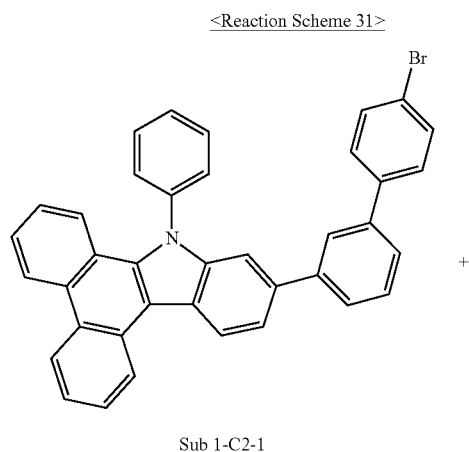

Sub 1-C2-1

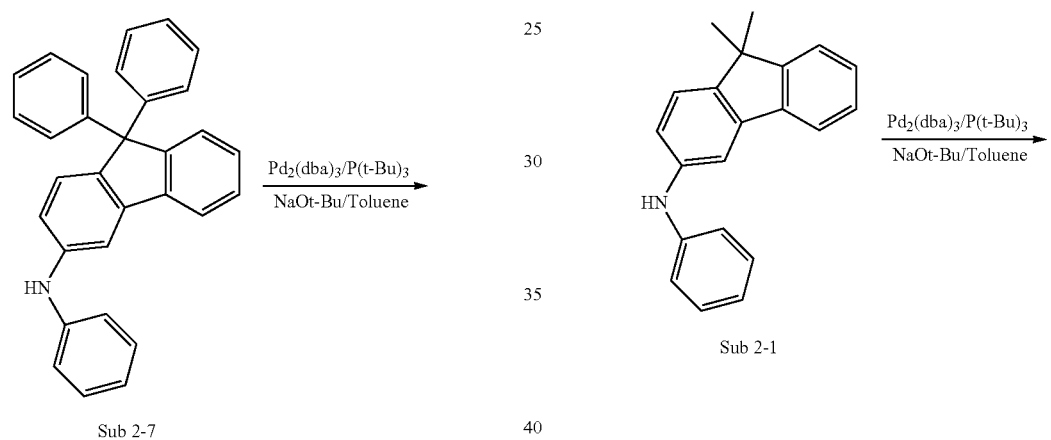

Sub 2-7

C2-3

<Reaction Scheme 31>

11. Product A3-1 Synthesis

<Reaction Scheme 32>

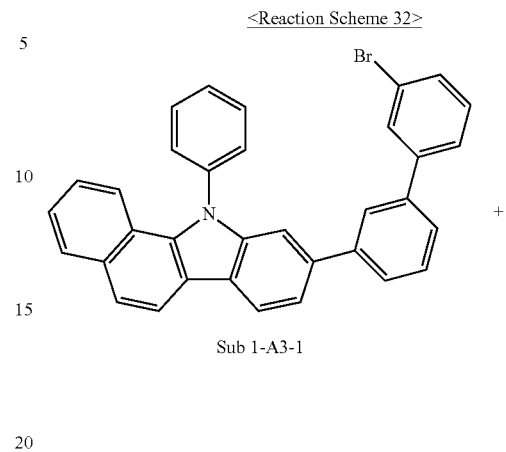

Sub 1-A3-1

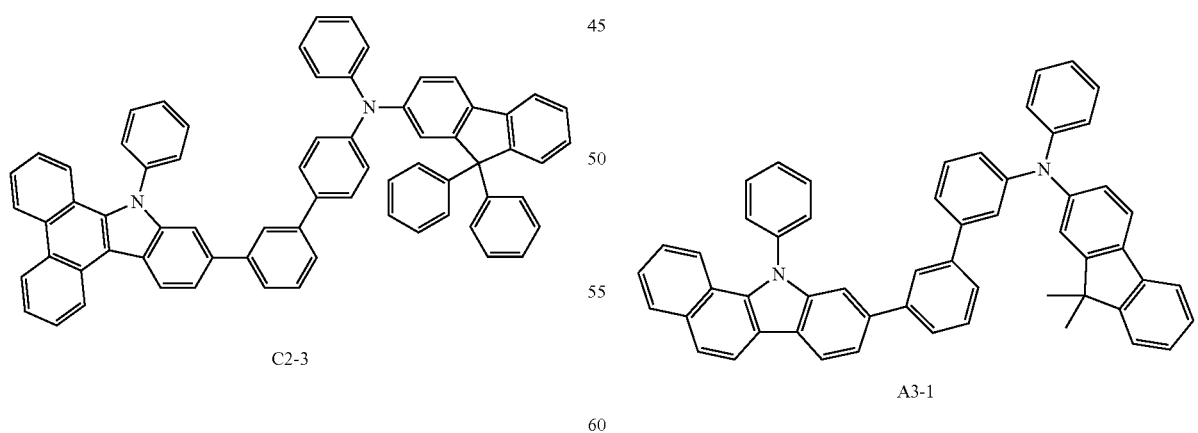

Sub 2-1

A3-1

Except for using the obtained Sub 2-7 (7.49 g, 18.3 mmol) plus Sub 1-C2-1 (12.61 g, 21.9 mmol), $Pd_2(dba)_3$ (0.5 g, 0.5 mmol), 50% P(t-Bu)$_3$ (0.7 ml, 1.5 mmol), NaOt-Bu (5.27 g, 54.9 mmol), and toluene the same procedure as in the Product A1-1 synthesis was repeated to afford the product. 11.23 g (yield: 68%).

Except for using the obtained Sub 2-1 (5.2 g, 18.3 mmol) plus Sub 1-A3-1 (11.5 g, 21.9 mmol), $Pd_2(dba)_3$ (0.5 g, 0.5 mmol), 50% P(t-Bu)$_3$ (0.7 ml, 1.5 mmol), NaOt-Bu (5.27 g, 54.9 mmol), and toluene, the same procedure as in the Product A1-1 synthesis was repeated to afford the product. 9.5 g (yield: 71%).

12. Product B4-1 Synthesis

<Reaction Scheme 33>

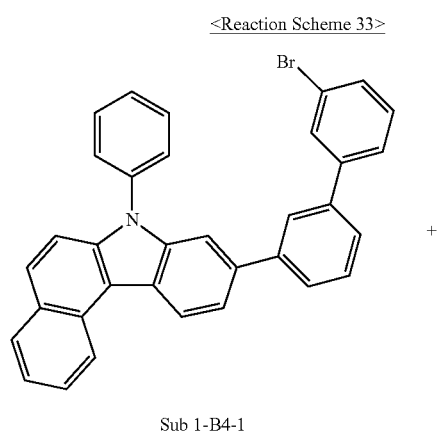

Sub 1-B4-1

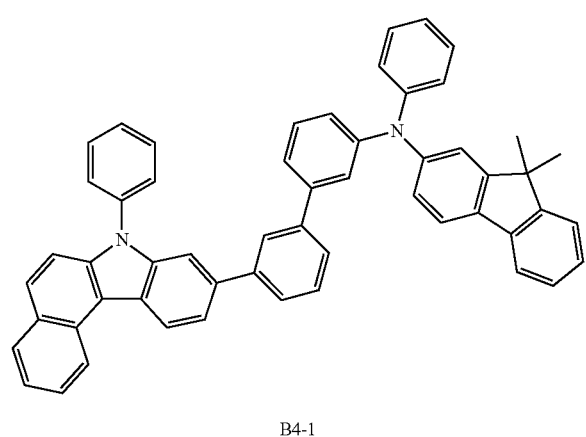

Sub 2-1

B4-1

Except for using the obtained Sub 2-1 (5.2 g, 18.3 mmol) plus Sub 1-B4-1 (11.5 g, 21.9 mmol), Pd$_2$(dba)$_3$ (0.5 g, 0.5 mmol), 50% P(t-Bu)$_3$ (0.7 ml, 1.5 mmol), NaOt-Bu (5.27 g, 54.9 mmol), and toluene, the same procedure as in the Product A1-1 synthesis was repeated to afford the product. 9.7 g (yield: 73%).

13. Product C5-3 Synthesis

<Reaction Scheme 34>

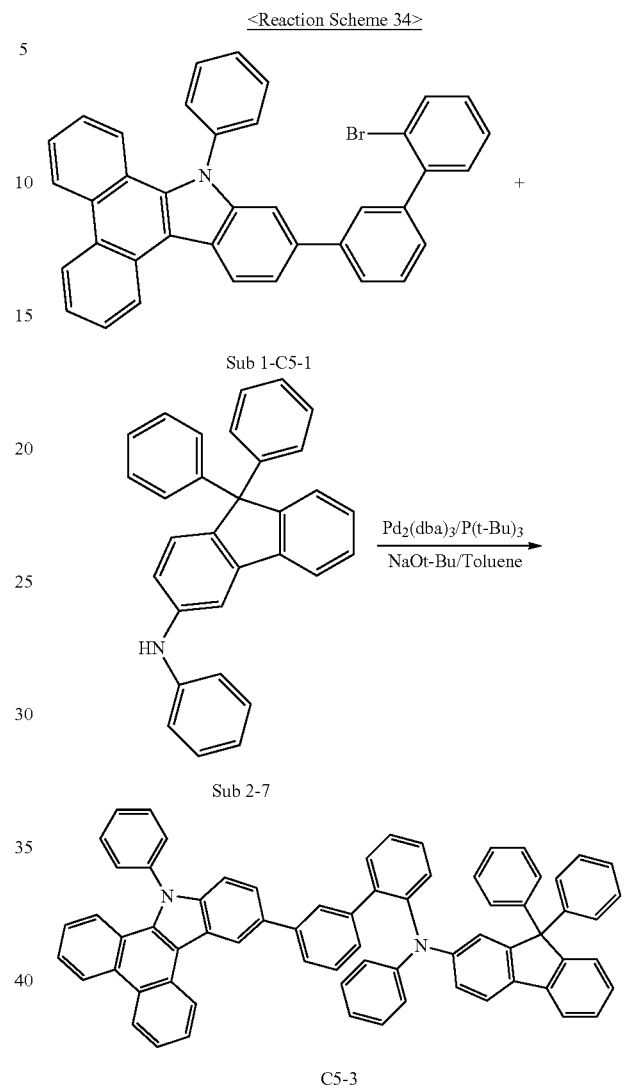

Except for using the obtained Sub 2-7 (7.5 g, 18.3 mmol) plus Sub 1-C5-1 (12.6 g, 21.9 mmol), Pd$_2$(dba)$_3$ (0.5 g, 0.5 mmol), 50% P(t-Bu)$_3$ (0.7 ml, 1.5 mmol), NaOt-Bu (5.27 g, 54.9 mmol), and toluene, the same procedure as in the Product A1-1 was repeated to afford the product. 10.7 g (yield: 65%).

14. Product A6-4 Synthesis

<Reaction Scheme 35>

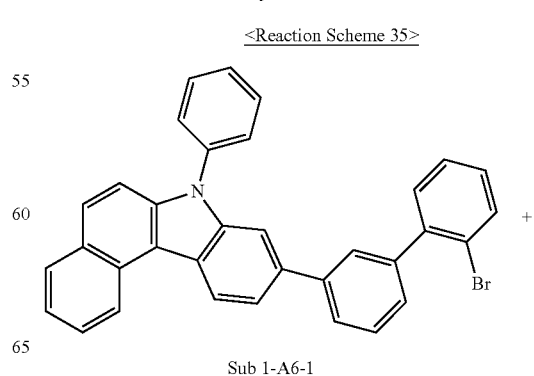

Sub 1-A6-1

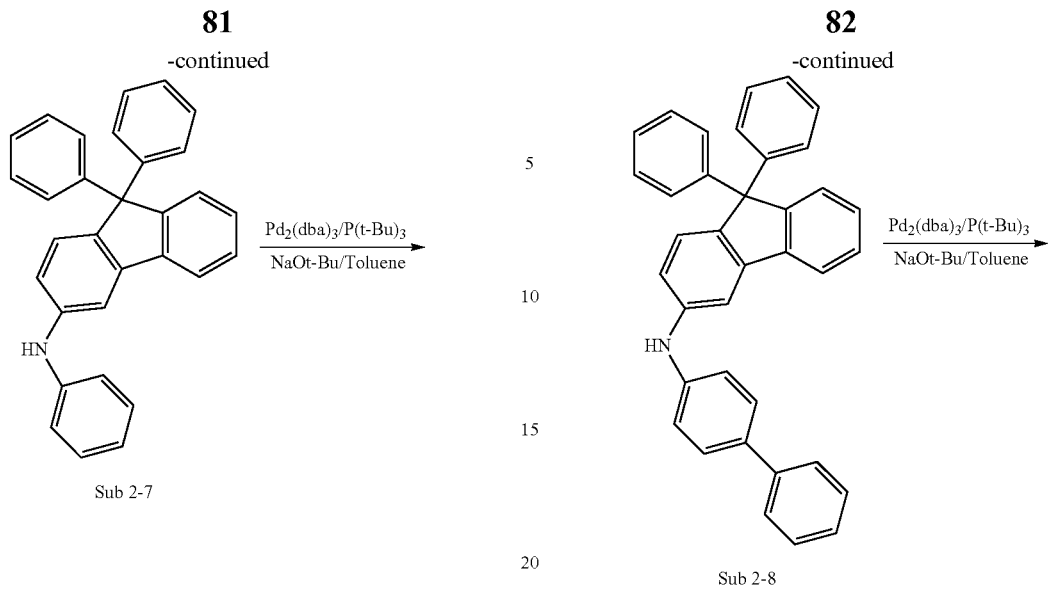

Sub 2-7

Sub 2-8

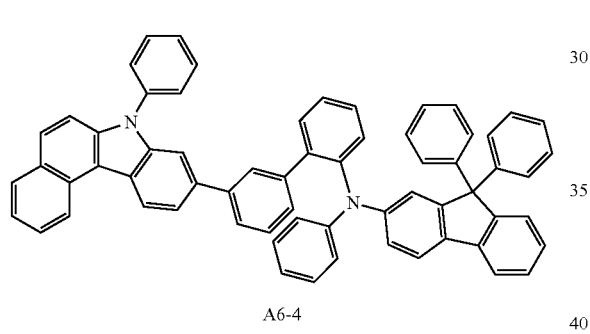

A6-4

Except for using the obtained Sub 2-7 (7.5 g, 18.3 mmol) plus Sub 1-A6-1 (11.5 g, 21.9 mmol), Pd$_2$(dba)$_3$ (0.5 g, 0.5 mmol), 50% P(t-Bu)$_3$ (0.7 ml, 1.5 mmol), NaOt-Bu (5.27 g, 54.9 mmol), and toluene, the same procedure as in the Product A1-1 synthesis was repeated to afford the product. 10.4 g (yield: 63%).

15. Product A7-2 Synthesis

<Reaction Scheme 36>

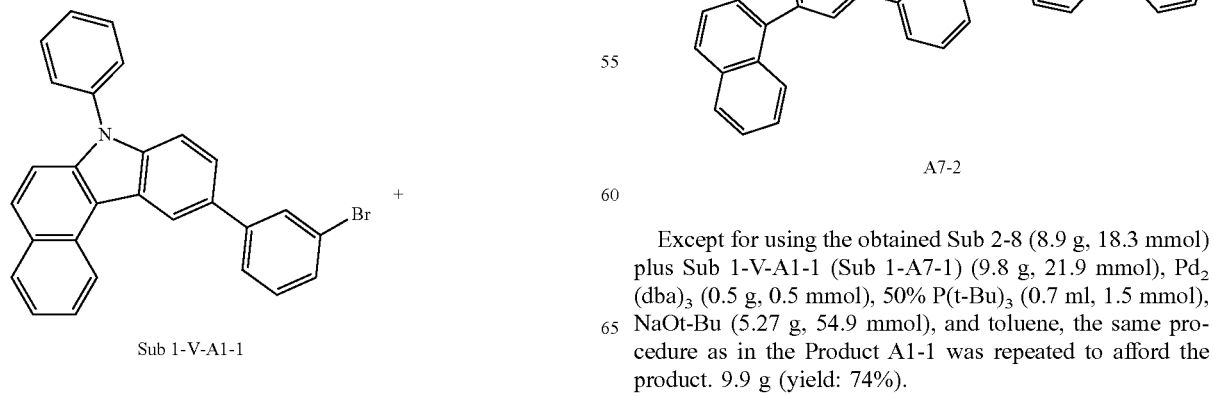

Sub 1-V-A1-1

A7-2

Except for using the obtained Sub 2-8 (8.9 g, 18.3 mmol) plus Sub 1-V-A1-1 (Sub 1-A7-1) (9.8 g, 21.9 mmol), Pd$_2$(dba)$_3$ (0.5 g, 0.5 mmol), 50% P(t-Bu)$_3$ (0.7 ml, 1.5 mmol), NaOt-Bu (5.27 g, 54.9 mmol), and toluene, the same procedure as in the Product A1-1 was repeated to afford the product. 9.9 g (yield: 74%).

16. Product C7-6 Synthesis

<Reaction Scheme 37>

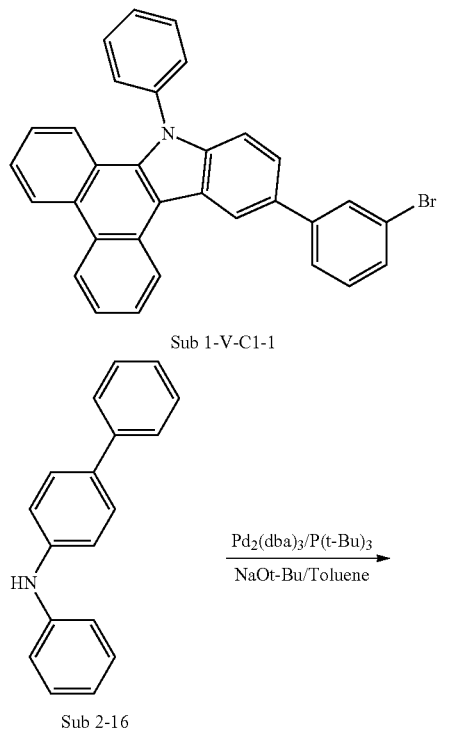

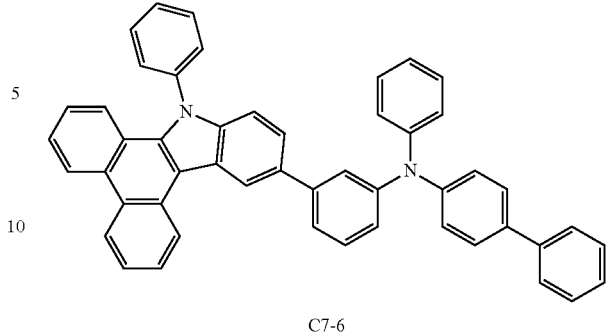

Except for using the obtained Sub 2-8 (4.5 g, 18.3 mmol) plus Sub 1-V-A1-1 (Sub 1-A7-1) (10.9 g, 21.9 mmol), Pd$_2$(dba)$_3$ (0.5 g, 0.5 mmol), 50% P(t-Bu)$_3$ (0.7 ml, 1.5 mmol), NaOt-Bu (5.27 g, 54.9 mmol), toluene, the same procedure as in the Product A1-1 synthesis was repeated to afford the product. 8.5 g (yield: 70%).

In Table 11 below, FD-MS data of the compounds prepared in the Synthesis Examples of the present invention are given.

TABLE 11

| Compound | FD-MS | Compound | FD-MS |
|---|---|---|---|
| A1-1 | m/z = 733.35($C_{55}H_{35}D_5N_2$ = 733.95) | A1-2 | m/z = 804.35($C_{61}H_{44}N_2$ = 805.02) |
| A1-3 | m/z = 778.33($C_{59}H_{42}N_2$ = 778.98) | A1-4 | m/z = 778.33($C_{59}H_{42}N_2$ = 778.98) |
| A1-5 | m/z = 804.35($C_{61}H_{44}N_2$ = 805.02) | A1-6 | m/z = 880.38($C_{67}H_{48}N_2$ = 881.11) |
| A1-7 | m/z = 854.37($C_{65}H_{46}N_2$ = 855.07) | A1-8 | m/z = 854.37($C_{65}H_{46}N_2$ = 855.07) |
| A1-9 | m/z = 778.33($C_{59}H_{42}N_2$ = 778.98) | A1-10 | m/z = 854.37($C_{65}H_{46}N_2$ = 855.07) |
| A1-11 | m/z = 828.35($C_{63}H_{44}N_2$ = 829.04) | A1-12 | m/z = 828.35($C_{63}H_{44}N_2$ = 829.04) |
| A1-13 | m/z = 852.35($C_{65}H_{44}N_2$ = 853.06) | A1-14 | m/z = 928.38($C_{71}H_{48}N_2$ = 929.15) |
| A1-15 | m/z = 902.37($C_{69}H_{46}N_2$ = 903.12) | A1-16 | m/z = 902.37($C_{69}H_{46}N_2$ = 903.12) |
| A1-17 | m/z = 928.38($C_{71}H_{48}N_2$ = 929.15) | A1-18 | m/z = 1004.41($C_{77}H_{52}N_2$ = 1005.25) |
| A1-19 | m/z = 978.40($C_{75}H_{50}N_2$ = 979.21) | A1-20 | m/z = 978.40($C_{75}H_{50}N_2$ = 979.21) |
| A1-21 | m/z = 902.37($C_{69}H_{46}N_2$ = 903.12) | A1-22 | m/z = 978.40($C_{75}H_{50}N_2$ = 979.21) |
| A1-23 | m/z = 952.38($C_{73}H_{48}N_2$ = 953.18) | A1-24 | m/z = 952.38($C_{73}H_{48}N_2$ = 953.18) |
| A1-25 | m/z = 850.33($C_{65}H_{42}N_2$ = 851.04) | A1-26 | m/z = 926.37($C_{71}H_{46}N_2$ = 927.14) |
| A1-27 | m/z = 900.35($C_{69}H_{44}N_2$ = 901.10) | A1-28 | m/z = 900.35($C_{69}H_{44}N_2$ = 901.10) |
| A1-29 | m/z = 900.35($C_{69}H_{44}N_2$ = 901.10) | A1-30 | m/z = 976.38($C_{75}H_{48}N_2$ = 977.20) |
| A1-31 | m/z = 950.37($C_{73}H_{46}N_2$ = 951.16) | A1-32 | m/z = 950.37($C_{73}H_{46}N_2$ = 951.16) |
| A1-33 | m/z = 926.37($C_{71}H_{46}N_2$ = 927.14) | A1-34 | m/z = 1002.40($C_{77}H_{50}N_2$ = 1003.23) |
| A1-35 | m/z = 976.38($C_{75}H_{48}N_2$ = 977.20) | A1-36 | m/z = 976.38($C_{75}H_{48}N_2$ = 977.20) |
| A1-37 | m/z = 688.29($C_{52}H_{36}N_2$ = 688.86) | A1-38 | m/z = 764.32($C_{58}H_{40}N_2$ = 764.95) |
| A1-39 | m/z = 738.30($C_{56}H_{38}N_2$ = 738.91) | A1-40 | m/z = 738.30($C_{56}H_{38}N_2$ = 738.91) |
| A1-41 | m/z = 764.32($C_{58}H_{40}N_2$ = 764.95) | A1-42 | m/z = 840.35($C_{64}H_{44}N_2$ = 841.05) |
| A1-43 | m/z = 814.33($C_{62}H_{42}N_2$ = 815.01) | A1-44 | m/z = 814.33($C_{62}H_{42}N_2$ = 815.01) |
| A1-45 | m/z = 738.30($C_{56}H_{38}N_2$ = 738.91) | A1-46 | m/z = 814.33($C_{62}H_{42}N_2$ = 815.01) |
| A1-47 | m/z = 788.32($C_{60}H_{40}N_2$ = 788.97) | A1-48 | m/z = 788.32($C_{60}H_{40}N_2$ = 788.97) |
| A1-49 | m/z = 738.30($C_{56}H_{38}N_2$ = 738.91) | A1-50 | m/z = 814.33($C_{62}H_{42}N_2$ = 815.01) |
| A1-51 | m/z = 788.32($C_{60}H_{40}N_2$ = 788.97) | A1-52 | m/z = 788.32($C_{60}H_{40}N_2$ = 788.97) |
| A1-53 | m/z = 662.27($C_{50}H_{34}N_2$ = 662.82) | A1-54 | m/z = 738.30($C_{56}H_{38}N_2$ = 738.91) |
| A1-55 | m/z = 712.29($C_{54}H_{36}N_2$ = 712.88) | A1-56 | m/z = 712.29($C_{54}H_{36}N_2$ = 712.88) |
| A1-57 | m/z = 662.27($C_{50}H_{34}N_2$ = 662.82) | A1-58 | m/z = 738.30($C_{56}H_{38}N_2$ = 738.91) |
| A1-59 | m/z = 712.29($C_{54}H_{36}N_2$ = 712.88) | A1-60 | m/z = 712.29($C_{54}H_{36}N_2$ = 712.88) |
| A1-61 | m/z = 712.29($C_{54}H_{36}N_2$ = 712.88) | A1-62 | m/z = 788.32($C_{60}H_{40}N_2$ = 788.97) |
| A1-63 | m/z = 762.30($C_{58}H_{38}N_2$ = 762.94) | A1-64 | m/z = 762.30($C_{58}H_{38}N_2$ = 762.94) |
| A1-65 | m/z = 712.29($C_{54}H_{36}N_2$ = 712.88) | A1-66 | m/z = 788.32($C_{60}H_{40}N_2$ = 788.97) |
| A1-67 | m/z = 762.30($C_{58}H_{38}N_2$ = 762.94) | A1-68 | m/z = 762.30($C_{58}H_{38}N_2$ = 762.94) |
| A1-69 | m/z = 712.29($C_{54}H_{36}N_2$ = 712.88) | A1-70 | m/z = 788.32($C_{60}H_{40}N_2$ = 788.97) |
| A1-71 | m/z = 762.30($C_{58}H_{38}N_2$ = 762.94) | A1-72 | m/z = 762.30($C_{58}H_{38}N_2$ = 762.94) |
| A1-73 | m/z = 718.24($C_{52}H_{34}N_2S$ = 718.90) | A1-74 | m/z = 794.28($C_{58}H_{38}N_2S$ = 795.00) |
| A1-75 | m/z = 768.26($C_{56}H_{36}N_2S$ = 768.96) | A1-76 | m/z = 768.26($C_{56}H_{36}N_2S$ = 768.96) |

TABLE 11-continued

| Compound | FD-MS | Compound | FD-MS |
|---|---|---|---|
| A1-77 | m/z = 702.27($C_{52}H_{34}N_2O$ = 702.84) | A1-78 | m/z = 778.30($C_{58}H_{38}N_2O$ = 778.94) |
| A1-79 | m/z = 752.28($C_{56}H_{36}N_2O$ = 752.90) | A1-80 | m/z = 752.28($C_{56}H_{36}N_2O$ = 752.90) |
| A1-81 | m/z = 794.28($C_{58}H_{38}N_2S$ = 795.00) | A1-82 | m/z = 870.31($C_{64}H_{42}N_2S$ = 871.10) |
| A1-83 | m/z = 844.29($C_{62}H_{40}N_2S$ = 845.06) | A1-84 | m/z = 844.29($C_{62}H_{40}N_2S$ = 845.06) |
| A1-85 | m/z = 778.30($C_{58}H_{38}N_2O$ = 778.94) | A1-86 | m/z = 854.33($C_{64}H_{42}N_2O$ = 855.03) |
| A1-87 | m/z = 828.31($C_{62}H_{40}N_2O$ = 828.99) | A1-88 | m/z = 828.31($C_{62}H_{40}N_2O$ = 828.99) |
| A1-89 | m/z = 768.26($C_{56}H_{36}N_2S$ = 768.96) | A1-90 | m/z = 844.29($C_{62}H_{40}N_2S$ = 845.06) |
| A1-91 | m/z = 818.28($C_{60}H_{38}N_2S$ = 819.02) | A1-92 | m/z = 818.28($C_{60}H_{38}N_2S$ = 819.02) |
| A1-93 | m/z = 752.28($C_{56}H_{36}N_2O$ = 752.90) | A1-94 | m/z = 828.31($C_{62}H_{40}N_2O$ = 828.99) |
| A1-95 | m/z = 802.30($C_{60}H_{38}N_2O$ = 802.96) | A1-96 | m/z = 802.30($C_{60}H_{38}N_2O$ = 802.96) |
| A1-97 | m/z = 718.24($C_{52}H_{34}N_2S$ = 718.90) | A1-98 | m/z = 870.31($C_{64}H_{42}N_2S$ = 871.10) |
| A1-99 | m/z = 612.26($C_{46}H_{32}N_2$ = 612.76) | A1-100 | m/z = 688.29($C_{52}H_{36}N_2$ = 688.86) |
| A1-101 | m/z = 742.33($C_{56}H_{42}N_2$ = 742.95) | A1-102 | m/z = 779.33($C_{58}H_{41}N_3$ = 779.97) |
| A1-103 | m/z = 809.38($C_{61}H_{39}D_5N_2$ = 810.05) | A1-104 | m/z = 893.38($C_{67}H_{47}N_3$ = 894.11) |
| B1-1 | m/z = 728.32($C_{55}H_{40}N_2$ = 728.92) | B1-2 | m/z = 804.35($C_{61}H_{44}N_2$ = 805.02) |
| B1-3 | m/z = 778.33($C_{59}H_{42}N_2$ = 778.98) | B1-4 | m/z = 778.33($C_{59}H_{42}N_2$ = 778.98) |
| B1-5 | m/z = 804.35($C_{61}H_{44}N_2$ = 805.02) | B1-6 | m/z = 880.38($C_{67}H_{48}N_2$ = 881.11) |
| B1-7 | m/z = 854.37($C_{65}H_{46}N_2$ = 855.07) | B1-8 | m/z = 854.37($C_{65}H_{46}N_2$ = 855.07) |
| B1-9 | m/z = 778.33($C_{59}H_{42}N_2$ = 778.98) | B1-10 | m/z = 854.37($C_{65}H_{46}N_2$ = 855.07) |
| B1-11 | m/z = 828.35($C_{63}H_{44}N_2$ = 829.04) | B1-12 | m/z = 828.35($C_{63}H_{44}N_2$ = 829.04) |
| B1-13 | m/z = 852.35($C_{65}H_{44}N_2$ = 853.06) | B1-14 | m/z = 928.38($C_{71}H_{48}N_2$ = 929.15) |
| B1-15 | m/z = 902.37($C_{69}H_{46}N_2$ = 903.12) | B1-16 | m/z = 902.37($C_{69}H_{46}N_2$ = 903.12) |
| B1-17 | m/z = 928.38($C_{71}H_{48}N_2$ = 929.15) | B1-18 | m/z = 1004.41($C_{77}H_{52}N_2$ = 1005.25) |
| B1-19 | m/z = 978.40($C_{75}H_{50}N_2$ = 979.21) | B1-20 | m/z = 978.40($C_{75}H_{50}N_2$ = 979.21) |
| B1-21 | m/z = 902.37($C_{69}H_{46}N_2$ = 903.12) | B1-22 | m/z = 978.40($C_{75}H_{50}N_2$ = 979.21) |
| B1-23 | m/z = 952.38($C_{73}H_{48}N_2$ = 953.18) | B1-24 | m/z = 952.38($C_{73}H_{48}N_2$ = 953.18) |
| B1-25 | m/z = 850.33($C_{65}H_{42}N_2$ = 851.04) | B1-26 | m/z = 926.37($C_{71}H_{46}N_2$ = 927.14) |
| B1-27 | m/z = 900.35($C_{69}H_{44}N_2$ = 901.10) | B1-28 | m/z = 900.35($C_{69}H_{44}N_2$ = 901.10) |
| B1-29 | m/z = 900.35($C_{69}H_{44}N_2$ = 901.10) | B1-30 | m/z = 976.38($C_{75}H_{48}N_2$ = 977.20) |
| B1-31 | m/z = 950.37($C_{73}H_{46}N_2$ = 951.16) | B1-32 | m/z = 950.37($C_{73}H_{46}N_2$ = 951.16) |
| B1-33 | m/z = 926.37($C_{71}H_{46}N_2$ = 927.14) | B1-34 | m/z = 1002.40($C_{77}H_{50}N_2$ = 1003.23) |
| B1-35 | m/z = 976.38($C_{75}H_{48}N_2$ = 977.20) | B1-36 | m/z = 976.38($C_{75}H_{48}N_2$ = 977.20) |
| B1-37 | m/z = 688.29($C_{52}H_{36}N_2$ = 688.86) | B1-38 | m/z = 764.32($C_{58}H_{40}N_2$ = 764.95) |
| B1-39 | m/z = 738.30($C_{56}H_{38}N_2$ = 738.91) | B1-40 | m/z = 738.30($C_{56}H_{38}N_2$ = 738.91) |
| B1-41 | m/z = 764.32($C_{58}H_{40}N_2$ = 764.95) | B1-42 | m/z = 840.35($C_{64}H_{44}N_2$ = 841.05) |
| B1-43 | m/z = 814.33($C_{62}H_{42}N_2$ = 815.01) | B1-44 | m/z = 814.33($C_{62}H_{42}N_2$ = 815.01) |
| B1-45 | m/z = 738.30($C_{56}H_{38}N_2$ = 738.91) | B1-46 | m/z = 814.33($C_{62}H_{42}N_2$ = 815.01) |
| B1-47 | m/z = 788.32($C_{60}H_{40}N_2$ = 788.97) | B1-48 | m/z = 788.32($C_{60}H_{40}N_2$ = 788.97) |
| B1-49 | m/z = 738.30($C_{56}H_{38}N_2$ = 738.91) | B1-50 | m/z = 814.33($C_{62}H_{42}N_2$ = 815.01) |
| B1-51 | m/z = 788.32($C_{60}H_{40}N_2$ = 788.97) | B1-52 | m/z = 788.32($C_{60}H_{40}N_2$ = 788.97) |
| B1-53 | m/z = 662.27($C_{50}H_{34}N_2$ = 662.82) | B1-54 | m/z = 738.30($C_{56}H_{38}N_2$ = 738.91) |
| B1-55 | m/z = 712.29($C_{54}H_{36}N_2$ = 712.88) | B1-56 | m/z = 712.29($C_{54}H_{36}N_2$ = 712.88) |
| B1-57 | m/z = 662.27($C_{50}H_{34}N_2$ = 662.82) | B1-58 | m/z = 738.30($C_{56}H_{38}N_2$ = 738.91) |
| B1-59 | m/z = 712.29($C_{54}H_{36}N_2$ = 712.88) | B1-60 | m/z = 712.29($C_{54}H_{36}N_2$ = 712.88) |
| B1-61 | m/z = 718.24($C_{52}H_{34}N_2S$ = 718.90) | B1-62 | m/z = 794.28($C_{58}H_{38}N_2S$ = 795.00) |
| B1-63 | m/z = 768.26($C_{56}H_{36}N_2S$ = 768.96) | B1-64 | m/z = 768.26($C_{56}H_{36}N_2S$ = 768.96) |
| B1-65 | m/z = 702.27($C_{52}H_{34}N_2O$ = 702.84) | B1-66 | m/z = 778.30($C_{58}H_{38}N_2O$ = 778.94) |
| B1-67 | m/z = 752.28($C_{56}H_{36}N_2O$ = 752.90) | B1-68 | m/z = 752.28($C_{56}H_{36}N_2O$ = 752.90) |
| B1-69 | m/z = 794.28($C_{58}H_{38}N_2S$ = 795.00) | B1-70 | m/z = 870.31($C_{64}H_{42}N_2S$ = 871.10) |
| B1-71 | m/z = 844.29($C_{62}H_{40}N_2S$ = 845.06) | B1-72 | m/z = 844.29($C_{62}H_{40}N_2S$ = 845.06) |
| B1-73 | m/z = 778.30($C_{58}H_{38}N_2O$ = 778.94) | B1-74 | m/z = 854.33($C_{64}H_{42}N_2O$ = 855.03) |
| B1-75 | m/z = 828.31($C_{62}H_{40}N_2O$ = 828.99) | B1-76 | m/z = 828.31($C_{62}H_{40}N_2O$ = 828.99) |
| B1-77 | m/z = 768.26($C_{56}H_{36}N_2S$ = 768.96) | B1-78 | m/z = 844.29($C_{62}H_{40}N_2S$ = 845.06) |
| B1-79 | m/z = 818.28($C_{60}H_{38}N_2S$ = 819.02) | B1-80 | m/z = 818.28($C_{60}H_{38}N_2S$ = 819.02) |
| B1-81 | m/z = 752.28($C_{56}H_{36}N_2O$ = 752.90) | B1-82 | m/z = 828.31($C_{62}H_{40}N_2O$ = 828.99) |
| B1-83 | m/z = 802.30($C_{60}H_{38}N_2O$ = 802.96) | B1-84 | m/z = 802.30($C_{60}H_{38}N_2O$ = 802.96) |
| B1-85 | m/z = 870.34($C_{64}H_{46}N_2Si$ = 871.15) | B1-86 | m/z = 855.36($C_{64}H_{45}N_3$ = 856.06) |
| C1-1 | m/z = 778.33($C_{59}H_{42}N_2$ = 778.98) | C1-2 | m/z = 854.37($C_{65}H_{46}N_2$ = 855.07) |
| C1-3 | m/z = 828.35($C_{63}H_{44}N_2$ = 829.04) | C1-4 | m/z = 828.35($C_{63}H_{44}N_2$ = 829.04) |
| C1-5 | m/z = 854.37($C_{65}H_{46}N_2$ = 855.07) | C1-6 | m/z = 930.40(C71H50N2 = 931.17) |
| C1-7 | m/z = 904.38($C_{69}H_{48}N_2$ = 905.13) | C1-8 | m/z = 904.38($C_{69}H_{48}N_2$ = 905.13) |
| C1-9 | m/z = 828.35($C_{63}H_{44}N_2$ = 829.04) | C1-10 | m/z = 904.38($C_{69}H_{48}N_2$ = 905.13) |
| C1-11 | m/z = 878.37($C_{67}H_{46}N_2$ = 879.10) | C1-12 | m/z = 878.37($C_{67}H_{46}N_2$ = 879.10) |
| C1-13 | m/z = 902.37($C_{69}H_{46}N_2$ = 903.12) | C1-14 | m/z = 978.40($C_{75}H_{50}N_2$ = 979.21) |
| C1-15 | m/z = 952.38($C_{73}H_{48}N_2$ = 953.18) | C1-16 | m/z = 952.38($C_{73}H_{48}N_2$ = 953.18) |
| C1-17 | m/z = 978.40($C_{75}H_{50}N_2$ = 979.21) | C1-18 | m/z = 1054.43($C_{81}H_{54}N_2$ = 1055.31) |
| C1-19 | m/z = 1028.41($C_{79}H_{52}N_2$ = 1029.27) | C1-20 | m/z = 1028.41($C_{79}H_{52}N_2$ = 1029.27) |
| C1-21 | m/z = 952.38($C_{73}H_{48}N_2$ = 953.18) | C1-22 | m/z = 1028.41($C_{79}H_{52}N_2$ = 1029.27) |
| C1-23 | m/z = 1002.40($C_{77}H_{50}N_2$ = 1003.23) | C1-24 | m/z = 1002.40($C_{77}H_{50}N_2$ = 1003.23) |
| C1-25 | m/z = 900.35($C_{69}H_{44}N_2$ = 901.10) | C1-26 | m/z = 976.38($C_{75}H_{48}N_2$ = 977.20) |
| C1-27 | m/z = 950.37($C_{73}H_{46}N_2$ = 951.16) | C1-28 | m/z = 950.37($C_{73}H_{46}N_2$ = 951.16) |
| C1-29 | m/z = 950.37(C73H46N2 = 951.16) | C1-30 | m/z = 1026.40($C_{79}H_{50}N_2$ = 1027.26) |
| C1-31 | m/z = 1000.38($C_{77}H_{48}N_2$ = 1001.22) | C1-32 | m/z = 1000.38($C_{77}H_{48}N_2$ = 1001.22) |
| C1-33 | m/z = 976.38($C_{75}H_{48}N_2$ = 977.20) | C1-34 | m/z = 1052.41($C_{81}H_{52}N_2$ = 1053.29) |
| C1-35 | m/z = 1026.40($C_{79}H_{50}N_2$ = 1027.26) | C1-36 | m/z = 1026.40($C_{79}H_{50}N_2$ = 1027.26) |
| C1-37 | m/z = 738.30($C_{56}H_{38}N_2$ = 738.91) | C1-38 | m/z = 814.33($C_{62}H_{42}N_2$ = 815.01) |
| C1-39 | m/z = 788.32($C_{60}H_{40}N_2$ = 788.97) | C1-40 | m/z = 788.32($C_{60}H_{40}N_2$ = 788.97) |
| C1-41 | m/z = 814.33($C_{62}H_{42}N_2$ = 815.01) | C1-42 | m/z = 890.37($C_{68}H_{46}N_2$ = 891.11) |

TABLE 11-continued

| Compound | FD-MS | Compound | FD-MS |
| --- | --- | --- | --- |
| C1-43 | m/z = 864.35($C_{66}H_{44}N_2$ = 865.07) | C1-44 | m/z = 864.35($C_{66}H_{44}N_2$ = 865.07) |
| C1-45 | m/z = 788.32($C_{60}H_{40}N_2$ = 788.97) | C1-46 | m/z = 864.35($C_{66}H_{44}N_2$ = 865.07) |
| C1-47 | m/z = 838.33($C_{64}H_{42}N_2$ = 839.03) | C1-48 | m/z = 838.33($C_{64}H_{42}N_2$ = 839.03) |
| C1-49 | m/z = 788.32($C_{60}H_{40}N_2$ = 788.97) | C1-50 | m/z = 864.35($C_{66}H_{44}N_2$ = 865.07) |
| C1-51 | m/z = 838.33($C_{64}H_{42}N_2$ = 839.03) | C1-52 | m/z = 838.33($C_{64}H_{42}N_2$ = 839.03) |
| C1-53 | m/z = 712.29($C_{54}H_{36}N_2$ = 712.88) | C1-54 | m/z = 788.32($C_{60}H_{40}N_2$ = 788.97) |
| C1-55 | m/z = 762.30($C_{58}H_{38}N_2$ = 762.94) | C1-56 | m/z = 762.30($C_{58}H_{38}N_2$ = 762.94) |
| C1-57 | m/z = 712.29($C_{54}H_{36}N_2$ = 712.88) | C1-58 | m/z = 788.32($C_{60}H_{40}N_2$ = 788.97) |
| C1-59 | m/z = 762.30($C_{58}H_{38}N_2$ = 762.94) | C1-60 | m/z = 762.30($C_{58}H_{38}N_2$ = 762.94) |
| C1-61 | m/z = 768.26($C_{56}H_{36}N_2S$ = 768.96) | C1-62 | m/z = 844.29($C_{62}H_{40}N_2S$ = 845.06) |
| C1-63 | m/z = 818.28($C_{60}H_{38}N_2S$ = 819.02) | C1-64 | m/z = 818.28($C_{60}H_{38}N_2S$ = 819.02) |
| C1-65 | m/z = 752.28($C_{56}H_{36}N_2O$ = 752.90) | C1-66 | m/z = 828.31($C_{62}H_{40}N_2O$ = 828.99) |
| C1-67 | m/z = 802.30($C_{60}H_{38}N_2O$ = 802.96) | C1-68 | m/z = 802.30($C_{60}H_{38}N_2O$ = 802.96) |
| C1-69 | m/z = 844.29($C_{62}H_{40}N_2S$ = 845.06) | C1-70 | m/z = 920.32($C_{68}H_{44}N_2S$ = 921.16) |
| C1-71 | m/z = 894.31($C_{66}H_{42}N_2S$ = 895.12) | C1-72 | m/z = 894.31($C_{66}H_{42}N_2S$ = 895.12) |
| C1-73 | m/z = 828.31($C_{62}H_{40}N_2O$ = 828.99) | C1-74 | m/z = 904.35($C_{68}H_{44}N_2O$ = 905.09) |
| C1-75 | m/z = 878.33($C_{66}H_{42}N_2O$ = 879.05) | C1-76 | m/z = 878.33($C_{66}H_{42}N_2O$ = 879.05) |
| C1-77 | m/z = 818.28($C_{60}H_{38}N_2S$ = 819.02) | C1-78 | m/z = 894.31($C_{66}H_{42}N_2S$ = 895.12) |
| C1-79 | m/z = 868.29($C_{64}H_{40}N_2S$ = 869.08) | C1-80 | m/z = 868.29($C_{64}H_{40}N_2S$ = 869.08) |
| C1-81 | m/z = 802.30($C_{60}H_{38}N_2O$ = 802.96) | C1-82 | m/z = 878.33($C_{66}H_{42}N_2O$ = 879.05) |
| C1-83 | m/z = 852.31($C_{64}H_{40}N_2O$ = 853.02) | C1-84 | m/z = 852.31($C_{64}H_{40}N_2O$ = 853.02) |
| C1-85 | m/z = 600.26($C_{45}H_{32}N_2$ = 600.75) | C1-86 | m/z = 626.27($C_{47}H_{34}N_2$ = 626.79) |
| A2-1 | m/z = 728.32($C_{55}H_{40}N_2$ = 728.92) | A2-2 | m/z = 804.35($C_{61}H_{44}N_2$ = 805.02) |
| A2-3 | m/z = 778.33($C_{59}H_{42}N_2$ = 778.98) | A2-4 | m/z = 852.35($C_{65}H_{44}N_2$ = 853.06) |
| A2-5 | m/z = 928.38($C_{71}H_{48}N_2$ = 929.15) | A2-6 | m/z = 902.37($C_{69}H_{46}N_2$ = 903.12) |
| A2-7 | m/z = 850.33($C_{65}H_{42}N_2$ = 851.04) | A2-8 | m/z = 900.35($C_{69}H_{44}N_2$ = 901.10) |
| A2-9 | m/z = 926.37($C_{71}H_{46}N_2$ = 927.14) | A2-10 | m/z = 688.29($C_{52}H_{36}N_2$ = 688.86) |
| A2-11 | m/z = 764.32($C_{58}H_{40}N_2$ = 764.95) | A2-12 | m/z = 764.32($C_{58}H_{40}N_2$ = 764.95) |
| A2-13 | m/z = 840.35($C_{64}H_{44}N_2$ = 841.05) | A2-14 | m/z = 738.30($C_{56}H_{38}N_2$ = 738.91) |
| A2-15 | m/z = 738.30($C_{56}H_{38}N_2$ = 738.91) | A2-16 | m/z = 662.27($C_{50}H_{34}N_2$ = 662.82) |
| A2-17 | m/z = 662.27($C_{50}H_{34}N_2$ = 662.82) | A2-18 | m/z = 718.24($C_{52}H_{34}N_2S$ = 718.90) |
| A2-19 | m/z = 702.27($C_{52}H_{34}N_2O$ = 702.84) | A2-20 | m/z = 794.28($C_{58}H_{38}N_2S$ = 795.00) |
| A2-21 | m/z = 778.30($C_{58}H_{38}N_2O$ = 778.94) | A2-22 | m/z = 768.26($C_{56}H_{36}N_2S$ = 768.96) |
| A2-23 | m/z = 752.28($C_{56}H_{36}N_2O$ = 752.90) | A2-24 | m/z = 612.26($C_{46}H_{32}N_2$ = 612.76) |
| B2-1 | m/z = 728.32($C_{55}H_{40}N_2$ = 728.92) | B2-2 | m/z = 852.35($C_{65}H_{44}N_2$ = 853.06) |
| B2-3 | m/z = 764.32($C_{58}H_{40}N_2$ = 764.95) | B2-4 | m/z = 840.35($C_{64}H_{44}N_2$ = 841.05) |
| B2-5 | m/z = 718.24($C_{52}H_{34}N_2S$ = 718.90) | B2-6 | m/z = 794.28($C_{58}H_{38}N_2S$ = 795.00) |
| B2-7 | m/z = 828.31($C_{62}H_{40}N_2O$ = 828.99) | B2-8 | m/z = 612.26($C_{46}H_{32}N_2$ = 612.76) |
| B2-9 | m/z = 630.25($C_{46}H_{31}FN_2$ = 630.75) | B2-10 | m/z = 652.29($C_{49}H_{36}N_2$ = 652.82) |
| C2-1 | m/z = 778.33($C_{59}H_{42}N_2$ = 778.98) | C2-2 | m/z = 854.37($C_{65}H_{46}N_2$ = 855.07) |
| C2-3 | m/z = 902.37($C_{69}H_{46}N_2$ = 903.12) | C2-4 | m/z = 978.40($C_{75}H_{50}N_2$ = 979.21) |
| C2-5 | m/z = 900.35($C_{69}H_{44}N_2$ = 901.10) | C2-6 | m/z = 738.30($C_{56}H_{38}N_2$ = 738.91) |
| C2-7 | m/z = 814.33($C_{62}H_{42}N_2$ = 815.01) | C2-8 | m/z = 712.29($C_{54}H_{36}N_2$ = 712.88) |
| C2-9 | m/z = 712.29($C_{54}H_{36}N_2$ = 712.88) | C2-10 | m/z = 768.26($C_{56}H_{36}N_2S$ = 768.96) |
| C2-11 | m/z = 752.28($C_{56}H_{36}N_2O$ = 752.90) | C2-12 | m/z = 662.27($C_{50}H_{34}N_2$ = 662.82) |
| A3-1 | m/z = 728.32($C_{55}H_{40}N_2$ = 728.92) | A3-2 | m/z = 804.35($C_{61}H_{44}N_2$ = 805.02) |
| A3-3 | m/z = 778.33($C_{59}H_{42}N_2$ = 778.98) | A3-4 | m/z = 852.35($C_{65}H_{44}N_2$ = 853.06) |
| A3-5 | m/z = 928.38($C_{71}H_{48}N_2$ = 929.15) | A3-6 | m/z = 902.37($C_{69}H_{46}N_2$ = 903.12) |
| A3-7 | m/z = 850.33($C_{65}H_{42}N_2$ = 851.04) | A3-8 | m/z = 900.35($C_{69}H_{44}N_2$ = 901.10) |
| A3-9 | m/z = 926.37($C_{71}H_{46}N_2$ = 927.14) | A3-10 | m/z = 688.29($C_{52}H_{36}N_2$ = 688.86) |
| A3-11 | m/z = 764.32($C_{58}H_{40}N_2$ = 764.95) | A3-12 | m/z = 764.32($C_{58}H_{40}N_2$ = 764.95) |
| A3-13 | m/z = 840.35($C_{64}H_{44}N_2$ = 841.05) | A3-14 | m/z = 738.30($C_{56}H_{38}N_2$ = 738.91) |
| A3-15 | m/z = 738.30($C_{56}H_{38}N_2$ = 738.91) | A3-16 | m/z = 662.27($C_{50}H_{34}N_2$ = 662.82) |
| A3-17 | m/z = 662.27($C_{50}H_{34}N_2$ = 662.82) | A3-18 | m/z = 718.24($C_{52}H_{34}N_2S$ = 718.90) |
| A3-19 | m/z = 702.27($C_{52}H_{34}N_2O$ = 702.84) | A3-20 | m/z = 794.28($C_{58}H_{38}N_2S$ = 795.00) |
| A3-21 | m/z = 778.30($C_{58}H_{38}N_2O$ = 778.94) | A3-22 | m/z = 768.26($C_{56}H_{36}N_2S$ = 768.96) |
| A3-23 | m/z = 752.28($C_{56}H_{36}N_2O$ = 752.90) | A3-24 | m/z = 612.26($C_{46}H_{32}N_2$ = 612.76) |
| B3-1 | m/z = 728.32($C_{55}H_{40}N_2$ = 728.92) | B3-2 | m/z = 852.35($C_{65}H_{44}N_2$ = 853.06) |
| B3-3 | m/z = 764.32($C_{58}H_{40}N_2$ = 764.95) | B3-4 | m/z = 840.35($C_{64}H_{44}N_2$ = 841.05) |
| B3-5 | m/z = 718.24($C_{52}H_{34}N_2S$ = 718.90) | B3-6 | m/z = 794.28($C_{58}H_{38}N_2S$ = 795.00) |
| B3-7 | m/z = 828.31($C_{62}H_{40}N_2O$ = 828.99) | B3-8 | m/z = 612.26($C_{46}H_{32}N_2$ = 612.76) |
| B3-9 | m/z = 630.25($C_{46}H_{31}FN_2$ = 630.75) | B3-10 | m/z = 652.29($C_{49}H_{36}N_2$ = 652.82) |
| C3-1 | m/z = 778.33($C_{59}H_{42}N_2$ = 778.98) | C3-2 | m/z = 854.37($C_{65}H_{46}N_2$ = 855.07) |
| C3-3 | m/z = 902.37($C_{69}H_{46}N_2$ = 903.12) | C3-4 | m/z = 978.40($C_{75}H_{50}N_2$ = 979.21) |
| C3-5 | m/z = 900.35($C_{69}H_{44}N_2$ = 901.10) | C3-6 | m/z = 738.30($C_{56}H_{38}N_2$ = 738.91) |
| C3-7 | m/z = 814.33($C_{62}H_{42}N_2$ = 815.01) | C3-8 | m/z = 712.29($C_{54}H_{36}N_2$ = 712.88) |
| C3-9 | m/z = 712.29($C_{54}H_{36}N_2$ = 712.88) | C3-10 | m/z = 768.26($C_{56}H_{36}N_2S$ = 768.96) |
| C3-11 | m/z = 752.28($C_{56}H_{36}N_2O$ = 752.90) | C3-12 | m/z = 662.27($C_{50}H_{34}N_2$ = 662.82) |
| A4-1 | m/z = 728.32($C_{55}H_{40}N_2$ = 728.92) | A4-2 | m/z = 804.35($C_{61}H_{44}N_2$ = 805.02) |
| A4-3 | m/z = 778.33($C_{59}H_{42}N_2$ = 778.98) | A4-4 | m/z = 852.35($C_{65}H_{44}N_2$ = 853.06) |
| A4-5 | m/z = 928.38($C_{71}H_{48}N_2$ = 929.15) | A4-6 | m/z = 902.37($C_{69}H_{46}N_2$ = 903.12) |
| A4-7 | m/z = 850.33($C_{65}H_{42}N_2$ = 851.04) | A4-8 | m/z = 900.35($C_{69}H_{44}N_2$ = 901.10) |
| A4-9 | m/z = 926.37($C_{71}H_{46}N_2$ = 927.14) | A4-10 | m/z = 688.29($C_{52}H_{36}N_2$ = 688.86) |
| A4-11 | m/z = 764.32($C_{58}H_{40}N_2$ = 764.95) | A4-12 | m/z = 764.32($C_{58}H_{40}N_2$ = 764.95) |
| A4-13 | m/z = 840.35($C_{64}H_{44}N_2$ = 841.05) | A4-14 | m/z = 738.30($C_{56}H_{38}N_2$ = 738.91) |
| A4-15 | m/z = 738.30($C_{56}H_{38}N_2$ = 738.91) | A4-16 | m/z = 662.27($C_{50}H_{34}N_2$ = 662.82) |
| A4-17 | m/z = 662.27($C_{50}H_{34}N_2$ = 662.82) | A4-18 | m/z = 718.24($C_{52}H_{34}N_2S$ = 718.90) |
| A4-19 | m/z = 702.27($C_{52}H_{34}N_2O$ = 702.84) | A4-20 | m/z = 794.28($C_{58}H_{38}N_2S$ = 795.00) |

TABLE 11-continued

| Compound | FD-MS | Compound | FD-MS |
|---|---|---|---|
| A4-21 | m/z = 778.30(C$_{58}$H$_{38}$N$_2$O = 778.94) | A4-22 | m/z = 768.26(C$_{56}$H$_{36}$N$_2$S = 768.96) |
| A4-23 | m/z = 752.28(C$_{56}$H$_{36}$N$_2$O = 752.90) | A4-24 | m/z = 612.26(C$_{46}$H$_{32}$N$_2$ = 612.76) |
| B4-1 | m/z = 728.32(C$_{55}$H$_{40}$N$_2$ = 728.92) | B4-2 | m/z = 852.35(C$_{65}$H$_{44}$N$_2$ = 853.06) |
| B4-3 | m/z = 764.32(C$_{58}$H$_{40}$N$_2$ = 764.95) | B4-4 | m/z = 840.35(C$_{64}$H$_{44}$N$_2$ = 841.05) |
| B4-5 | m/z = 718.24(C$_{52}$H$_{34}$N$_2$S = 718.90) | B4-6 | m/z = 794.28(C$_{58}$H$_{38}$N$_2$S = 795.00) |
| B4-7 | m/z = 828.31(C$_{62}$H$_{40}$N$_2$O = 828.99) | B4-8 | m/z = 612.26(C$_{46}$H$_{32}$N$_2$ = 612.76) |
| B4-9 | m/z = 630.25(C$_{46}$H$_{31}$FN$_2$ = 630.75) | B4-10 | m/z = 652.29(C$_{49}$H$_{36}$N$_2$ = 652.82) |
| C4-1 | m/z = 778.33(C$_{59}$H$_{42}$N$_2$ = 778.98) | C4-2 | m/z = 854.37(C$_{65}$H$_{46}$N$_2$ = 855.07) |
| C4-3 | m/z = 902.37(C$_{69}$H$_{46}$N$_2$ = 903.12) | C4-4 | m/z = 978.40(C$_{75}$H$_{50}$N$_2$ = 979.21) |
| C4-5 | m/z = 900.35(C$_{69}$H$_{44}$N$_2$ = 901.10) | C4-6 | m/z = 738.30(C$_{56}$H$_{38}$N$_2$ = 738.91) |
| C4-7 | m/z = 814.33(C$_{62}$H$_{42}$N$_2$ = 815.01) | C4-8 | m/z = 712.29(C$_{54}$H$_{36}$N$_2$ = 712.88) |
| C4-9 | m/z = 712.29(C$_{54}$H$_{36}$N$_2$ = 712.88) | C4-10 | m/z = 768.26(C$_{56}$H$_{36}$N$_2$S = 768.96) |
| C4-11 | m/z = 752.28(C$_{56}$H$_{36}$N$_2$O = 752.90) | C4-12 | m/z = 662.27(C$_{50}$H$_{34}$N$_2$ = 662.82) |
| A5-1 | m/z = 728.32(C$_{55}$H$_{40}$N$_2$ = 728.92) | A5-2 | m/z = 804.35(C$_{61}$H$_{44}$N$_2$ = 805.02) |
| A5-3 | m/z = 778.33(C$_{59}$H$_{42}$N$_2$ = 778.98) | A5-4 | m/z = 852.35(C$_{65}$H$_{44}$N$_2$ = 853.06) |
| A5-5 | m/z = 928.38(C$_{71}$H$_{48}$N$_2$ = 929.15) | A5-6 | m/z = 902.37(C$_{69}$H$_{46}$N$_2$ = 903.12) |
| A5-7 | m/z = 850.33(C$_{65}$H$_{42}$N$_2$ = 851.04) | A5-8 | m/z = 900.35(C$_{69}$H$_{44}$N$_2$ = 901.10) |
| A5-9 | m/z = 926.37(C$_{71}$H$_{46}$N$_2$ = 927.14) | A5-10 | m/z = 688.29(C$_{52}$H$_{36}$N$_2$ = 688.86) |
| A5-11 | m/z = 764.32(C$_{58}$H$_{40}$N$_2$ = 764.95) | A5-12 | m/z = 764.32(C$_{58}$H$_{40}$N$_2$ = 764.95) |
| A5-13 | m/z = 840.35(C$_{64}$H$_{44}$N$_2$ = 841.05) | A5-14 | m/z = 738.30(C$_{56}$H$_{38}$N$_2$ = 738.91) |
| A5-15 | m/z = 738.30(C$_{56}$H$_{38}$N$_2$ = 738.91) | A5-16 | m/z = 662.27(C$_{50}$H$_{34}$N$_2$ = 662.82) |
| A5-17 | m/z = 662.27(C$_{50}$H$_{34}$N$_2$ = 662.82) | A5-18 | m/z = 718.24(C$_{52}$H$_{34}$N$_2$S = 718.90) |
| A5-19 | m/z = 702.27(C$_{52}$H$_{34}$N$_2$O = 702.84) | A5-20 | m/z = 794.28(C$_{58}$H$_{38}$N$_2$S = 795.00) |
| A5-21 | m/z = 778.30(C$_{58}$H$_{38}$N$_2$O = 778.94) | A5-22 | m/z = 768.26(C$_{56}$H$_{36}$N$_2$S = 768.96) |
| A5-23 | m/z = 752.28(C$_{56}$H$_{36}$N$_2$O = 752.90) | A5-24 | m/z = 612.26(C$_{46}$H$_{32}$N$_2$ = 612.76) |
| B5-1 | m/z = 728.32(C$_{55}$H$_{40}$N$_2$ = 728.92) | B5-2 | m/z = 852.35(C$_{65}$H$_{44}$N$_2$ = 853.06) |
| B5-3 | m/z = 764.32(C$_{58}$H$_{40}$N$_2$ = 764.95) | B5-4 | m/z = 840.35(C$_{64}$H$_{44}$N$_2$ = 841.05) |
| B5-5 | m/z = 718.24(C$_{52}$H$_{34}$N$_2$S = 718.90) | B5-6 | m/z = 794.28(C$_{58}$H$_{38}$N$_2$S = 795.00) |
| B5-7 | m/z = 828.31(C$_{62}$H$_{40}$N$_2$O = 828.99) | B5-8 | m/z = 612.26(C$_{46}$H$_{32}$N$_2$ = 612.76) |
| B5-9 | m/z = 630.25(C$_{46}$H$_{31}$FN$_2$ = 630.75) | B5-10 | m/z = 652.29(C$_{49}$H$_{36}$N$_2$ = 652.82) |
| C5-1 | m/z = 778.33(C$_{59}$H$_{42}$N$_2$ = 778.98) | C5-2 | m/z = 854.37(C$_{65}$H$_{46}$N$_2$ = 855.07) |
| C5-3 | m/z = 902.37(C$_{69}$H$_{46}$N$_2$ = 903.12) | C5-4 | m/z = 978.40(C$_{75}$H$_{50}$N$_2$ = 979.21) |
| C5-5 | m/z = 900.35(C$_{69}$H$_{44}$N$_2$ = 901.10) | C5-6 | m/z = 738.30(C$_{56}$H$_{38}$N$_2$ = 738.91) |
| C5-7 | m/z = 814.33(C$_{62}$H$_{42}$N$_2$ = 815.01) | C5-8 | m/z = 712.29(C$_{54}$H$_{36}$N$_2$ = 712.88) |
| C5-9 | m/z = 712.29(C$_{54}$H$_{36}$N$_2$ = 712.88) | C5-10 | m/z = 768.26(C$_{56}$H$_{36}$N$_2$S = 768.96) |
| C5-11 | m/z = 752.28(C$_{56}$H$_{36}$N$_2$O = 752.90) | C5-12 | m/z = 662.27(C$_{50}$H$_{34}$N$_2$ = 662.82) |
| A6-1 | m/z = 728.32(C$_{55}$H$_{40}$N$_2$ = 728.92) | A6-2 | m/z = 804.35(C$_{61}$H$_{44}$N$_2$ = 805.02) |
| A6-3 | m/z = 778.33(C$_{59}$H$_{42}$N$_2$ = 778.98) | A6-4 | m/z = 852.35(C$_{65}$H$_{44}$N$_2$ = 853.06) |
| A6-5 | m/z = 928.38(C$_{71}$H$_{48}$N$_2$ = 929.15) | A6-6 | m/z = 902.37(C$_{69}$H$_{46}$N$_2$ = 903.12) |
| A6-7 | m/z = 850.33(C$_{65}$H$_{42}$N$_2$ = 851.04) | A6-8 | m/z = 900.35(C$_{69}$H$_{44}$N$_2$ = 901.10) |
| A6-9 | m/z = 926.37(C$_{71}$H$_{46}$N$_2$ = 927.14) | A6-10 | m/z = 688.29(C$_{52}$H$_{36}$N$_2$ = 688.86) |
| A6-11 | m/z = 764.32(C$_{58}$H$_{40}$N$_2$ = 764.95) | A6-12 | m/z = 764.32(C$_{58}$H$_{40}$N$_2$ = 764.95) |
| A6-13 | m/z = 840.35(C$_{64}$H$_{44}$N$_2$ = 841.05) | A6-14 | m/z = 738.30(C$_{56}$H$_{38}$N$_2$ = 738.91) |
| A6-15 | m/z = 738.30(C$_{56}$H$_{38}$N$_2$ = 738.91) | A6-16 | m/z = 662.27(C$_{50}$H$_{34}$N$_2$ = 662.82) |
| A6-17 | m/z = 662.27(C$_{50}$H$_{34}$N$_2$ = 662.82) | A6-18 | m/z = 718.24(C$_{52}$H$_{34}$N$_2$S = 718.90) |
| A6-19 | m/z = 702.27(C$_{52}$H$_{34}$N$_2$O = 702.84) | A6-20 | m/z = 794.28(C$_{58}$H$_{38}$N$_2$S = 795.00) |
| A6-21 | m/z = 778.30(C$_{58}$H$_{38}$N$_2$O = 778.94) | A6-22 | m/z = 768.26(C$_{56}$H$_{36}$N$_2$S = 768.96) |
| A6-23 | m/z = 752.28(C$_{56}$H$_{36}$N$_2$O = 752.90) | A6-24 | m/z = 612.26(C$_{46}$H$_{32}$N$_2$ = 612.76) |
| B6-1 | m/z = 728.32(C$_{55}$H$_{40}$N$_2$ = 728.92) | B6-2 | m/z = 852.35(C$_{65}$H$_{44}$N$_2$ = 853.06) |
| B6-3 | m/z = 764.32(C$_{58}$H$_{40}$N$_2$ = 764.95) | B6-4 | m/z = 840.35(C$_{64}$H$_{44}$N$_2$ = 841.05) |
| B6-5 | m/z = 718.24(C$_{52}$H$_{34}$N$_2$S = 718.90) | B6-6 | m/z = 794.28(C$_{58}$H$_{38}$N$_2$S = 795.00) |
| B6-7 | m/z = 828.31(C$_{62}$H$_{40}$N$_2$O = 828.99) | B6-8 | m/z = 612.26(C$_{46}$H$_{32}$N$_2$ = 612.76) |
| B6-9 | m/z = 630.25(C$_{46}$H$_{31}$FN$_2$ = 630.75) | B6-10 | m/z = 652.29(C$_{49}$H$_{36}$N$_2$ = 652.82) |
| C6-1 | m/z = 778.33(C$_{59}$H$_{42}$N$_2$ = 778.98) | C6-2 | m/z = 854.37(C$_{65}$H$_{46}$N$_2$ = 855.07) |
| C6-3 | m/z = 902.37(C$_{69}$H$_{46}$N$_2$ = 903.12) | C6-4 | m/z = 978.40(C$_{75}$H$_{50}$N$_2$ = 979.21) |
| C6-5 | m/z = 900.35(C$_{69}$H$_{44}$N$_2$ = 901.10) | C6-6 | m/z = 738.30(C$_{56}$H$_{38}$N$_2$ = 738.91) |
| C6-7 | m/z = 814.33(C$_{62}$H$_{42}$N$_2$ = 815.01) | C6-8 | m/z = 712.29(C$_{54}$H$_{36}$N$_2$ = 712.88) |
| C6-9 | m/z = 712.29(C$_{54}$H$_{36}$N$_2$ = 712.88) | C6-10 | m/z = 768.26(C$_{56}$H$_{36}$N$_2$S = 768.96) |
| C6-11 | m/z = 752.28(C$_{56}$H$_{36}$N$_2$O = 752.90) | C6-12 | m/z = 662.27(C$_{50}$H$_{34}$N$_2$ = 662.82) |
| A7-1 | m/z = 652.29(C$_{49}$H$_{36}$N$_2$ = 652.82) | A7-2 | m/z = 728.32(C$_{55}$H$_{40}$N$_2$ = 728.92) |
| A7-3 | m/z = 702.30(C$_{53}$H$_{38}$N$_2$ = 702.88) | A7-4 | m/z = 776.32(C$_{59}$H$_{40}$N$_2$ = 776.96) |
| A7-5 | m/z = 852.35(C$_{65}$H$_{44}$N$_2$ = 853.06) | A7-6 | m/z = 826.33(C$_{63}$H$_{42}$N$_2$ = 827.02) |
| A7-7 | m/z = 774.30(C$_{59}$H$_{38}$N$_2$ = 774.95) | A7-8 | m/z = 824.32(C$_{63}$H$_{40}$N$_2$ = 825.01) |
| A7-9 | m/z = 850.33(C$_{65}$H$_{42}$N$_2$ = 851.04) | A7-10 | m/z = 612.26(C$_{46}$H$_{32}$N$_2$ = 612.76) |
| A7-11 | m/z = 688.29(C$_{52}$H$_{36}$N$_2$ = 688.86) | A7-12 | m/z = 688.29(C$_{52}$H$_{36}$N$_2$ = 688.86) |
| A7-13 | m/z = 764.32(C$_{58}$H$_{40}$N$_2$ = 764.95) | A7-14 | m/z = 662.27(C$_{50}$H$_{34}$N$_2$ = 662.82) |
| A7-15 | m/z = 662.27(C$_{50}$H$_{34}$N$_2$ = 662.82) | A7-16 | m/z = 586.24(C$_{44}$H$_{30}$N$_2$ = 586.72) |
| A7-17 | m/z = 586.24(C$_{44}$H$_{30}$N$_2$ = 586.72) | A7-18 | m/z = 642.21(C$_{46}$H$_{30}$N$_2$S = 642.81) |
| A7-19 | m/z = 626.24(C$_{46}$H$_{30}$N$_2$O = 626.74) | A7-20 | m/z = 718.24(C$_{52}$H$_{34}$N$_2$S = 718.90) |
| A7-21 | m/z = 702.27(C$_{52}$H$_{34}$N$_2$O = 702.84) | A7-22 | m/z = 692.23(C$_{50}$H$_{32}$N$_2$S = 692.87) |
| A7-23 | m/z = 676.25(C$_{50}$H$_{32}$N$_2$O = 676.80) | A7-24 | m/z = 536.23(C$_{40}$H$_{28}$N$_2$ = 536.66) |
| B7-1 | m/z = 652.29(C$_{49}$H$_{36}$N$_2$ = 652.82) | B7-2 | m/z = 776.32(C$_{59}$H$_{40}$N$_2$ = 776.96) |
| B7-3 | m/z = 688.29(C$_{52}$H$_{36}$N$_2$ = 688.86) | B7-4 | m/z = 764.32(C$_{58}$H$_{40}$N$_2$ = 764.95) |
| B7-5 | m/z = 642.21(C$_{46}$H$_{30}$N$_2$S = 642.81) | B7-6 | m/z = 718.24(C$_{52}$H$_{34}$N$_2$S = 718.90) |
| B7-7 | m/z = 752.28(C$_{56}$H$_{36}$N$_2$O = 752.90) | B7-8 | m/z = 536.23(C$_{40}$H$_{28}$N$_2$ = 536.66) |
| B7-9 | m/z = 554.22(C$_{40}$H$_{27}$FN$_2$ = 554.65) | B7-10 | m/z = 576.26(C$_{43}$H$_{32}$N$_2$ = 576.73) |
| C7-1 | m/z = 702.30(C$_{53}$H$_{38}$N$_2$ = 702.88) | C7-2 | m/z = 778.33(C$_{59}$H$_{42}$N$_2$ = 778.98) |
| C7-3 | m/z = 826.33(C$_{63}$H$_{42}$N$_2$ = 827.02) | C7-4 | m/z = 902.37(C$_{69}$H$_{46}$N$_2$ = 903.12) |

TABLE 11-continued

| Compound | FD-MS | Compound | FD-MS |
|---|---|---|---|
| C7-5 | m/z = 824.32($C_{63}H_{40}N_2$ = 825.01) | C7-6 | m/z = 662.27($C_{50}H_{34}N_2$ = 662.82) |
| C7-7 | m/z = 738.30($C_{56}H_{38}N_2$ = 738.91) | C7-8 | m/z = 636.26($C_{48}H_{32}N_2$ = 636.78) |
| C7-9 | m/z = 636.26($C_{48}H_{32}N_2$ = 636.78) | C7-10 | m/z = 692.23($C_{50}H_{32}N_2S$ = 692.87) |
| C7-11 | m/z = 676.25($C_{50}H_{32}N_2O$ = 676.80) | C7-12 | m/z = 586.24($C_{44}H_{30}N_2$ = 586.72) |
| A8-1 | m/z = 652.29($C_{49}H_{36}N_2$ = 652.82) | A8-2 | m/z = 728.32($C_{55}H_{40}N_2$ = 728.92) |
| A8-3 | m/z = 702.30($C_{53}H_{38}N_2$ = 702.88) | A8-4 | m/z = 776.32($C_{59}H_{40}N_2$ = 776.96) |
| A8-5 | m/z = 852.35($C_{65}H_{44}N_2$ = 853.06) | A8-6 | m/z = 826.33($C_{63}H_{42}N_2$ = 827.02) |
| A8-7 | m/z = 774.30($C_{59}H_{38}N_2$ = 774.95) | A8-8 | m/z = 824.32($C_{63}H_{40}N_2$ = 825.01) |
| A8-9 | m/z = 850.33($C_{65}H_{42}N_2$ = 851.04) | A8-10 | m/z = 612.26($C_{46}H_{32}N_2$ = 612.76) |
| A8-11 | m/z = 688.29($C_{52}H_{36}N_2$ = 688.86) | A8-12 | m/z = 688.29($C_{52}H_{36}N_2$ = 688.86) |
| A8-13 | m/z = 764.32($C_{58}H_{40}N_2$ = 764.95) | A8-14 | m/z = 662.27($C_{50}H_{34}N_2$ = 662.82) |
| A8-15 | m/z = 662.27($C_{50}H_{34}N_2$ = 662.82) | A8-16 | m/z = 586.24($C_{44}H_{30}N_2$ = 586.72) |
| A8-17 | m/z = 586.24($C_{44}H_{30}N_2$ = 586.72) | A8-18 | m/z = 642.21($C_{46}H_{30}N_2S$ = 642.81) |
| A8-19 | m/z = 626.24($C_{46}H_{30}N_2O$ = 626.74) | A8-20 | m/z = 718.24($C_{52}H_{34}N_2S$ = 718.90) |
| A8-21 | m/z = 702.27($C_{52}H_{34}N_2O$ = 702.84) | A8-22 | m/z = 692.23($C_{50}H_{32}N_2S$ = 692.87) |
| A8-23 | m/z = 676.25($C_{50}H_{32}N_2O$ = 676.80) | A8-24 | m/z = 536.23($C_{40}H_{28}N_2$ = 536.66) |
| B8-1 | m/z = 652.29($C_{49}H_{36}N_2$ = 652.82) | B8-2 | m/z = 776.32($C_{59}H_{40}N_2$ = 776.96) |
| B8-3 | m/z = 688.29($C_{52}H_{36}N_2$ = 688.86) | B8-4 | m/z = 764.32($C_{58}H_{40}N_2$ = 764.95) |
| B8-5 | m/z = 642.21($C_{46}H_{30}N_2S$ = 642.81) | B8-6 | m/z = 718.24($C_{52}H_{34}N_2S$ = 718.90) |
| B8-7 | m/z = 752.28($C_{56}H_{36}N_2O$ = 752.90) | B8-8 | m/z = 536.23($C_{40}H_{28}N_2$ = 536.66) |
| B8-9 | m/z = 554.22($C_{40}H_{27}FN_2$ = 554.65) | B8-10 | m/z = 576.26($C_{43}H_{32}N_2$ = 576.73) |
| C8-1 | m/z = 702.30($C_{53}H_{38}N_2$ = 702.88) | C8-2 | m/z = 778.33($C_{59}H_{42}N_2$ = 778.98) |
| C8-3 | m/z = 826.33($C_{63}H_{42}N_2$ = 827.02) | C8-4 | m/z = 902.37($C_{69}H_{46}N_2$ = 903.12) |
| C8-5 | m/z = 824.32($C_{63}H_{40}N_2$ = 825.01) | C8-6 | m/z = 662.27($C_{50}H_{34}N_2$ = 662.82) |
| C8-7 | m/z = 738.30($C_{56}H_{38}N_2$ = 738.91) | C8-8 | m/z = 636.26($C_{48}H_{32}N_2$ = 636.78) |
| C8-9 | m/z = 636.26($C_{48}H_{32}N_2$ = 636.78) | C8-10 | m/z = 692.23($C_{50}H_{32}N_2S$ = 692.87) |
| C8-11 | m/z = 676.25($C_{50}H_{32}N_2O$ = 676.80) | C8-12 | m/z = 586.24($C_{44}H_{30}N_2$ = 586.72) |

Fabrication and Evaluation of Organic Electronic Element

Test Example I

Green Organic Light Emitting Diode (a Hole Transport Layer)

Organic light emitting diodes (OLEDs) were fabricated according to a conventional method by using a compound of the present invention as a hole transport layer material. First, an ITO layer (anode) was formed on a glass substrate, and a film of $N^1$-(naphthalene-2-yl)-$N^4$,$N^4$-bis(4-(naphthalene-2-yl(phenyl)amino)phenyl)-$N^1$-phenylbenzene-1,4-diamine (hereinafter abbreviated as "2-TNATA") was vacuum-deposited on the ITO layer to form a hole injection layer with a thickness of 60 nm. Subsequently, a film of the compound of the present invention was vacuum-deposited on the hole injection layer to form a hole transport layer with a thickness of 60 nm. Subsequently, a light emitting layer with a thickness of 30 nm was deposited on the hole transport layer by doping the hole transport layer with the 4,4'-N,N'-dicarbazole-biphenyl (hereinafter abbreviated as "CBP") as a host material and tris(2-phenylpyridine)-iridium (hereinafter abbreviated as "Ir(ppy)$_3$") as a dopant material in a weight ratio of 90:10. Next, a film of (1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato)aluminum (hereinafter abbreviated as "Alq$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

The organic light emitting diode fabricated according to [Test Example I] is described as Ex. (1) to (120) in the Table below 12.

Comparative Example I

Comparative Examples (1) to (4)

Comparative Examples (1)

An OLED was manufactured in the same manner as described in Test Example I, except that Comparative Compound A represented below was used as the hole transport layer material, instead of the inventive compound.

<Comparative Compound A>

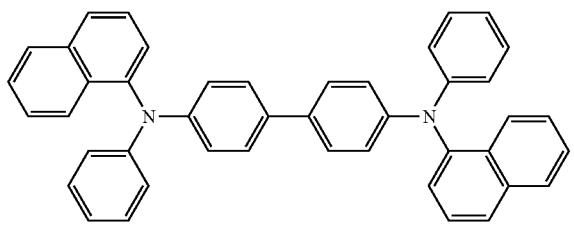 [SMILES: c1ccc(N(c2ccc(-c3ccc(N(c4ccccc4)c4cccc5ccccc45)cc3)cc2)c2cccc3ccccc23)cc1]

Comparative Examples (2)

An OLED was manufactured in the same manner as described in Test Example I, except that Comparative Compound B represented below was used as the hole transport layer material, instead of the inventive compound.

<Comparative Compound B>

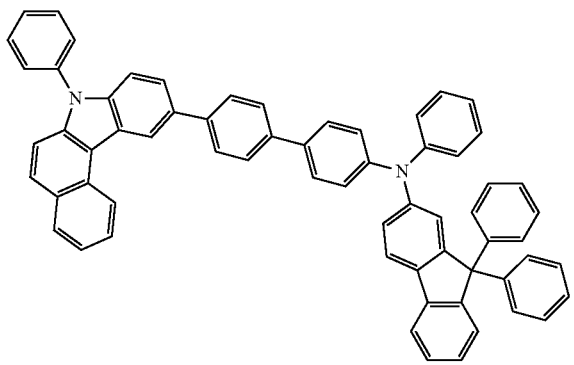 [SMILES: c1ccc(N(c2ccc(-c3ccc(-c4ccc5c(c4)c4c6ccccc6ccc4n5-c4ccccc4)cc3)cc2)c2ccc3c(c2)C(c2ccccc2)(c2ccccc2)c2ccccc2-3)cc1]

Comparative Examples (3)

An OLED was manufactured in the same manner as described in Test Example I, except that Comparative Compound C represented below was used as the hole transport layer material, instead of the inventive compound.
<Comparative Compound C>

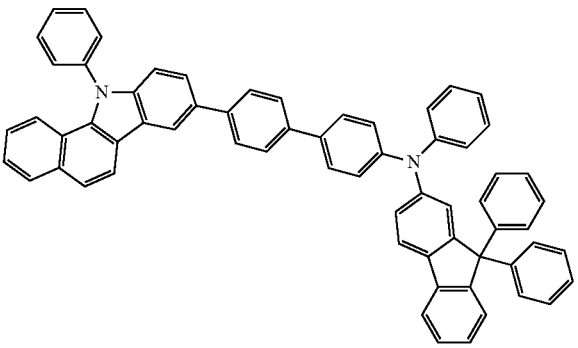 [SMILES: c1ccc(N(c2ccc(-c3ccc(-c4ccc5c(c4)c4ccc6ccccc6c4n5-c4ccccc4)cc3)cc2)c2ccc3c(c2)C(c2ccccc2)(c2ccccc2)c2ccccc2-3)cc1]

Comparative Examples (4)

An OLED was manufactured in the same manner as described in Test Example I, except that Comparative Compound D represented below was used as the hole transport layer material, instead of the inventive compound.

<Comparative Compound D>

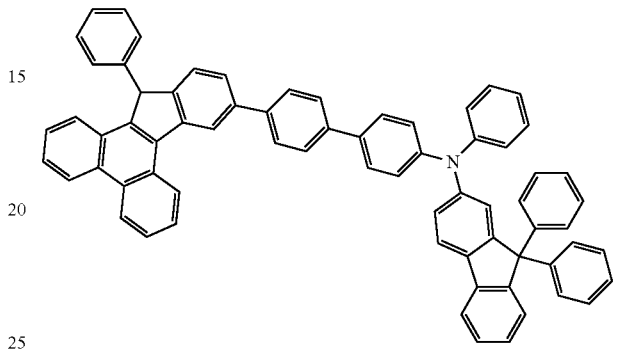

A forward bias DC voltage was applied to each of the OLEDs manufactured through Test Example I (Test Examples (1) to (120)) and Comparative Example I (Comparative Examples (1) to (4)), and electro-luminescence (EL) characteristics of the OLED were measured by PR-650 (Photoresearch). Also, T95 life span was measured by life span measuring equipment (Mcscience) at a reference brightness of 5000 cd/m².

Table 12 below shows fabrications and evaluation results of OLEDs manufactured by Test Example I (Test Examples (1) to (120)) and Comparative Example I (Comparative Examples (1) to (4)).

TABLE 12

|  | Compound | Voltage (V) | Current Density (mA/cm²) | Brightness (cd/m²) | Efficiency (cd/A) | Lifetime T(95) | CIE (x, y) |
|---|---|---|---|---|---|---|---|
| comp. Ex(1) | comp. Com A | 5.7 | 21.7 | 5000.0 | 23.0 | 51.1 | (0.31, 0.60) |
| comp. Ex(2) | comp. Com B | 5.1 | 12.7 | 5000.0 | 39.3 | 89.5 | (0.31, 0.61) |
| comp. Ex(3) | comp. Com C | 5.2 | 15.8 | 5000.0 | 31.7 | 88.4 | (0.31, 0.60) |
| comp. Ex(4) | comp. Com D | 5.4 | 16.4 | 5000.0 | 30.6 | 86.0 | (0.31, 0.60) |
| Ex. (1) | Com. (A1-1) | 4.7 | 11.3 | 5000.0 | 44.2 | 137.8 | (0.30, 0.60) |
| Ex. (2) | Com. (A1-2) | 4.6 | 11.1 | 5000.0 | 44.9 | 95.3 | (0.31, 0.61) |
| Ex. (3) | Com. (A1-3) | 4.5 | 12.2 | 5000.0 | 40.9 | 92.9 | (0.31, 0.60) |
| Ex. (4) | Com. (A1-4) | 4.7 | 11.9 | 5000.0 | 42.1 | 128.5 | (0.33, 0.61) |
| Ex. (5) | Com. (A1-5) | 4.7 | 10.2 | 5000.0 | 49.2 | 138.3 | (0.32, 0.61) |
| Ex. (6) | Com. (B1-1) | 4.8 | 10.5 | 5000.0 | 47.7 | 121.3 | (0.33, 0.60) |
| Ex. (7) | Com. (B1-2) | 4.7 | 11.0 | 5000.0 | 45.3 | 90.9 | (0.32, 0.61) |
| Ex. (8) | Com. (B1-3) | 4.5 | 10.1 | 5000.0 | 49.3 | 107.4 | (0.31, 0.60) |
| Ex. (9) | Com. (B1-4) | 4.6 | 11.9 | 5000.0 | 42.2 | 149.3 | (0.31, 0.61) |
| Ex. (10) | Com. (B1-5) | 4.7 | 11.7 | 5000.0 | 42.7 | 141.1 | (0.31, 0.60) |
| Ex. (11) | Com. (C1-1) | 4.6 | 11.8 | 5000.0 | 42.4 | 134.7 | (0.33, 0.61) |
| Ex. (12) | Com. (C1-2) | 4.6 | 12.2 | 5000.0 | 40.8 | 110.0 | (0.32, 0.61) |
| Ex. (13) | Com. (C1-3) | 4.7 | 11.4 | 5000.0 | 43.9 | 111.5 | (0.33, 0.60) |
| Ex. (14) | Com. (C1-4) | 4.7 | 11.5 | 5000.0 | 43.5 | 141.0 | (0.32, 0.61) |
| Ex. (15) | Com. (C1-5) | 4.5 | 11.5 | 5000.0 | 43.6 | 135.9 | (0.31, 0.60) |
| Ex. (16) | Com. (A2-1) | 4.6 | 11.5 | 5000.0 | 43.4 | 142.0 | (0.31, 0.61) |
| Ex. (17) | Com. (A2-2) | 4.7 | 11.1 | 5000.0 | 45.2 | 143.7 | (0.31, 0.60) |
| Ex. (18) | Com. (A2-3) | 4.6 | 11.0 | 5000.0 | 45.6 | 113.8 | (0.33, 0.61) |

TABLE 12-continued

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (19) | Com. (A2-4) | 4.6 | 10.1 | 5000.0 | 49.6 | 140.7 | (0.32, 0.61) |
| Ex. (20) | Com. (A2-5) | 4.6 | 12.4 | 5000.0 | 40.2 | 139.0 | (0.33, 0.60) |
| Ex. (21) | Com. (B2-1) | 4.8 | 10.2 | 5000.0 | 48.8 | 132.4 | (0.31, 0.61) |
| Ex. (22) | Com. (B2-2) | 4.6 | 10.3 | 5000.0 | 48.4 | 100.9 | (0.31, 0.60) |
| Ex. (23) | Com. (B2-3) | 4.7 | 11.2 | 5000.0 | 44.6 | 99.9 | (0.33, 0.61) |
| Ex. (24) | Com. (B2-4) | 4.6 | 11.3 | 5000.0 | 44.2 | 94.0 | (0.32, 0.61) |
| Ex. (25) | Com. (B2-5) | 4.7 | 12.1 | 5000.0 | 41.4 | 138.3 | (0.31, 0.60) |
| Ex. (26) | Com. (C2-6) | 4.8 | 12.4 | 5000.0 | 40.3 | 97.9 | (0.33, 0.61) |
| Ex. (27) | Com. (C2-7) | 4.8 | 10.9 | 5000.0 | 45.7 | 118.8 | (0.30, 0.60) |
| Ex. (28) | Com. (C2-8) | 4.7 | 11.4 | 5000.0 | 43.8 | 93.6 | (0.31, 0.61) |
| Ex. (29) | Com. (C2-9) | 4.5 | 11.9 | 5000.0 | 41.9 | 104.6 | (0.31, 0.60) |
| Ex. (30) | Com. (C2-10) | 4.5 | 12.0 | 5000.0 | 41.7 | 93.4 | (0.33, 0.61) |
| Ex. (31) | Com. (A3-1) | 4.7 | 12.0 | 5000.0 | 41.8 | 146.2 | (0.32, 0.61) |
| Ex. (32) | Com. (A3-2) | 4.6 | 12.1 | 5000.0 | 41.4 | 105.2 | (0.33, 0.61) |
| Ex. (33) | Com. (A3-3) | 4.8 | 11.2 | 5000.0 | 44.6 | 107.6 | (0.30, 0.60) |
| Ex. (34) | Com. (A3-4) | 4.6 | 11.8 | 5000.0 | 42.5 | 122.2 | (0.31, 0.61) |
| Ex. (35) | Com. (A3-5) | 4.5 | 11.6 | 5000.0 | 42.9 | 139.8 | (0.31, 0.60) |
| Ex. (36) | Com. (B3-1) | 4.8 | 11.4 | 5000.0 | 43.8 | 99.7 | (0.33, 0.61) |
| Ex. (37) | Com. (B3-2) | 4.7 | 11.4 | 5000.0 | 44.0 | 94.4 | (0.32, 0.61) |
| Ex. (38) | Com. (B3-3) | 4.7 | 11.8 | 5000.0 | 42.2 | 103.5 | (0.33, 0.60) |
| Ex. (39) | Com. (B3-4) | 4.8 | 10.1 | 5000.0 | 49.4 | 105.0 | (0.32, 0.61) |
| Ex. (40) | Com. (B3-5) | 4.5 | 12.1 | 5000.0 | 41.4 | 138.2 | (0.31, 0.60) |
| Ex. (41) | Com. (C3-1) | 4.7 | 10.2 | 5000.0 | 49.1 | 141.4 | (0.33, 0.61) |
| Ex. (42) | Com. (C3-2) | 4.6 | 11.5 | 5000.0 | 43.4 | 94.5 | (0.32, 0.61) |
| Ex. (43) | Com. (C3-3) | 4.6 | 11.1 | 5000.0 | 45.1 | 130.6 | (0.33, 0.61) |
| Ex. (44) | Com. (C3-4) | 4.6 | 12.5 | 5000.0 | 40.1 | 105.1 | (0.32, 0.61) |
| Ex. (45) | Com. (C3-5) | 4.6 | 11.1 | 5000.0 | 45.0 | 120.6 | (0.31, 0.60) |
| Ex. (46) | Com. (A4-1) | 4.6 | 10.2 | 5000.0 | 49.0 | 119.8 | (0.31, 0.61) |
| Ex. (47) | Com. (A4-2) | 4.5 | 11.8 | 5000.0 | 42.3 | 103.4 | (0.31, 0.60) |
| Ex. (48) | Com. (A4-3) | 4.7 | 12.4 | 5000.0 | 40.2 | 124.9 | (0.33, 0.61) |
| Ex. (49) | Com. (A4-4) | 4.6 | 11.9 | 5000.0 | 41.9 | 105.7 | (0.32, 0.61) |
| Ex. (50) | Com. (A4-5) | 4.5 | 10.5 | 5000.0 | 47.4 | 129.2 | (0.33, 0.61) |
| Ex. (51) | Com. (B4-1) | 4.6 | 10.9 | 5000.0 | 45.8 | 97.0 | (0.30, 0.60) |
| Ex. (52) | Com. (B4-2) | 4.6 | 10.7 | 5000.0 | 46.8 | 121.3 | (0.33, 0.61) |
| Ex. (53) | Com. (B4-3) | 4.6 | 12.1 | 5000.0 | 41.4 | 98.1 | (0.30, 0.60) |
| Ex. (54) | Com. (B4-4) | 4.5 | 11.0 | 5000.0 | 45.3 | 131.2 | (0.31, 0.61) |
| Ex. (55) | Com. (B4-5) | 4.6 | 11.5 | 5000.0 | 43.6 | 137.6 | (0.31, 0.60) |
| Ex. (56) | Com. (C4-6) | 4.6 | 11.2 | 5000.0 | 44.6 | 134.5 | (0.30, 0.60) |
| Ex. (57) | Com. (C4-7) | 4.7 | 11.9 | 5000.0 | 42.0 | 113.7 | (0.31, 0.61) |
| Ex. (58) | Com. (C4-8) | 4.7 | 12.0 | 5000.0 | 41.7 | 113.0 | (0.31, 0.61) |
| Ex. (59) | Com. (C4-9) | 4.7 | 10.2 | 5000.0 | 49.1 | 149.2 | (0.33, 0.61) |
| Ex. (60) | Com. (C4-10) | 4.6 | 11.8 | 5000.0 | 42.4 | 131.5 | (0.32, 0.61) |
| Ex. (61) | Com. (A5-1) | 4.7 | 12.2 | 5000.0 | 41.1 | 146.1 | (0.33, 0.61) |
| Ex. (62) | Com. (A5-2) | 4.8 | 12.0 | 5000.0 | 41.6 | 139.7 | (0.32, 0.61) |
| Ex. (63) | Com. (A5-3) | 4.5 | 11.6 | 5000.0 | 43.1 | 104.8 | (0.31, 0.60) |
| Ex. (64) | Com. (A5-4) | 4.7 | 11.1 | 5000.0 | 45.1 | 90.7 | (0.31, 0.61) |
| Ex. (65) | Com. (A5-5) | 4.7 | 11.2 | 5000.0 | 44.8 | 97.4 | (0.31, 0.61) |
| Ex. (66) | Com. (B5-1) | 4.7 | 10.5 | 5000.0 | 47.8 | 129.8 | (0.33, 0.61) |
| Ex. (67) | Com. (B5-2) | 4.5 | 10.3 | 5000.0 | 48.3 | 145.7 | (0.32, 0.61) |
| Ex. (68) | Com. (B5-3) | 4.6 | 12.1 | 5000.0 | 41.4 | 132.2 | (0.33, 0.60) |
| Ex. (69) | Com. (B5-4) | 4.7 | 10.4 | 5000.0 | 48.0 | 108.2 | (0.32, 0.61) |
| Ex. (70) | Com. (B5-5) | 4.6 | 11.0 | 5000.0 | 45.5 | 127.9 | (0.31, 0.60) |
| Ex. (71) | Com. (C5-1) | 4.6 | 10.2 | 5000.0 | 49.2 | 109.9 | (0.31, 0.61) |
| Ex. (72) | Com. (C5-2) | 4.5 | 11.7 | 5000.0 | 42.6 | 93.5 | (0.31, 0.61) |
| Ex. (73) | Com. (C5-3) | 4.8 | 12.3 | 5000.0 | 40.7 | 121.5 | (0.33, 0.61) |
| Ex. (74) | Com. (C5-4) | 4.8 | 11.7 | 5000.0 | 42.6 | 130.2 | (0.32, 0.61) |
| Ex. (75) | Com. (C5-5) | 4.6 | 11.5 | 5000.0 | 43.5 | 148.5 | (0.33, 0.60) |
| Ex. (76) | Com. (A6-1) | 4.8 | 12.4 | 5000.0 | 40.3 | 147.9 | (0.31, 0.61) |
| Ex. (77) | Com. (A6-2) | 4.7 | 10.5 | 5000.0 | 47.5 | 139.2 | (0.31, 0.60) |
| Ex. (78) | Com. (A6-3) | 4.7 | 10.4 | 5000.0 | 48.1 | 104.9 | (0.33, 0.61) |
| Ex. (79) | Com. (A6-4) | 4.7 | 10.8 | 5000.0 | 46.5 | 141.1 | (0.32, 0.61) |
| Ex. (80) | Com. (A6-5) | 4.6 | 10.3 | 5000.0 | 48.5 | 128.1 | (0.31, 0.60) |
| Ex. (81) | Com. (B6-1) | 4.7 | 11.9 | 5000.0 | 42.1 | 116.9 | (0.33, 0.61) |
| Ex. (82) | Com. (B6-2) | 4.5 | 10.1 | 5000.0 | 49.5 | 137.8 | (0.30, 0.60) |
| Ex. (83) | Com. (B6-3) | 4.7 | 10.0 | 5000.0 | 49.9 | 105.1 | (0.31, 0.61) |
| Ex. (84) | Com. (B6-4) | 4.6 | 12.0 | 5000.0 | 41.5 | 117.1 | (0.31, 0.60) |
| Ex. (85) | Com. (B6-5) | 4.6 | 10.1 | 5000.0 | 49.7 | 129.5 | (0.33, 0.61) |
| Ex. (86) | Com. (C6-6) | 4.6 | 11.4 | 5000.0 | 43.9 | 142.0 | (0.32, 0.61) |
| Ex. (87) | Com. (C6-7) | 4.7 | 11.3 | 5000.0 | 44.3 | 131.6 | (0.33, 0.61) |
| Ex. (88) | Com. (C6-8) | 4.8 | 10.9 | 5000.0 | 45.8 | 103.5 | (0.30, 0.60) |
| Ex. (89) | Com. (C6-9) | 4.7 | 11.6 | 5000.0 | 43.3 | 129.9 | (0.31, 0.60) |
| Ex. (90) | Com. (C6-10) | 4.6 | 10.3 | 5000.0 | 48.4 | 108.0 | (0.31, 0.60) |
| Ex. (91) | Com. (A7-1) | 4.7 | 10.5 | 5000.0 | 47.5 | 97.0 | (0.33, 0.61) |
| Ex. (92) | Com. (A7-2) | 4.8 | 10.7 | 5000.0 | 46.8 | 147.9 | (0.32, 0.61) |
| Ex. (93) | Com. (A7-3) | 4.6 | 12.4 | 5000.0 | 40.2 | 91.2 | (0.33, 0.60) |
| Ex. (94) | Com. (A7-4) | 4.7 | 10.9 | 5000.0 | 45.7 | 131.2 | (0.32, 0.61) |

TABLE 12-continued

| | Compound | Voltage (V) | Current Density (mA/cm²) | Brightness (cd/m²) | Efficiency (cd/A) | Lifetime T(95) | CIE (x, y) |
|---|---|---|---|---|---|---|---|
| Ex. (95) | Com. (A7-5) | 4.6 | 12.0 | 5000.0 | 41.8 | 122.5 | (0.31, 0.60) |
| Ex. (96) | Com. (B7-1) | 4.6 | 11.1 | 5000.0 | 45.1 | 95.0 | (0.33, 0.61) |
| Ex. (97) | Com. (B7-2) | 4.6 | 10.5 | 5000.0 | 47.5 | 100.8 | (0.32, 0.61) |
| Ex. (98) | Com. (B7-3) | 4.6 | 11.5 | 5000.0 | 43.4 | 109.8 | (0.33, 0.60) |
| Ex. (99) | Com. (B7-4) | 4.7 | 10.5 | 5000.0 | 47.6 | 119.6 | (0.32, 0.61) |
| Ex. (100) | Com. (B7-5) | 4.7 | 10.7 | 5000.0 | 46.6 | 104.2 | (0.31, 0.60) |
| Ex. (101) | Com. (C7-1) | 4.7 | 11.5 | 5000.0 | 43.5 | 128.0 | (0.31, 0.61) |
| Ex. (102) | Com. (C7-2) | 4.8 | 11.3 | 5000.0 | 44.1 | 103.4 | (0.31, 0.60) |
| Ex. (103) | Com. (C7-3) | 4.5 | 11.0 | 5000.0 | 45.5 | 140.1 | (0.33, 0.61) |
| Ex. (104) | Com. (C7-4) | 4.6 | 11.9 | 5000.0 | 42.0 | 133.5 | (0.32, 0.61) |
| Ex. (105) | Com. (C7-5) | 4.8 | 11.8 | 5000.0 | 42.4 | 111.6 | (0.33, 0.61) |
| Ex. (106) | Com. (A8-1) | 4.8 | 12.0 | 5000.0 | 41.8 | 104.1 | (0.30, 0.60) |
| Ex. (107) | Com. (A8-2) | 4.6 | 12.0 | 5000.0 | 41.6 | 110.1 | (0.33, 0.61) |
| Ex. (108) | Com. (A8-3) | 4.7 | 11.5 | 5000.0 | 43.5 | 126.1 | (0.30, 0.60) |
| Ex. (109) | Com. (A8-4) | 4.6 | 10.9 | 5000.0 | 45.8 | 90.6 | (0.31, 0.61) |
| Ex. (110) | Com. (A8-5) | 4.8 | 10.3 | 5000.0 | 48.4 | 145.0 | (0.31, 0.60) |
| Ex. (111) | Com. (B8-1) | 4.7 | 10.3 | 5000.0 | 48.5 | 110.9 | (0.30, 0.60) |
| Ex. (112) | Com. (B8-2) | 4.6 | 12.1 | 5000.0 | 41.4 | 102.4 | (0.31, 0.61) |
| Ex. (113) | Com. (B8-3) | 4.6 | 10.0 | 5000.0 | 49.8 | 111.1 | (0.31, 0.60) |
| Ex. (114) | Com. (B8-4) | 4.7 | 10.1 | 5000.0 | 49.4 | 96.7 | (0.33, 0.61) |
| Ex. (115) | Com. (B8-5) | 4.6 | 10.5 | 5000.0 | 47.7 | 124.3 | (0.32, 0.61) |
| Ex. (116) | Com. (C8-1) | 4.7 | 10.8 | 5000.0 | 46.3 | 135.3 | (0.33, 0.60) |
| Ex. (117) | Com. (C8-2) | 4.6 | 10.4 | 5000.0 | 47.9 | 127.4 | (0.32, 0.61) |
| Ex. (118) | Com. (C8-3) | 4.6 | 10.7 | 5000.0 | 46.7 | 113.3 | (0.31, 0.60) |
| Ex. (119) | Com. (C8-4) | 4.8 | 11.6 | 5000.0 | 42.9 | 138.1 | (0.31, 0.61) |
| Ex. (120) | Com. (C8-5) | 4.8 | 11.2 | 5000.0 | 44.7 | 143.5 | (0.31, 0.60) |

As understood from the data of Table 12, the organic light-emitting diodes fabricated using the compounds of the present invention as hole transport layer materials were found to be significantly improved in luminous efficiency and life span, compared to those of Comparative Examples 1 to 4. That is, far better diode properties were obtained with the compounds of the present invention that has the linker L at a non-linear position than the comparative compound A NPB, and the comparative compounds B, C and D, all having the linker L at the para-position (linear).

Than the linear compounds, the non-linear compounds are shorter in conjugation length and thus have wider band gaps, deeper HOMO energy levels and higher T1 values. Accordingly, the deeper HOMO energy levels make it possible to more readily transfer holes to the light emitting layer while the higher T1 values enhance the electron blocking performance, which, in turn, makes it possible to more easily form excitons, leading to an improvement in luminous efficiency and life span.

Test Example II

Red Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, 4,4-bis[N-(1-naphthyl)-N-phenylamino]biphenyl (hereinafter abbreviated as "NPD") was vacuum-deposited with a thickness of 60 nm on the hole injection layer to form a hole transport layer. Next, the inventive compound was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with CBP as a host material and bis-(1-phenylisoquinolyl)iridium(III) acetylacetonate (hereinafter abbreviated as "(piq)₂Ir(acac)") as a dopant material in a weight ratio of 95:5. Also, BAlq was vacuum-deposited with a thickness of 10 nm on the light emitting layer to form a hole blocking layer, and then a film of Alq₃ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

The organic light emitting diode fabricated according to [Test Example II] is described as Ex. (121) to (240) in the Table below 13.

Comparative Example II

Comparative Examples (5) to (9)

Comparative Example (5)

An OLED was manufactured in the same manner as described in Test Example II, except that an emission-auxiliary layer was not formed.

Comparative Example (6)

An OLED was manufactured in the same manner as described in Test Example II, except that Comparative Compound A was used as the emission-auxiliary layer material, instead of the inventive compound.

Comparative Example (7)

An OLED was manufactured in the same manner as described in Test Example II, except that Comparative Compound B was used as the emission-auxiliary layer material, instead of the inventive compound.

Comparative Example (8)

An OLED was manufactured in the same manner as described in Test Example II, except that Comparative Compound C was used as the emission-auxiliary layer material, instead of the inventive compound.

Comparative Example (9)

An OLED was manufactured in the same manner as described in Test Example II, except that Comparative Compound D was used as the emission-auxiliary layer material, instead of the inventive compound.

A forward bias DC voltage was applied to each of the OLEDs manufactured in Test Example II (Test Examples (121) to (240)) and Comparative Example II (Comparative Examples (5) to (9)), and EL characteristics of the OLED were measured by PR-650 (Photoresearch). Also, T95 life span was measured by life span measuring equipment (Mcscience) at a reference brightness of 2500 cd/m².

Table 13 below shows fabrications and evaluation results of OLEDs manufactured by Test Example II (Test Examples (121) to (240)) and Comparative Example II (Comparative Examples (5) to (9)).

TABLE 13

| | Compound | Voltage (V) | Current Density (mA/cm²) | Brightness (cd/m²) | Efficiency (cd/A) | Lifetime T(95) | CIE (x, y) |
|---|---|---|---|---|---|---|---|
| comp. Ex(5) | — | 5.9 | 31.3 | 2500.0 | 8.0 | 73.5 | (0.66, 0.32) |
| comp. Ex(6) | comp. Com A | 6.3 | 29.4 | 2500.0 | 8.5 | 86.9 | (0.66, 0.32) |
| comp. Ex(7) | comp. Com B | 6.3 | 25.5 | 2500.0 | 9.8 | 83.1 | (0.67, 0.32) |
| comp. Ex(8) | comp. Com C | 6.1 | 25.4 | 2500.0 | 9.8 | 89.6 | (0.66, 0.32) |
| comp. Ex(9) | comp. Com D | 6.1 | 26.9 | 2500.0 | 9.3 | 89.3 | (0.66, 0.33) |
| Ex. (121) | Com. (A1-21) | 6.1 | 16.4 | 2500.0 | 15.3 | 131.8 | (0.65, 0.32) |
| Ex. (122) | Com. (A1-22) | 6.2 | 14.7 | 2500.0 | 17.0 | 118.9 | (0.66, 0.32) |
| Ex. (123) | Com. (A1-23) | 6.0 | 15.1 | 2500.0 | 16.5 | 122.2 | (0.66, 0.33) |
| Ex. (124) | Com. (A1-24) | 5.9 | 13.5 | 2500.0 | 18.5 | 99.0 | (0.66, 0.32) |
| Ex. (125) | Com. (A1-25) | 6.0 | 15.4 | 2500.0 | 16.2 | 136.1 | (0.65, 0.32) |
| Ex. (126) | Com. (B1-21) | 5.9 | 13.5 | 2500.0 | 18.5 | 147.1 | (0.66, 0.32) |
| Ex. (127) | Com. (B1-22) | 6.1 | 13.3 | 2500.0 | 18.8 | 147.9 | (0.66, 0.32) |
| Ex. (128) | Com. (B1-23) | 5.8 | 13.1 | 2500.0 | 19.1 | 105.9 | (0.67, 0.32) |
| Ex. (129) | Com. (B1-24) | 6.1 | 12.5 | 2500.0 | 19.9 | 123.4 | (0.66, 0.32) |
| Ex. (130) | Com. (B1-25) | 6.3 | 16.6 | 2500.0 | 15.0 | 130.6 | (0.66, 0.32) |
| Ex. (131) | Com. (C1-21) | 6.0 | 14.2 | 2500.0 | 17.6 | 130.9 | (0.66, 0.33) |
| Ex. (132) | Com. (C1-22) | 5.8 | 14.9 | 2500.0 | 16.8 | 142.0 | (0.66, 0.32) |
| Ex. (133) | Com. (C1-23) | 6.3 | 14.9 | 2500.0 | 16.8 | 119.5 | (0.65, 0.32) |
| Ex. (134) | Com. (C1-24) | 6.2 | 15.6 | 2500.0 | 16.0 | 137.3 | (0.66, 0.32) |
| Ex. (135) | Com. (C1-25) | 6.0 | 13.9 | 2500.0 | 18.0 | 140.6 | (0.66, 0.32) |
| Ex. (136) | Com. (A2-20) | 6.1 | 13.8 | 2500.0 | 18.2 | 106.1 | (0.67, 0.32) |
| Ex. (137) | Com. (A2-21) | 5.8 | 15.5 | 2500.0 | 16.1 | 121.6 | (0.66, 0.32) |
| Ex. (138) | Com. (A2-22) | 6.1 | 16.6 | 2500.0 | 15.0 | 110.6 | (0.67, 0.32) |
| Ex. (139) | Com. (A2-23) | 6.2 | 14.7 | 2500.0 | 17.1 | 95.4 | (0.66, 0.32) |
| Ex. (140) | Com. (A2-24) | 6.0 | 13.5 | 2500.0 | 18.5 | 146.4 | (0.66, 0.32) |
| Ex. (141) | Com. (B2-6) | 6.3 | 13.1 | 2500.0 | 19.0 | 103.5 | (0.66, 0.33) |
| Ex. (142) | Com. (B2-7) | 6.1 | 16.6 | 2500.0 | 15.1 | 100.0 | (0.66, 0.32) |
| Ex. (143) | Com. (B2-8) | 6.0 | 15.4 | 2500.0 | 16.3 | 125.6 | (0.65, 0.32) |
| Ex. (144) | Com. (B2-9) | 6.0 | 13.4 | 2500.0 | 18.7 | 145.8 | (0.66, 0.32) |
| Ex. (145) | Com. (B2-10) | 6.0 | 13.8 | 2500.0 | 18.1 | 139.8 | (0.66, 0.32) |
| Ex. (146) | Com. (C2-8) | 6.3 | 12.7 | 2500.0 | 19.6 | 105.3 | (0.67, 0.32) |
| Ex. (147) | Com. (C2-9) | 5.8 | 13.7 | 2500.0 | 18.3 | 121.9 | (0.66, 0.32) |
| Ex. (148) | Com. (C2-10) | 5.9 | 14.8 | 2500.0 | 16.9 | 142.6 | (0.67, 0.32) |
| Ex. (149) | Com. (C2-11) | 6.1 | 12.8 | 2500.0 | 19.6 | 126.6 | (0.66, 0.32) |
| Ex. (150) | Com. (C2-12) | 5.9 | 13.3 | 2500.0 | 18.8 | 115.4 | (0.66, 0.32) |
| Ex. (151) | Com. (A3-20) | 5.9 | 13.2 | 2500.0 | 18.9 | 145.1 | (0.66, 0.33) |
| Ex. (152) | Com. (A3-21) | 5.8 | 13.4 | 2500.0 | 18.7 | 93.0 | (0.66, 0.32) |
| Ex. (153) | Com. (A3-22) | 6.0 | 15.4 | 2500.0 | 16.2 | 140.8 | (0.65, 0.32) |
| Ex. (154) | Com. (A3-23) | 6.0 | 13.7 | 2500.0 | 18.3 | 140.1 | (0.66, 0.32) |
| Ex. (155) | Com. (A3-24) | 6.1 | 13.2 | 2500.0 | 19.0 | 127.3 | (0.66, 0.32) |
| Ex. (156) | Com. (B3-6) | 6.2 | 12.6 | 2500.0 | 19.8 | 149.6 | (0.67, 0.32) |
| Ex. (157) | Com. (B3-7) | 6.3 | 15.6 | 2500.0 | 16.1 | 136.6 | (0.66, 0.32) |
| Ex. (158) | Com. (B3-8) | 6.2 | 12.5 | 2500.0 | 19.9 | 136.4 | (0.67, 0.32) |
| Ex. (159) | Com. (B3-9) | 5.8 | 14.5 | 2500.0 | 17.3 | 141.3 | (0.66, 0.32) |
| Ex. (160) | Com. (B3-10) | 6.2 | 13.4 | 2500.0 | 18.7 | 113.2 | (0.67, 0.32) |
| Ex. (161) | Com. (C3-8) | 6.1 | 16.0 | 2500.0 | 15.6 | 145.0 | (0.66, 0.32) |
| Ex. (162) | Com. (C3-9) | 6.2 | 13.4 | 2500.0 | 18.7 | 90.2 | (0.66, 0.33) |
| Ex. (163) | Com. (C3-10) | 6.3 | 13.4 | 2500.0 | 18.7 | 91.4 | (0.65, 0.32) |
| Ex. (164) | Com. (C3-11) | 6.2 | 12.8 | 2500.0 | 19.5 | 115.0 | (0.66, 0.32) |
| Ex. (165) | Com. (C3-12) | 6.2 | 13.5 | 2500.0 | 18.5 | 143.1 | (0.66, 0.33) |
| Ex. (166) | Com. (A4-20) | 6.1 | 14.8 | 2500.0 | 16.9 | 101.7 | (0.66, 0.32) |
| Ex. (167) | Com. (A4-21) | 6.2 | 12.7 | 2500.0 | 19.7 | 95.1 | (0.65, 0.32) |
| Ex. (168) | Com. (A4-22) | 5.9 | 12.7 | 2500.0 | 19.6 | 99.9 | (0.66, 0.32) |
| Ex. (169) | Com. (A4-23) | 5.9 | 15.2 | 2500.0 | 16.5 | 141.2 | (0.66, 0.32) |
| Ex. (170) | Com. (A4-24) | 6.2 | 13.3 | 2500.0 | 18.8 | 148.0 | (0.67, 0.32) |
| Ex. (171) | Com. (B4-6) | 6.0 | 15.8 | 2500.0 | 15.8 | 131.3 | (0.66, 0.32) |
| Ex. (172) | Com. (B4-7) | 6.1 | 13.5 | 2500.0 | 18.5 | 103.1 | (0.66, 0.32) |
| Ex. (173) | Com. (B4-8) | 6.1 | 15.0 | 2500.0 | 16.7 | 111.2 | (0.66, 0.33) |

TABLE 13-continued

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (174) | Com. (B4-9) | 6.1 | 13.1 | 2500.0 | 19.1 | 131.2 | (0.66, 0.32) |
| Ex. (175) | Com. (B4-10) | 6.1 | 14.4 | 2500.0 | 17.4 | 105.2 | (0.65, 0.32) |
| Ex. (176) | Com. (C4-8) | 6.0 | 13.2 | 2500.0 | 19.0 | 146.7 | (0.66, 0.32) |
| Ex. (177) | Com. (C4-9) | 6.0 | 12.5 | 2500.0 | 20.0 | 139.7 | (0.66, 0.32) |
| Ex. (178) | Com. (C4-10) | 6.1 | 14.2 | 2500.0 | 17.6 | 141.1 | (0.67, 0.32) |
| Ex. (179) | Com. (C4-11) | 6.1 | 14.1 | 2500.0 | 17.7 | 108.4 | (0.66, 0.32) |
| Ex. (180) | Com. (C4-12) | 5.9 | 13.5 | 2500.0 | 18.6 | 141.6 | (0.67, 0.32) |
| Ex. (181) | Com. (A5-20) | 6.0 | 16.0 | 2500.0 | 15.6 | 101.4 | (0.66, 0.32) |
| Ex. (182) | Com. (A5-21) | 6.0 | 12.8 | 2500.0 | 19.5 | 93.6 | (0.66, 0.32) |
| Ex. (183) | Com. (A5-22) | 6.1 | 13.9 | 2500.0 | 18.0 | 90.0 | (0.66, 0.33) |
| Ex. (184) | Com. (A5-23) | 6.1 | 13.4 | 2500.0 | 18.6 | 146.0 | (0.66, 0.32) |
| Ex. (185) | Com. (A5-24) | 6.3 | 16.0 | 2500.0 | 15.6 | 108.5 | (0.65, 0.32) |
| Ex. (186) | Com. (B5-6) | 6.1 | 15.1 | 2500.0 | 16.5 | 143.5 | (0.66, 0.32) |
| Ex. (187) | Com. (B5-7) | 6.3 | 13.2 | 2500.0 | 18.9 | 119.3 | (0.66, 0.32) |
| Ex. (188) | Com. (B5-8) | 6.1 | 13.6 | 2500.0 | 18.4 | 112.3 | (0.67, 0.32) |
| Ex. (189) | Com. (B5-9) | 6.0 | 15.1 | 2500.0 | 16.6 | 143.4 | (0.66, 0.32) |
| Ex. (190) | Com. (B5-10) | 6.0 | 12.7 | 2500.0 | 19.7 | 136.6 | (0.67, 0.32) |
| Ex. (191) | Com. (C5-8) | 6.2 | 12.7 | 2500.0 | 19.7 | 118.0 | (0.66, 0.32) |
| Ex. (192) | Com. (C5-9) | 6.2 | 15.9 | 2500.0 | 15.7 | 135.5 | (0.67, 0.32) |
| Ex. (193) | Com. (C5-10) | 6.0 | 12.7 | 2500.0 | 19.6 | 113.6 | (0.66, 0.32) |
| Ex. (194) | Com. (C5-11) | 5.8 | 15.4 | 2500.0 | 16.3 | 99.4 | (0.66, 0.33) |
| Ex. (195) | Com. (C5-12) | 5.8 | 15.9 | 2500.0 | 15.7 | 111.1 | (0.65, 0.32) |
| Ex. (196) | Com. (A6-20) | 5.9 | 13.8 | 2500.0 | 18.1 | 124.6 | (0.66, 0.32) |
| Ex. (197) | Com. (A6-21) | 6.1 | 14.0 | 2500.0 | 17.9 | 128.2 | (0.66, 0.33) |
| Ex. (198) | Com. (A6-22) | 6.0 | 15.3 | 2500.0 | 16.4 | 129.4 | (0.66, 0.32) |
| Ex. (199) | Com. (A6-23) | 6.2 | 12.6 | 2500.0 | 19.8 | 135.3 | (0.65, 0.32) |
| Ex. (200) | Com. (A6-24) | 6.0 | 13.7 | 2500.0 | 18.2 | 97.2 | (0.66, 0.32) |
| Ex. (201) | Com. (B6-6) | 6.1 | 13.1 | 2500.0 | 19.1 | 90.9 | (0.66, 0.32) |
| Ex. (202) | Com. (B6-7) | 6.2 | 15.3 | 2500.0 | 16.4 | 96.5 | (0.67, 0.32) |
| Ex. (203) | Com. (B6-8) | 6.0 | 13.9 | 2500.0 | 17.9 | 114.1 | (0.66, 0.32) |
| Ex. (204) | Com. (B6-9) | 6.1 | 16.6 | 2500.0 | 15.1 | 133.7 | (0.66, 0.32) |
| Ex. (205) | Com. (B6-10) | 6.3 | 15.3 | 2500.0 | 16.3 | 118.8 | (0.66, 0.33) |
| Ex. (206) | Com. (C6-8) | 6.1 | 12.7 | 2500.0 | 19.7 | 138.2 | (0.66, 0.32) |
| Ex. (207) | Com. (C6-9) | 5.8 | 14.8 | 2500.0 | 16.9 | 136.2 | (0.65, 0.32) |
| Ex. (208) | Com. (C6-10) | 6.1 | 12.9 | 2500.0 | 19.4 | 132.7 | (0.66, 0.32) |
| Ex. (209) | Com. (C6-11) | 6.2 | 16.2 | 2500.0 | 15.5 | 106.5 | (0.66, 0.32) |
| Ex. (210) | Com. (C6-12) | 6.3 | 13.7 | 2500.0 | 18.3 | 97.7 | (0.67, 0.32) |
| Ex. (211) | Com. (A7-20) | 6.2 | 14.1 | 2500.0 | 17.8 | 97.8 | (0.66, 0.32) |
| Ex. (212) | Com. (A7-21) | 6.1 | 13.4 | 2500.0 | 18.6 | 108.4 | (0.67, 0.32) |
| Ex. (213) | Com. (A7-22) | 6.1 | 14.0 | 2500.0 | 17.8 | 131.0 | (0.66, 0.32) |
| Ex. (214) | Com. (A7-23) | 6.3 | 15.8 | 2500.0 | 15.8 | 129.1 | (0.66, 0.32) |
| Ex. (215) | Com. (A7-24) | 6.1 | 14.7 | 2500.0 | 17.0 | 101.8 | (0.66, 0.33) |
| Ex. (216) | Com. (B7-6) | 5.8 | 13.0 | 2500.0 | 19.2 | 103.0 | (0.66, 0.32) |
| Ex. (217) | Com. (B7-7) | 5.9 | 13.2 | 2500.0 | 18.9 | 100.9 | (0.65, 0.32) |
| Ex. (218) | Com. (B7-8) | 6.2 | 16.1 | 2500.0 | 15.5 | 133.7 | (0.66, 0.32) |
| Ex. (219) | Com. (B7-9) | 6.1 | 12.7 | 2500.0 | 19.7 | 137.4 | (0.66, 0.32) |
| Ex. (220) | Com. (B7-10) | 6.0 | 15.3 | 2500.0 | 16.3 | 111.8 | (0.67, 0.32) |
| Ex. (221) | Com. (C7-8) | 6.2 | 13.5 | 2500.0 | 18.5 | 139.3 | (0.66, 0.32) |
| Ex. (222) | Com. (C7-9) | 5.8 | 14.0 | 2500.0 | 17.8 | 120.6 | (0.67, 0.32) |
| Ex. (223) | Com. (C7-10) | 6.0 | 12.5 | 2500.0 | 20.0 | 147.5 | (0.66, 0.32) |
| Ex. (224) | Com. (C7-11) | 5.9 | 15.7 | 2500.0 | 15.9 | 113.0 | (0.66, 0.32) |
| Ex. (225) | Com. (C7-12) | 6.3 | 15.9 | 2500.0 | 15.8 | 102.4 | (0.66, 0.33) |
| Ex. (226) | Com. (A8-20) | 6.2 | 15.6 | 2500.0 | 16.0 | 147.5 | (0.66, 0.32) |
| Ex. (227) | Com. (A8-21) | 6.0 | 12.9 | 2500.0 | 19.3 | 100.7 | (0.65, 0.32) |
| Ex. (228) | Com. (A8-22) | 6.1 | 16.1 | 2500.0 | 15.5 | 90.2 | (0.66, 0.32) |
| Ex. (229) | Com. (A8-23) | 6.0 | 14.6 | 2500.0 | 17.2 | 99.4 | (0.66, 0.32) |
| Ex. (230) | Com. (A8-24) | 6.0 | 15.6 | 2500.0 | 16.0 | 144.9 | (0.67, 0.32) |
| Ex. (231) | Com. (B8-6) | 5.9 | 14.0 | 2500.0 | 17.8 | 113.5 | (0.66, 0.32) |
| Ex. (232) | Com. (B8-7) | 6.0 | 15.8 | 2500.0 | 15.8 | 107.6 | (0.67, 0.32) |
| Ex. (233) | Com. (B8-8) | 5.9 | 15.0 | 2500.0 | 16.6 | 118.8 | (0.66, 0.32) |
| Ex. (234) | Com. (B8-9) | 6.2 | 13.9 | 2500.0 | 18.0 | 140.3 | (0.67, 0.32) |
| Ex. (235) | Com. (B8-10) | 6.3 | 15.7 | 2500.0 | 15.9 | 94.1 | (0.66, 0.32) |
| Ex. (236) | Com. (C8-8) | 6.3 | 13.8 | 2500.0 | 18.1 | 137.8 | (0.66, 0.33) |
| Ex. (237) | Com. (C8-9) | 6.3 | 16.0 | 2500.0 | 15.6 | 136.2 | (0.65, 0.32) |
| Ex. (238) | Com. (C8-10) | 6.0 | 15.6 | 2500.0 | 16.1 | 135.7 | (0.66, 0.32) |
| Ex. (239) | Com. (C8-11) | 6.3 | 16.5 | 2500.0 | 15.1 | 134.7 | (0.66, 0.33) |
| Ex. (240) | Com. (C8-12) | 6.0 | 16.4 | 2500.0 | 15.2 | 90.6 | (0.66, 0.32) |

Test Example III

Green Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, NPD was vacuum-deposited with a thickness of 60 nm on the hole injection layer to form a hole transport layer. Next, the inventive compound was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with CBP as a host material and Ir(ppy)$_3$ as a dopant material in a weight ratio of 95:5. Also, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

The organic light emitting diode fabricated according to [Test Example III] is described as Ex. (241) to (360) in the Table below 14.

Comparative Example III

Comparative Examples (10) to (14)

Comparative Example (10)

An OLED was manufactured in the same manner as described in Test Example III, except that an emission-auxiliary layer was not formed.

Comparative Example (11)

An OLED was manufactured in the same manner as described in Test Example III, except that Comparative Compound A was used as the emission-auxiliary layer material, instead of the inventive compound.

Comparative Example (12)

An OLED was manufactured in the same manner as described in Test Example III, except that Comparative Compound B was used as the emission-auxiliary layer material, instead of the inventive compound.

Comparative Example (13)

An OLED was manufactured in the same manner as described in Test Example III, except that Comparative Compound C was used as the emission-auxiliary layer material, instead of the inventive compound.

Comparative Example (14)

An OLED was manufactured in the same manner as described in Test Example III, except that Comparative Compound D was used as the emission-auxiliary layer material, instead of the inventive compound.

A forward bias DC voltage was applied to each of the OLEDs manufactured in Test Example III (Test Examples (241) to (360)) and Comparative Example III (Comparative Examples (10) to (14)), and EL characteristics of the OLED were measured by PR-650 (Photoresearch). Also, T95 life span was measured by life span measuring equipment (Mc-science) at a reference brightness of 5000 cd/m$^2$.

Table 14 below shows fabrications and evaluation results of OLEDs manufactured by Test Example III (Test Examples (241) to (360)) and Comparative Example III (Comparative Examples (10) to (14)).

TABLE 14

|  | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| comp. Ex(10) | — | 5.7 | 21.7 | 5000.0 | 23.0 | 51.1 | (0.31, 0.60) |
| comp. Ex(11) | comp. Com A | 5.8 | 17.9 | 5000.0 | 28.0 | 58.5 | (0.31, 0.61) |
| comp. Ex(12) | comp. Com B | 5.6 | 13.6 | 5000.0 | 36.7 | 91.8 | (0.31, 0.60) |
| comp. Ex(13) | comp. Com C | 6.0 | 14.3 | 5000.0 | 34.9 | 94.6 | (0.33, 0.61) |
| comp. Ex(14) | comp. Com D | 5.8 | 12.8 | 5000.0 | 39.1 | 90.6 | (0.30, 0.60) |
| Ex. (241) | Com. (A1-26) | 5.9 | 10.1 | 5000.0 | 49.7 | 142.7 | (0.31, 0.61) |
| Ex. (242) | Com. (A1-27) | 5.8 | 10.6 | 5000.0 | 47.2 | 108.5 | (0.31, 0.60) |
| Ex. (243) | Com. (A1-28) | 5.9 | 10.1 | 5000.0 | 49.5 | 126.9 | (0.33, 0.61) |
| Ex. (244) | Com. (A1-29) | 5.8 | 10.3 | 5000.0 | 48.7 | 116.1 | (0.32, 0.61) |
| Ex. (245) | Com. (A1-30) | 5.8 | 12.4 | 5000.0 | 40.2 | 116.9 | (0.33, 0.60) |
| Ex. (246) | Com. (B1-26) | 5.8 | 12.2 | 5000.0 | 41.0 | 110.2 | (0.32, 0.61) |
| Ex. (247) | Com. (B1-27) | 5.7 | 11.0 | 5000.0 | 45.4 | 133.9 | (0.31, 0.60) |
| Ex. (248) | Com. (B1-28) | 5.6 | 10.2 | 5000.0 | 48.9 | 131.6 | (0.31, 0.61) |
| Ex. (249) | Com. (B1-29) | 5.7 | 11.2 | 5000.0 | 44.6 | 142.6 | (0.31, 0.60) |
| Ex. (250) | Com. (B1-30) | 5.9 | 11.4 | 5000.0 | 43.7 | 94.1 | (0.33, 0.61) |
| Ex. (251) | Com. (C1-26) | 5.7 | 10.5 | 5000.0 | 47.7 | 117.7 | (0.30, 0.60) |
| Ex. (252) | Com. (C1-27) | 5.8 | 12.1 | 5000.0 | 41.3 | 106.8 | (0.31, 0.61) |
| Ex. (253) | Com. (C1-28) | 6.0 | 11.1 | 5000.0 | 44.9 | 148.4 | (0.31, 0.60) |
| Ex. (254) | Com. (C1-29) | 5.8 | 10.9 | 5000.0 | 45.7 | 132.8 | (0.33, 0.61) |
| Ex. (255) | Com. (C1-30) | 5.9 | 10.5 | 5000.0 | 47.5 | 148.2 | (0.32, 0.61) |
| Ex. (256) | Com. (A2-1) | 5.9 | 12.3 | 5000.0 | 40.5 | 134.4 | (0.31, 0.60) |
| Ex. (257) | Com. (A2-2) | 5.7 | 12.2 | 5000.0 | 41.1 | 145.4 | (0.31, 0.61) |
| Ex. (258) | Com. (A2-3) | 5.8 | 10.2 | 5000.0 | 49.2 | 144.2 | (0.31, 0.60) |
| Ex. (259) | Com. (A2-4) | 5.9 | 11.4 | 5000.0 | 43.7 | 129.7 | (0.33, 0.61) |

TABLE 14-continued

|  | Compound | Voltage (V) | Current Density (mA/cm²) | Brightness (cd/m²) | Efficiency (cd/A) | Lifetime T(95) | CIE (x, y) |
|---|---|---|---|---|---|---|---|
| Ex. (260) | Com. (A2-5) | 5.6 | 11.9 | 5000.0 | 42.1 | 136.8 | (0.30, 0.60) |
| Ex. (261) | Com. (B2-1) | 5.9 | 11.5 | 5000.0 | 43.3 | 90.7 | (0.31, 0.61) |
| Ex. (262) | Com. (B2-2) | 5.9 | 10.8 | 5000.0 | 46.1 | 103.4 | (0.31, 0.60) |
| Ex. (263) | Com. (B2-3) | 5.7 | 10.8 | 5000.0 | 46.3 | 131.0 | (0.33, 0.61) |
| Ex. (264) | Com. (B2-4) | 5.7 | 10.7 | 5000.0 | 46.9 | 136.0 | (0.32, 0.61) |
| Ex. (265) | Com. (B2-5) | 5.6 | 12.3 | 5000.0 | 40.6 | 132.7 | (0.33, 0.60) |
| Ex. (266) | Com. (C2-6) | 6.0 | 11.1 | 5000.0 | 45.2 | 146.2 | (0.32, 0.61) |
| Ex. (267) | Com. (C2-7) | 5.7 | 10.7 | 5000.0 | 46.9 | 135.5 | (0.31, 0.60) |
| Ex. (268) | Com. (C2-8) | 5.7 | 11.8 | 5000.0 | 42.2 | 110.0 | (0.31, 0.61) |
| Ex. (269) | Com. (C2-9) | 5.9 | 11.2 | 5000.0 | 44.7 | 97.0 | (0.31, 0.60) |
| Ex. (270) | Com. (C2-10) | 5.8 | 11.2 | 5000.0 | 44.7 | 144.0 | (0.33, 0.61) |
| Ex. (271) | Com. (A3-1) | 5.9 | 10.8 | 5000.0 | 46.5 | 124.1 | (0.30, 0.60) |
| Ex. (272) | Com. (A3-2) | 5.9 | 10.9 | 5000.0 | 45.8 | 114.1 | (0.31, 0.61) |
| Ex. (273) | Com. (A3-3) | 5.7 | 10.1 | 5000.0 | 49.5 | 121.4 | (0.31, 0.60) |
| Ex. (274) | Com. (A3-4) | 5.8 | 10.5 | 5000.0 | 47.7 | 148.5 | (0.33, 0.61) |
| Ex. (275) | Com. (A3-5) | 5.6 | 10.8 | 5000.0 | 46.4 | 107.4 | (0.32, 0.61) |
| Ex. (276) | Com. (B3-1) | 5.7 | 10.2 | 5000.0 | 49.3 | 142.3 | (0.31, 0.60) |
| Ex. (277) | Com. (B3-2) | 5.7 | 12.0 | 5000.0 | 41.5 | 145.0 | (0.31, 0.61) |
| Ex. (278) | Com. (B3-3) | 5.6 | 11.7 | 5000.0 | 42.8 | 92.8 | (0.31, 0.60) |
| Ex. (279) | Com. (B3-4) | 5.7 | 11.0 | 5000.0 | 45.6 | 114.9 | (0.33, 0.61) |
| Ex. (280) | Com. (B3-5) | 5.8 | 11.2 | 5000.0 | 44.8 | 90.7 | (0.30, 0.60) |
| Ex. (281) | Com. (C3-1) | 5.7 | 10.3 | 5000.0 | 48.4 | 117.5 | (0.31, 0.61) |
| Ex. (282) | Com. (C3-2) | 5.8 | 10.2 | 5000.0 | 49.2 | 94.3 | (0.31, 0.60) |
| Ex. (283) | Com. (C3-3) | 6.0 | 10.7 | 5000.0 | 46.6 | 140.3 | (0.33, 0.61) |
| Ex. (284) | Com. (C3-4) | 5.6 | 11.2 | 5000.0 | 44.6 | 123.0 | (0.32, 0.61) |
| Ex. (285) | Com. (C3-5) | 6.0 | 11.9 | 5000.0 | 41.9 | 91.9 | (0.33, 0.60) |
| Ex. (286) | Com. (A4-1) | 5.8 | 12.2 | 5000.0 | 41.1 | 148.0 | (0.32, 0.61) |
| Ex. (287) | Com. (A4-2) | 5.9 | 10.9 | 5000.0 | 46.0 | 90.5 | (0.31, 0.60) |
| Ex. (288) | Com. (A4-3) | 5.7 | 10.5 | 5000.0 | 47.6 | 93.0 | (0.31, 0.61) |
| Ex. (289) | Com. (A4-4) | 5.6 | 10.9 | 5000.0 | 46.0 | 129.4 | (0.31, 0.60) |
| Ex. (290) | Com. (A4-5) | 5.7 | 10.1 | 5000.0 | 49.4 | 120.5 | (0.33, 0.61) |
| Ex. (291) | Com. (B4-1) | 5.7 | 10.2 | 5000.0 | 48.9 | 148.9 | (0.30, 0.60) |
| Ex. (292) | Com. (B4-2) | 5.9 | 11.6 | 5000.0 | 43.0 | 100.2 | (0.31, 0.61) |
| Ex. (293) | Com. (B4-3) | 5.8 | 11.8 | 5000.0 | 42.5 | 90.1 | (0.31, 0.60) |
| Ex. (294) | Com. (B4-4) | 5.9 | 10.0 | 5000.0 | 49.8 | 115.4 | (0.33, 0.61) |
| Ex. (295) | Com. (B4-5) | 5.9 | 10.0 | 5000.0 | 49.8 | 110.2 | (0.32, 0.61) |
| Ex. (296) | Com. (C4-6) | 5.8 | 10.4 | 5000.0 | 48.1 | 102.2 | (0.31, 0.60) |
| Ex. (297) | Com. (C4-7) | 5.9 | 10.0 | 5000.0 | 49.9 | 127.6 | (0.31, 0.61) |
| Ex. (298) | Com. (C4-8) | 5.9 | 10.8 | 5000.0 | 46.1 | 149.8 | (0.31, 0.60) |
| Ex. (299) | Com. (C4-9) | 5.7 | 11.8 | 5000.0 | 42.3 | 100.0 | (0.33, 0.61) |
| Ex. (300) | Com. (C4-10) | 5.6 | 10.5 | 5000.0 | 47.7 | 136.3 | (0.30, 0.60) |
| Ex. (301) | Com. (A5-1) | 5.7 | 11.0 | 5000.0 | 45.3 | 104.3 | (0.31, 0.61) |
| Ex. (302) | Com. (A5-2) | 5.8 | 10.2 | 5000.0 | 49.2 | 92.3 | (0.31, 0.60) |
| Ex. (303) | Com. (A5-3) | 5.8 | 12.1 | 5000.0 | 41.2 | 99.5 | (0.33, 0.61) |
| Ex. (304) | Com. (A5-4) | 5.7 | 12.3 | 5000.0 | 40.5 | 133.0 | (0.32, 0.61) |
| Ex. (305) | Com. (A5-5) | 5.9 | 10.9 | 5000.0 | 45.9 | 148.1 | (0.33, 0.60) |
| Ex. (306) | Com. (B5-1) | 6.0 | 11.0 | 5000.0 | 45.4 | 124.1 | (0.32, 0.61) |
| Ex. (307) | Com. (B5-2) | 5.9 | 10.8 | 5000.0 | 46.4 | 93.6 | (0.31, 0.60) |
| Ex. (308) | Com. (B5-3) | 5.9 | 12.2 | 5000.0 | 41.0 | 99.6 | (0.31, 0.61) |
| Ex. (309) | Com. (B5-4) | 5.9 | 12.4 | 5000.0 | 40.4 | 136.1 | (0.31, 0.60) |
| Ex. (310) | Com. (B5-5) | 6.0 | 12.4 | 5000.0 | 40.3 | 127.0 | (0.31, 0.61) |
| Ex. (311) | Com. (C5-1) | 5.9 | 11.9 | 5000.0 | 41.9 | 104.6 | (0.31, 0.61) |
| Ex. (312) | Com. (C5-2) | 5.7 | 11.6 | 5000.0 | 43.1 | 99.4 | (0.31, 0.60) |
| Ex. (313) | Com. (C5-3) | 5.7 | 10.4 | 5000.0 | 47.9 | 131.0 | (0.33, 0.61) |
| Ex. (314) | Com. (C5-4) | 5.8 | 10.7 | 5000.0 | 46.9 | 126.5 | (0.30, 0.60) |
| Ex. (315) | Com. (C5-5) | 5.6 | 10.0 | 5000.0 | 49.9 | 131.5 | (0.31, 0.61) |
| Ex. (316) | Com. (A6-1) | 5.6 | 10.5 | 5000.0 | 47.6 | 131.4 | (0.31, 0.60) |
| Ex. (317) | Com. (A6-2) | 5.7 | 10.0 | 5000.0 | 49.9 | 142.8 | (0.33, 0.61) |
| Ex. (318) | Com. (A6-3) | 5.7 | 12.1 | 5000.0 | 41.2 | 104.9 | (0.32, 0.61) |
| Ex. (319) | Com. (A6-4) | 5.7 | 11.3 | 5000.0 | 44.3 | 91.5 | (0.33, 0.61) |
| Ex. (320) | Com. (A6-5) | 5.7 | 11.2 | 5000.0 | 44.5 | 146.5 | (0.32, 0.61) |
| Ex. (321) | Com. (B6-1) | 5.9 | 10.8 | 5000.0 | 46.4 | 148.8 | (0.31, 0.60) |
| Ex. (322) | Com. (B6-2) | 5.7 | 10.7 | 5000.0 | 46.7 | 106.3 | (0.31, 0.61) |
| Ex. (323) | Com. (B6-3) | 6.0 | 10.5 | 5000.0 | 47.6 | 144.5 | (0.31, 0.60) |
| Ex. (324) | Com. (B6-4) | 5.7 | 10.3 | 5000.0 | 48.5 | 99.2 | (0.33, 0.61) |
| Ex. (325) | Com. (B6-5) | 5.8 | 10.8 | 5000.0 | 46.3 | 94.2 | (0.30, 0.60) |
| Ex. (326) | Com. (C6-6) | 5.9 | 10.3 | 5000.0 | 48.5 | 138.0 | (0.31, 0.61) |
| Ex. (327) | Com. (C6-7) | 5.9 | 10.1 | 5000.0 | 49.4 | 116.9 | (0.31, 0.61) |
| Ex. (328) | Com. (C6-8) | 5.7 | 11.5 | 5000.0 | 43.3 | 123.4 | (0.33, 0.61) |
| Ex. (329) | Com. (C6-9) | 5.9 | 10.0 | 5000.0 | 49.8 | 123.7 | (0.32, 0.61) |
| Ex. (330) | Com. (C6-10) | 5.9 | 11.8 | 5000.0 | 42.5 | 110.0 | (0.31, 0.60) |
| Ex. (331) | Com. (A7-1) | 5.9 | 12.3 | 5000.0 | 40.6 | 142.8 | (0.31, 0.61) |
| Ex. (332) | Com. (A7-2) | 5.9 | 10.6 | 5000.0 | 47.1 | 107.0 | (0.31, 0.60) |
| Ex. (333) | Com. (A7-3) | 6.0 | 10.9 | 5000.0 | 45.9 | 107.4 | (0.33, 0.61) |
| Ex. (334) | Com. (A7-4) | 5.6 | 12.5 | 5000.0 | 40.1 | 142.0 | (0.30, 0.60) |
| Ex. (335) | Com. (A7-5) | 6.0 | 11.1 | 5000.0 | 44.9 | 143.1 | (0.31, 0.61) |

TABLE 14-continued

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (336) | Com. (B7-1) | 5.8 | 10.5 | 5000.0 | 47.5 | 130.7 | (0.31, 0.60) |
| Ex. (337) | Com. (B7-2) | 5.7 | 12.0 | 5000.0 | 41.8 | 134.3 | (0.33, 0.61) |
| Ex. (338) | Com. (B7-3) | 5.7 | 10.1 | 5000.0 | 49.4 | 128.8 | (0.32, 0.61) |
| Ex. (339) | Com. (B7-4) | 6.0 | 11.0 | 5000.0 | 45.6 | 145.4 | (0.33, 0.60) |
| Ex. (340) | Com. (B7-5) | 5.6 | 11.7 | 5000.0 | 42.7 | 110.6 | (0.32, 0.61) |
| Ex. (341) | Com. (C7-1) | 5.9 | 11.8 | 5000.0 | 42.6 | 103.7 | (0.31, 0.60) |
| Ex. (342) | Com. (C7-2) | 6.0 | 10.6 | 5000.0 | 47.1 | 113.3 | (0.31, 0.61) |
| Ex. (343) | Com. (C7-3) | 5.6 | 12.1 | 5000.0 | 41.4 | 118.5 | (0.31, 0.60) |
| Ex. (344) | Com. (C7-4) | 6.0 | 10.7 | 5000.0 | 46.9 | 145.9 | (0.33, 0.61) |
| Ex. (345) | Com. (C7-5) | 6.0 | 11.7 | 5000.0 | 42.9 | 119.8 | (0.30, 0.60) |
| Ex. (346) | Com. (A8-1) | 5.7 | 10.6 | 5000.0 | 47.0 | 134.0 | (0.31, 0.61) |
| Ex. (347) | Com. (A8-2) | 5.7 | 11.4 | 5000.0 | 44.0 | 93.8 | (0.31, 0.60) |
| Ex. (348) | Com. (A8-3) | 5.8 | 12.3 | 5000.0 | 40.8 | 92.0 | (0.33, 0.61) |
| Ex. (349) | Com. (A8-4) | 5.6 | 10.8 | 5000.0 | 46.4 | 120.0 | (0.32, 0.61) |
| Ex. (350) | Com. (A8-5) | 5.8 | 10.6 | 5000.0 | 47.2 | 146.2 | (0.31, 0.61) |
| Ex. (351) | Com. (B8-1) | 5.7 | 11.2 | 5000.0 | 44.5 | 107.0 | (0.31, 0.61) |
| Ex. (352) | Com. (B8-2) | 6.0 | 10.7 | 5000.0 | 46.5 | 144.1 | (0.31, 0.60) |
| Ex. (353) | Com. (B8-3) | 5.6 | 10.7 | 5000.0 | 46.9 | 108.8 | (0.33, 0.61) |
| Ex. (354) | Com. (B8-4) | 5.8 | 12.0 | 5000.0 | 41.5 | 100.2 | (0.30, 0.60) |
| Ex. (355) | Com. (B8-5) | 5.9 | 10.9 | 5000.0 | 45.9 | 129.5 | (0.31, 0.61) |
| Ex. (356) | Com. (C8-1) | 5.7 | 10.3 | 5000.0 | 48.4 | 146.0 | (0.31, 0.60) |
| Ex. (357) | Com. (C8-2) | 6.0 | 10.6 | 5000.0 | 47.1 | 143.2 | (0.33, 0.61) |
| Ex. (358) | Com. (C8-3) | 5.7 | 10.4 | 5000.0 | 48.1 | 124.9 | (0.32, 0.61) |
| Ex. (359) | Com. (C8-4) | 5.8 | 10.6 | 5000.0 | 47.2 | 142.9 | (0.33, 0.60) |
| Ex. (360) | Com. (C8-5) | 5.9 | 12.4 | 5000.0 | 40.2 | 105.8 | (0.32, 0.61) |

Test Example IV

Blue Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, NPD was vacuum-deposited with a thickness of 60 nm on the hole injection layer to form a hole transport layer. Next, the inventive compound was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with 9, 10-di(naphthalen-2-yl)anthracene as a host material and BD-052X (made by Idemitsu kosan) as a dopant material in a weight ratio of 93:7. Also, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

The organic light emitting diode fabricated according to [Test Example IV] is described as Ex. (361) to (480) in the Table below 15.

Comparative Example IV

Comparative Examples (15) to (19)

Comparative Example (15)

An OLED was manufactured in the same manner as described in Test Example IV, except that an emission-auxiliary layer was not formed.

Comparative Example (16)

An OLED was manufactured in the same manner as described in Test Example IV, except that Comparative Compound A was used as the emission-auxiliary layer material, instead of the inventive compound.

Comparative Example (17)

An OLED was manufactured in the same manner as described in Test Example IV, except that Comparative Compound B was used as the emission-auxiliary layer material, instead of the inventive compound.

Comparative Example (18)

An OLED was manufactured in the same manner as described in Test Example IV, except that Comparative Compound C was used as the emission-auxiliary layer material, instead of the inventive compound.

Comparative Example (19)

An OLED was manufactured in the same manner as described in Test Example IV, except that Comparative Compound D was used as the emission-auxiliary layer material, instead of the inventive compound.

A forward bias DC voltage was applied to each of the OLEDs manufactured in Test Example IV (Test Examples (361) to (480)) and Comparative Example IV (Comparative Examples (15) to (19)), and EL characteristics of the OLED were measured by PR-650 (Photoresearch). Also, T95 life span was measured by life span measuring equipment (Mcscience) at a reference brightness of 500 cd/m².

Table 15 below shows fabrications and evaluation results of OLEDs manufactured by Test Example IV (Test Examples (361) to (480)) and Comparative Example IV (Comparative Examples (15) to (19)).

TABLE 15

| | Compound | Voltage (V) | Current Density (mA/cm²) | Brightness (cd/m²) | Efficiency (cd/A) | Lifetime T(95) | CIE (x, y) |
|---|---|---|---|---|---|---|---|
| comp. Ex(15) | — | 5.1 | 13.9 | 500.0 | 3.6 | 70.4 | (0.15, 0.16) |
| comp. Ex(16) | comp. Com A | 5.0 | 12.8 | 500.0 | 3.9 | 73.7 | (0.15, 0.14) |
| comp. Ex(17) | comp. Com B | 5.4 | 12.2 | 500.0 | 4.1 | 93.0 | (0.15, 0.13) |
| comp. Ex(18) | comp. Com C | 5.5 | 12.5 | 500.0 | 4.0 | 85.4 | (0.14, 0.14) |
| comp. Ex(19) | comp. Com D | 5.2 | 12.2 | 500.0 | 4.1 | 85.8 | (0.15, 0.14) |
| Ex. (361) | Com. (A1-6) | 5.4 | 8.0 | 500.0 | 6.2 | 111.3 | (0.15, 0.13) |
| Ex. (362) | Com. (A1-7) | 5.1 | 9.8 | 500.0 | 5.1 | 97.9 | (0.14, 0.14) |
| Ex. (363) | Com. (A1-8) | 5.1 | 7.7 | 500.0 | 6.5 | 131.1 | (0.15, 0.13) |
| Ex. (364) | Com. (A1-9) | 5.3 | 8.4 | 500.0 | 6.0 | 96.9 | (0.14, 0.14) |
| Ex. (365) | Com. (A1-10) | 5.3 | 7.4 | 500.0 | 6.7 | 135.3 | (0.14, 0.14) |
| Ex. (366) | Com. (B1-6) | 5.2 | 7.3 | 500.0 | 6.8 | 132.6 | (0.14, 0.14) |
| Ex. (367) | Com. (B1-7) | 5.1 | 8.8 | 500.0 | 5.7 | 142.2 | (0.15, 0.13) |
| Ex. (368) | Com. (B1-8) | 5.1 | 9.9 | 500.0 | 5.1 | 119.9 | (0.15, 0.14) |
| Ex. (369) | Com. (B1-9) | 5.5 | 7.4 | 500.0 | 6.7 | 105.8 | (0.15, 0.14) |
| Ex. (370) | Com. (B1-10) | 5.2 | 9.6 | 500.0 | 5.2 | 96.9 | (0.15, 0.13) |
| Ex. (371) | Com. (C1-6) | 5.1 | 8.4 | 500.0 | 6.0 | 97.5 | (0.14, 0.14) |
| Ex. (372) | Com. (C1-7) | 5.4 | 8.9 | 500.0 | 5.6 | 141.9 | (0.15, 0.14) |
| Ex. (373) | Com. (C1-8) | 5.3 | 7.3 | 500.0 | 6.9 | 145.2 | (0.15, 0.14) |
| Ex. (374) | Com. (C1-9) | 5.1 | 7.7 | 500.0 | 6.5 | 121.5 | (0.14, 0.14) |
| Ex. (375) | Com. (C1-10) | 5.1 | 7.4 | 500.0 | 6.8 | 149.2 | (0.15, 0.13) |
| Ex. (376) | Com. (A2-1) | 5.5 | 8.9 | 500.0 | 5.6 | 145.9 | (0.15, 0.16) |
| Ex. (377) | Com. (A2-2) | 5.3 | 8.5 | 500.0 | 5.9 | 144.6 | (0.15, 0.14) |
| Ex. (378) | Com. (A2-3) | 5.1 | 9.3 | 500.0 | 5.4 | 108.1 | (0.15, 0.13) |
| Ex. (379) | Com. (A2-4) | 5.2 | 8.8 | 500.0 | 5.7 | 146.3 | (0.14, 0.14) |
| Ex. (380) | Com. (A2-5) | 5.3 | 9.0 | 500.0 | 5.6 | 106.0 | (0.15, 0.14) |
| Ex. (381) | Com. (B2-1) | 5.4 | 9.2 | 500.0 | 5.4 | 107.6 | (0.15, 0.13) |
| Ex. (382) | Com. (B2-2) | 5.3 | 7.6 | 500.0 | 6.6 | 101.4 | (0.14, 0.14) |
| Ex. (383) | Com. (B2-3) | 5.2 | 9.4 | 500.0 | 5.3 | 90.2 | (0.14, 0.14) |
| Ex. (384) | Com. (B2-4) | 5.5 | 7.3 | 500.0 | 6.8 | 114.6 | (0.15, 0.13) |
| Ex. (385) | Com. (B2-5) | 5.4 | 7.2 | 500.0 | 7.0 | 114.6 | (0.15, 0.14) |
| Ex. (386) | Com. (C2-6) | 5.5 | 8.6 | 500.0 | 5.8 | 136.8 | (0.14, 0.14) |
| Ex. (387) | Com. (C2-7) | 5.2 | 9.7 | 500.0 | 5.2 | 105.2 | (0.15, 0.13) |
| Ex. (388) | Com. (C2-8) | 5.2 | 9.4 | 500.0 | 5.3 | 101.3 | (0.14, 0.14) |
| Ex. (389) | Com. (C2-9) | 5.3 | 7.3 | 500.0 | 6.8 | 139.1 | (0.15, 0.14) |
| Ex. (390) | Com. (C2-10) | 5.4 | 8.7 | 500.0 | 5.7 | 140.1 | (0.14, 0.14) |
| Ex. (391) | Com. (A3-1) | 5.1 | 7.4 | 500.0 | 6.7 | 98.6 | (0.15, 0.14) |
| Ex. (392) | Com. (A3-2) | 5.1 | 9.2 | 500.0 | 5.5 | 139.1 | (0.15, 0.16) |
| Ex. (393) | Com. (A3-3) | 5.0 | 8.5 | 500.0 | 5.9 | 90.6 | (0.14, 0.14) |
| Ex. (394) | Com. (A3-4) | 5.4 | 7.3 | 500.0 | 6.9 | 122.4 | (0.14, 0.14) |
| Ex. (395) | Com. (A3-5) | 5.5 | 9.5 | 500.0 | 5.3 | 130.3 | (0.15, 0.14) |
| Ex. (396) | Com. (B3-1) | 5.3 | 9.3 | 500.0 | 5.4 | 138.8 | (0.15, 0.13) |
| Ex. (397) | Com. (B3-2) | 5.2 | 7.3 | 500.0 | 6.8 | 136.5 | (0.15, 0.16) |
| Ex. (398) | Com. (B3-3) | 5.4 | 7.6 | 500.0 | 6.5 | 117.6 | (0.15, 0.14) |
| Ex. (399) | Com. (B3-4) | 5.5 | 9.7 | 500.0 | 5.2 | 113.8 | (0.15, 0.13) |
| Ex. (400) | Com. (B3-5) | 5.3 | 7.8 | 500.0 | 6.4 | 100.2 | (0.14, 0.14) |
| Ex. (401) | Com. (C3-1) | 5.1 | 9.5 | 500.0 | 5.2 | 148.5 | (0.15, 0.14) |
| Ex. (402) | Com. (C3-2) | 5.2 | 8.0 | 500.0 | 6.2 | 111.2 | (0.15, 0.13) |
| Ex. (403) | Com. (C3-3) | 5.2 | 8.4 | 500.0 | 5.9 | 137.1 | (0.14, 0.14) |
| Ex. (404) | Com. (C3-4) | 5.5 | 7.6 | 500.0 | 6.5 | 134.3 | (0.15, 0.13) |
| Ex. (405) | Com. (C3-5) | 5.4 | 7.2 | 500.0 | 6.9 | 91.4 | (0.14, 0.14) |
| Ex. (406) | Com. (A4-1) | 5.1 | 7.8 | 500.0 | 6.4 | 102.9 | (0.14, 0.14) |
| Ex. (407) | Com. (A4-2) | 5.4 | 9.8 | 500.0 | 5.1 | 120.0 | (0.14, 0.14) |
| Ex. (408) | Com. (A4-3) | 5.4 | 7.3 | 500.0 | 6.9 | 99.4 | (0.15, 0.13) |
| Ex. (409) | Com. (A4-4) | 5.3 | 7.4 | 500.0 | 6.7 | 118.2 | (0.15, 0.14) |
| Ex. (410) | Com. (A4-5) | 5.2 | 7.8 | 500.0 | 6.5 | 92.1 | (0.15, 0.14) |
| Ex. (411) | Com. (B4-1) | 5.2 | 9.8 | 500.0 | 5.1 | 97.8 | (0.15, 0.13) |
| Ex. (412) | Com. (B4-2) | 5.1 | 7.3 | 500.0 | 6.9 | 133.3 | (0.14, 0.14) |
| Ex. (413) | Com. (B4-3) | 5.3 | 8.0 | 500.0 | 6.2 | 92.2 | (0.15, 0.14) |
| Ex. (414) | Com. (B4-4) | 5.4 | 8.0 | 500.0 | 6.2 | 140.0 | (0.15, 0.14) |
| Ex. (415) | Com. (B4-5) | 5.3 | 8.0 | 500.0 | 6.2 | 92.3 | (0.14, 0.14) |
| Ex. (416) | Com. (C4-6) | 5.2 | 7.6 | 500.0 | 6.6 | 91.2 | (0.15, 0.13) |
| Ex. (417) | Com. (C4-7) | 5.4 | 9.4 | 500.0 | 5.3 | 122.5 | (0.15, 0.16) |
| Ex. (418) | Com. (C4-8) | 5.3 | 7.4 | 500.0 | 6.7 | 93.9 | (0.15, 0.14) |
| Ex. (419) | Com. (C4-9) | 5.3 | 7.7 | 500.0 | 6.5 | 106.3 | (0.15, 0.13) |
| Ex. (420) | Com. (C4-10) | 5.1 | 7.2 | 500.0 | 6.9 | 130.9 | (0.14, 0.14) |
| Ex. (421) | Com. (A5-1) | 5.5 | 7.4 | 500.0 | 6.7 | 130.5 | (0.15, 0.14) |
| Ex. (422) | Com. (A5-2) | 5.3 | 9.8 | 500.0 | 5.1 | 90.8 | (0.15, 0.13) |
| Ex. (423) | Com. (A5-3) | 5.4 | 8.3 | 500.0 | 6.0 | 95.1 | (0.14, 0.14) |
| Ex. (424) | Com. (A5-4) | 5.3 | 7.7 | 500.0 | 6.5 | 107.3 | (0.14, 0.14) |
| Ex. (425) | Com. (A5-5) | 5.4 | 9.2 | 500.0 | 5.4 | 126.7 | (0.15, 0.13) |

TABLE 15-continued

|  | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (426) | Com. (B5-1) | 5.1 | 8.9 | 500.0 | 5.6 | 119.5 | (0.15, 0.14) |
| Ex. (427) | Com. (B5-2) | 5.3 | 7.4 | 500.0 | 6.8 | 102.0 | (0.14, 0.14) |
| Ex. (428) | Com. (B5-3) | 5.3 | 7.4 | 500.0 | 6.8 | 148.4 | (0.15, 0.16) |
| Ex. (429) | Com. (B5-4) | 5.5 | 7.9 | 500.0 | 6.4 | 139.3 | (0.15, 0.14) |
| Ex. (430) | Com. (B5-5) | 5.2 | 7.6 | 500.0 | 6.6 | 145.5 | (0.15, 0.13) |
| Ex. (431) | Com. (C5-1) | 5.3 | 7.4 | 500.0 | 6.7 | 146.1 | (0.14, 0.14) |
| Ex. (432) | Com. (C5-2) | 5.4 | 7.2 | 500.0 | 6.9 | 100.5 | (0.15, 0.14) |
| Ex. (433) | Com. (C5-3) | 5.2 | 7.6 | 500.0 | 6.6 | 131.7 | (0.15, 0.13) |
| Ex. (434) | Com. (C5-4) | 5.2 | 7.4 | 500.0 | 6.7 | 147.3 | (0.14, 0.14) |
| Ex. (435) | Com. (C5-5) | 5.5 | 8.8 | 500.0 | 5.7 | 112.1 | (0.15, 0.13) |
| Ex. (436) | Com. (A6-1) | 5.1 | 8.5 | 500.0 | 5.9 | 113.5 | (0.14, 0.14) |
| Ex. (437) | Com. (A6-2) | 5.0 | 8.8 | 500.0 | 5.7 | 126.9 | (0.14, 0.14) |
| Ex. (438) | Com. (A6-3) | 5.4 | 8.0 | 500.0 | 6.2 | 95.4 | (0.14, 0.14) |
| Ex. (439) | Com. (A6-4) | 5.1 | 7.6 | 500.0 | 6.5 | 112.9 | (0.15, 0.13) |
| Ex. (440) | Com. (A6-5) | 5.4 | 7.4 | 500.0 | 6.8 | 146.0 | (0.15, 0.14) |
| Ex. (441) | Com. (B6-1) | 5.2 | 9.7 | 500.0 | 5.2 | 145.6 | (0.15, 0.14) |
| Ex. (442) | Com. (B6-2) | 5.0 | 9.5 | 500.0 | 5.3 | 123.6 | (0.15, 0.13) |
| Ex. (443) | Com. (B6-3) | 5.2 | 8.2 | 500.0 | 6.1 | 94.5 | (0.14, 0.14) |
| Ex. (444) | Com. (B6-4) | 5.2 | 8.5 | 500.0 | 5.9 | 143.8 | (0.15, 0.14) |
| Ex. (445) | Com. (B6-5) | 5.2 | 9.0 | 500.0 | 5.6 | 126.4 | (0.15, 0.14) |
| Ex. (446) | Com. (C6-6) | 5.2 | 8.3 | 500.0 | 6.1 | 111.3 | (0.14, 0.14) |
| Ex. (447) | Com. (C6-7) | 5.4 | 7.2 | 500.0 | 7.0 | 92.9 | (0.15, 0.13) |
| Ex. (448) | Com. (C6-8) | 5.5 | 7.7 | 500.0 | 6.5 | 143.6 | (0.15, 0.16) |
| Ex. (449) | Com. (C6-9) | 5.3 | 8.7 | 500.0 | 5.7 | 102.9 | (0.15, 0.14) |
| Ex. (450) | Com. (C6-10) | 5.4 | 7.2 | 500.0 | 7.0 | 112.9 | (0.15, 0.13) |
| Ex. (451) | Com. (A7-1) | 5.3 | 8.9 | 500.0 | 5.6 | 92.0 | (0.14, 0.14) |
| Ex. (452) | Com. (A7-2) | 5.4 | 8.0 | 500.0 | 6.2 | 141.6 | (0.15, 0.14) |
| Ex. (453) | Com. (A7-3) | 5.3 | 8.2 | 500.0 | 6.1 | 142.9 | (0.15, 0.13) |
| Ex. (454) | Com. (A7-4) | 5.5 | 8.4 | 500.0 | 6.0 | 106.8 | (0.14, 0.14) |
| Ex. (455) | Com. (A7-5) | 5.1 | 8.0 | 500.0 | 6.2 | 99.6 | (0.14, 0.14) |
| Ex. (456) | Com. (B7-1) | 5.0 | 9.9 | 500.0 | 5.1 | 125.6 | (0.15, 0.13) |
| Ex. (457) | Com. (B7-2) | 5.4 | 10.0 | 500.0 | 5.0 | 105.9 | (0.15, 0.14) |
| Ex. (458) | Com. (B7-3) | 5.1 | 9.2 | 500.0 | 5.4 | 141.1 | (0.14, 0.14) |
| Ex. (459) | Com. (B7-4) | 5.0 | 7.2 | 500.0 | 6.9 | 149.7 | (0.15, 0.13) |
| Ex. (460) | Com. (B7-5) | 5.2 | 8.4 | 500.0 | 6.0 | 98.6 | (0.14, 0.14) |
| Ex. (461) | Com. (C7-1) | 5.3 | 7.2 | 500.0 | 6.9 | 129.4 | (0.15, 0.14) |
| Ex. (462) | Com. (C7-2) | 5.1 | 9.9 | 500.0 | 5.0 | 128.5 | (0.14, 0.14) |
| Ex. (463) | Com. (C7-3) | 5.4 | 8.0 | 500.0 | 6.3 | 107.0 | (0.15, 0.14) |
| Ex. (464) | Com. (C7-4) | 5.2 | 7.5 | 500.0 | 6.7 | 113.0 | (0.15, 0.16) |
| Ex. (465) | Com. (C7-5) | 5.1 | 7.4 | 500.0 | 6.7 | 122.8 | (0.14, 0.14) |
| Ex. (466) | Com. (A8-1) | 5.3 | 9.2 | 500.0 | 5.4 | 120.1 | (0.14, 0.14) |
| Ex. (467) | Com. (A8-2) | 5.1 | 9.0 | 500.0 | 5.5 | 149.6 | (0.15, 0.14) |
| Ex. (468) | Com. (A8-3) | 5.5 | 8.2 | 500.0 | 6.1 | 140.7 | (0.15, 0.13) |
| Ex. (469) | Com. (A8-4) | 5.1 | 8.9 | 500.0 | 5.6 | 99.5 | (0.15, 0.16) |
| Ex. (470) | Com. (A8-5) | 5.3 | 9.1 | 500.0 | 5.5 | 125.5 | (0.15, 0.14) |
| Ex. (471) | Com. (B8-1) | 5.3 | 9.6 | 500.0 | 5.2 | 112.0 | (0.15, 0.13) |
| Ex. (472) | Com. (B8-2) | 5.4 | 8.7 | 500.0 | 5.8 | 115.2 | (0.14, 0.14) |
| Ex. (473) | Com. (B8-3) | 5.1 | 9.0 | 500.0 | 5.6 | 116.2 | (0.15, 0.14) |
| Ex. (474) | Com. (B8-4) | 5.3 | 7.5 | 500.0 | 6.6 | 148.1 | (0.15, 0.13) |
| Ex. (475) | Com. (B8-5) | 5.1 | 8.5 | 500.0 | 5.9 | 112.6 | (0.14, 0.14) |
| Ex. (476) | Com. (C8-1) | 5.2 | 8.4 | 500.0 | 6.0 | 129.9 | (0.15, 0.13) |
| Ex. (477) | Com. (C8-2) | 5.1 | 7.2 | 500.0 | 6.9 | 140.3 | (0.14, 0.14) |
| Ex. (478) | Com. (C8-3) | 5.3 | 8.6 | 500.0 | 5.8 | 92.9 | (0.14, 0.14) |
| Ex. (479) | Com. (C8-4) | 5.1 | 7.5 | 500.0 | 6.6 | 149.8 | (0.14, 0.14) |
| Ex. (480) | Com. (C8-5) | 5.5 | 8.0 | 500.0 | 6.3 | 99.0 | (0.15, 0.13) |

As is apparent from data of Tables 13 to 15, the organic light-emitting diodes fabricated using the compounds of the present invention as emission-auxiliary layer materials were found to be significantly improved in luminous efficiency and life span, compared to those of Comparative Examples 5 to 19. This is believed to be attributed to the fact that, as explained in Test Example 1, the non-linear linkages elicit deep HOMO energy levels and high T1 values, and thus enhance the electron blocking performance, which, in turn, makes it possible to easily form excitons, leading to an improvement in luminous efficiency and life span.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound represented by Formula 1 below:

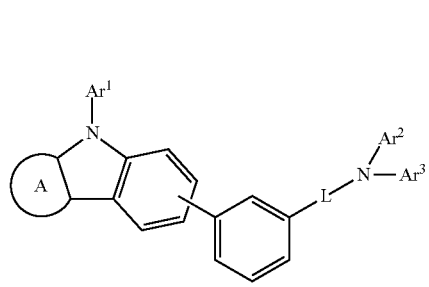

[Formula 1]

In Formula 1,
A ring is a $C_{10}$-$C_{60}$ aromatic ring; or a $C_2$-$C_{60}$ heterocyclic group containing at least one heteroatom selected from the group consisting of O, N, S, Si, and P,
$Ar^1$ to $Ar^3$ are each independently selected from the group consisting of a $C_6$-$C_{60}$ aryl group; a fluorenyl group; a $C_2$-$C_{60}$ heterocyclic group containing at least one heteroatom selected from O, N, S, Si, and P; a fused ring group of a $C_3$-$C_{60}$ aliphatic ring and a $C_6$-$C_{60}$ aromatic ring; a $C_1$-$C_{20}$ alkyl group; and a $C_2$-$C_{20}$ alkenyl group,
L is selected from the group consisting of a single bond; a $C_6$-$C_{60}$ arylene group; and a fluorenylene group,
the above aromatic ring, aryl group, fluorenyl group, heterocyclic group, fused ring group, alkyl group, alkenyl group, arylene group, and fluorenylene group may be substituted by one or more substituents selected from the group consisting of deuterium, halogen, a silane group, a boron group, a germanium group, a cyano group, a nitro group, -L'-N($R^a$)($R^b$) (wherein, L' may be selected from the group consisting of a single bond; a $C_6$-$C_{60}$ arylene group; a fluorenylene group; a $C_2$-$C_{60}$ heterocyclic group containing at least one heteroatom selected from O, N, S, Si, and P; a fused ring group of a $C_3$-$C_{60}$ aliphatic ring and a $C_6$-$C_{60}$ aromatic ring; and a $C_1$-$C_{60}$ aliphatic hydrocarbon group, and the $R^a$ and $R^b$ may be independently selected from the group consisting of a $C_6$-$C_{60}$ aryl group; a fluorenyl group; a $C_2$-$C_{60}$ heterocyclic group containing at least one heteroatom selected from O, N, S, Si, and P; a $C_1$-$C_{20}$ alkyl group; and a $C_2$-$C_{20}$ alkenyl group), a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

2. The compound as claimed in claim 1, wherein A ring is naphthalene or phenanthrene.

3. The compound as claimed in claim 1, wherein the compound is represented by one of Formulas below:

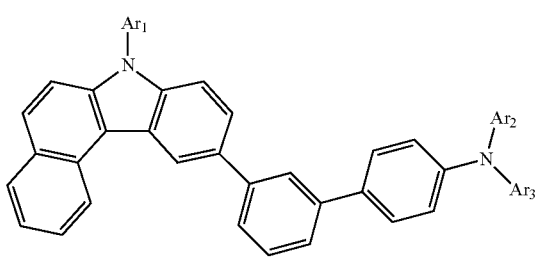

<Formula A1>

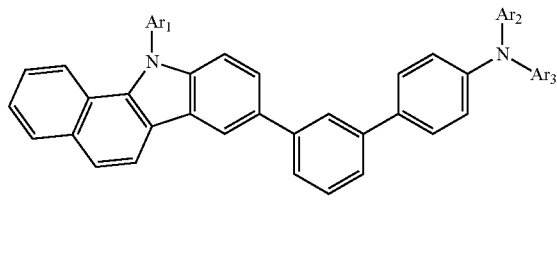

<Formula B1>

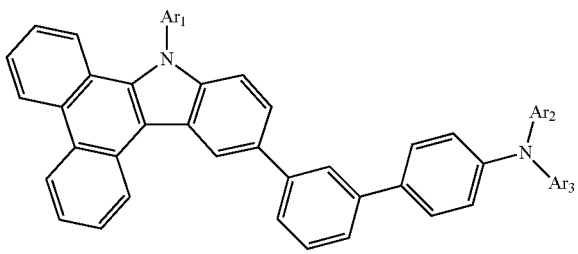

<Formula C1>

<Formula A2>

<Formula B2>

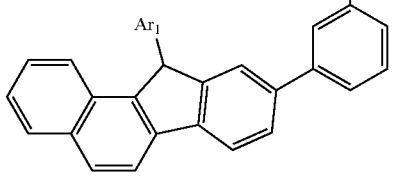

<Formula C2>
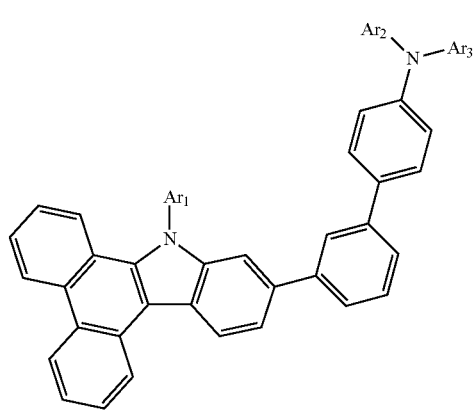
<Formula A3>
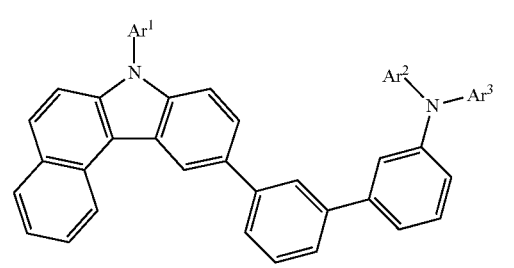
<Formula B3>
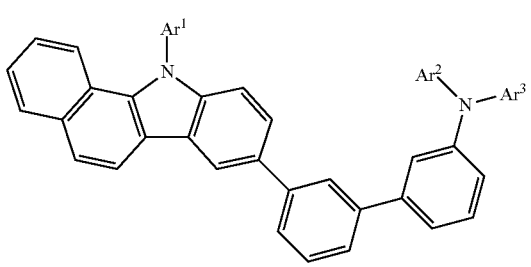
<Formula C3>
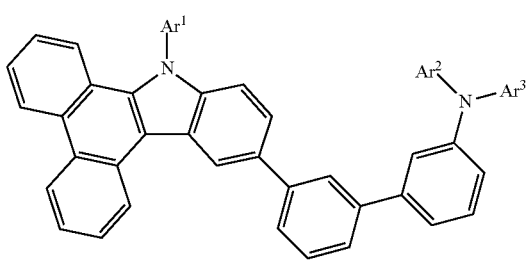
<Formula A4>
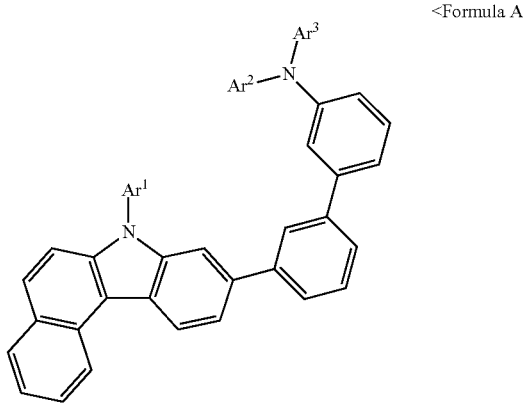
<Formula B4>
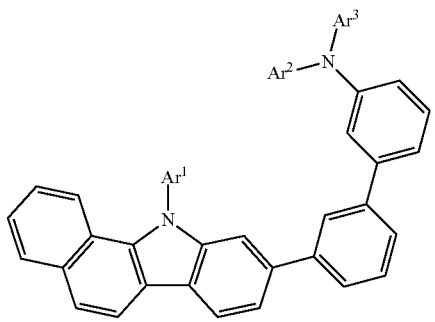
<Formula C4>
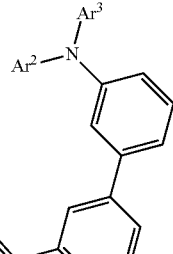
<Formula A5>
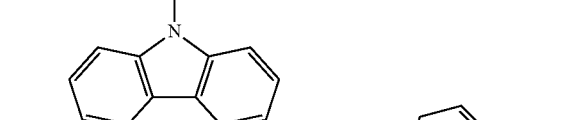
<Formula B5>
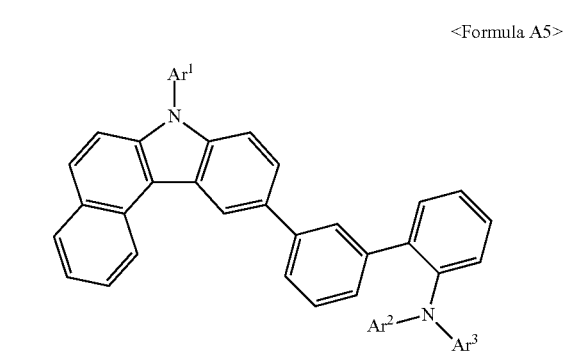

<Formula C5>
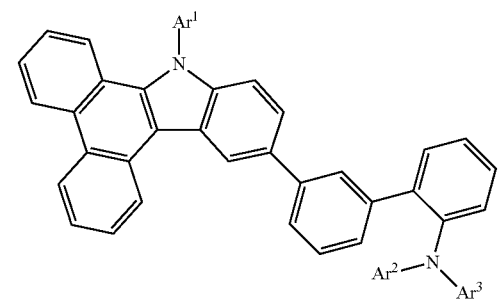
<Formula A6>
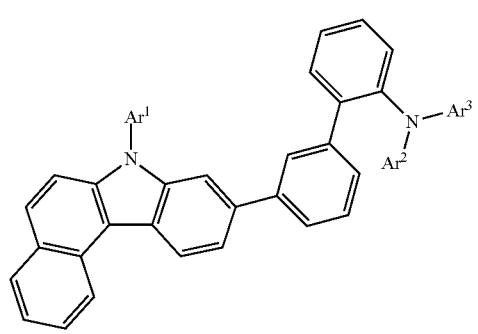
<Formula B6>
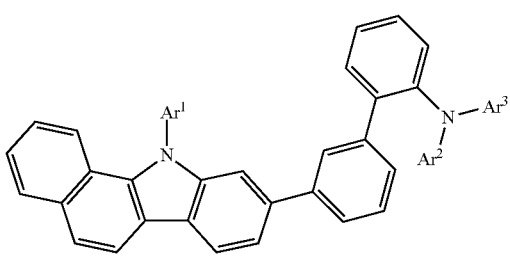
<Formula C6>
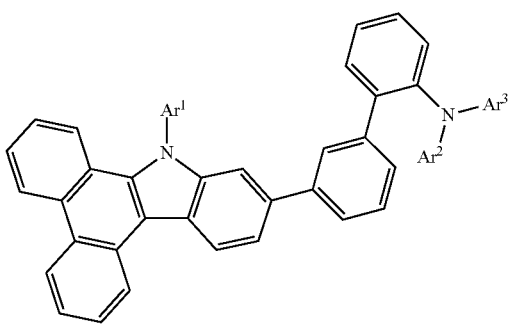
<Formula A7>
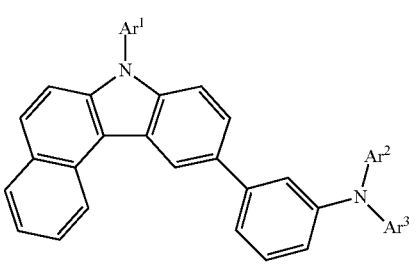
<Formula B7>
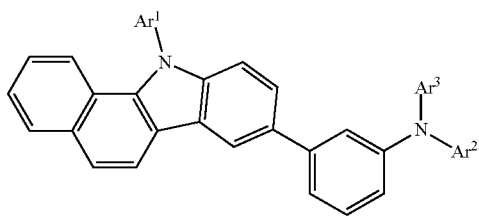
<Formula C7>
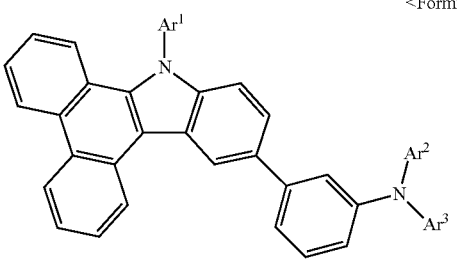
<Formula A8>
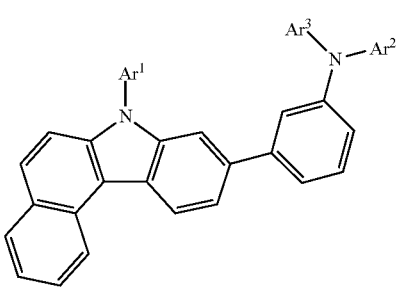
<Formula B8>
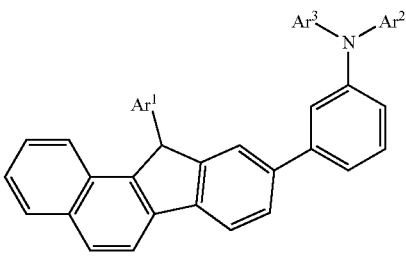
<Formula C8>
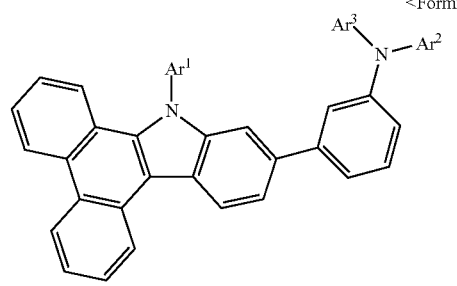
In Formulas above, Ar¹ to Ar³ are as defined in Formula 1.
4. The compound as claimed in claim 1, wherein Ar¹ to Ar³ are each independently one of the following H1 to H22:

-continued
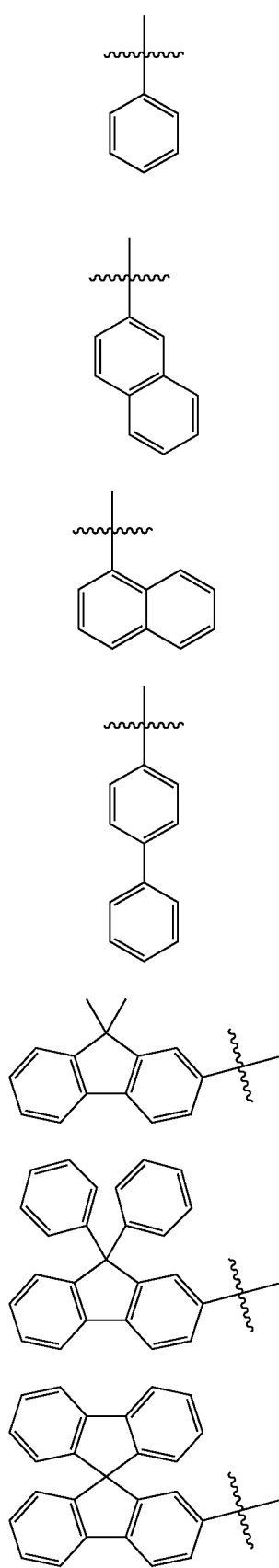
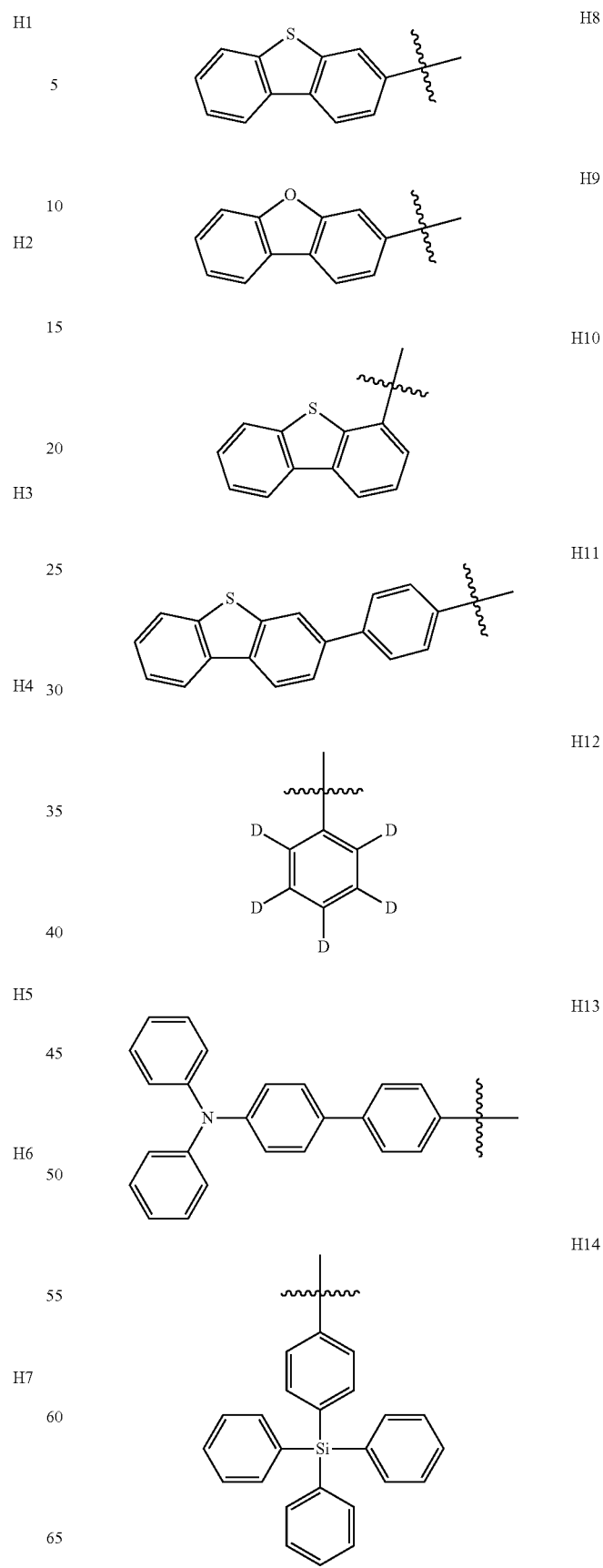

121
-continued
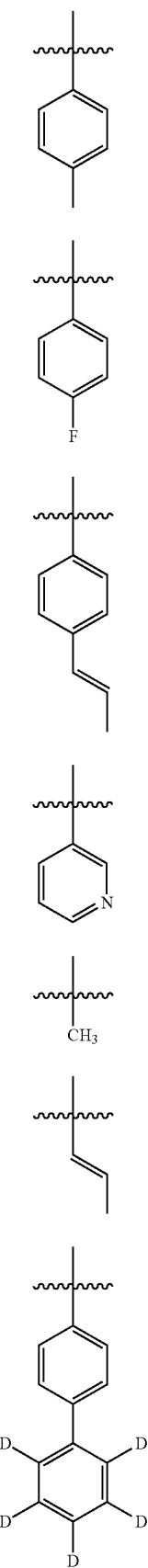
122
-continued
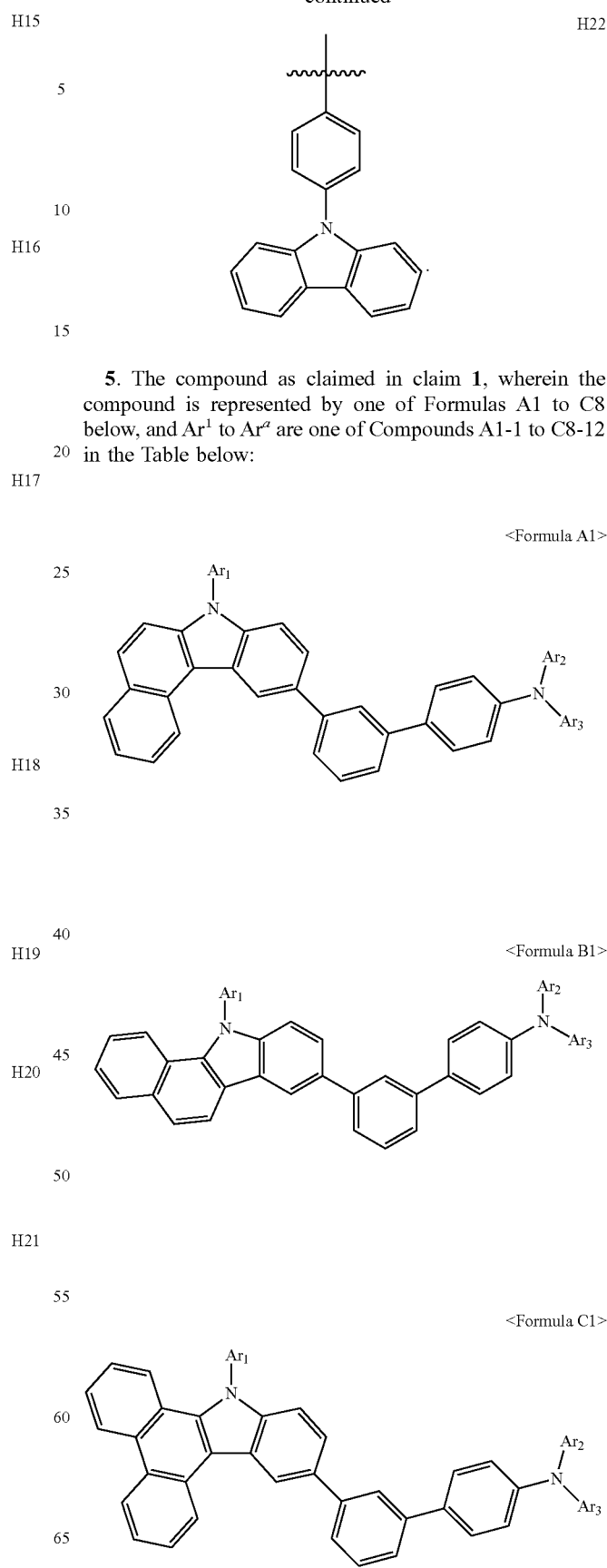
5. The compound as claimed in claim 1, wherein the compound is represented by one of Formulas A1 to C8 below, and $Ar^1$ to $Ar^a$ are one of Compounds A1-1 to C8-12 in the Table below:

<Formula A2>
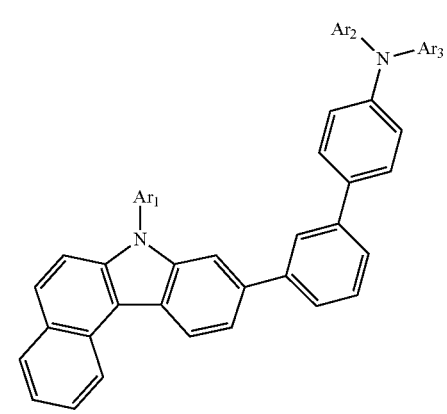
<Formula B2>
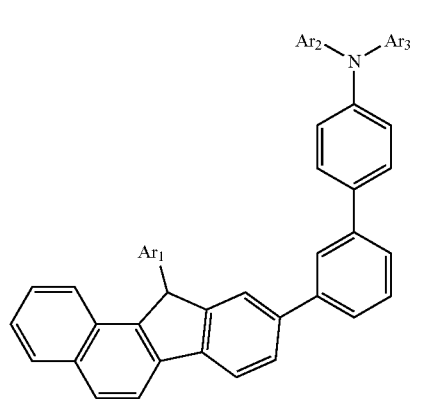
<Formula C2>
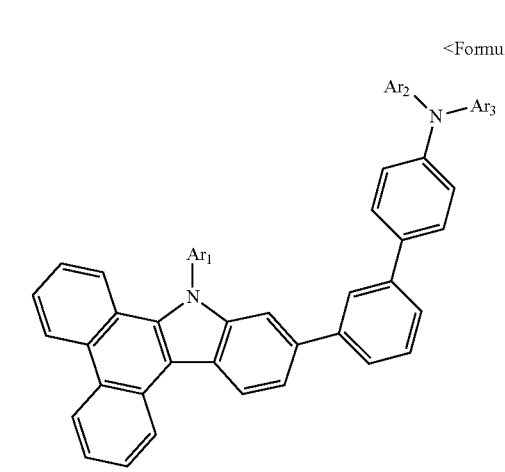
<Formula A3>
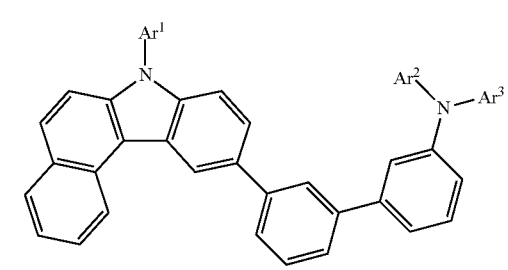
<Formula B3>
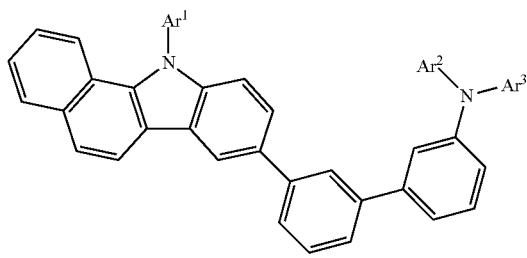
<Formula C3>
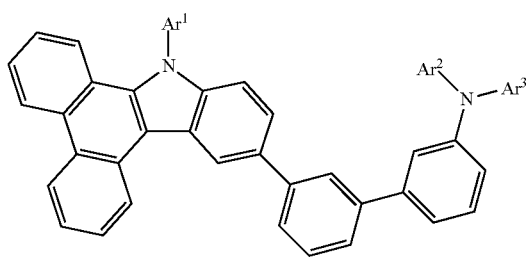
<Formula A4>
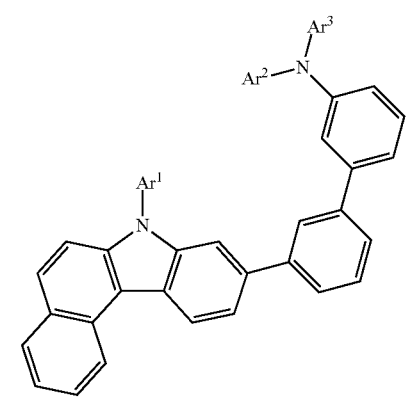
<Formula B4>
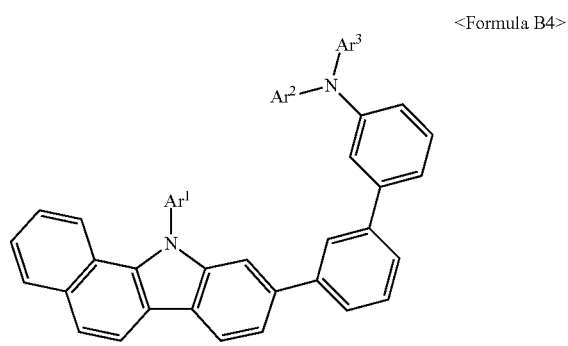

<Formula C4>
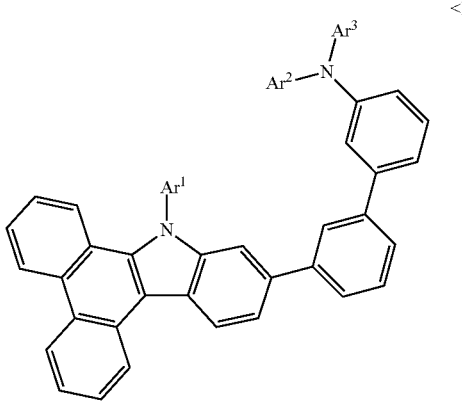
<Formula A5>
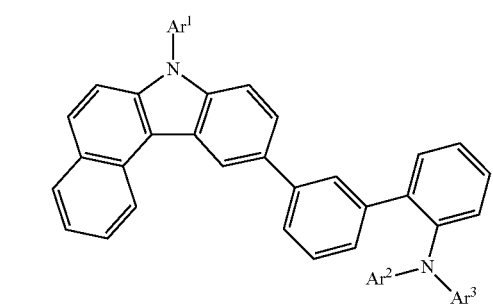
<Formula B5>
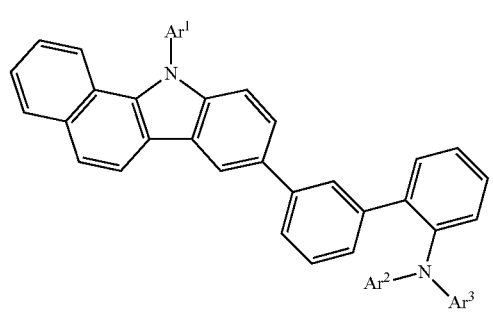
<Formula C5>
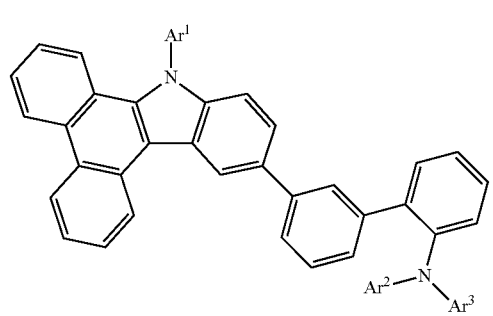
<Formula A6>
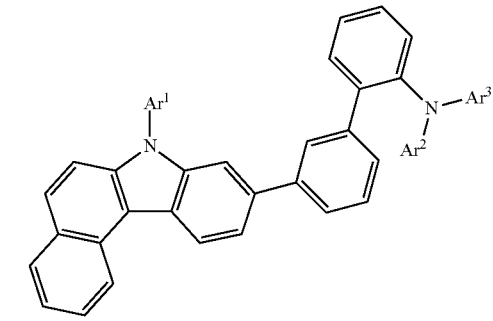
<Formula B6>
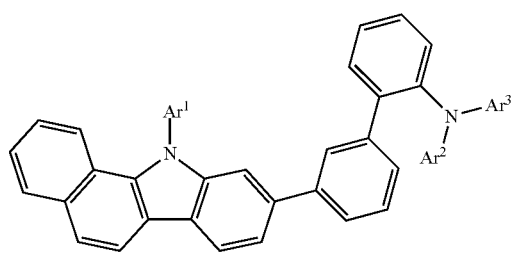
<Formula C6>
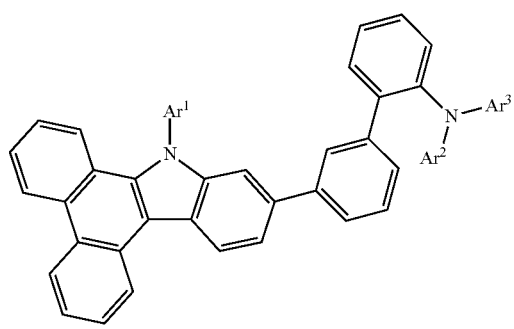
<Formula A7>
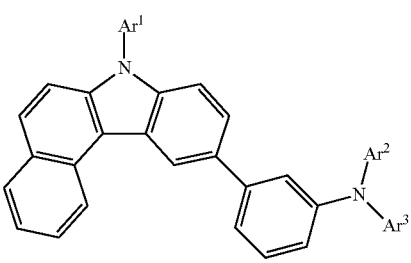
<Formula B7>
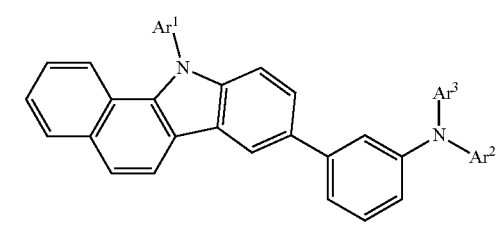

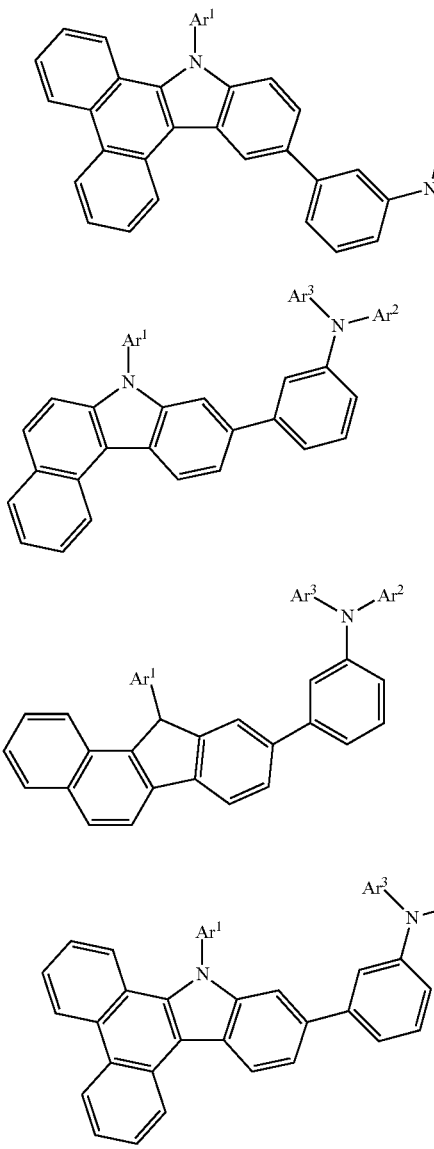

<Formula C7>

<Formula A8>

<Formula B8>

<Formula C8>

| Compound | Ar¹ | Ar² | Ar³ | Compound | Ar¹ | Ar² | Ar³ |
|---|---|---|---|---|---|---|---|
| A1-1 | H1 | H5 | H12 | A1-2 | H4 | H5 | H1 |
| A1-3 | H2 | H5 | H1 | A1-4 | H3 | H5 | H1 |
| A1-5 | H1 | H5 | H4 | A1-6 | H4 | H5 | H4 |
| A1-7 | H2 | H5 | H4 | A1-8 | H3 | H5 | H4 |
| A1-9 | H1 | H5 | H3 | A1-10 | H4 | H5 | H3 |
| A1-11 | H2 | H5 | H3 | A1-12 | H3 | H5 | H3 |
| A1-13 | H1 | H6 | H1 | A1-14 | H4 | H6 | H1 |
| A1-15 | H2 | H6 | H1 | A1-16 | H3 | H6 | H1 |
| A1-17 | H1 | H6 | H4 | A1-18 | H4 | H6 | H4 |
| A1-19 | H2 | H6 | H4 | A1-20 | H3 | H6 | H4 |
| A1-21 | H1 | H6 | H3 | A1-22 | H4 | H6 | H3 |
| A1-23 | H2 | H6 | H3 | A1-24 | H3 | H6 | H3 |
| A1-25 | H1 | H7 | H1 | A1-26 | H4 | H7 | H1 |
| A1-27 | H2 | H7 | H1 | A1-28 | H3 | H7 | H1 |
| A1-29 | H1 | H7 | H3 | A1-30 | H4 | H7 | H3 |
| A1-31 | H2 | H7 | H3 | A1-32 | H3 | H7 | H3 |
| A1-33 | H1 | H7 | H4 | A1-34 | H4 | H7 | H4 |
| A1-35 | H2 | H7 | H4 | A1-36 | H3 | H7 | H4 |
| A1-37 | H1 | H4 | H1 | A1-38 | H4 | H4 | H1 |
| A1-39 | H2 | H4 | H1 | A1-40 | H3 | H4 | H1 |
| A1-41 | H1 | H4 | H4 | A1-42 | H4 | H4 | H4 |
| A1-43 | H2 | H4 | H4 | A1-44 | H3 | H4 | H4 |
| A1-45 | H1 | H4 | H3 | A1-46 | H4 | H4 | H3 |
| A1-47 | H2 | H4 | H3 | A1-48 | H3 | H4 | H3 |
| A1-49 | H1 | H4 | H2 | A1-50 | H4 | H4 | H2 |
| A1-51 | H2 | H4 | H2 | A1-52 | H3 | H4 | H2 |
| A1-53 | H1 | H1 | H3 | A1-54 | H4 | H1 | H3 |
| A1-55 | H2 | H1 | H3 | A1-56 | H3 | H1 | H3 |
| A1-57 | H1 | H1 | H2 | A1-58 | H4 | H1 | H2 |
| A1-59 | H2 | H1 | H2 | A1-60 | H3 | H1 | H2 |
| A1-61 | H1 | H3 | H3 | A1-62 | H4 | H3 | H3 |
| A1-63 | H2 | H3 | H3 | A1-64 | H3 | H3 | H3 |
| A1-65 | H1 | H3 | H2 | A1-66 | H4 | H3 | H2 |
| A1-67 | H2 | H3 | H2 | A1-68 | H3 | H3 | H2 |
| A1-69 | H1 | H2 | H2 | A1-70 | H4 | H2 | H2 |
| A1-71 | H2 | H2 | H2 | A1-72 | H3 | H2 | H2 |
| A1-73 | H1 | H8 | H1 | A1-74 | H4 | H8 | H1 |
| A1-75 | H2 | H8 | H1 | A1-76 | H3 | H8 | H1 |
| A1-77 | H1 | H9 | H1 | A1-78 | H4 | H9 | H1 |
| A1-79 | H2 | H9 | H1 | A1-80 | H3 | H9 | H1 |
| A1-81 | H1 | H8 | H4 | A1-82 | H4 | H8 | H4 |
| A1-83 | H2 | H8 | H4 | A1-84 | H3 | H8 | H4 |
| A1-85 | H1 | H9 | H4 | A1-86 | H4 | H9 | H4 |
| A1-87 | H2 | H9 | H4 | A1-88 | H3 | H9 | H4 |
| A1-89 | H1 | H8 | H3 | A1-90 | H4 | H8 | H3 |
| A1-91 | H2 | H8 | H3 | A1-92 | H3 | H8 | H3 |
| A1-93 | H1 | H9 | H3 | A1-94 | H4 | H9 | H3 |
| A1-95 | H2 | H9 | H3 | A1-96 | H3 | H9 | H3 |
| A1-97 | H1 | H11 | H1 | A1-98 | H4 | H10 | H1 |
| A1-99 | H1 | H1 | H1 | A1-100 | H4 | H1 | H1 |
| A1-101 | H1 | H5 | H15 | A1-102 | H18 | H5 | H2 |
| A1-103 | H1 | H5 | H21 | A1-104 | H1 | H5 | H22 |
| B1-1 | H1 | H5 | H1 | B1-2 | H4 | H5 | H1 |
| B1-3 | H2 | H5 | H1 | B1-4 | H3 | H5 | H1 |
| B1-5 | H1 | H5 | H4 | B1-6 | H4 | H5 | H4 |
| B1-7 | H2 | H5 | H4 | B1-8 | H3 | H5 | H4 |
| B1-9 | H1 | H5 | H3 | B1-10 | H4 | H5 | H3 |
| B1-11 | H2 | H5 | H3 | B1-12 | H3 | H5 | H3 |
| B1-13 | H1 | H6 | H1 | B1-14 | H4 | H6 | H1 |
| B1-15 | H2 | H6 | H1 | B1-16 | H3 | H6 | H1 |
| B1-17 | H1 | H6 | H4 | B1-18 | H4 | H6 | H4 |
| B1-19 | H2 | H6 | H4 | B1-20 | H3 | H6 | H4 |
| B1-21 | H1 | H6 | H3 | B1-22 | H4 | H6 | H3 |
| B1-23 | H2 | H6 | H3 | B1-24 | H3 | H6 | H3 |
| B1-25 | H1 | H7 | H1 | B1-26 | H4 | H7 | H1 |
| B1-27 | H2 | H7 | H1 | B1-28 | H3 | H7 | H1 |
| B1-29 | H1 | H7 | H3 | B1-30 | H4 | H7 | H3 |
| B1-31 | H2 | H7 | H3 | B1-32 | H3 | H7 | H3 |
| B1-33 | H1 | H7 | H4 | B1-34 | H4 | H7 | H4 |
| B1-35 | H2 | H7 | H4 | B1-36 | H3 | H7 | H4 |
| B1-37 | H1 | H4 | H1 | B1-38 | H4 | H4 | H1 |
| B1-39 | H2 | H4 | H1 | B1-40 | H3 | H4 | H1 |
| B1-41 | H1 | H4 | H4 | B1-42 | H4 | H4 | H4 |
| B1-43 | H2 | H4 | H4 | B1-44 | H3 | H4 | H4 |
| B1-45 | H1 | H4 | H3 | B1-46 | H4 | H4 | H3 |
| B1-47 | H2 | H4 | H3 | B1-48 | H3 | H4 | H3 |
| B1-49 | H1 | H4 | H2 | B1-50 | H4 | H4 | H2 |
| B1-51 | H2 | H4 | H2 | B1-52 | H3 | H4 | H2 |
| B1-53 | H1 | H1 | H3 | B1-54 | H4 | H1 | H3 |
| B1-55 | H2 | H1 | H3 | B1-56 | H3 | H1 | H3 |
| B1-57 | H1 | H1 | H2 | B1-58 | H4 | H1 | H2 |
| B1-59 | H2 | H1 | H2 | B1-60 | H3 | H1 | H2 |
| B1-61 | H1 | H8 | H1 | B1-62 | H4 | H8 | H1 |
| B1-63 | H2 | H8 | H1 | B1-64 | H3 | H8 | H1 |
| B1-65 | H1 | H9 | H1 | B1-66 | H4 | H9 | H1 |
| B1-67 | H2 | H9 | H1 | B1-68 | H3 | H9 | H1 |
| B1-69 | H1 | H8 | H4 | B1-70 | H4 | H8 | H4 |
| B1-71 | H2 | H8 | H4 | B1-72 | H3 | H8 | H4 |
| B1-73 | H1 | H9 | H4 | B1-74 | H4 | H9 | H4 |
| B1-75 | H2 | H9 | H4 | B1-76 | H3 | H9 | H4 |
| B1-77 | H1 | H8 | H3 | B1-78 | H4 | H8 | H3 |
| B1-79 | H2 | H8 | H3 | B1-80 | H3 | H8 | H3 |
| B1-81 | H1 | H9 | H3 | B1-82 | H4 | H9 | H3 |
| B1-83 | H2 | H9 | H3 | B1-84 | H3 | H9 | H3 |
| B1-85 | H1 | H1 | H14 | B1-86 | H1 | H1 | H13 |
| C1-1 | H1 | H5 | H1 | C1-2 | H4 | H5 | H1 |

-continued

| Compound | Ar¹ | Ar² | Ar³ | Compound | Ar¹ | Ar² | Ar³ |
|---|---|---|---|---|---|---|---|
| C1-3 | H2 | H5 | H1 | C1-4 | H3 | H5 | H1 |
| C1-5 | H1 | H5 | H4 | C1-6 | H4 | H5 | H4 |
| C1-7 | H2 | H5 | H4 | C1-8 | H3 | H5 | H4 |
| C1-9 | H1 | H5 | H3 | C1-10 | H4 | H5 | H3 |
| C1-11 | H2 | H5 | H3 | C1-12 | H3 | H5 | H3 |
| C1-13 | H1 | H6 | H1 | C1-14 | H4 | H6 | H1 |
| C1-15 | H2 | H6 | H1 | C1-16 | H3 | H6 | H1 |
| C1-17 | H1 | H6 | H4 | C1-18 | H4 | H6 | H4 |
| C1-19 | H2 | H6 | H4 | C1-20 | H3 | H6 | H4 |
| C1-21 | H1 | H6 | H3 | C1-22 | H4 | H6 | H3 |
| C1-23 | H2 | H6 | H3 | C1-24 | H3 | H6 | H3 |
| C1-25 | H1 | H7 | H1 | C1-26 | H4 | H7 | H1 |
| C1-27 | H2 | H7 | H1 | C1-28 | H3 | H7 | H1 |
| C1-29 | H1 | H7 | H3 | C1-30 | H4 | H7 | H3 |
| C1-31 | H2 | H7 | H3 | C1-32 | H3 | H7 | H3 |
| C1-33 | H1 | H7 | H4 | C1-34 | H4 | H7 | H4 |
| C1-35 | H2 | H7 | H4 | C1-36 | H3 | H7 | H4 |
| C1-37 | H1 | H4 | H1 | C1-38 | H4 | H4 | H1 |
| C1-39 | H2 | H4 | H1 | C1-40 | H3 | H4 | H1 |
| C1-41 | H1 | H4 | H4 | C1-42 | H4 | H4 | H4 |
| C1-43 | H2 | H4 | H4 | C1-44 | H3 | H4 | H4 |
| C1-45 | H1 | H4 | H3 | C1-46 | H4 | H4 | H3 |
| C1-47 | H2 | H4 | H3 | C1-48 | H3 | H4 | H3 |
| C1-49 | H1 | H4 | H2 | C1-50 | H4 | H4 | H2 |
| C1-51 | H2 | H4 | H2 | C1-52 | H3 | H4 | H2 |
| C1-53 | H1 | H1 | H3 | C1-54 | H4 | H1 | H3 |
| C1-55 | H2 | H1 | H3 | C1-56 | H3 | H1 | H3 |
| C1-57 | H1 | H1 | H2 | C1-58 | H4 | H1 | H2 |
| C1-59 | H2 | H1 | H2 | C1-60 | H3 | H1 | H2 |
| C1-61 | H1 | H8 | H1 | C1-62 | H4 | H8 | H1 |
| C1-63 | H2 | H8 | H1 | C1-64 | H3 | H8 | H1 |
| C1-65 | H1 | H9 | H1 | C1-66 | H4 | H9 | H1 |
| C1-67 | H2 | H9 | H1 | C1-68 | H3 | H9 | H1 |
| C1-69 | H1 | H8 | H4 | C1-70 | H4 | H8 | H4 |
| C1-71 | H2 | H8 | H4 | C1-72 | H3 | H8 | H4 |
| C1-73 | H1 | H9 | H4 | C1-74 | H4 | H9 | H4 |
| C1-75 | H2 | H9 | H4 | C1-76 | H3 | H9 | H4 |
| C1-77 | H1 | H8 | H3 | C1-78 | H4 | H8 | H3 |
| C1-79 | H2 | H8 | H3 | C1-80 | H3 | H8 | H3 |
| C1-81 | H1 | H9 | H3 | C1-82 | H4 | H9 | H3 |
| C1-83 | H2 | H9 | H3 | C1-84 | H3 | H9 | H3 |
| C1-85 | H19 | H1 | H1 | C1-86 | H2O | H1 | H1 |
| A2-1 | H1 | H5 | H1 | A2-2 | H1 | H5 | H4 |
| A2-3 | H1 | H5 | H3 | A2-4 | H1 | H6 | H1 |
| A2-5 | H1 | H6 | H4 | A2-6 | H1 | H6 | H3 |
| A2-7 | H1 | H7 | H1 | A2-8 | H1 | H7 | H3 |
| A2-9 | H1 | H7 | H4 | A2-10 | H1 | H4 | H1 |
| A2-11 | H4 | H4 | H1 | A2-12 | H1 | H4 | H4 |
| A2-13 | H4 | H4 | H4 | A2-14 | H1 | H4 | H3 |
| A2-15 | H1 | H4 | H2 | A2-16 | H1 | H1 | H3 |
| A2-17 | H1 | H1 | H2 | A2-18 | H1 | H8 | H1 |
| A2-19 | H1 | H9 | H1 | A2-20 | H1 | H8 | H4 |
| A2-21 | H1 | H9 | H4 | A2-22 | H1 | H8 | H3 |
| A2-23 | H1 | H9 | H3 | A2-24 | H1 | H1 | H1 |
| B2-1 | H1 | H5 | H1 | B2-2 | H1 | H6 | H1 |
| B2-3 | H4 | H4 | H1 | B2-4 | H4 | H4 | H4 |
| B2-5 | H1 | H8 | H1 | B2-6 | H1 | H8 | H4 |
| B2-7 | H3 | H9 | H4 | B2-8 | H1 | H1 | H1 |
| B2-9 | H1 | H1 | H16 | B2-10 | H1 | H1 | H17 |
| C2-1 | H1 | H5 | H1 | C2-2 | H1 | H5 | H4 |
| C2-3 | H1 | H6 | H1 | C2-4 | H1 | H6 | H4 |
| C2-5 | H1 | H7 | H1 | C2-6 | H1 | H4 | H1 |
| C2-7 | H1 | H4 | H4 | C2-8 | H1 | H1 | H3 |
| C2-9 | H1 | H1 | H2 | C2-10 | H1 | H8 | H1 |
| C2-11 | H1 | H9 | H1 | C2-12 | H1 | H1 | H1 |
| A3-1 | H1 | H5 | H1 | A3-2 | H1 | H5 | H4 |
| A3-3 | H1 | H5 | H3 | A3-4 | H1 | H6 | H1 |
| A3-5 | H1 | H6 | H4 | A3-6 | H1 | H6 | H3 |
| A3-7 | H1 | H7 | H1 | A3-8 | H1 | H7 | H3 |
| A3-9 | H1 | H7 | H4 | A3-10 | H1 | H4 | H1 |
| A3-11 | H4 | H4 | H1 | A3-12 | H1 | H4 | H4 |
| A3-13 | H4 | H4 | H4 | A3-14 | H1 | H4 | H3 |
| A3-15 | H1 | H4 | H2 | A3-16 | H1 | H1 | H3 |
| A3-17 | H1 | H1 | H2 | A3-18 | H1 | H8 | H1 |
| A3-19 | H1 | H9 | H1 | A3-20 | H1 | H8 | H4 |
| A3-21 | H1 | H9 | H4 | A3-22 | H1 | H8 | H3 |
| A3-23 | H1 | H9 | H3 | A3-24 | H1 | H1 | H1 |
| B3-1 | H1 | H5 | H1 | B3-2 | H1 | H6 | H1 |
| B3-3 | H4 | H4 | H1 | B3-4 | H4 | H4 | H4 |
| B3-5 | H1 | H8 | H1 | B3-6 | H1 | H8 | H4 |
| B3-7 | H3 | H9 | H4 | B3-8 | H1 | H1 | H1 |
| B3-9 | H1 | H1 | H16 | B3-10 | H1 | H1 | H17 |
| C3-1 | H1 | H5 | H1 | C3-2 | H1 | H5 | H4 |
| C3-3 | H1 | H6 | H1 | C3-4 | H1 | H6 | H4 |
| C3-5 | H1 | H7 | H1 | C3-6 | H1 | H4 | H1 |
| C3-7 | H1 | H4 | H4 | C3-8 | H1 | H1 | H3 |
| C3-9 | H1 | H1 | H2 | C3-10 | H1 | H8 | H1 |
| C3-11 | H1 | H9 | H1 | C3-12 | H1 | H1 | H1 |
| A4-1 | H1 | H5 | H1 | A4-2 | H1 | H5 | H4 |
| A4-3 | H1 | H5 | H3 | A4-4 | H1 | H6 | H1 |
| A4-5 | H1 | H6 | H4 | A4-6 | H1 | H6 | H3 |
| A4-7 | H1 | H7 | H1 | A4-8 | H1 | H7 | H3 |
| A4-9 | H1 | H7 | H4 | A4-10 | H1 | H4 | H1 |
| A4-11 | H4 | H4 | H1 | A4-12 | H1 | H4 | H4 |
| A4-13 | H4 | H4 | H4 | A4-14 | H1 | H4 | H3 |
| A4-15 | H1 | H4 | H2 | A4-16 | H1 | H1 | H3 |
| A4-17 | H1 | H1 | H2 | A4-18 | H1 | H8 | H1 |
| A4-19 | H1 | H9 | H1 | A4-20 | H1 | H8 | H4 |
| A4-21 | H1 | H9 | H4 | A4-22 | H1 | H8 | H3 |
| A4-23 | H1 | H9 | H3 | A4-24 | H1 | H1 | H1 |
| B4-1 | H1 | H5 | H1 | B4-2 | H1 | H6 | H1 |
| B4-3 | H4 | H4 | H1 | B4-4 | H4 | H4 | H4 |
| B4-5 | H1 | H8 | H1 | B4-6 | H1 | H8 | H4 |
| B4-7 | H3 | H9 | H4 | B4-8 | H1 | H1 | H1 |
| B4-9 | H1 | H1 | H16 | B4-10 | H1 | H1 | H17 |
| C4-1 | H1 | H5 | H1 | C4-2 | H1 | H5 | H4 |
| C4-3 | H1 | H6 | H1 | C4-4 | H1 | H6 | H4 |
| C4-5 | H1 | H7 | H1 | C4-6 | H1 | H4 | H1 |
| C4-7 | H1 | H4 | H4 | C4-8 | H1 | H1 | H3 |
| C4-9 | H1 | H1 | H2 | C4-10 | H1 | H8 | H1 |
| C4-11 | H1 | H9 | H1 | C4-12 | H1 | H1 | H1 |
| A5-1 | H1 | H5 | H1 | A5-2 | H1 | H5 | H4 |
| A5-3 | H1 | H5 | H3 | A5-4 | H1 | H6 | H1 |
| A5-5 | H1 | H6 | H4 | A5-6 | H1 | H6 | H3 |
| A5-7 | H1 | H7 | H1 | A5-8 | H1 | H7 | H3 |
| A5-9 | H1 | H7 | H4 | A5-10 | H1 | H4 | H1 |
| A5-11 | H4 | H4 | H1 | A5-12 | H1 | H4 | H4 |
| A5-13 | H4 | H4 | H4 | A5-14 | H1 | H4 | H3 |
| A5-15 | H1 | H4 | H2 | A5-16 | H1 | H1 | H3 |
| A5-17 | H1 | H1 | H2 | A5-18 | H1 | H8 | H1 |
| A5-19 | H1 | H9 | H1 | A5-20 | H1 | H8 | H4 |
| A5-21 | H1 | H9 | H4 | A5-22 | H1 | H8 | H3 |
| A5-23 | H1 | H9 | H3 | A5-24 | H1 | H1 | H1 |
| B5-1 | H1 | H5 | H1 | B5-2 | H1 | H6 | H1 |
| B5-3 | H4 | H4 | H1 | B5-4 | H4 | H4 | H4 |
| B5-5 | H1 | H8 | H1 | B5-6 | H1 | H8 | H4 |
| B5-7 | H3 | H9 | H4 | B5-8 | H1 | H1 | H1 |
| B5-9 | H1 | H1 | H16 | B5-10 | H1 | H1 | H17 |
| C5-1 | H1 | H5 | H1 | C5-2 | H1 | H5 | H4 |
| C5-3 | H1 | H6 | H1 | C5-4 | H1 | H6 | H4 |
| C5-5 | H1 | H7 | H1 | C5-6 | H1 | H4 | H1 |
| C5-7 | H1 | H4 | H4 | C5-8 | H1 | H1 | H3 |
| C5-9 | H1 | H1 | H2 | C5-10 | H1 | H8 | H1 |
| C5-11 | H1 | H9 | H1 | C5-12 | H1 | H1 | H1 |
| A6-1 | H1 | H5 | H1 | A6-2 | H1 | H5 | H4 |
| A6-3 | H1 | H5 | H3 | A6-4 | H1 | H6 | H1 |
| A6-5 | H1 | H6 | H4 | A6-6 | H1 | H6 | H3 |
| A6-7 | H1 | H7 | H1 | A6-8 | H1 | H7 | H3 |
| A6-9 | H1 | H7 | H4 | A6-10 | H1 | H4 | H1 |
| A6-11 | H4 | H4 | H1 | A6-12 | H1 | H4 | H4 |
| A6-13 | H4 | H4 | H4 | A6-14 | H1 | H4 | H3 |
| A6-15 | H1 | H4 | H2 | A6-16 | H1 | H1 | H3 |
| A6-17 | H1 | H1 | H2 | A6-18 | H1 | H8 | H1 |
| A6-19 | H1 | H9 | H1 | A6-20 | H1 | H8 | H4 |
| A6-21 | H1 | H9 | H4 | A6-22 | H1 | H8 | H3 |
| A6-23 | H1 | H9 | H3 | A6-24 | H1 | H1 | H1 |
| B6-1 | H1 | H5 | H1 | B6-2 | H1 | H6 | H1 |
| B6-3 | H4 | H4 | H1 | B6-4 | H4 | H4 | H4 |
| B6-5 | H1 | H8 | H1 | B6-6 | H1 | H8 | H4 |
| B6-7 | H3 | H9 | H4 | B6-8 | H1 | H1 | H1 |
| B6-9 | H1 | H1 | H16 | B6-10 | H1 | H1 | H17 |
| C6-1 | H1 | H5 | H1 | C6-2 | H1 | H5 | H4 |
| C6-3 | H1 | H6 | H1 | C6-4 | H1 | H6 | H4 |
| C6-5 | H1 | H7 | H1 | C6-6 | H1 | H4 | H1 |

-continued

| Compound | Ar¹ | Ar² | Ar³ | Compound | Ar¹ | Ar² | Ar³ |
|---|---|---|---|---|---|---|---|
| C6-7 | H1 | H4 | H4 | C6-8 | H1 | H1 | H3 |
| C6-9 | H1 | H1 | H2 | C6-10 | H1 | H8 | H1 |
| C6-11 | H1 | H9 | H1 | C6-12 | H1 | H1 | H1 |
| A7-1 | H1 | H5 | H1 | A7-2 | H1 | H5 | H4 |
| A7-3 | H1 | H5 | H3 | A7-4 | H1 | H6 | H1 |
| A7-5 | H1 | H6 | H4 | A7-6 | H1 | H6 | H3 |
| A7-7 | H1 | H7 | H1 | A7-8 | H1 | H7 | H3 |
| A7-9 | H1 | H7 | H4 | A7-10 | H1 | H4 | H1 |
| A7-11 | H4 | H4 | H1 | A7-12 | H1 | H4 | H4 |
| A7-13 | H4 | H4 | H4 | A7-14 | H1 | H4 | H3 |
| A7-15 | H1 | H4 | H2 | A7-16 | H1 | H1 | H3 |
| A7-17 | H1 | H1 | H2 | A7-18 | H1 | H8 | H1 |
| A7-19 | H1 | H9 | H1 | A7-20 | H1 | H8 | H4 |
| A7-21 | H1 | H9 | H4 | A7-22 | H1 | H8 | H3 |
| A7-23 | H1 | H9 | H3 | A7-24 | H1 | H1 | H1 |
| B7-1 | H1 | H5 | H1 | B7-2 | H1 | H6 | H1 |
| B7-3 | H4 | H4 | H1 | B7-4 | H4 | H4 | H4 |
| B7-5 | H1 | H8 | H1 | B7-6 | H1 | H8 | H4 |
| B7-7 | H3 | H9 | H4 | B7-8 | H1 | H1 | H1 |
| B7-9 | H1 | H1 | H16 | B7-10 | H1 | H1 | H17 |
| C7-1 | H1 | H5 | H1 | C7-2 | H1 | H5 | H4 |
| C7-3 | H1 | H6 | H1 | C7-4 | H1 | H6 | H4 |
| C7-5 | H1 | H7 | H1 | C7-6 | H1 | H4 | H1 |
| C7-7 | H1 | H4 | H4 | C7-8 | H1 | H1 | H3 |
| C7-9 | H1 | H1 | H2 | C7-10 | H1 | H8 | H1 |
| C7-11 | H1 | H9 | H1 | C7-12 | H1 | H1 | H1 |
| A8-1 | H1 | H5 | H1 | A8-2 | H1 | H5 | H4 |
| A8-3 | H1 | H5 | H3 | A8-4 | H1 | H6 | H1 |
| A8-5 | H1 | H6 | H4 | A8-6 | H1 | H6 | H3 |
| A8-7 | H1 | H7 | H1 | A8-8 | H1 | H7 | H3 |
| A8-9 | H1 | H7 | H4 | A8-10 | H1 | H4 | H1 |
| A8-11 | H4 | H4 | H1 | A8-12 | H1 | H4 | H4 |
| A8-13 | H4 | H4 | H4 | A8-14 | H1 | H4 | H3 |
| A8-15 | H1 | H4 | H2 | A8-16 | H1 | H1 | H3 |
| A8-17 | H1 | H1 | H2 | A8-18 | H1 | H8 | H1 |
| A8-19 | H1 | H9 | H1 | A8-20 | H1 | H8 | H4 |
| A8-21 | H1 | H9 | H4 | A8-22 | H1 | H8 | H3 |
| A8-23 | H1 | H9 | H3 | A8-24 | H1 | H1 | H1 |
| B8-1 | H1 | H5 | H1 | B8-2 | H1 | H6 | H1 |
| B8-3 | H4 | H4 | H1 | B8-4 | H4 | H4 | H4 |
| B8-5 | H1 | H8 | H1 | B8-6 | H1 | H8 | H4 |
| B8-7 | H3 | H9 | H4 | B8-8 | H1 | H1 | H1 |
| B8-9 | H1 | H1 | H16 | B8-10 | H1 | H1 | H17 |
| C8-1 | H1 | H5 | H1 | C8-2 | H1 | H5 | H4 |
| C8-3 | H1 | H6 | H1 | C8-4 | H1 | H6 | H4 |
| C8-5 | H1 | H7 | H1 | C8-6 | H1 | H4 | H1 |
| C8-7 | H1 | H4 | H4 | C8-8 | H1 | H1 | H3 |
| C8-9 | H1 | H1 | H2 | C8-10 | H1 | H8 | H1 |
| C8-11 | H1 | H9 | H1 | C8-12 | H1 | H1 | H1. |

6. An organic electric element comprising a first electrode, a second electrode, and an organic material layer disposed between the first electrode and the second electrode, wherein the organic material layer comprises the compound according to claim 1.

7. The organic electric element as claimed in claim 6, wherein the organic electric element further comprises a layer to improve luminous efficiency which is formed on at least one of the sides of the first and the second electrodes opposite to the organic material layer.

8. The organic electric element as claimed in claim 6, wherein the organic material layer is formed by one of the processes of spin coating, nozzle printing, inkjet printing, slot coating, dip coating and roll-to-roll.

9. The organic electric element as claimed in claim 6, wherein the organic material layer comprises an emission-auxiliary layer, and the emission-auxiliary layer comprises the compound.

10. The organic electric element as claimed in claim 6, wherein the organic material layer comprises a hole transport layer, and the hole transport layer comprises the compound.

11. An electronic device comprising a display device, the display device comprising the organic electric element as claimed in claim 6 and a control unit for driving the display device.

12. The electronic device as claimed in claim 11, wherein the organic electric element comprises at least one of an organic light emitting diode (OLED), an organic solar cell, an organic photo conductor (OPC), an organic transistor (organic TFT), and an element for monochromatic or white illumination.

* * * * *